(12) United States Patent
Wisniewski et al.

(10) Patent No.: US 10,870,709 B2
(45) Date of Patent: Dec. 22, 2020

(54) SPECIFIC MURINE AND HUMANIZED MONOCLONAL ANTIBODIES DETECTING PATHOLOGY ASSOCIATED SECONDARY STRUCTURE CHANGES IN PROTEINS AND PEPTIDES

(71) Applicant: NEW YORK UNIVERSITY, New York, NY (US)

(72) Inventors: Thomas M. Wisniewski, Staten Island, NY (US); Fernando Goni, New York, NY (US)

(73) Assignee: NEW YORK UNIVERSITY, New York, NY (US)

( * ) Notice: Subject to any disclaimer, the term of this patent is extended or adjusted under 35 U.S.C. 154(b) by 0 days.

(21) Appl. No.: 16/319,682

(22) PCT Filed: Jul. 22, 2017

(86) PCT No.: PCT/US2017/043416
§ 371 (c)(1),
(2) Date: Jan. 22, 2019

(87) PCT Pub. No.: WO2018/018031
PCT Pub. Date: Jan. 25, 2018

(65) Prior Publication Data
US 2019/0256612 A1 Aug. 22, 2019

Related U.S. Application Data

(60) Provisional application No. 62/365,465, filed on Jul. 22, 2016.

(51) Int. Cl.
| | | |
|---|---|---|
| *C07K 16/44* | (2006.01) | |
| *A61P 25/28* | (2006.01) | |
| *C07K 7/06* | (2006.01) | |
| *C07K 16/18* | (2006.01) | |
| *C07K 14/00* | (2006.01) | |
| *A61K 39/00* | (2006.01) | |

(52) U.S. Cl.
CPC .............. *C07K 16/44* (2013.01); *A61P 25/28* (2018.01); *C07K 7/06* (2013.01); *C07K 14/00* (2013.01); *C07K 16/18* (2013.01); *A61K 2039/505* (2013.01); *C07K 2317/30* (2013.01); *C07K 2317/33* (2013.01); *C07K 2317/34* (2013.01)

(58) Field of Classification Search
None
See application file for complete search history.

(56) References Cited

U.S. PATENT DOCUMENTS

| 8,951,519 B2 | 2/2015 | Wisniewski et al. |
| 9,834,582 B2 | 12/2017 | Wisniewski et al. |
| 2007/0110750 A1 | 5/2007 | Glabe et al. |
| 2007/0166311 A1 | 7/2007 | Greferath et al. |
| 2015/0118239 A1 | 4/2015 | Bayer |
| 2015/0166661 A1 | 6/2015 | Chen et al. |
| 2015/0196663 A1* | 7/2015 | Shusta .................... C07K 16/28 424/178.1 |
| 2015/0266947 A1* | 9/2015 | Sierks ................ G01N 33/6896 424/135.1 |
| 2017/0355756 A1* | 12/2017 | Julien ..................... C07K 16/18 |

FOREIGN PATENT DOCUMENTS

WO    WO 2008068048    *  6/2008

OTHER PUBLICATIONS

Kussie "A Single Engineered Amino Acid Substitution Changes Antibody Fine Specificity" J immunol 152(1):146-52 (Year: 1994).*
Chen "Enhancement and destruction of antibody function by somatic mutation: unequal occurrence is controlled by V gene combinatorial associations" EMBO 14(12):2784-2794 (Year: 1995).*
Koenig "Mutational landscape of antibody variable domains reveals a switch modulating the interdomain conformational dynamics and antigen binding" PNAS E486-E495 (Year: 2017).*
Reitz "toward precision medicine in Alzheimer's disease" ann tran med 4(6):107 (Year: 2016).*
Stanford "Alzheimer's Prevention, Treatment and Research—A Q&A with Dr. Frank Longo" stanfordhealthcare.org accessed on May 3, 2016 (Year: 2016).*
PCT International Search Report and Written Opinion for corresponding PCT/US2017/043416, dated Nov. 27, 2017.

* cited by examiner

*Primary Examiner* — Adam Weidner
(74) *Attorney, Agent, or Firm* — Troutman Pepper Hamilton Sanders LLP (Rochester)

(57) ABSTRACT

The present invention relates to antibodies and binding fragments thereof that bind the β-sheet secondary structure of a pathological monomeric or oligomeric non-fibrillar proteins without binding to the non-toxic, non-pathological forms of these proteins or peptides These antibodies and binding fragments thereof are suitable for the diagnosis, prevention, and treatment of protein conformational disorders including all amyloid diseases.

19 Claims, 38 Drawing Sheets
(38 of 38 Drawing Sheet(s) Filed in Color)
Specification includes a Sequence Listing.

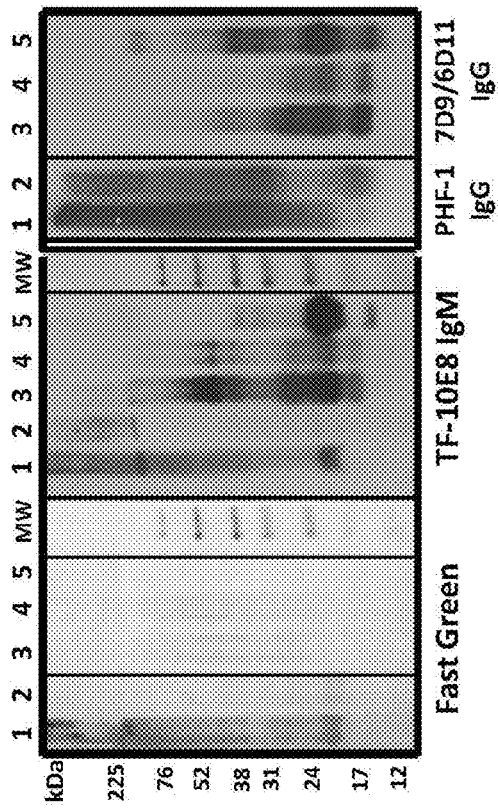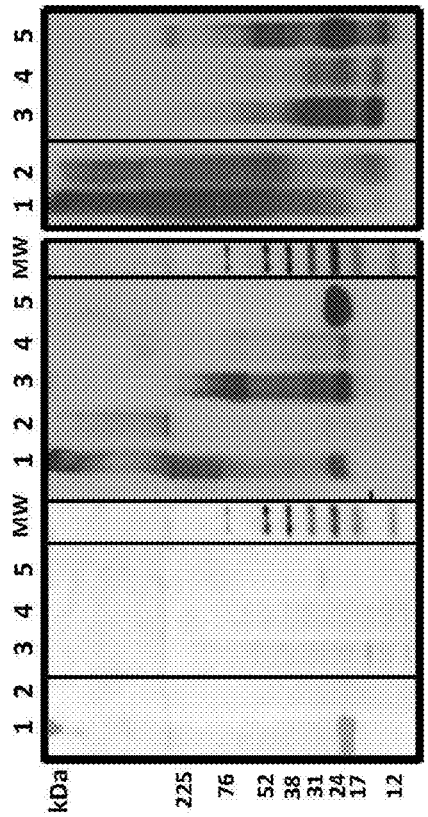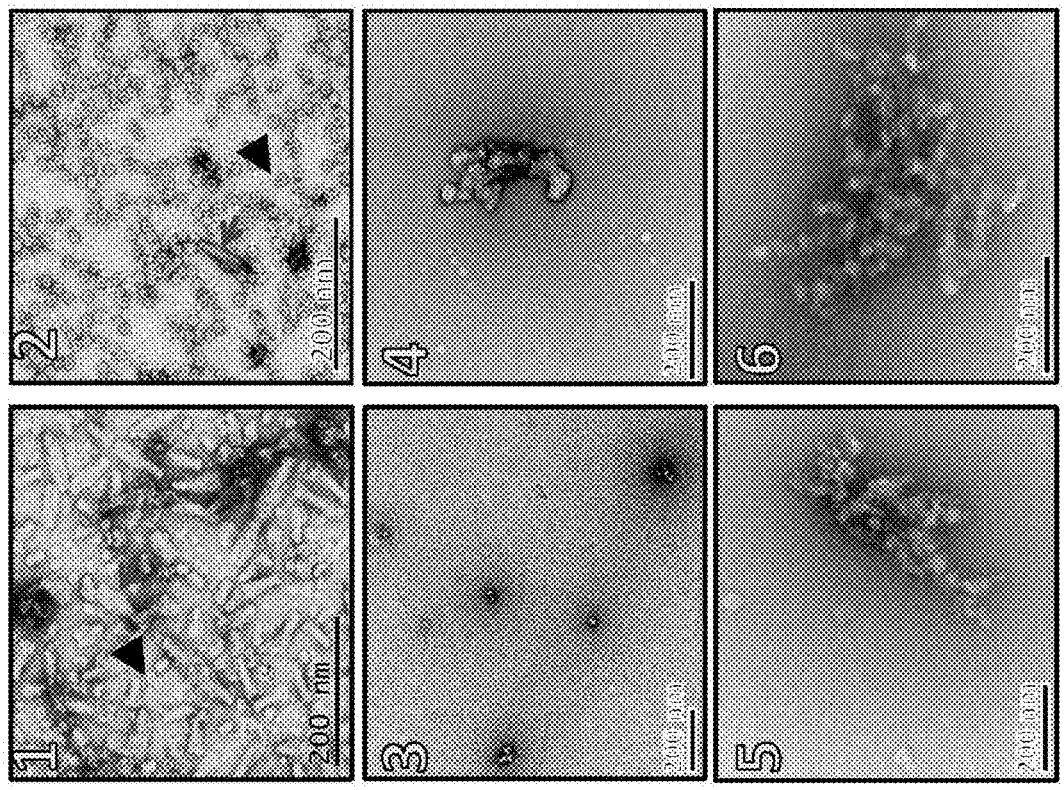
Figure 26A
Figure 26B
Figure 26C

SEQUENCE LISTING

```
<160> NUMBER OF SEQ ID NOS: 112

<210> SEQ ID NO 1
<211> LENGTH: 348
<212> TYPE: DNA
<213> ORGANISM: Artificial
<220> FEATURE:
<223> OTHER INFORMATION: Antibody Sequence

<400> SEQUENCE: 1
caggtccagc tgcagcagtc tggacctgag ctggtgaagc ctggggcttc agtgaagata        60
tcctgcaagg cttctggcta cagcttcaca agctactata tacactgggt gaagcagagg       120
cctggacagg gacttgagtg gattggatgg atttatcctg gaagtggtaa tactaagtac       180
aatgagaagt tcaagggcaa ggccacactg acggcagaca catcctccag cactgcctac       240
atgcagctca gcagcctaac atctgaggac tctgcggtct attactgtgc aaggagctat       300
ggtgactacg actactgggg ccaaggcacc actctcacag tctcctca                    348

<210> SEQ ID NO 2
<211> LENGTH: 116
<212> TYPE: PRT
<213> ORGANISM: Artificial
<220> FEATURE:
<223> OTHER INFORMATION: Antibody Sequence
```

<400> SEQUENCE: 2

Gln Val Gln Leu Gln Gln Ser Gly Pro Glu Leu Val Lys Pro Gly Ala
1               5                   10                  15

Ser Val Lys Ile Ser Cys Lys Ala Ser Gly Tyr Ser Phe Thr Ser Tyr
            20                  25                  30

Tyr Ile His Trp Val Lys Gln Arg Pro Gly Gln Gly Leu Glu Trp Ile
        35                  40                  45

Gly Trp Ile Tyr Pro Gly Ser Gly Asn Thr Lys Tyr Asn Glu Lys Phe
    50                  55                  60

Lys Gly Lys Ala Thr Leu Thr Ala Asp Thr Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Ser Tyr Gly Asp Tyr Asp Tyr Trp Gly Gln Gly Thr Thr Leu
            100                 105                 110

Thr Val Ser Ser
        115

<210> SEQ ID NO 3
<211> LENGTH: 336
<212> TYPE: DNA
<213> ORGANISM: Artificial
<220> FEATURE:
<223> OTHER INFORMATION: Antibody Sequence

<400> SEQUENCE: 3
gatgttgtga tgacccaaac tccactctcc ctgcctgtca gtcttggaga tcaagcctcc      60
atctcttgca gatctagtca gagccttgta cacagtaatg aaacaccta tttacattgg     120 tacctgcaga agccaggcca gtctccaaag ctcctgatct acaaagtttc caaccgattt    180
tctggggtcc cagacaggtt cagtggcagt ggatcaggga cagatttcac actcaagatc    240
agcagagtgg aggctgagga tctgggagtt tatttctgct ctcaaagtac acatgttcct    300
cggacgttcg gtggaggcac caagctggaa atcaaa                              336

<210> SEQ ID NO 4
<211> LENGTH: 112
<212> TYPE: PRT
<213> ORGANISM: Artificial
<220> FEATURE:
<223> OTHER INFORMATION: Antibody Sequence

<400> SEQUENCE: 4

Asp Val Val Met Thr Gln Thr Pro Leu Ser Leu Pro Val Ser Leu Gly
1               5                   10                  15

Asp Gln Ala Ser Ile Ser Cys Arg Ser Ser Gln Ser Leu Val His Ser
            20                  25                  30

Asn Gly Asn Thr Tyr Leu His Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Phe Cys Ser Gln Ser
                85                  90                  95

Thr His Val Pro Arg Thr Phe Gly Gly Gly Thr Lys Leu Glu Ile Lys
            100                 105                 110

<210> SEQ ID NO 5
<211> LENGTH: 363
<212> TYPE: DNA
<213> ORGANISM: Artificial
<220> FEATURE:
<223> OTHER INFORMATION: Antibody Sequence

<400> SEQUENCE: 5

```
caggtgcagc tgaaacagtc aggacctggc ctagtgccgc cctcacagag cctgtccatc    60
acctgcacag tttctggttt ctcattaact agctatggtg tacactgggt tcgccagtct   120
ccaggaaagg gtctggagtg gctgggagtg atatggagtg gtggaagcac agactacaat   180
gcagctttca tatccagact gagcatcagc aaggacaact ccaagagcca agttttcttt   240
aaaatgaaca gtctgcaagc tgatgacaca gccatatact actgtgccag aaatccctcc   300
gcctactata gtaactactg gtttgcttac tggggccaag gactctggt cactgtctct   360
gca                                                                  363
```

<210> SEQ ID NO 6
<211> LENGTH: 121
<212> TYPE: PRT
<213> ORGANISM: Artificial
<220> FEATURE:
<223> OTHER INFORMATION: Antibody Sequence

<400> SEQUENCE: 6

Gln Val Gln Leu Lys Gln Ser Gly Pro Gly Leu Val Pro Pro Ser Gln
1               5                   10                  15

Ser Leu Ser Ile Thr Cys Thr Val Ser Gly Phe Ser Leu Thr Ser Tyr
            20                  25                  30

Gly Val His Trp Val Arg Gln Ser Pro Gly Lys Gly Leu Glu Trp Leu
        35                  40                  45

Gly Val Ile Trp Ser Gly Gly Ser Thr Asp Tyr Asn Ala Ala Phe Ile
    50                  55                  60

Ser Arg Leu Ser Ile Ser Lys Asp Asn Ser Lys Ser Gln Val Phe Phe
65                  70                  75                  80

Lys Met Asn Ser Leu Gln Ala Asp Asp Thr Ala Ile Tyr Tyr Cys Ala
                85                  90                  95

Arg Asn Pro Ser Ala Tyr Tyr Ser Asn Tyr Trp Phe Ala Tyr Trp Gly
            100                 105                 110

Gln Gly Thr Leu Val Thr Val Ser Ala
        115                 120

<210> SEQ ID NO 7
<211> LENGTH: 321
<212> TYPE: DNA
<213> ORGANISM: Artificial
<220> FEATURE:
<223> OTHER INFORMATION: Antibody Sequence

<400> SEQUENCE: 7

```
gacattgtga tgacccagtc tcaaaatttc atgtccacat cagtaggaga cagggtcagc    60
gtcacctgca aggccagtca gtatgtgggt acttatgtag cctggtatca acagaaacca   120
gggcaatctc ctaaagcact gatttactcg gcatcctacc ggcatactgg agtccctgat   180
cgcttcacag gcagtggatc tgggacagat tcactctca ccatcagcaa tgtgcagtct   240
gaagacctgg cagattattt ctgtcagcaa tatagcagct cctctcac gttcggctcg   300
gggacaaagt tggaaataaa a                                              321
```

<210> SEQ ID NO 8
<211> LENGTH: 107
<212> TYPE: PRT
<213> ORGANISM: Artificial
<220> FEATURE:
<223> OTHER INFORMATION: Antibody Sequence

<400> SEQUENCE: 8

Asp Ile Val Met Thr Gln Ser Gln Asn Phe Met Ser Thr Ser Val Gly
1               5                   10                  15

Asp Arg Val Ser Val Thr Cys Lys Ala Ser Gln Tyr Val Gly Thr Tyr
            20                  25                  30

Val Ala Trp Tyr Gln Gln Lys Pro Gly Gln Ser Pro Lys Ala Leu Ile
        35                  40                  45

Tyr Ser Ala Ser Tyr Arg His Thr Gly Val Pro Asp Arg Phe Thr Gly
    50                  55                  60

Ser Gly Ser Gly Thr Asp Phe Thr Leu Thr Ile Ser Asn Val Gln Ser
65                  70                  75                  80

Glu Asp Leu Ala Asp Tyr Phe Cys Gln Gln Tyr Ser Ser Ser Pro Leu
                85                  90                  95

Thr Phe Gly Ser Gly Thr Lys Leu Glu Ile Lys
            100                 105

<210> SEQ ID NO 9
<211> LENGTH: 348
<212> TYPE: DNA
<213> ORGANISM: Artificial
<220> FEATURE:
<223> OTHER INFORMATION: Antibody Sequence

<400> SEQUENCE: 9
gaggtcaagc tgcagcagtc tggacctgag ctggtgaagc ctggggcttc agtgaagata         60
tcctgcaagg cttctggtta ctcattcact ggctactaca tgcactgggt gaagcaaagt        120
tctgaaaaga gccttgagtg gattggagag attaatccta gcactggtgg tactagctac        180
aaccagaagt tcaagggcaa ggccacatta actgtagaca gtcatccag cacagcctac         240 atgcagctca agagcctgac atctgaggac tctgctgtct attactgtgc aagagactac        300
tatagtaagg cttactgggg ccaagggact ctggtcactg tctctgca                     348

<210> SEQ ID NO 10
<211> LENGTH: 116
<212> TYPE: PRT
<213> ORGANISM: Artificial
<220> FEATURE:
<223> OTHER INFORMATION: Antibody Sequence

<400> SEQUENCE: 10

Glu Val Lys Leu Gln Gln Ser Gly Pro Glu Leu Val Lys Pro Gly Ala
1               5                   10                  15

Ser Val Lys Ile Ser Cys Lys Ala Ser Gly Tyr Ser Phe Thr Gly Tyr
            20                  25                  30

Tyr Met His Trp Val Lys Gln Ser Ser Glu Lys Ser Leu Glu Trp Ile
        35                  40                  45

Gly Glu Ile Asn Pro Ser Thr Gly Gly Thr Ser Tyr Asn Gln Lys Phe
    50                  55                  60

Lys Gly Lys Ala Thr Leu Thr Val Asp Lys Ser Ser Ser Thr Ala Tyr
65                  70                  75                  80

```
Met Gln Leu Lys Ser Leu Thr Ser Glu Asp Ser Ala Val Tyr Tyr Cys
                 85                  90                  95

Ala Arg Asp Tyr Tyr Ser Lys Ala Tyr Trp Gly Gln Gly Thr Leu Val
            100                 105                 110

Thr Val Ser Ala
        115

<210> SEQ ID NO 11
<211> LENGTH: 321
<212> TYPE: DNA
<213> ORGANISM: Artificial
<220> FEATURE:
<223> OTHER INFORMATION: Antibody Sequence

<400> SEQUENCE: 11
agtattgtga tgacccagac tcccaaattc ctgcttgtat cagcaggaga cagggttacc    60
ataacctgca aggccagtca gagtgtgagt aatgatgtag cttggtacca acagaagcca   120
gggcagtctc ctaaactgct gatatactat gcatccaatc gctacactgg agtccctgat   180
cgcttcactg gcagtggata tgggacggat ttcacttttca ccatcagcac tgtgcaggct   240
gaagacctgg cagtttattt ctgtcagcag gattatagct ctccgtacac gttcggaggg   300
gggaccaagc tggaaataaa a                                             321

<210> SEQ ID NO 12
<211> LENGTH: 107
<212> TYPE: PRT
<213> ORGANISM: Artificial
<220> FEATURE:
<223> OTHER INFORMATION: Antibody Sequence

<400> SEQUENCE: 12

Ser Ile Val Met Thr Gln Thr Pro Lys Phe Leu Leu Val Ser Ala Gly
1               5                   10                  15

Asp Arg Val Thr Ile Thr Cys Lys Ala Ser Gln Ser Val Ser Asn Asp
            20                  25                  30

Val Ala Trp Tyr Gln Gln Lys Pro Gly Gln Ser Pro Lys Leu Leu Ile
        35                  40                  45

Tyr Tyr Ala Ser Asn Arg Tyr Thr Gly Val Pro Asp Arg Phe Thr Gly
    50                  55                  60

Ser Gly Tyr Gly Thr Asp Phe Thr Phe Thr Ile Ser Thr Val Gln Ala
65                  70                  75                  80

Glu Asp Leu Ala Val Tyr Phe Cys Gln Gln Asp Tyr Ser Ser Pro Tyr
                85                  90                  95

Thr Phe Gly Gly Gly Thr Lys Leu Glu Ile Lys
            100                 105

<210> SEQ ID NO 13
<211> LENGTH: 360
<212> TYPE: DNA
<213> ORGANISM: Artificial
<220> FEATURE:
<223> OTHER INFORMATION: Antibody Sequence

<400> SEQUENCE: 13
caggtcactc tgaaagagtc tggccctggg atattgcagc cctcccagac cctcagtctg    60
acttgttctt tctctgggtt ttcactgagc acttatggta tgggtgtagg ttggattcgt   120
cagccttcag ggaagggtct ggagtggctg gccaacattt ggtggaatga tgataagtac   180
tataactcag ccctgaagag ccggctcaca atctccaagg atacctccaa caaccaggta   240
```
ttcctcaaga tctccagtgt ggacactgca gatactgcca catactactg tgctcaaata    300
gggtggttac tagcctggtt tgcttactgg ggccaaggga ctctggtcac tgtctctgca    360

<210> SEQ ID NO 14
<211> LENGTH: 120
<212> TYPE: PRT
<213> ORGANISM: Artificial
<220> FEATURE:
<223> OTHER INFORMATION: Antibody Sequence

<400> SEQUENCE: 14

Gln Val Thr Leu Lys Glu Ser Gly Pro Gly Ile Leu Gln Pro Ser Gln
1               5                   10                  15

Thr Leu Ser Leu Thr Cys Ser Phe Ser Gly Phe Ser Leu Ser Thr Tyr
            20                  25                  30

Gly Met Gly Val Gly Trp Ile Arg Gln Pro Ser Gly Lys Gly Leu Glu
        35                  40                  45

Trp Leu Ala Asn Ile Trp Trp Asn Asp Asp Lys Tyr Tyr Asn Ser Ala
    50                  55                  60

Leu Lys Ser Arg Leu Thr Ile Ser Lys Asp Thr Ser Asn Asn Gln Val
65                  70                  75                  80

Phe Leu Lys Ile Ser Ser Val Asp Thr Ala Asp Thr Ala Thr Tyr Tyr
                85                  90                  95

Cys Ala Gln Ile Gly Trp Leu Leu Ala Trp Phe Ala Tyr Trp Gly Gln
            100                 105                 110

Gly Thr Leu Val Thr Val Ser Ala
        115                 120

<210> SEQ ID NO 15
<211> LENGTH: 336
<212> TYPE: DNA
<213> ORGANISM: Artificial
<220> FEATURE:
<223> OTHER INFORMATION: Antibody Sequence

<400> SEQUENCE: 15
gacattgtga tgtcacagtc tccatcctcc ctggctgtgt cagcaggaga gaaggtcact     60
atgagctgca aatccagtca gagtctgctc aacagtagaa cccgaaagaa ctacttggct    120
tggtaccagc agaaaccagg gcagtctcct aaactgctga tctactgggc atccactagg    180
gaatctgggg tccctgatcg cttcacaggc agtggatctg ggacagattt cactctcacc    240
atcagcagtg tgcaggctga agacctggca gtttattact gcaagcaatc ttataatctg    300
ctcacgttcg gtgctgggac caagctggag ctgaaa                              336

<210> SEQ ID NO 16
<211> LENGTH: 112
<212> TYPE: PRT
<213> ORGANISM: Artificial
<220> FEATURE:
<223> OTHER INFORMATION: Antibody Sequence

<400> SEQUENCE: 16

Asp Ile Val Met Ser Gln Ser Pro Ser Ser Leu Ala Val Ser Ala Gly
1               5                   10                  15

Glu Lys Val Thr Met Ser Cys Lys Ser Ser Gln Ser Leu Leu Asn Ser
            20                  25                  30

Arg Thr Arg Lys Asn Tyr Leu Ala Trp Tyr Gln Gln Lys Pro Gly Gln
        35                  40                  45

```
Ser Pro Lys Leu Leu Ile Tyr Trp Ala Ser Thr Arg Glu Ser Gly Val
        50                  55                  60

Pro Asp Arg Phe Thr Gly Ser Gly Ser Gly Thr Asp Phe Thr Leu Thr
 65              70                  75                  80

Ile Ser Ser Val Gln Ala Glu Asp Leu Ala Val Tyr Tyr Cys Lys Gln
                    85                  90                  95

Ser Tyr Asn Leu Leu Thr Phe Gly Ala Gly Thr Lys Leu Glu Leu Lys
            100                 105                 110
```

<210> SEQ ID NO 17
<211> LENGTH: 333
<212> TYPE: DNA
<213> ORGANISM: Artificial
<220> FEATURE:
<223> OTHER INFORMATION: Antibody Sequence

<400> SEQUENCE: 17

```
gacattgtgc tgacacagtc tcctgcttcc ttagctgtat ctctggggca gagggccacc    60
atctcataca gggccagcaa aagtgtcagt acatctggct atagttatat gcactggaac   120
caacagaaac caggacagcc acccagactc ctcatctatc ttgtatccaa cctagaatct   180
ggggtccctg ccaggttcag tggcagtgga tcagggacag atttcacact caagatcagc   240
agagtggagg ctgaggatct gggagtttat ttctgctctc aaagtacaca tgttcctcgg   300
acgttcggtg gaggcaccaa gctggaaatc aaa                                333
```

<210> SEQ ID NO 18
<211> LENGTH: 111
<212> TYPE: PRT
<213> ORGANISM: Artificial
<220> FEATURE:
<223> OTHER INFORMATION: Antibody Sequence

<400> SEQUENCE: 18

```
Asp Ile Val Leu Thr Gln Ser Pro Ala Ser Leu Ala Val Ser Leu Gly
  1               5                  10                  15

Gln Arg Ala Thr Ile Ser Tyr Arg Ala Ser Lys Ser Val Ser Thr Ser
                20                  25                  30

Gly Tyr Ser Tyr Met His Trp Asn Gln Gln Lys Pro Gly Gln Pro Pro
            35                  40                  45

Arg Leu Leu Ile Tyr Leu Val Ser Asn Leu Glu Ser Gly Val Pro Ala
        50                  55                  60

Arg Phe Ser Gly Ser Gly Ser Gly Thr Asp Phe Thr Leu Lys Ile Ser
 65              70                  75                  80

Arg Val Glu Ala Glu Asp Leu Gly Val Tyr Phe Cys Ser Gln Ser Thr
                    85                  90                  95

His Val Pro Arg Thr Phe Gly Gly Gly Thr Lys Leu Glu Ile Lys
            100                 105                 110
```

<210> SEQ ID NO 19
<211> LENGTH: 351
<212> TYPE: DNA
<213> ORGANISM: Artificial
<220> FEATURE:
<223> OTHER INFORMATION: Antibody Sequence

<400> SEQUENCE: 19

```
gaggttcagc tgcagcagtc tgtggcagag cttgtgaggc caggggcctc agtcaagttg    60
tcctgcacag cttctggctt caacattaaa aacacctata tgcactgggt gaagcagagg   120
```

```
cctgaacagg gcctggagtg gattggaagg attgatcctg cgaatggtaa tactaaatat    180
gccccgaagt tccagggcaa ggccactata actgcagaca catcctccaa cacagcctac    240
ctgcagctca gcagcctgac atctgaggac actgccatct attactgtgc tagagggagt    300
ttttatgcta tggactactg gggtcaagga acctcagtca ccgtctcctc a             351
```

```
<210> SEQ ID NO 20
<211> LENGTH: 117
<212> TYPE: PRT
<213> ORGANISM: Artificial
<220> FEATURE:
<223> OTHER INFORMATION: Antibody Sequence

<400> SEQUENCE: 20
```

Glu Val Gln Leu Gln Gln Ser Val Ala Glu Leu Val Arg Pro Gly Ala
1               5                   10                  15

Ser Val Lys Leu Ser Cys Thr Ala Ser Gly Phe Asn Ile Lys Asn Thr
            20                  25                  30

Tyr Met His Trp Val Lys Gln Arg Pro Glu Gln Gly Leu Glu Trp Ile
        35                  40                  45

Gly Arg Ile Asp Pro Ala Asn Gly Asn Thr Lys Tyr Ala Pro Lys Phe
    50                  55                  60

Gln Gly Lys Ala Thr Ile Thr Ala Asp Thr Ser Ser Asn Thr Ala Tyr
65                  70                  75                  80

Leu Gln Leu Ser Ser Leu Thr Ser Glu Asp Thr Ala Ile Tyr Tyr Cys
                85                  90                  95

Ala Arg Gly Ser Phe Tyr Ala Met Asp Tyr Trp Gly Gln Gly Thr Ser
            100                 105                 110

Val Thr Val Ser Ser
        115

```
<210> SEQ ID NO 21
<211> LENGTH: 321
<212> TYPE: DNA
<213> ORGANISM: Artificial
<220> FEATURE:
<223> OTHER INFORMATION: Antibody Sequence
<400> SEQUENCE: 21
gatgtccaga taacccagtc tccatcttat cttgctgcat ctcctggaga aaccattact    60
attaattgca gggcaagtaa gagcattaac aaatatttag cctggtatca agagaaacct    120
gggaaaacta taagcttct tatctactct ggatccacct tgcaatctgg aattccatca    180
aggttcagtg gcagtggatc tggtacagat tttactctca ccatcagtag cctggagcct    240
gaagattttg caatgtatca ctgtcaacag cataatgaat acccgtggac gttcggtgga    300
ggcaccaagc tggaaatcaa a                                               321
```

```
<210> SEQ ID NO 22
<211> LENGTH: 107
<212> TYPE: PRT
<213> ORGANISM: Artificial
<220> FEATURE:
<223> OTHER INFORMATION: Antibody Sequence

<400> SEQUENCE: 22
```

Asp Val Gln Ile Thr Gln Ser Pro Ser Tyr Leu Ala Ala Ser Pro Gly
1               5                   10                  15

Glu Thr Ile Thr Ile Asn Cys Arg Ala Ser Lys Ser Ile Asn Lys Tyr

```
            20                  25                  30
Leu Ala Trp Tyr Gln Glu Lys Pro Gly Lys Thr Asn Lys Leu Leu Ile
            35                  40                  45

Tyr Ser Gly Ser Thr Leu Gln Ser Gly Ile Pro Ser Arg Phe Ser Gly
            50                  55                  60

Ser Gly Ser Gly Thr Asp Phe Thr Leu Thr Ile Ser Ser Leu Glu Pro
 65                  70                  75                  80

Glu Asp Phe Ala Met Tyr His Cys Gln Gln His Asn Glu Tyr Pro Trp
                85                  90                  95

Thr Phe Gly Gly Gly Thr Lys Leu Glu Ile Lys
                100                 105
```

<210> SEQ ID NO 23
<211> LENGTH: 10
<212> TYPE: PRT
<213> ORGANISM: Artificial
<220> FEATURE:
<223> OTHER INFORMATION: Antibody Sequence

<400> SEQUENCE: 23

```
Gly Tyr Ser Phe Thr Ser Tyr Tyr Ile His
 1               5                  10
```

<210> SEQ ID NO 24
<211> LENGTH: 10
<212> TYPE: PRT
<213> ORGANISM: Artificial
<220> FEATURE:
<223> OTHER INFORMATION: Antibody Sequence

<400> SEQUENCE: 24

```
Gly Phe Ser Leu Thr Ser Tyr Gly Val His
 1               5                  10
```

<210> SEQ ID NO 25
<211> LENGTH: 10
<212> TYPE: PRT
<213> ORGANISM: Artificial
<220> FEATURE:
<223> OTHER INFORMATION: Antibody Sequence

<400> SEQUENCE: 25

```
Gly Tyr Ser Phe Thr Gly Tyr Tyr Met His
 1               5                  10
```

<210> SEQ ID NO 26
<211> LENGTH: 10
<212> TYPE: PRT
<213> ORGANISM: Artificial
<220> FEATURE:
<223> OTHER INFORMATION: Antibody Sequence

<400> SEQUENCE: 26

```
Gly Phe Asn Ile Lys Asn Thr Tyr Met His
 1               5                  10
```

<210> SEQ ID NO 27
<211> LENGTH: 17
<212> TYPE: PRT
<213> ORGANISM: Artificial
<220> FEATURE:
<223> OTHER INFORMATION: Antibody Sequence

<400> SEQUENCE: 27

```
Trp Ile Tyr Pro Gly Ser Gly Asn Thr Lys Tyr Asn Glu Lys Phe Lys
1               5                   10                  15

Gly

<210> SEQ ID NO 28
<211> LENGTH: 16
<212> TYPE: PRT
<213> ORGANISM: Artificial
<220> FEATURE:
<223> OTHER INFORMATION: Antibody Sequence

<400> SEQUENCE: 28

Val Ile Trp Ser Gly Gly Ser Thr Asp Tyr Asn Ala Ala Phe Ile Ser
1               5                   10                  15

<210> SEQ ID NO 29
<211> LENGTH: 17
<212> TYPE: PRT
<213> ORGANISM: Artificial
<220> FEATURE:
<223> OTHER INFORMATION: Antibody Sequence

<400> SEQUENCE: 29

Glu Ile Asn Pro Ser Thr Gly Gly Thr Ser Tyr Asn Gln Lys Phe Lys
1               5                   10                  15

Gly

<210> SEQ ID NO 30
<211> LENGTH: 17
<212> TYPE: PRT
<213> ORGANISM: Artificial
<220> FEATURE:
<223> OTHER INFORMATION: Antibody Sequence

<400> SEQUENCE: 30

Arg Ile Asp Pro Ala Asn Gly Asn Thr Lys Tyr Ala Pro Lys Phe Gln
1               5                   10                  15

Gly

<210> SEQ ID NO 31
<211> LENGTH: 7
<212> TYPE: PRT
<213> ORGANISM: Artificial
<220> FEATURE:
<223> OTHER INFORMATION: Antibody Sequence

<400> SEQUENCE: 31

Ser Tyr Gly Asp Tyr Asp Tyr
1               5

<210> SEQ ID NO 32
<211> LENGTH: 13
<212> TYPE: PRT
<213> ORGANISM: Artificial
<220> FEATURE:
<223> OTHER INFORMATION: Antibody Sequence

<400> SEQUENCE: 32

Asn Pro Ser Ala Tyr Tyr Ser Asn Tyr Trp Phe Ala Tyr
1               5                   10

<210> SEQ ID NO 33
<211> LENGTH: 7
<212> TYPE: PRT
<213> ORGANISM: Artificial
```

```
<220> FEATURE:
<223> OTHER INFORMATION: Antibody Sequence

<400> SEQUENCE: 33

Asp Tyr Tyr Ser Lys Ala Tyr
1               5

<210> SEQ ID NO 34
<211> LENGTH: 6
<212> TYPE: PRT
<213> ORGANISM: Artificial
<220> FEATURE:
<223> OTHER INFORMATION: Antibody Sequence

<400> SEQUENCE: 34

Phe Tyr Ala Met Asp Tyr
1               5

<210> SEQ ID NO 35
<211> LENGTH: 16
<212> TYPE: PRT
<213> ORGANISM: Artificial
<220> FEATURE:
<223> OTHER INFORMATION: Antibody Sequence

<400> SEQUENCE: 35

Arg Ser Ser Gln Ser Leu Val His Ser Asn Gly Asn Thr Tyr Leu His
1               5                   10                  15

<210> SEQ ID NO 36
<211> LENGTH: 11
<212> TYPE: PRT
<213> ORGANISM: Artificial
<220> FEATURE:
<223> OTHER INFORMATION: Antibody Sequence

<400> SEQUENCE: 36

Lys Ala Ser Gln Tyr Val Gly Thr Tyr Val Ala
1               5                   10

<210> SEQ ID NO 37
<211> LENGTH: 11
<212> TYPE: PRT
<213> ORGANISM: Artificial
<220> FEATURE:
<223> OTHER INFORMATION: Antibody Sequence

<400> SEQUENCE: 37

Lys Ala Ser Gln Ser Val Ser Asn Asp Val Ala
1               5                   10

<210> SEQ ID NO 38
<211> LENGTH: 15
<212> TYPE: PRT
<213> ORGANISM: Artificial
<220> FEATURE:
<223> OTHER INFORMATION: Antibody Sequence

<400> SEQUENCE: 38

Arg Ala Ser Lys Ser Val Ser Thr Ser Gly Tyr Ser Tyr Met His
1               5                   10                  15

<210> SEQ ID NO 39
<211> LENGTH: 11
<212> TYPE: PRT
<213> ORGANISM: Artificial
<220> FEATURE:
```

```
<223> OTHER INFORMATION: Antibody Sequence

<400> SEQUENCE: 39

Arg Ala Ser Lys Ser Ile Asn Lys Tyr Leu Ala
1               5                   10

<210> SEQ ID NO 40
<211> LENGTH: 7
<212> TYPE: PRT
<213> ORGANISM: Artificial
<220> FEATURE:
<223> OTHER INFORMATION: Antibody Sequence

<400> SEQUENCE: 40

Lys Val Ser Asn Arg Phe Ser
1               5

<210> SEQ ID NO 41
<211> LENGTH: 7
<212> TYPE: PRT
<213> ORGANISM: Artificial
<220> FEATURE:
<223> OTHER INFORMATION: Antibody Sequence

<400> SEQUENCE: 41

Ser Ala Ser Tyr Arg His Thr
1               5

<210> SEQ ID NO 42
<211> LENGTH: 7
<212> TYPE: PRT
<213> ORGANISM: Artificial
<220> FEATURE:
<223> OTHER INFORMATION: Antibody Sequence

<400> SEQUENCE: 42

Tyr Ala Ser Asn Arg Tyr Thr
1               5

<210> SEQ ID NO 43
<211> LENGTH: 7
<212> TYPE: PRT
<213> ORGANISM: Artificial
<220> FEATURE:
<223> OTHER INFORMATION: Antibody Sequence

<400> SEQUENCE: 43

Leu Val Ser Asn Leu Glu Ser
1               5

<210> SEQ ID NO 44
<211> LENGTH: 7
<212> TYPE: PRT
<213> ORGANISM: Artificial
<220> FEATURE:
<223> OTHER INFORMATION: Antibody Sequence

<400> SEQUENCE: 44

Ser Gly Ser Thr Leu Gln Ser
1               5

<210> SEQ ID NO 45
<211> LENGTH: 9
<212> TYPE: PRT
<213> ORGANISM: Artificial
<220> FEATURE:
<223> OTHER INFORMATION: Antibody Sequence
```

<400> SEQUENCE: 45

Ser Gln Ser Thr His Val Pro Arg Thr
1               5

<210> SEQ ID NO 46
<211> LENGTH: 9
<212> TYPE: PRT
<213> ORGANISM: Artificial
<220> FEATURE:
<223> OTHER INFORMATION: Antibody Sequence

<400> SEQUENCE: 46

Gln Gln Tyr Ser Ser Ser Pro Leu Thr
1               5

<210> SEQ ID NO 47
<211> LENGTH: 9
<212> TYPE: PRT
<213> ORGANISM: Artificial
<220> FEATURE:
<223> OTHER INFORMATION: Antibody Sequence

<400> SEQUENCE: 47

Gln Gln Asp Tyr Ser Ser Pro Tyr Thr
1               5

<210> SEQ ID NO 48
<211> LENGTH: 9
<212> TYPE: PRT
<213> ORGANISM: Artificial
<220> FEATURE:
<223> OTHER INFORMATION: Antibody Sequence

<400> SEQUENCE: 48

Ser Gln Ser Thr His Val Pro Arg Thr
1               5

<210> SEQ ID NO 49
<211> LENGTH: 9
<212> TYPE: PRT
<213> ORGANISM: Artificial
<220> FEATURE:
<223> OTHER INFORMATION: Antibody Sequence

<400> SEQUENCE: 49

Gln Gln His Asn Glu Tyr Pro Trp Thr
1               5

<210> SEQ ID NO 50
<211> LENGTH: 12
<212> TYPE: PRT
<213> ORGANISM: Artificial
<220> FEATURE:
<223> OTHER INFORMATION: Antibody Sequence

<400> SEQUENCE: 50

Gly Phe Ser Leu Ser Thr Tyr Gly Met Gly Val Gly
1               5                   10

<210> SEQ ID NO 51
<211> LENGTH: 16
<212> TYPE: PRT
<213> ORGANISM: Artificial
<220> FEATURE:
<223> OTHER INFORMATION: Antibody Sequence -continued

<400> SEQUENCE: 51

Asn Ile Trp Trp Asn Asp Asp Lys Tyr Tyr Asn Ser Ala Leu Lys Ser
1               5                   10                  15

<210> SEQ ID NO 52
<211> LENGTH: 10
<212> TYPE: PRT
<213> ORGANISM: Artificial
<220> FEATURE:
<223> OTHER INFORMATION: Antibody Sequence

<400> SEQUENCE: 52

Ile Gly Trp Leu Leu Ala Trp Phe Ala Tyr
1               5                   10

<210> SEQ ID NO 53
<211> LENGTH: 17
<212> TYPE: PRT
<213> ORGANISM: Artificial
<220> FEATURE:
<223> OTHER INFORMATION: Antibody Sequence

<400> SEQUENCE: 53

Lys Ser Ser Gln Ser Leu Leu Asn Ser Arg Thr Arg Lys Asn Tyr Leu
1               5                   10                  15

Ala

<210> SEQ ID NO 54
<211> LENGTH: 7
<212> TYPE: PRT
<213> ORGANISM: Artificial
<220> FEATURE:
<223> OTHER INFORMATION: Antibody Sequence

<400> SEQUENCE: 54

Trp Ala Ser Thr Arg Glu Ser
1               5

<210> SEQ ID NO 55
<211> LENGTH: 8
<212> TYPE: PRT
<213> ORGANISM: Artificial
<220> FEATURE:
<223> OTHER INFORMATION: Antibody Sequence

<400> SEQUENCE: 55

Lys Gln Ser Tyr Asn Leu Leu Thr
1               5

<210> SEQ ID NO 56
<211> LENGTH: 1773
<212> TYPE: DNA
<213> ORGANISM: Artificial
<220> FEATURE:
<223> OTHER INFORMATION: Antibody Sequence

<400> SEQUENCE: 56
atgggatgga gctggatctt tctcttcctc ctgtcaggaa ctgcaggtgt ccattgccag      60
gtccagctgc agcagtctgg acctgagctg gtgaagcctg ggcttcagt gaagatatcc     120 tgcaaggctt ctggctacag cttcacaagc tactatatac actgggtgaa gcagaggcct     180
ggacagggac ttgagtggat tgatggatt tatcctggaa gtggtaatac taagtacaat     240
gagaagttca aggcaaggc cacactgacg gcagacacat cctccagcac tgcctacatg     300

```
cagctcagca gcctaacatc tgaggactct gcggtctatt actgtgcaag gagctatggt    360
gactacgact actggggcca aggcaccact ctcacagtct cctcagagag tcagtccttc    420
ccaaatgtct ttcccctcgt ctcctgcgag agcccctgt  ctgataagaa tctggtggcc    480
atgggctgcc tggcccggga cttcctgccc agcaccattt ccttcacctg gaactaccag    540
aacaacactg aagtcatcca gggtatcaga accttcccaa cactgaggac aggggggcaag   600 tacctagcca cctcgcaggt gttgctgtct cccaagagca tccttgaagg ttcagatgaa    660
tacctggtat gcaaaatcca ctacggaggc aaaaacagag atctgcatgt gcccattcca    720
gctgtcgcag agatgaaccc caatgtaaat gtgttcgtcc caccacggga tggcttctct    780
ggccctgcac cacgcaagtc taaactcatc tgcgaggcca cgaacttcac tccaaaaccg    840
atcacagtat cctggctaaa ggatgggaag ctcgtggaat ctggcttcac cacagatccg    900
gtgaccatcg agaacaaagg atccacaccc caaacctaca aggtcataag cacacttacc    960
atctctgaaa tcgactggct gaacctgaat gtgtacacct gccgtgtgga tcacaggggt   1020 ctcacccttct tgaagaacgt gtcctccaca tgtgctgcca gtccctccac agacatccta   1080
accttcacca tccccccctc ctttgccgac atcttcctca gcaagtccgc taacctgacc   1140
tgtctggtct caaacctggc aacctatgaa accctgaata tctcctgggc ttctcaaagt   1200
ggtgaaccac tggaaaccaa aattaaaatc atggaaagtc atcccaatgg caccttcagt   1260
gctaagggtg tggctagtgt ttgtgtggaa gactggaata caggaagga  atttgtgtgt   1320 actgtgactc acagggatct gccttcacca cagaagaaat tcatctcaaa acccaatgag   1380
gtgcacaaac atccacctgc tgtgtacctg ctgccaccag ctcgtgagca actgaacctg   1440
agggagtcag ccacagtcac ctgcctggtg aagggcttct ctcctgcaga catcagtgtg   1500
cagtggcttc agagagggca actcttgccc aagagaagt  atgtgaccag tgcccccgatg  1560 ccagagcctg ggcccccagg cttctacttt acccacagca tcctgactgt gacagaggag   1620
gaatggaact ccggagagac ctatacctgt gttgtaggcc acgaggccct gccacacctg   1680
gtgaccgaga ggaccgtgga caagtccact ggtaaaccca cactgtacaa tgtctccctg   1740
atcatgtctg acacaggcgg cacctgctat tga                                1773
```

<210> SEQ ID NO 57
<211> LENGTH: 590
<212> TYPE: PRT
<213> ORGANISM: Artificial
<220> FEATURE:
<223> OTHER INFORMATION: Antibody Sequence

<400> SEQUENCE: 57

```
Met Gly Trp Ser Trp Ile Phe Leu Phe Leu Leu Ser Gly Thr Ala Gly
1               5                   10                  15

Val His Cys Gln Val Gln Leu Gln Gln Ser Gly Pro Glu Leu Val Lys
            20                  25                  30

Pro Gly Ala Ser Val Lys Ile Ser Cys Lys Ala Ser Gly Tyr Ser Phe
        35                  40                  45

Thr Ser Tyr Tyr Ile His Trp Val Lys Gln Arg Pro Gly Gln Gly Leu
    50                  55                  60

Glu Trp Ile Gly Trp Ile Tyr Pro Gly Ser Gly Asn Thr Lys Tyr Asn
65                  70                  75                  80

Glu Lys Phe Lys Gly Lys Ala Thr Leu Thr Ala Asp Thr Ser Ser Ser
                85                  90                  95

Thr Ala Tyr Met Gln Leu Ser Ser Leu Thr Ser Glu Asp Ser Ala Val
```

-continued

```
                100                 105                 110
Tyr Tyr Cys Ala Arg Ser Tyr Gly Asp Tyr Asp Tyr Trp Gly Gln Gly
            115                 120                 125

Thr Thr Leu Thr Val Ser Ser Glu Ser Gln Ser Phe Pro Asn Val Phe
130                 135                 140

Pro Leu Val Ser Cys Glu Ser Pro Leu Ser Asp Lys Asn Leu Val Ala
145                 150                 155                 160

Met Gly Cys Leu Ala Arg Asp Phe Leu Pro Ser Thr Ile Ser Phe Thr
                165                 170                 175

Trp Asn Tyr Gln Asn Asn Thr Glu Val Ile Gln Gly Ile Arg Thr Phe
                180                 185                 190

Pro Thr Leu Arg Thr Gly Gly Lys Tyr Leu Ala Thr Ser Gln Val Leu
                195                 200                 205

Leu Ser Pro Lys Ser Ile Leu Glu Gly Ser Asp Glu Tyr Leu Val Cys
            210                 215                 220

Lys Ile His Tyr Gly Gly Lys Asn Arg Asp Leu His Val Pro Ile Pro
225                 230                 235                 240

Ala Val Ala Glu Met Asn Pro Asn Val Asn Val Phe Val Pro Pro Arg
                245                 250                 255

Asp Gly Phe Ser Gly Pro Ala Pro Arg Lys Ser Lys Leu Ile Cys Glu
                260                 265                 270

Ala Thr Asn Phe Thr Pro Lys Pro Ile Thr Val Ser Trp Leu Lys Asp
                275                 280                 285

Gly Lys Leu Val Glu Ser Gly Phe Thr Thr Asp Pro Val Thr Ile Glu
            290                 295                 300

Asn Lys Gly Ser Thr Pro Gln Thr Tyr Lys Val Ile Ser Thr Leu Thr
305                 310                 315                 320

Ile Ser Glu Ile Asp Trp Leu Asn Leu Asn Val Tyr Thr Cys Arg Val
                325                 330                 335

Asp His Arg Gly Leu Thr Phe Leu Lys Asn Val Ser Ser Thr Cys Ala
                340                 345                 350

Ala Ser Pro Ser Thr Asp Ile Leu Thr Phe Thr Ile Pro Pro Ser Phe
            355                 360                 365

Ala Asp Ile Phe Leu Ser Lys Ser Ala Asn Leu Thr Cys Leu Val Ser
            370                 375                 380

Asn Leu Ala Thr Tyr Glu Thr Leu Asn Ile Ser Trp Ala Ser Gln Ser
385                 390                 395                 400

Gly Glu Pro Leu Glu Thr Lys Ile Lys Ile Met Glu Ser His Pro Asn
                405                 410                 415

Gly Thr Phe Ser Ala Lys Gly Val Ala Ser Val Cys Val Glu Asp Trp
                420                 425                 430

Asn Asn Arg Lys Glu Phe Val Cys Thr Val Thr His Arg Asp Leu Pro
            435                 440                 445

Ser Pro Gln Lys Lys Phe Ile Ser Lys Pro Asn Glu Val His Lys His
            450                 455                 460

Pro Pro Ala Val Tyr Leu Leu Pro Pro Ala Arg Glu Gln Leu Asn Leu
465                 470                 475                 480

Arg Glu Ser Ala Thr Val Thr Cys Leu Val Lys Gly Phe Ser Pro Ala
                485                 490                 495

Asp Ile Ser Val Gln Trp Leu Gln Arg Gly Gln Leu Leu Pro Gln Glu
            500                 505                 510

Lys Tyr Val Thr Ser Ala Pro Met Pro Glu Pro Gly Ala Pro Gly Phe
            515                 520                 525
```

Tyr Phe Thr His Ser Ile Leu Thr Val Thr Glu Glu Trp Asn Ser
            530                 535                 540

Gly Glu Thr Tyr Thr Cys Val Val Gly His Glu Ala Leu Pro His Leu
545                 550                 555                 560

Val Thr Glu Arg Thr Val Asp Lys Ser Thr Gly Lys Pro Thr Leu Tyr
                565                 570                 575

Asn Val Ser Leu Ile Met Ser Asp Thr Gly Gly Thr Cys Tyr
            580                 585                 590

<210> SEQ ID NO 58
<211> LENGTH: 717
<212> TYPE: DNA
<213> ORGANISM: Artificial
<220> FEATURE:
<223> OTHER INFORMATION: Antibody Sequence

<400> SEQUENCE: 58
atgaagttgc ctgttaggct gttggtgctg atgttctgga ttcctgcttc cagcagtgat      60
gttgtgatga cccaaactcc actctccctg cctgtcagtc ttggagatca agcctccatc     120
tcttgcagat ctagtcagag ccttgtacac agtaatggaa acacctattt acattggtac     180
ctgcagaagc caggccagtc tccaaagctc ctgatctaca agtttccaa ccgattttct      240 ggggtcccag acaggttcag tggcagtgga tcaggacag atttcacact caagatcagc      300
agagtggagg ctgaggatct gggagtttat ttctgctctc aaagtacaca tgttcctcgg     360
acgttcggtg gaggcaccaa gctggaaatc aaacgggctg atgctgcacc aactgtatcc     420
atcttcccac catccagtga gcagttaaca tctggaggtg cctcagtcgt gtgcttcttg     480
aacaacttct accccaaaga catcaatgtc aagtggaaga ttgatggcag tgaacgacaa     540
aatggcgtcc tgaacagttg gactgatcag gacagcaaag acagcaccta cagcatgagc     600 agcacccte cgttgaccaa ggacgagtat gaacgacata cagctatac ctgtgaggcc       660 actcacaaga catcaacttc acccattgtc aagagcttca caggaatga gtgttag         717

<210> SEQ ID NO 59
<211> LENGTH: 238
<212> TYPE: PRT
<213> ORGANISM: Artificial
<220> FEATURE:
<223> OTHER INFORMATION: Antibody Sequence

<400> SEQUENCE: 59

Met Lys Leu Pro Val Arg Leu Leu Val Leu Met Phe Trp Ile Pro Ala
1               5                   10                  15

Ser Ser Ser Asp Val Val Met Thr Gln Thr Pro Leu Ser Leu Pro Val
            20                  25                  30

Ser Leu Gly Asp Gln Ala Ser Ile Ser Cys Arg Ser Ser Gln Ser Leu
        35                  40                  45

Val His Ser Asn Gly Asn Thr Tyr Leu His Trp Tyr Leu Gln Lys Pro
    50                  55                  60

Gly Gln Ser Pro Lys Leu Leu Ile Tyr Lys Val Ser Asn Arg Phe Ser
65                  70                  75                  80

Gly Val Pro Asp Arg Phe Ser Gly Ser Gly Ser Gly Thr Asp Phe Thr
                85                  90                  95

Leu Lys Ile Ser Arg Val Glu Ala Glu Asp Leu Gly Val Tyr Phe Cys
            100                 105                 110

Ser Gln Ser Thr His Val Pro Arg Thr Phe Gly Gly Gly Thr Lys Leu

|     |     |     | 115 |     |     |     | 120 |     |     |     | 125 |     |     |
| --- | --- | --- | --- | --- | --- | --- | --- | --- | --- | --- | --- | --- | --- |
| Glu | Ile | Lys | Arg | Ala | Asp | Ala | Ala | Pro | Thr | Val | Ser | Ile | Phe | Pro | Pro |
|     |     |     | 130 |     |     |     | 135 |     |     |     | 140 |     |     |

Ser Ser Glu Gln Leu Thr Ser Gly Gly Ala Ser Val Val Cys Phe Leu
145                 150                 155                 160

Asn Asn Phe Tyr Pro Lys Asp Ile Asn Val Lys Trp Lys Ile Asp Gly
                165                 170                 175

Ser Glu Arg Gln Asn Gly Val Leu Asn Ser Trp Thr Asp Gln Asp Ser
            180                 185                 190

Lys Asp Ser Thr Tyr Ser Met Ser Ser Thr Leu Thr Leu Thr Lys Asp
        195                 200                 205

Glu Tyr Glu Arg His Asn Ser Tyr Thr Cys Glu Ala Thr His Lys Thr
210                 215                 220

Ser Thr Ser Pro Ile Val Lys Ser Phe Asn Arg Asn Glu Cys
225                 230                 235

```
<210> SEQ ID NO 60
<211> LENGTH: 1788
<212> TYPE: DNA
<213> ORGANISM: Artificial
<220> FEATURE:
<223> OTHER INFORMATION: Antibody Sequence

<400> SEQUENCE: 60
atggctgtcc tggtgctgct cctctgcctg gtgacattcc caagctgtgt cctgtcccag      60
gtgcagctga acagtcagg acctggccta gtgccgccct cacagagcct gtccatcacc     120
tgcacagttt ctggtttctc attaactagc tatggtgtac actgggttcg ccagtctcca    180
ggaaagggtc tggagtggct gggagtgata tggagtggtg aagcacaga ctacaatgca    240 gctttcatat ccagactgag catcagcaag acaactcca agagccaagt tttcttaaa      300 atgaacagtc tgcaagctga tgacacagcc atatactact gtgccagaaa tccctccgcc    360
tactatagta actactggtt tgcttactgg ggccaaggga ctctggtcac tgtctctgca    420
gagagtcagt ccttcccaaa tgtctttcc ctcgtctcct gcgagagccc cctgtctgat      480
aagaatctgg tggccatggg ctgcctggcc cgggacttcc tgcccagcac catttccttc    540
acctggaact accagaacaa cactgaagtc atccagggta tcagaacctt cccaacactg    600
aggacagggg gcaagtacct agccacctcg caggtgttgc tgtctcccaa gagcatcctt    660
gaaggttcag atgaatacct ggtatgcaaa atccactacg aggcaaaaa cagagatctg    720 catgtgccca ttccagctgt cgcagagatg aaccccaatg taaatgtgtt cgtcccacca    780
cgggatggct ctctggccc tgcaccacgc aagtctaaac tcatctgcga ggccacgaac    840
ttcactccaa aaccgatcac agtatcctgg ctaaaggatg ggaagctcgt ggaatctggc    900
ttcaccacag atccggtgac catcgagaac aaaggatcca cccccaaac ctacaaggtc     960 ataagcacac ttaccatctc tgaaatcgac tggctgaacc tgaatgtgta cacctgccgt   1020
gtggatcaca ggggtctcac cttcttgaag aacgtgtcct ccacatgtgc tgccagtccc   1080
tccacagaca tcctaacctt caccatcccc cctccttg ccgacatctt cctcagcaag    1140
tccgctaacc tgacctgtct ggtctcaaac ctggcaacct atgaaccct gaatatctcc   1200 tgggcttctc aaagtggtga accactggaa accaaaatta aaatcatgga agtcatccc   1260 aatggcacct tcagtgctaa gggtgtggct agtgtttgtg tggaagactg gaataacagg  1320
aaggaatttg tgtgtactgt gactcacagg gatctgcctt caccacagaa gaaattcatc  1380
```

```
tcaaaaccca atgaggtgca caaacatcca cctgctgtgt acctgctgcc accagctcgt    1440
gagcaactga acctgaggga gtcagccaca gtcacctgcc tggtgaaggg cttctctcct    1500
gcagacatca gtgtgcagtg gcttcagaga gggcaactct tgccccaaga gaagtatgtg    1560
accagtgccc cgatgccaga gcctggggcc ccaggcttct actttaccca cagcatcctg    1620
actgtgacag aggaggaatg gaactccgga gagacctata cctgtgttgt aggccacgag    1680
gccctgccac acctggtgac cgagaggacc gtggacaagt ccactggtaa acccacactg    1740
tacaatgtct ccctgatcat gtctgacaca ggcggcacct gctattga                1788
```

<210> SEQ ID NO 61
<211> LENGTH: 595
<212> TYPE: PRT
<213> ORGANISM: Artificial
<220> FEATURE:
<223> OTHER INFORMATION: Antibody Sequence

<400> SEQUENCE: 61

```
Met Ala Val Leu Val Leu Leu Cys Leu Val Thr Phe Pro Ser Cys
1               5                   10                  15

Val Leu Ser Gln Val Gln Leu Lys Gln Ser Gly Pro Gly Leu Val Pro
            20                  25                  30

Pro Ser Gln Ser Leu Ser Ile Thr Cys Thr Val Ser Gly Phe Ser Leu
        35                  40                  45

Thr Ser Tyr Gly Val His Trp Val Arg Gln Ser Pro Gly Lys Gly Leu
    50                  55                  60

Glu Trp Leu Gly Val Ile Trp Ser Gly Gly Ser Thr Asp Tyr Asn Ala
65                  70                  75                  80

Ala Phe Ile Ser Arg Leu Ser Ile Ser Lys Asp Asn Ser Lys Ser Gln
                85                  90                  95

Val Phe Phe Lys Met Asn Ser Leu Gln Ala Asp Asp Thr Ala Ile Tyr
            100                 105                 110

Tyr Cys Ala Arg Asn Pro Ser Ala Tyr Tyr Ser Asn Tyr Trp Phe Ala
        115                 120                 125

Tyr Trp Gly Gln Gly Thr Leu Val Thr Val Ser Ala Glu Ser Gln Ser
    130                 135                 140

Phe Pro Asn Val Phe Pro Leu Val Ser Cys Glu Ser Pro Leu Ser Asp
145                 150                 155                 160

Lys Asn Leu Val Ala Met Gly Cys Leu Ala Arg Asp Phe Leu Pro Ser
                165                 170                 175

Thr Ile Ser Phe Thr Trp Asn Tyr Gln Asn Asn Thr Glu Val Ile Gln
            180                 185                 190

Gly Ile Arg Thr Phe Pro Thr Leu Arg Thr Gly Gly Lys Tyr Leu Ala
        195                 200                 205

Thr Ser Gln Val Leu Leu Ser Pro Lys Ser Ile Leu Glu Gly Ser Asp
    210                 215                 220

Glu Tyr Leu Val Cys Lys Ile His Tyr Gly Gly Lys Asn Arg Asp Leu
225                 230                 235                 240

His Val Pro Ile Pro Ala Val Ala Glu Met Asn Pro Asn Val Asn Val
                245                 250                 255

Phe Val Pro Pro Arg Asp Gly Phe Gly Pro Ala Pro Arg Lys Ser
            260                 265                 270

Lys Leu Ile Cys Glu Ala Thr Asn Phe Thr Pro Lys Pro Ile Thr Val
        275                 280                 285

Ser Trp Leu Lys Asp Gly Lys Leu Val Glu Ser Gly Phe Thr Thr Asp
```

Pro Val Thr Ile Glu Asn Lys Gly Ser Thr Pro Gln Thr Tyr Lys Val
305             310                 315                 320

Ile Ser Thr Leu Thr Ile Ser Glu Ile Asp Trp Leu Asn Leu Asn Val
                325                 330                 335

Tyr Thr Cys Arg Val Asp His Arg Gly Leu Thr Phe Leu Lys Asn Val
            340                 345                 350

Ser Ser Thr Cys Ala Ala Ser Pro Ser Thr Asp Ile Leu Thr Phe Thr
        355                 360                 365

Ile Pro Pro Ser Phe Ala Asp Ile Phe Leu Ser Lys Ser Ala Asn Leu
    370                 375                 380

Thr Cys Leu Val Ser Asn Leu Ala Thr Tyr Glu Thr Leu Asn Ile Ser
385                 390                 395                 400

Trp Ala Ser Gln Ser Gly Glu Pro Leu Glu Thr Lys Ile Lys Ile Met
                405                 410                 415

Glu Ser His Pro Asn Gly Thr Phe Ser Ala Lys Gly Val Ala Ser Val
            420                 425                 430

Cys Val Glu Asp Trp Asn Asn Arg Lys Glu Phe Val Cys Thr Val Thr
        435                 440                 445

His Arg Asp Leu Pro Ser Pro Gln Lys Lys Phe Ile Ser Lys Pro Asn
    450                 455                 460

Glu Val His Lys His Pro Pro Ala Val Tyr Leu Leu Pro Pro Ala Arg
465                 470                 475                 480

Glu Gln Leu Asn Leu Arg Glu Ser Ala Thr Val Thr Cys Leu Val Lys
                485                 490                 495

Gly Phe Ser Pro Ala Asp Ile Ser Val Gln Trp Leu Gln Arg Gly Gln
            500                 505                 510

Leu Leu Pro Gln Glu Lys Tyr Val Thr Ser Ala Pro Met Pro Glu Pro
        515                 520                 525

Gly Ala Pro Gly Phe Tyr Phe Thr His Ser Ile Leu Thr Val Thr Glu
    530                 535                 540

Glu Glu Trp Asn Ser Gly Glu Thr Tyr Thr Cys Val Val Gly His Glu
545                 550                 555                 560

Ala Leu Pro His Leu Val Thr Glu Arg Thr Val Asp Lys Ser Thr Gly
                565                 570                 575

Lys Pro Thr Leu Tyr Asn Val Ser Leu Ile Met Ser Asp Thr Gly Gly
            580                 585                 590

Thr Cys Tyr
    595

<210> SEQ ID NO 62
<211> LENGTH: 705
<212> TYPE: DNA
<213> ORGANISM: Artificial
<220> FEATURE:
<223> OTHER INFORMATION: Antibody Sequence

<400> SEQUENCE: 62
atggagacac attctcaggt ctttgtatac atgttgctgt ggttgtctgg tgttgatgga     60
gacattgtga tgacccagtc tcaaaatttc atgtccacat cagtaggaga cagggtcagc    120
gtcacctgca aggccagtca gtatgtgggt acttatgtag cctggtatca acagaaacca    180
gggcaatctc ctaaagcact gatttactcg catcctacc ggcatactgg agtccctgat    240
cgcttcacag gcagtggatc tgggacagat ttcactctca ccatcagcaa tgtgcagtct    300

```
gaagacctgg cagattattt ctgtcagcaa tatagcagct ctcctctcac gttcggctcg    360
gggacaaagt tggaaataaa acgggctgat gctgcaccaa ctgtatccat cttcccacca    420
tccagtgagc agttaacatc tggaggtgcc tcagtcgtgt gcttcttgaa caacttctac    480
cccagagaca tcaatgtcaa gtggaagatt gatggcagtg aacgacaaaa tggtgtcctg    540
aacagttgga ctgatcagga cagcaaagac agcacctaca gcatgagcag caccctcaca    600
ttgaccaagg acgagtatga acgacataac agctatacct gtgaggccac tcacaagaca    660
tcaacttcac ccatcgtcaa gagcttcaac aggaatgagt gttag                    705

<210> SEQ ID NO 63
<211> LENGTH: 234
<212> TYPE: PRT
<213> ORGANISM: Artificial
<220> FEATURE:
<223> OTHER INFORMATION: Antibody Sequence

<400> SEQUENCE: 63
```

Met Glu Thr His Ser Gln Val Phe Val Tyr Met Leu Leu Trp Leu Ser
1               5                   10                  15

Gly Val Asp Gly Asp Ile Val Met Thr Gln Ser Gln Asn Phe Met Ser
                20                  25                  30

Thr Ser Val Gly Asp Arg Val Ser Val Thr Cys Lys Ala Ser Gln Tyr
            35                  40                  45

Val Gly Thr Tyr Val Ala Trp Tyr Gln Gln Lys Pro Gly Gln Ser Pro
        50                  55                  60

Lys Ala Leu Ile Tyr Ser Ala Ser Tyr Arg His Thr Gly Val Pro Asp
65                  70                  75                  80

Arg Phe Thr Gly Ser Gly Ser Gly Thr Asp Phe Thr Leu Thr Ile Ser
                85                  90                  95

Asn Val Gln Ser Glu Asp Leu Ala Asp Tyr Phe Cys Gln Gln Tyr Ser
            100                 105                 110

Ser Ser Pro Leu Thr Phe Gly Ser Gly Thr Lys Leu Glu Ile Lys Arg
        115                 120                 125

Ala Asp Ala Ala Pro Thr Val Ser Ile Phe Pro Pro Ser Ser Glu Gln
    130                 135                 140

Leu Thr Ser Gly Gly Ala Ser Val Val Cys Phe Leu Asn Asn Phe Tyr
145                 150                 155                 160

Pro Arg Asp Ile Asn Val Lys Trp Lys Ile Asp Gly Ser Glu Arg Gln
                165                 170                 175

Asn Gly Val Leu Asn Ser Trp Thr Asp Gln Asp Ser Lys Asp Ser Thr
            180                 185                 190

Tyr Ser Met Ser Ser Thr Leu Thr Leu Thr Lys Asp Glu Tyr Glu Arg
        195                 200                 205

His Asn Ser Tyr Thr Cys Glu Ala Thr His Lys Thr Ser Thr Ser Pro
    210                 215                 220

Ile Val Lys Ser Phe Asn Arg Asn Glu Cys
225                 230

```
<210> SEQ ID NO 64
<211> LENGTH: 1773
<212> TYPE: DNA
<213> ORGANISM: Artificial
<220> FEATURE:
<223> OTHER INFORMATION: Antibody Sequence

<400> SEQUENCE: 64
```

```
atggaatgga gctgggtctt tctcttcctc ctgtcagtaa ctacaggtgt ccactctgag      60
gtcaagctgc agcagtctgg acctgagctg gtgaagcctg gggcttcagt gaagatatcc     120
tgcaaggctt ctggttactc attcactggc tactacatgc actgggtgaa gcaaagttct     180
gaaaagagcc ttgagtggat tggagagatt aatcctagca ctggtggtac tagctacaac     240
cagaagttca agggcaaggc cacattaact gtagacaagt catccagcac agcctacatg     300
cagctcaaga gcctgacatc tgaggactct gctgtctatt actgtgcaag agactactat     360
agtaaggctt actggggcca agggactctg gtcactgtct ctgcagagag tcagtccttc     420
ccaaatgtct ttcccctcgt ctcctgcgag agccccctgt ctgataagaa tctggtggcc     480
atgggctgcc tggcccggga cttcctgccc agcaccattt ccttcacctg gaactaccag     540
aacaacactg aagtcatcca gggtatcaga accttcccaa cactgaggac aggggggaag     600
tacctagcca cctcgcaggt gttgctgtct cccaagagca tccttgaagg ttcagatgaa     660
tacctggtat gcaaaatcca ctacggaggc aaaaacagag atctgcatgt gcccattcca     720
gctgtcgcag agatgaaccc caatgtaaat gtgttcgtcc caccacggga tggcttctct     780
ggccctgcac cacgcaagtc taaactcatc tgcgaggcca cgaacttcac tccaaaaccg     840
atcacagtat cctggctaaa ggatgggaag ctcgtggaat ctggcttcac cacagatccg     900
gtgaccatcg agaacaaagg atccacaccc aaacctacaa ggtcataagc acacttacc      960
atctctgaaa tcgactggct gaacctgaat gtgtacacct gccgtgtgga tcacaggggt    1020
ctcaccttct tgaagaacgt gtcctccaca tgtgctgcca gtccctccac agacatccta    1080
accttcacca tccccccctc ctttgccgac atcttcctca gcaagtccgc taacctgacc    1140
tgtctggtct caaacctggc aacctatgaa accctgaata tctcctgggc ttctcaaagt    1200
ggtgaaccac tggaaaccaa aattaaaatc atggaaagtc atcccaatgg cacccttcagt  1260
gctaagggtg tggctagtgt ttgtgtggaa gactggaata caggaaggaa atttgtgtgt    1320
actgtgactc acagggatct gccttcacca cagaagaaat tcatctcaaa acccaatgag    1380
gtgcacaaac atccacctgc tgtgtacctg ctgccaccag ctcgtgagca actgaacctg    1440
agggagtcag ccacagtcac ctgcctggtg aagggcttct ctcctgcaga catcagtgtg    1500
cagtggcttc agagagggca actcttgccc caagagaagt atgtgaccag tgccccgatg    1560
ccagagcctg ggccccagg cttctacttt acccacagca tcctgactgt gacagaggag    1620
gaatggaact ccggagagac ctatacctgt gttgtaggcc acgaggccct gccacacctg    1680
gtgaccgaga ggaccgtgga caagtccact ggtaaaccca cactgtacaa tgtctccctg    1740
atcatgtctg acacaggcgg cacctgctat tga                                 1773
```

<210> SEQ ID NO 65
<211> LENGTH: 590
<212> TYPE: PRT
<213> ORGANISM: Artificial
<220> FEATURE:
<223> OTHER INFORMATION: Antibody Sequence

<400> SEQUENCE: 65

Met Glu Trp Ser Trp Val Phe Leu Phe Leu Leu Ser Val Thr Thr Gly
1               5                   10                  15

Val His Ser Glu Val Lys Leu Gln Gln Ser Gly Pro Glu Leu Val Lys
            20                  25                  30

Pro Gly Ala Ser Val Lys Ile Ser Cys Lys Ala Ser Gly Tyr Ser Phe
        35                  40                  45

```
Thr Gly Tyr Tyr Met His Trp Val Lys Gln Ser Ser Glu Lys Ser Leu
 50              55                  60

Glu Trp Ile Gly Glu Ile Asn Pro Ser Thr Gly Gly Thr Ser Tyr Asn
 65              70                  75                  80

Gln Lys Phe Lys Gly Lys Ala Thr Leu Thr Val Asp Lys Ser Ser Ser
             85                  90                  95

Thr Ala Tyr Met Gln Leu Lys Ser Leu Thr Ser Glu Asp Ser Ala Val
            100                 105                 110

Tyr Tyr Cys Ala Arg Asp Tyr Tyr Ser Lys Ala Tyr Trp Gly Gln Gly
            115                 120                 125

Thr Leu Val Thr Val Ser Ala Glu Ser Gln Ser Phe Pro Asn Val Phe
130                 135                 140

Pro Leu Val Ser Cys Glu Ser Pro Leu Ser Asp Lys Asn Leu Val Ala
145                 150                 155                 160

Met Gly Cys Leu Ala Arg Asp Phe Leu Pro Ser Thr Ile Ser Phe Thr
            165                 170                 175

Trp Asn Tyr Gln Asn Asn Thr Glu Val Ile Gln Gly Ile Arg Thr Phe
            180                 185                 190

Pro Thr Leu Arg Thr Gly Gly Lys Tyr Leu Ala Thr Ser Gln Val Leu
            195                 200                 205

Leu Ser Pro Lys Ser Ile Leu Glu Gly Ser Asp Glu Tyr Leu Val Cys
210                 215                 220

Lys Ile His Tyr Gly Gly Lys Asn Arg Asp Leu His Val Pro Ile Pro
225                 230                 235                 240

Ala Val Ala Glu Met Asn Pro Asn Val Asn Val Phe Val Pro Pro Arg
            245                 250                 255

Asp Gly Phe Ser Gly Pro Ala Pro Arg Lys Ser Lys Leu Ile Cys Glu
            260                 265                 270

Ala Thr Asn Phe Thr Pro Lys Pro Ile Thr Val Ser Trp Leu Lys Asp
            275                 280                 285

Gly Lys Leu Val Glu Ser Gly Phe Thr Thr Asp Pro Val Thr Ile Glu
290                 295                 300

Asn Lys Gly Ser Thr Pro Gln Thr Tyr Lys Val Ile Ser Thr Leu Thr
305                 310                 315                 320

Ile Ser Glu Ile Asp Trp Leu Asn Leu Asn Val Tyr Thr Cys Arg Val
            325                 330                 335

Asp His Arg Gly Leu Thr Phe Leu Lys Asn Val Ser Ser Thr Cys Ala
            340                 345                 350

Ala Ser Pro Ser Thr Asp Ile Leu Thr Phe Thr Ile Pro Pro Ser Phe
            355                 360                 365

Ala Asp Ile Phe Leu Ser Lys Ser Ala Asn Leu Thr Cys Leu Val Ser
370                 375                 380

Asn Leu Ala Thr Tyr Glu Thr Leu Asn Ile Ser Trp Ala Ser Gln Ser
385                 390                 395                 400

Gly Glu Pro Leu Glu Thr Lys Ile Lys Ile Met Glu Ser His Pro Asn
            405                 410                 415

Gly Thr Phe Ser Ala Lys Gly Val Ala Ser Val Cys Val Glu Asp Trp
            420                 425                 430

Asn Asn Arg Lys Glu Phe Val Cys Thr Val Thr His Arg Asp Leu Pro
            435                 440                 445

Ser Pro Gln Lys Lys Phe Ile Ser Lys Pro Asn Glu Val His Lys His
450                 455                 460

Pro Pro Ala Val Tyr Leu Leu Pro Pro Ala Arg Glu Gln Leu Asn Leu
```

Arg Glu Ser Ala Thr Val Thr Cys Leu Val Lys Gly Phe Ser Pro Ala
465                 470                 475                 480

Asp Ile Ser Val Gln Trp Leu Gln Arg Gly Gln Leu Leu Pro Gln Glu
            485                 490                 495

Lys Tyr Val Thr Ser Ala Pro Met Pro Glu Pro Gly Ala Pro Gly Phe
        500                 505                 510

Tyr Phe Thr His Ser Ile Leu Thr Val Thr Glu Glu Trp Asn Ser
    515                 520                 525

Gly Glu Thr Tyr Thr Cys Val Val Gly His Glu Ala Leu Pro His Leu
530                 535                 540

Val Thr Glu Arg Thr Val Asp Lys Ser Thr Gly Lys Pro Thr Leu Tyr
545                 550                 555                 560

Asn Val Ser Leu Ile Met Ser Asp Thr Gly Gly Thr Cys Tyr
            565                 570                 575

580                 585                 590

<210> SEQ ID NO 66
<211> LENGTH: 705
<212> TYPE: DNA
<213> ORGANISM: Artificial
<220> FEATURE:
<223> OTHER INFORMATION: Antibody Sequence

<400> SEQUENCE: 66
atgaagtcac agacccaggt cttcgtattt ctactgctct gtgtgtctgg tgctcatggg    60
agtattgtga tgacccagac tcccaaattc ctgcttgtat cagcaggaga cagggttacc   120
ataacctgca aggccagtca gagtgtgagt aatgatgtag cttggtacca acagaagcca   180
gggcagtctc ctaaactgct gatatactat gcatccaatc gctacactgg agtccctgat   240
cgcttcactg gcagtggata tgggacggat ttcactttca ccatcagcac tgtgcaggct   300
gaagacctgg cagtttattt ctgtcagcag gattatagct ctccgtacac gttcggaggg   360
gggaccaagc tggaaataaa acgggctgat gctgcaccaa ctgtatccat cttcccacca   420
tccagtgagc agttaacatc tggaggtgcc tcagtcgtgt gcttcttgaa caacttctac   480
cccaaagaca tcaatgtcaa gtggaagatt gatggcagtg aacgacaaaa tggcgtcctg   540
aacagttgga ctgatcagga cagcaaagac agcacctaca gcatgagcag caccctcacg   600
ttgaccaagg acgagtatga acgacataac agctatacct gtgaggccac tcacaagaca   660
tcaacttcac ccattgtcaa gagcttcaac aggaatgagt gttag               705

<210> SEQ ID NO 67
<211> LENGTH: 234
<212> TYPE: PRT
<213> ORGANISM: Artificial
<220> FEATURE:
<223> OTHER INFORMATION: Antibody Sequence

<400> SEQUENCE: 67

Met Lys Ser Gln Thr Gln Val Phe Val Phe Leu Leu Leu Cys Val Ser
1               5                   10                  15

Gly Ala His Gly Ser Ile Val Met Thr Gln Thr Pro Lys Phe Leu Leu
            20                  25                  30

Val Ser Ala Gly Asp Arg Val Thr Ile Thr Cys Lys Ala Ser Gln Ser
        35                  40                  45

Val Ser Asn Asp Val Ala Trp Tyr Gln Gln Lys Pro Gly Gln Ser Pro
    50                  55                  60

```
Lys Leu Leu Ile Tyr Tyr Ala Ser Asn Arg Tyr Thr Gly Val Pro Asp
 65                  70                  75                  80

Arg Phe Thr Gly Ser Gly Tyr Gly Thr Asp Phe Thr Phe Thr Ile Ser
                 85                  90                  95

Thr Val Gln Ala Glu Asp Leu Ala Val Tyr Phe Cys Gln Gln Asp Tyr
            100                 105                 110

Ser Ser Pro Tyr Thr Phe Gly Gly Gly Thr Lys Leu Glu Ile Lys Arg
        115                 120                 125

Ala Asp Ala Ala Pro Thr Val Ser Ile Phe Pro Pro Ser Ser Glu Gln
    130                 135                 140

Leu Thr Ser Gly Gly Ala Ser Val Val Cys Phe Leu Asn Asn Phe Tyr
145                 150                 155                 160

Pro Lys Asp Ile Asn Val Lys Trp Lys Ile Asp Gly Ser Glu Arg Gln
                165                 170                 175

Asn Gly Val Leu Asn Ser Trp Thr Asp Gln Asp Ser Lys Asp Ser Thr
            180                 185                 190

Tyr Ser Met Ser Ser Thr Leu Thr Leu Thr Lys Asp Glu Tyr Glu Arg
        195                 200                 205

His Asn Ser Tyr Thr Cys Glu Ala Thr His Lys Thr Ser Thr Ser Pro
    210                 215                 220

Ile Val Lys Ser Phe Asn Arg Asn Glu Cys
225                 230

<210> SEQ ID NO 68
<211> LENGTH: 1773
<212> TYPE: DNA
<213> ORGANISM: Artificial
<220> FEATURE:
<223> OTHER INFORMATION: Antibody Sequence

<400> SEQUENCE: 68
atgggatgga gctggatctt tctcttcctc ctgtcaggaa ctgcaggtgt ccattgccag      60
gtccagctgc agcagtctgg acctgagctg gtgaagcctg ggcttcagt gaagatatcc     120 tgcaaggctt ctggctacag cttcacaagc tactatatac actgggtgaa gcagaggcct    180
ggacagggac ttgagtggat tggatggatt tatcctggaa gtggtaatac taagtacaat    240
gagaagttca gggcaaggc cacactgacg gcagacacat cctccagcac tgcctacatg    300
cagctcagca gcctaacatc tgaggactct gcggtctatt actgtgcaag gagctatggt    360
gactacgact actggggcca aggcaccact ctcacagtct cctcagagag tcagtccttc    420
ccaaatgtct tcccctcgt ctcctgcgag agccccctgt ctgataagaa tctggtggcc     480
atgggctgcc tggcccggga cttcctgccc agcaccattt ccttcacctg aactaccag    540 aacaacactg aagtcatcca gggtatcaga accttcccaa cactgaggac aggggggcaag    600 tacctagcca cctcgcaggt gttgctgtct cccaagagca tccttgaagg ttcagatgaa    660
tacctggtat gcaaaatcca ctacggaggc aaaaacagag atctgcatgt gcccattcca    720
gctgtcgcag agatgaaccc caatgtaaat gtgttcgtcc caccacggga tggcttctct    780
ggccctgcac cacgcaagtc taaactcatc tgcgaggcca cgaacttcac tccaaaaccg    840
atcacagtat cctggctaaa ggatgggaag ctcgtggaat ctggcttcac cacagatccg    900
gtgaccatcg agaacaaagg atccacaccc caaacctaca aggtcataag cacacttacc    960
atctctgaaa tcgactggct gaacctgaat gtgtacacct gccgtgtgga tcacaggggt   1020
ctcaccttct tgaagaacgt gtcctccaca tgtgctgcca gtccctccac agacatccta   1080
```

```
accttcacca tcccccctc ctttgccgac atcttcctca gcaagtccgc taacctgacc    1140
tgtctggtct caaacctggc aacctatgaa accctgaata tctcctgggc ttctcaaagt    1200
ggtgaaccac tggaaaccaa aattaaaatc atggaaagtc atcccaatgg caccttcagt    1260
gctaagggtg tggctagtgt ttgtgtggaa gactggaata acaggaagga atttgtgtgt    1320
actgtgactc acagggatct gccttcacca cagaagaaat tcatctcaaa acccaatgag    1380
gtgcacaaac atccacctgc tgtgtacctg ctgccaccag ctcgtgagca actgaacctg    1440
agggagtcag ccacagtcac ctgcctggtg aagggcttct ctcctgcaga catcagtgtg    1500
cagtggcttc agagagggca actcttgccc caagagaagt atgtgaccag tgcccccgatg   1560 ccagagcctg ggccccagg cttctacttt acccacagca tcctgactgt gacagaggag    1620
gaatggaact ccggagagac ctatacctgt gttgtaggcc acgaggccct gccacacctg    1680
gtgaccgaga ggaccgtgga caagtccact ggtaaaccca cactgtacaa tgtctccctg    1740
atcatgtctg acacaggcgg cacctgctat tga                                1773
```

<210> SEQ ID NO 69
<211> LENGTH: 590
<212> TYPE: PRT
<213> ORGANISM: Artificial
<220> FEATURE:
<223> OTHER INFORMATION: Antibody Sequence

<400> SEQUENCE: 69

```
Met Gly Trp Ser Trp Ile Phe Leu Phe Leu Leu Ser Gly Thr Ala Gly
1               5                   10                  15

Val His Cys Gln Val Gln Leu Gln Gln Ser Gly Pro Glu Leu Val Lys
            20                  25                  30

Pro Gly Ala Ser Val Lys Ile Ser Cys Lys Ala Ser Gly Tyr Ser Phe
        35                  40                  45

Thr Ser Tyr Tyr Ile His Trp Val Lys Gln Arg Pro Gly Gln Gly Leu
    50                  55                  60

Glu Trp Ile Gly Trp Ile Tyr Pro Gly Ser Gly Asn Thr Lys Tyr Asn
65                  70                  75                  80

Glu Lys Phe Lys Gly Lys Ala Thr Leu Thr Ala Asp Thr Ser Ser Ser
                85                  90                  95

Thr Ala Tyr Met Gln Leu Ser Ser Leu Thr Ser Glu Asp Ser Ala Val
            100                 105                 110

Tyr Tyr Cys Ala Arg Ser Tyr Gly Asp Tyr Asp Tyr Trp Gly Gln Gly
        115                 120                 125

Thr Thr Leu Thr Val Ser Ser Glu Ser Gln Ser Phe Pro Asn Val Phe
    130                 135                 140

Pro Leu Val Ser Cys Glu Ser Pro Leu Ser Asp Lys Asn Leu Val Ala
145                 150                 155                 160

Met Gly Cys Leu Ala Arg Asp Phe Leu Pro Ser Thr Ile Ser Phe Thr
                165                 170                 175

Trp Asn Tyr Gln Asn Asn Thr Glu Val Ile Gln Gly Ile Arg Thr Phe
            180                 185                 190

Pro Thr Leu Arg Thr Gly Gly Lys Tyr Leu Ala Thr Ser Gln Val Leu
        195                 200                 205

Leu Ser Pro Lys Ser Ile Leu Glu Gly Ser Asp Glu Tyr Leu Val Cys
    210                 215                 220

Lys Ile His Tyr Gly Gly Lys Asn Arg Asp Leu His Val Pro Ile Pro
225                 230                 235                 240
```

```
Ala Val Ala Glu Met Asn Pro Asn Val Asn Val Phe Val Pro Pro Arg
                 245                 250                 255

Asp Gly Phe Ser Gly Pro Ala Pro Arg Lys Ser Lys Leu Ile Cys Glu
            260                 265                 270

Ala Thr Asn Phe Thr Pro Lys Pro Ile Thr Val Ser Trp Leu Lys Asp
        275                 280                 285

Gly Lys Leu Val Glu Ser Gly Phe Thr Thr Asp Pro Val Thr Ile Glu
    290                 295                 300

Asn Lys Gly Ser Thr Pro Gln Thr Tyr Lys Val Ile Ser Thr Leu Thr
305                 310                 315                 320

Ile Ser Glu Ile Asp Trp Leu Asn Leu Asn Val Tyr Thr Cys Arg Val
                325                 330                 335

Asp His Arg Gly Leu Thr Phe Leu Lys Asn Val Ser Ser Thr Cys Ala
            340                 345                 350

Ala Ser Pro Ser Thr Asp Ile Leu Thr Phe Thr Ile Pro Pro Ser Phe
        355                 360                 365

Ala Asp Ile Phe Leu Ser Lys Ser Ala Asn Leu Thr Cys Leu Val Ser
    370                 375                 380

Asn Leu Ala Thr Tyr Glu Thr Leu Asn Ile Ser Trp Ala Ser Gln Ser
385                 390                 395                 400

Gly Glu Pro Leu Glu Thr Lys Ile Lys Ile Met Glu Ser His Pro Asn
                405                 410                 415

Gly Thr Phe Ser Ala Lys Gly Val Ala Ser Val Cys Val Glu Asp Trp
            420                 425                 430

Asn Asn Arg Lys Glu Phe Val Cys Thr Val Thr His Arg Asp Leu Pro
        435                 440                 445

Ser Pro Gln Lys Lys Phe Ile Ser Lys Pro Asn Glu Val His Lys His
    450                 455                 460

Pro Pro Ala Val Tyr Leu Leu Pro Pro Ala Arg Glu Gln Leu Asn Leu
465                 470                 475                 480

Arg Glu Ser Ala Thr Val Thr Cys Leu Val Lys Gly Phe Ser Pro Ala
                485                 490                 495

Asp Ile Ser Val Gln Trp Leu Gln Arg Gly Gln Leu Leu Pro Gln Glu
            500                 505                 510

Lys Tyr Val Thr Ser Ala Pro Met Pro Glu Pro Gly Ala Pro Gly Phe
        515                 520                 525

Tyr Phe Thr His Ser Ile Leu Thr Val Thr Glu Glu Glu Trp Asn Ser
    530                 535                 540

Gly Glu Thr Tyr Thr Cys Val Val Gly His Glu Ala Leu Pro His Leu
545                 550                 555                 560

Val Thr Glu Arg Thr Val Asp Lys Ser Thr Gly Lys Pro Thr Leu Tyr
                565                 570                 575

Asn Val Ser Leu Ile Met Ser Asp Thr Gly Gly Thr Cys Tyr
            580                 585                 590

<210> SEQ ID NO 70
<211> LENGTH: 717
<212> TYPE: DNA
<213> ORGANISM: Artificial
<220> FEATURE:
<223> OTHER INFORMATION: Antibody Sequence

<400> SEQUENCE: 70
atggagacag acacactcct gttatgggta ctgctgctct gggttccagg ttccactggt      60
gacattgtgc tgacacagtc tcctgcttcc ttagctgtat ctctggggca gagggccacc    120
```

```
atctcataca gggccagcaa aagtgtcagt acatctggct atagttatat gcactggaac    180
caacagaaac caggacagcc acccagactc ctcatctatc ttgtatccaa cctagaatct    240
ggggtccctg ccaggttcag tggcagtgga tcagggacag atttcacact caagatcagc    300
agagtggagg ctgaggatct gggagtttat ttctgctctc aaagtacaca tgttcctcgg    360
acgttcggtg gaggcaccaa gctggaaatc aaacgggctg atgctgcacc aactgtatcc    420
atcttcccac catccagtga gcagttaaca tctggaggtg cctcagtcgt gtgcttcttg    480
aacaacttct accccaaaga catcaatgtc aagtggaaga ttgatggcag tgaacgacaa    540
aatggcgtcc tgaacagttg gactgatcag gacagcaaag acagcaccta cagcatgagc    600
agcaccctca cgttgaccaa ggacgagtat gaacgacata cagctatac ctgtgaggcc    660 actcacaaga catcaacttc acccattgtc aagagcttca caggaatga gtgttag      717
```

<210> SEQ ID NO 71
<211> LENGTH: 238
<212> TYPE: PRT
<213> ORGANISM: Artificial
<220> FEATURE:
<223> OTHER INFORMATION: Antibody Sequence

<400> SEQUENCE: 71

```
Met Glu Thr Asp Thr Leu Leu Leu Trp Val Leu Leu Leu Trp Val Pro
  1               5                  10                  15

Gly Ser Thr Gly Asp Ile Val Leu Thr Gln Ser Pro Ala Ser Leu Ala
             20                  25                  30

Val Ser Leu Gly Gln Arg Ala Thr Ile Ser Tyr Arg Ala Ser Lys Ser
         35                  40                  45

Val Ser Thr Ser Gly Tyr Ser Tyr Met His Trp Asn Gln Gln Lys Pro
     50                  55                  60

Gly Gln Pro Pro Arg Leu Leu Ile Tyr Leu Val Ser Asn Leu Glu Ser
 65                  70                  75                  80

Gly Val Pro Ala Arg Phe Ser Gly Ser Gly Ser Gly Thr Asp Phe Thr
                 85                  90                  95

Leu Lys Ile Ser Arg Val Glu Ala Glu Asp Leu Gly Val Tyr Phe Cys
            100                 105                 110

Ser Gln Ser Thr His Val Pro Arg Thr Phe Gly Gly Gly Thr Lys Leu
        115                 120                 125

Glu Ile Lys Arg Ala Asp Ala Ala Pro Thr Val Ser Ile Phe Pro Pro
    130                 135                 140

Ser Ser Glu Gln Leu Thr Ser Gly Gly Ala Ser Val Val Cys Phe Leu
145                 150                 155                 160

Asn Asn Phe Tyr Pro Lys Asp Ile Asn Val Lys Trp Lys Ile Asp Gly
                165                 170                 175

Ser Glu Arg Gln Asn Gly Val Leu Asn Ser Trp Thr Asp Gln Asp Ser
            180                 185                 190

Lys Asp Ser Thr Tyr Ser Met Ser Ser Thr Leu Thr Leu Thr Lys Asp
        195                 200                 205

Glu Tyr Glu Arg His Asn Ser Tyr Thr Cys Glu Ala Thr His Lys Thr
    210                 215                 220

Ser Thr Ser Pro Ile Val Lys Ser Phe Asn Arg Asn Glu Cys
225                 230                 235
```

<210> SEQ ID NO 72
<211> LENGTH: 1776

<212> TYPE: DNA
<213> ORGANISM: Artificial
<220> FEATURE:
<223> OTHER INFORMATION: Antibody Sequence

<400> SEQUENCE: 72

```
atgaaattca gctgggtcat cttcttcctg atggcagtgg ttacaggggt caattcagag      60
gttcagctgc agcagtctgt ggcagagctt gtgaggccag ggcctcagt caagttgtcc     120
tgcacagctt ctggcttcaa cattaaaaac acctatatgc actgggtgaa gcagaggcct     180
gaacagggcc tggagtggat tggaaggatt gatcctgcga atggtaatac taaatatgcc     240
ccgaagttcc agggcaaggc cactataact gcagacacat cctccaacac agcctacctg     300
cagctcagca gcctgacatc tgaggacact gccatctatt actgtgctag agggagtttt     360
tatgctatgg actactgggg tcaaggaacc tcagtcaccg tctcctcaga gagtcagtcc     420
ttcccaaatg tctttcccct cgtctcctgc gagagccccc tgtctgataa aatctggtg     480
gccatgggct gcctggcccg ggacttcctg cccagcacca tttccttcac ctggaactac     540
cagaacaaca ctgaagtcat ccagggtatc agaaccttcc caacactgag acaggggc      600
aagtacctag ccacctcgca ggtgttgctg tctcccaaga gcatccttga aggttcagat     660
gaatacctgg tatgcaaaat ccactacgga ggcaaaaaca gagatctgca tgtgcccatt     720
ccagctgtcg cagagatgaa ccccaatgta aatgtgttcg tcccaccacg ggatggcttc     780
tctggccctg caccacgcaa gtctaaactc atctgcgagg ccacgaactt cactccaaaa     840
ccgatcacag tatcctggct aaaggatggg aagctcgtgg aatctggctt caccacagat     900
ccggtgacca tcgagaacaa aggatccaca ccccaaaacct acaaggtcat aagcacactt     960
accatctctg aaatcgactg gctgaacctg aatgtgtaca cctgccgtgt ggatcacagg    1020
ggtctcacct tcttgaagaa cgtgtcctcc acatgtgctg ccagtccctc cacagacatc    1080
ctaaccttca ccatcccccc ctcctttgcc gacatcttcc tcagcaagtc cgctaacctg    1140
acctgtctgg tctcaaacct ggcaacctat gaaaccctga atatctcctg ggcttctcaa    1200
agtggtgaac cactggaaac caaaattaaa atcatggaaa gtcatcccaa tggcaccttc    1260
agtgctaagg gtgtggctag tgtttgtgtg aagactgga ataacaggaa ggaatttgtg     1320
tgtactgtga ctcacaggga tctgccttca ccacagaaga aattcatctc aaaacccaat    1380
gaggtgcaca acatccacc tgctgtgtac ctgctgccac cagctcgtga gcaactgaac    1440
ctgagggagt cagccacagt cacctgcctg gtgaagggct ctctcctgc agacatcagt     1500
gtgcagtggc ttcagagagg gcaactcttg ccccaagaga gtatgtgac cagtgccccg    1560
atgccagagc tgggccccc aggcttctac tttacccaca gcatcctgac tgtgacagag    1620
gaggaatgga ctccggaga gacctatacc tgtgttgtag ccacgaggc cctgccacac    1680
ctggtgaccg agaggaccgt ggacaagtcc actggtaaac ccacactgta caatgtctcc    1740
ctgatcatgt ctgacacagg cggcaccctg tattga                              1776
```

<210> SEQ ID NO 73
<211> LENGTH: 591
<212> TYPE: PRT
<213> ORGANISM: Artificial
<220> FEATURE:
<223> OTHER INFORMATION: Antibody Sequence

<400> SEQUENCE: 73

```
Met Lys Phe Ser Trp Val Ile Phe Phe Leu Met Ala Val Val Thr Gly
1               5                   10                  15
```

-continued

Val Asn Ser Glu Val Gln Leu Gln Gln Ser Val Ala Glu Leu Val Arg
              20                  25                  30

Pro Gly Ala Ser Val Lys Leu Ser Cys Thr Ala Ser Gly Phe Asn Ile
              35                  40                  45

Lys Asn Thr Tyr Met His Trp Val Lys Gln Arg Pro Glu Gln Gly Leu
 50                  55                  60

Glu Trp Ile Gly Arg Ile Asp Pro Ala Asn Gly Asn Thr Lys Tyr Ala
 65                  70                  75                  80

Pro Lys Phe Gln Gly Lys Ala Thr Ile Thr Ala Asp Thr Ser Ser Asn
              85                  90                  95

Thr Ala Tyr Leu Gln Leu Ser Ser Leu Thr Ser Glu Asp Thr Ala Ile
              100                 105                 110

Tyr Tyr Cys Ala Arg Gly Ser Phe Tyr Ala Met Asp Tyr Trp Gly Gln
              115                 120                 125

Gly Thr Ser Val Thr Val Ser Ser Glu Ser Gln Ser Phe Pro Asn Val
 130                 135                 140

Phe Pro Leu Val Ser Cys Glu Ser Pro Leu Ser Asp Lys Asn Leu Val
145                  150                 155                 160

Ala Met Gly Cys Leu Ala Arg Asp Phe Leu Pro Ser Thr Ile Ser Phe
              165                 170                 175

Thr Trp Asn Tyr Gln Asn Asn Thr Glu Val Ile Gln Gly Ile Arg Thr
              180                 185                 190

Phe Pro Thr Leu Arg Thr Gly Gly Lys Tyr Leu Ala Thr Ser Gln Val
              195                 200                 205

Leu Leu Ser Pro Lys Ser Ile Leu Glu Gly Ser Asp Glu Tyr Leu Val
              210                 215                 220

Cys Lys Ile His Tyr Gly Gly Lys Asn Arg Asp Leu His Val Pro Ile
225                  230                 235                 240

Pro Ala Val Ala Glu Met Asn Pro Asn Val Asn Val Phe Val Pro Pro
              245                 250                 255

Arg Asp Gly Phe Ser Gly Pro Ala Pro Arg Lys Ser Lys Leu Ile Cys
              260                 265                 270

Glu Ala Thr Asn Phe Thr Pro Lys Pro Ile Thr Val Ser Trp Leu Lys
              275                 280                 285

Asp Gly Lys Leu Val Glu Ser Gly Phe Thr Thr Asp Pro Val Thr Ile
              290                 295                 300

Glu Asn Lys Gly Ser Thr Pro Gln Thr Tyr Lys Val Ile Ser Thr Leu
305                  310                 315                 320

Thr Ile Ser Glu Ile Asp Trp Leu Asn Leu Asn Val Tyr Thr Cys Arg
              325                 330                 335

Val Asp His Arg Gly Leu Thr Phe Leu Lys Asn Val Ser Ser Thr Cys
              340                 345                 350

Ala Ala Ser Pro Ser Thr Asp Ile Leu Thr Phe Thr Ile Pro Pro Ser
              355                 360                 365

Phe Ala Asp Ile Phe Leu Ser Lys Ser Ala Asn Leu Thr Cys Leu Val
              370                 375                 380

Ser Asn Leu Ala Thr Tyr Glu Thr Leu Asn Ile Ser Trp Ala Ser Gln
385                  390                 395                 400

Ser Gly Glu Pro Leu Glu Thr Lys Ile Lys Ile Met Glu Ser His Pro
              405                 410                 415

Asn Gly Thr Phe Ser Ala Lys Gly Val Ala Ser Val Cys Val Glu Asp
              420                 425                 430

Trp Asn Asn Arg Lys Glu Phe Val Cys Thr Val Thr His Arg Asp Leu
            435                 440                 445
Pro Ser Pro Gln Lys Lys Phe Ile Ser Lys Pro Asn Glu Val His Lys
    450                 455                 460
His Pro Pro Ala Val Tyr Leu Leu Pro Pro Ala Arg Glu Gln Leu Asn
465                 470                 475                 480
Leu Arg Glu Ser Ala Thr Val Thr Cys Leu Val Lys Gly Phe Ser Pro
                485                 490                 495
Ala Asp Ile Ser Val Gln Trp Leu Gln Arg Gly Gln Leu Pro Gln
            500                 505                 510
Glu Lys Tyr Val Thr Ser Ala Pro Met Pro Glu Pro Gly Ala Pro Gly
    515                 520                 525
Phe Tyr Phe Thr His Ser Ile Leu Thr Val Thr Glu Glu Trp Asn
    530                 535                 540
Ser Gly Glu Thr Tyr Thr Cys Val Val Gly His Glu Ala Leu Pro His
545                 550                 555                 560
Leu Val Thr Glu Arg Thr Val Asp Lys Ser Thr Gly Lys Pro Thr Leu
                565                 570                 575
Tyr Asn Val Ser Leu Ile Met Ser Asp Thr Gly Gly Thr Cys Tyr
            580                 585                 590

<210> SEQ ID NO 74
<211> LENGTH: 705
<212> TYPE: DNA
<213> ORGANISM: Artificial
<220> FEATURE:
<223> OTHER INFORMATION: Antibody Sequence

<400> SEQUENCE: 74

```
atgaggttcc aggttcaggt tctggggctc cttctgctct ggataccagg tgcccagtgt    60
gatgtccaga taacccagtc tccatcttat cttgctgcat ctcctggaga accattact   120
attaattgca gggcaagtaa gagcattaac aaatatttag cctggtatca agagaaacct   180
gggaaaacta ataagcttct tatctactct ggatccacct tgcaatctgg aattccatca   240
aggttcagtg gcagtggatc tggtacagat tttactctca ccatcagtag cctggagcct   300
gaagattttg caatgtatca ctgtcaacag cataatgaat acccgtggac gttcggtgga   360
ggcaccaagc tggaaatcaa acgggctgat gctgcaccaa ctgtatccat cttcccacca   420
tccagtgagc agttaacatc tggaggtgcc tcagtcgtgt gcttcttgaa caacttctac   480
cccagagaca tcaatgtcaa gtggaagatt gatggcagtg aacgacaaaa tggtgtcctg   540
aacagttgga ctgatcagga cagcaaagac agcacctaca gcatgagcag caccctcaca   600
ttgaccaagg acgagtatga acgacataac agctatacct gtgaggccac tcacaagaca   660
tcaacttcac ccatcgtcaa gagcttcaac aggaatgagt gttag              705
```

<210> SEQ ID NO 75
<211> LENGTH: 234
<212> TYPE: PRT
<213> ORGANISM: Artificial
<220> FEATURE:
<223> OTHER INFORMATION: Antibody Sequence

<400> SEQUENCE: 75

Met Arg Phe Gln Val Gln Val Leu Gly Leu Leu Leu Trp Ile Pro
1               5                   10                  15
Gly Ala Gln Cys Asp Val Gln Ile Thr Gln Ser Pro Ser Tyr Leu Ala
            20                  25                  30

-continued

```
Ala Ser Pro Gly Glu Thr Ile Thr Ile Asn Cys Arg Ala Ser Lys Ser
            35                  40                  45

Ile Asn Lys Tyr Leu Ala Trp Tyr Gln Glu Lys Pro Gly Lys Thr Asn
 50                  55                  60

Lys Leu Leu Ile Tyr Ser Gly Ser Thr Leu Gln Ser Gly Ile Pro Ser
 65                  70                  75                  80

Arg Phe Ser Gly Ser Gly Ser Gly Thr Asp Phe Thr Leu Thr Ile Ser
                85                  90                  95

Ser Leu Glu Pro Glu Asp Phe Ala Met Tyr His Cys Gln Gln His Asn
            100                 105                 110

Glu Tyr Pro Trp Thr Phe Gly Gly Gly Thr Lys Leu Glu Ile Lys Arg
        115                 120                 125

Ala Asp Ala Ala Pro Thr Val Ser Ile Phe Pro Pro Ser Ser Glu Gln
130                 135                 140

Leu Thr Ser Gly Gly Ala Ser Val Val Cys Phe Leu Asn Asn Phe Tyr
145                 150                 155                 160

Pro Arg Asp Ile Asn Val Lys Trp Lys Ile Asp Gly Ser Glu Arg Gln
                165                 170                 175

Asn Gly Val Leu Asn Ser Trp Thr Asp Gln Asp Ser Lys Asp Ser Thr
            180                 185                 190

Tyr Ser Met Ser Ser Thr Leu Thr Leu Thr Lys Asp Glu Tyr Glu Arg
        195                 200                 205

His Asn Ser Tyr Thr Cys Glu Ala Thr His Lys Thr Ser Thr Ser Pro
210                 215                 220

Ile Val Lys Ser Phe Asn Arg Asn Glu Cys
225                 230

<210> SEQ ID NO 76
<211> LENGTH: 30
<212> TYPE: DNA
<213> ORGANISM: Artificial
<220> FEATURE:
<223> OTHER INFORMATION: Antibody Sequence

<400> SEQUENCE: 76
ggctacagct tcacaagcta ctatatacac                                    30

<210> SEQ ID NO 77
<211> LENGTH: 30
<212> TYPE: DNA
<213> ORGANISM: Artificial
<220> FEATURE:
<223> OTHER INFORMATION: Antibody Sequence

<400> SEQUENCE: 77
ggtttctcat taactagcta tggtgtacac                                    30

<210> SEQ ID NO 78
<211> LENGTH: 30
<212> TYPE: DNA
<213> ORGANISM: Artificial
<220> FEATURE:
<223> OTHER INFORMATION: Antibody Sequence

<400> SEQUENCE: 78
ggttactcat tcactggcta ctacatgcac                                    30

<210> SEQ ID NO 79
<211> LENGTH: 30
```

```
<212> TYPE: DNA
<213> ORGANISM: Artificial
<220> FEATURE:
<223> OTHER INFORMATION: Antibody Sequence

<400> SEQUENCE: 79
ggcttcaaca ttaaaaacac ctatatgcac                              30

<210> SEQ ID NO 80
<211> LENGTH: 21
<212> TYPE: DNA
<213> ORGANISM: Artificial
<220> FEATURE:
<223> OTHER INFORMATION: Antibody Sequence

<400> SEQUENCE: 80
acttatggta tgggtgtagg t                                       21

<210> SEQ ID NO 81
<211> LENGTH: 51
<212> TYPE: DNA
<213> ORGANISM: Artificial
<220> FEATURE:
<223> OTHER INFORMATION: Antibody Sequence

<400> SEQUENCE: 81
tggatttatc ctggaagtgg taatactaag tacaatgaga agttcaaggg c       51

<210> SEQ ID NO 82
<211> LENGTH: 48
<212> TYPE: DNA
<213> ORGANISM: Artificial
<220> FEATURE:
<223> OTHER INFORMATION: Antibody Sequence

<400> SEQUENCE: 82
gtgatatgga gtggtggaag cacagactac aatgcagctt tcatatcc           48

<210> SEQ ID NO 83
<211> LENGTH: 51
<212> TYPE: DNA
<213> ORGANISM: Artificial
<220> FEATURE:
<223> OTHER INFORMATION: Antibody Sequence

<400> SEQUENCE: 83
gagattaatc ctagcactgg tggtactagc tacaaccaga agttcaaggg c       51

<210> SEQ ID NO 84
<211> LENGTH: 51
<212> TYPE: DNA
<213> ORGANISM: Artificial
<220> FEATURE:
<223> OTHER INFORMATION: Antibody Sequence

<400> SEQUENCE: 84
aggattgatc ctgcgaatgg taatactaaa tatgccccga agttccaggg c       51

<210> SEQ ID NO 85
<211> LENGTH: 48
<212> TYPE: DNA
<213> ORGANISM: Artificial
<220> FEATURE:
<223> OTHER INFORMATION: Antibody Sequence

<400> SEQUENCE: 85
```

```
aacatttggt ggaatgatga taagtactat aactcagccc tgaagagc          48
```

<210> SEQ ID NO 86
<211> LENGTH: 21
<212> TYPE: DNA
<213> ORGANISM: Artificial
<220> FEATURE:
<223> OTHER INFORMATION: Antibody Sequence

<400> SEQUENCE: 86

```
agctatggtg actacgacta c                                      21
```

<210> SEQ ID NO 87
<211> LENGTH: 39
<212> TYPE: DNA
<213> ORGANISM: Artificial
<220> FEATURE:
<223> OTHER INFORMATION: Antibody Sequence

<400> SEQUENCE: 87

```
aatccctccg cctactatag taactactgg tttgcttac                    39
```

<210> SEQ ID NO 88
<211> LENGTH: 21
<212> TYPE: DNA
<213> ORGANISM: Artificial
<220> FEATURE:
<223> OTHER INFORMATION: Antibody Sequence

<400> SEQUENCE: 88

```
gactactata gtaaggctta c                                      21
```

<210> SEQ ID NO 89
<211> LENGTH: 18
<212> TYPE: DNA
<213> ORGANISM: Artificial
<220> FEATURE:
<223> OTHER INFORMATION: Antibody Sequence

<400> SEQUENCE: 89

```
tttatgcta tggactac                                           18
```

<210> SEQ ID NO 90
<211> LENGTH: 30
<212> TYPE: DNA
<213> ORGANISM: Artificial
<220> FEATURE:
<223> OTHER INFORMATION: Antibody Sequence

<400> SEQUENCE: 90

```
atagggtggt tactagcctg gtttgcttac                             30
```

<210> SEQ ID NO 91
<211> LENGTH: 48
<212> TYPE: DNA
<213> ORGANISM: Artificial
<220> FEATURE:
<223> OTHER INFORMATION: Antibody Sequence

<400> SEQUENCE: 91

```
agatctagtc agagccttgt acacagtaat ggaaacacct atttacat          48
```

<210> SEQ ID NO 92
<211> LENGTH: 33
<212> TYPE: DNA
<213> ORGANISM: Artificial

```
<220> FEATURE:
<223> OTHER INFORMATION: Antibody Sequence

<400> SEQUENCE: 92
aaggccagtc agtatgtggg tacttatgta gcc                              33

<210> SEQ ID NO 93
<211> LENGTH: 33
<212> TYPE: DNA
<213> ORGANISM: Artificial
<220> FEATURE:
<223> OTHER INFORMATION: Antibody Sequence

<400> SEQUENCE: 93
aaggccagtc agagtgtgag taatgatgta gct                              33

<210> SEQ ID NO 94
<211> LENGTH: 45
<212> TYPE: DNA
<213> ORGANISM: Artificial
<220> FEATURE:
<223> OTHER INFORMATION: Antibody Sequence

<400> SEQUENCE: 94
agggccagca aaagtgtcag tacatctggc tatagttata tgcac                 45

<210> SEQ ID NO 95
<211> LENGTH: 33
<212> TYPE: DNA
<213> ORGANISM: Artificial
<220> FEATURE:
<223> OTHER INFORMATION: Antibody Sequence

<400> SEQUENCE: 95
agggcaagta agagcattaa caaatattta gcc                              33

<210> SEQ ID NO 96
<211> LENGTH: 51
<212> TYPE: DNA
<213> ORGANISM: Artificial
<220> FEATURE:
<223> OTHER INFORMATION: Antibody Sequence

<400> SEQUENCE: 96
aaatccagtc agagtctgct caacagtaga acccgaaaga actacttggc t          51

<210> SEQ ID NO 97
<211> LENGTH: 21
<212> TYPE: DNA
<213> ORGANISM: Artificial
<220> FEATURE:
<223> OTHER INFORMATION: Antibody Sequence

<400> SEQUENCE: 97
aaagtttcca accgattttc t                                           21

<210> SEQ ID NO 98
<211> LENGTH: 21
<212> TYPE: DNA
<213> ORGANISM: Artificial
<220> FEATURE:
<223> OTHER INFORMATION: Antibody Sequence

<400> SEQUENCE: 98
tcggcatcct accggcatac t                                           21
```

```
<210> SEQ ID NO 99
<211> LENGTH: 21
<212> TYPE: DNA
<213> ORGANISM: Artificial
<220> FEATURE:
<223> OTHER INFORMATION: Antibody Sequence

<400> SEQUENCE: 99
tatgcatcca atcgctacac t                                             21

<210> SEQ ID NO 100
<211> LENGTH: 21
<212> TYPE: DNA
<213> ORGANISM: Artificial
<220> FEATURE:
<223> OTHER INFORMATION: Antibody Sequence

<400> SEQUENCE: 100
cttgtatcca acctagaatc t                                             21

<210> SEQ ID NO 101
<211> LENGTH: 21
<212> TYPE: DNA
<213> ORGANISM: Artificial
<220> FEATURE:
<223> OTHER INFORMATION: Antibody Sequence

<400> SEQUENCE: 101
tctggatcca ccttgcaatc t                                             21

<210> SEQ ID NO 102
<211> LENGTH: 21
<212> TYPE: DNA
<213> ORGANISM: Artificial
<220> FEATURE:
<223> OTHER INFORMATION: Antibody Sequence

<400> SEQUENCE: 102
tgggcatcca ctagggaatc t                                             21

<210> SEQ ID NO 103
<211> LENGTH: 27
<212> TYPE: DNA
<213> ORGANISM: Artificial
<220> FEATURE:
<223> OTHER INFORMATION: Antibody Sequence

<400> SEQUENCE: 103
tctcaaagta cacatgttcc tcggacg                                       27

<210> SEQ ID NO 104
<211> LENGTH: 27
<212> TYPE: DNA
<213> ORGANISM: Artificial
<220> FEATURE:
<223> OTHER INFORMATION: Antibody Sequence

<400> SEQUENCE: 104
cagcaatata gcagctctcc tctcacg                                       27

<210> SEQ ID NO 105
<211> LENGTH: 27
<212> TYPE: DNA
<213> ORGANISM: Artificial
<220> FEATURE:
<223> OTHER INFORMATION: Antibody Sequence
```

-continued

<400> SEQUENCE: 105
cagcaggatt atagctctcc gtacacg　　　　　　　　　　　　　　　　　　27

<210> SEQ ID NO 106
<211> LENGTH: 27
<212> TYPE: DNA
<213> ORGANISM: Artificial
<220> FEATURE:
<223> OTHER INFORMATION: Antibody Sequence

<400> SEQUENCE: 106
tctcaaagta cacatgttcc tcggacg　　　　　　　　　　　　　　　　　　27

<210> SEQ ID NO 107
<211> LENGTH: 27
<212> TYPE: DNA
<213> ORGANISM: Artificial
<220> FEATURE:
<223> OTHER INFORMATION: Antibody Sequence

<400> SEQUENCE: 107
caacagcata atgaataccc gtggacg　　　　　　　　　　　　　　　　　　27

<210> SEQ ID NO 108
<211> LENGTH: 24
<212> TYPE: DNA
<213> ORGANISM: Artificial
<220> FEATURE:
<223> OTHER INFORMATION: Antibody Sequence

<400> SEQUENCE: 108
aagcaatctt ataatctgct cacg　　　　　　　　　　　　　　　　　　　24

<210> SEQ ID NO 109
<211> LENGTH: 109
<212> TYPE: PRT
<213> ORGANISM: Artificial
<220> FEATURE:
<223> OTHER INFORMATION: Antibody Sequence

<400> SEQUENCE: 109

Asp Ile Val Met Ser Gln Ser Pro Ser Ser Leu Ala Val Ser Ala Gly
1               5                   10                  15

Asp Lys Val Thr Met Ser Cys Lys Ser Ser Gln Ser Leu Leu Asn Ser
            20                  25                  30

Arg Thr Arg Lys Asn Tyr Leu Ala Trp Tyr Gln Gln Lys Pro Gly Gln
        35                  40                  45

Ser Pro Lys Val Leu Val Tyr Trp Gly Ser Thr Arg Tyr Ser Gly Val
    50                  55                  60

Pro Asp Arg Phe Thr Gly Ser Gly Ser Gly Thr Asp Tyr Thr Leu Thr
65                  70                  75                  80

Val Ser Ser Val Gln Ala Glu Asp Leu Ala Val Tyr Phe Cys Lys Gln
                85                  90                  95

Ser Tyr Asn Leu Leu Thr Phe Gly Ala Gly Thr Lys Leu
            100                 105

<210> SEQ ID NO 110
<211> LENGTH: 327
<212> TYPE: DNA
<213> ORGANISM: Artificial
<220> FEATURE:
<223> OTHER INFORMATION: Antibody Sequence

```
<400> SEQUENCE: 110
gacattgtga tgtcacagtc tccatcctcc ctggctgtgt cagcaggaga caaggtcact    60
atgagctgca aatccagtca gagtctgctc aacagtagaa cccgaaagaa ctacttggct   120
tggtaccagc agaaaccagg gcagtctcct aaagtgctgg tctactgggg atccactagg   180
gactctgggg tccctgatcg cttcacaggc agtggatctg ggacagatta cactctcacc   240
gtcagcagtg tgcaggctga agacctggca gtttatttct gcaagcaatc ttataatctg   300
ctcacgttcg gtgctgggac caagctg                                       327

<210> SEQ ID NO 111
<211> LENGTH: 13
<212> TYPE: PRT
<213> ORGANISM: Artificial
<220> FEATURE:
<223> OTHER INFORMATION: Antibody Sequence

<400> SEQUENCE: 111

Cys Ser Arg Thr Val Lys Lys Asn Ile Ile Glu Glu Asn
1               5                   10

<210> SEQ ID NO 112
<211> LENGTH: 7
<212> TYPE: PRT
<213> ORGANISM: Artificial
<220> FEATURE:
<223> OTHER INFORMATION: Antibody Sequence

<400> SEQUENCE: 112

Trp Gly Ser Thr Arg Tyr Ser
1               5
```

SPECIFIC MURINE AND HUMANIZED MONOCLONAL ANTIBODIES DETECTING PATHOLOGY ASSOCIATED SECONDARY STRUCTURE CHANGES IN PROTEINS AND PEPTIDES

This application is a national stage application under 35 U.S.C. § 371 of PCT Application No. PCT/US2017/043416, filed Jul. 22, 2017, which claims the priority benefit of U.S. Provisional Patent Application Ser. No. 62/365,465, filed Jul. 22, 2016, which are hereby incorporated by reference in their entirety.

This invention was made with government support under NS073502 awarded by the National Institutes of Health. The government has certain rights in the invention.

FIELD OF THE INVENTION

The present invention relates to antibodies and binding fragments thereof that bind β-sheet secondary structures on pathological proteins, such as the β-sheet secondary structures found in toxic oligomeric forms of amyloidogenic proteins or in infectious, toxic or necrotic protein complexes. These antibodies and binding fragments thereof are suitable for the diagnosis, prevention, and treatment of protein conformational disorders including all amyloid disease and some foreign infective complexes.

BACKGROUND OF THE INVENTION

Amyloidosis broadly encompasses a variety of diseases that are characterized by the extracellular or intracellular deposition of amyloid proteins in tissues and/or organs. Amyloidosis starts with the conformational change of an otherwise soluble physiological peptide/protein into a pre-pathological or pathological conformer that has acquired a higher percentage of β-sheet structure, which is evident by the secondary and/or the tertiary structure of the peptide/protein. This conformational change leads to the generation of a toxic oligomeric form and ultimately to a fibrillary structure that becomes insoluble and precipitates in the milieu where the change was initiated. Thus, an initial conformational disorder might end up being an amyloid disease and/or a toxic conformational disease of pre-fibrillar amyloidotic material (Wisniewski and Goñi, "Immunotherapy for Alzheimer's Disease," *Biochem Pharmacol* 88:499-507 (2014)). Amyloids are insoluble protein/peptide aggregates in fibrillar form, and their deposition may occur in localized sites or systemically. The fibrillar composition of these deposits is an identifying characteristic for the various forms of amyloid disease. In some cases the amyloid protein/peptide accumulates intracellularly, resulting in cell dysfunction and ultimately cell death. Examples of intracellular amyloid proteins include, among others, α-synuclein, forming Lewy bodies in Parkinson's disease, and huntingtin, forming neuronal inclusions in Huntington disease. The pathogenesis of Alzheimer's disease (AD), the most common of the conformational amyloid related neurodegenerative disorders, is linked to the forming of two different pathological conformers. The first of these is characterized by the cleavage of the amyloid precursor protein (APP) generating amyloid-β (Aβ) peptides of about 30 to 55 amino acids, which undergo a shape change into a pathological conformer having high β-sheet content. Intracerebral and cerebrovascular deposits composed primarily of fibrils of the pathological Aβ peptide are characteristic of both familial and sporadic forms of AD. In addition to Aβ, conformationally abnormal hyper-phosphorylated tau protein forms toxic oligomeric structures and intraneuronal deposited neurofibrillary tangles in AD as well as in fronto-temporal dementias. Similar to AD, prion-associated diseases, such as Creutzfeldt-Jacob disease, have also been characterized as amyloid diseases. The pathogenesis of prion disease is linked to a conformational change of the cellular prion protein ($PrP^C$) into the disease associated $PrP^{Sc}$ (Sc for scrapie). Currently there is no effective therapy for any of these disorders.

An active area of translational research and current clinical trials for amyloid disease has focused on immunotherapy, using both passive and active immunization against amyloid proteins, particularly Aβ in AD (Wisniewski and Goñi, "Immunotherapeutic Approaches for Alzheimer's Disease," *Neuron* 85:1162-1170 (2015)). Although conventional anti-Aβ specific immunotherapy held great promise as a means of reducing amyloid deposition, it, unfortunately, has been accompanied by major obstacles. Specific problems associated with immunotherapy that were identified in a clinical trial for AD include the potential of toxicity from encephalitis (related to excessive cell mediated immunity), the immunological targeting of both the normal and abnormal Aβ peptide, the failure to address tau related pathology, and the apparent poor efficacy. Moreover, although autopsy data from this early immunotherapy vaccine trial suggested that many patients had a significant reduction in amyloid burden, these patients exhibited only minor cognitive benefits (Wisniewski et al., "Amyloid-β Immunization for Alzheimer's Disease," *Lancet Neurol* 7:805-811 (2008) and Holmes et al., "Long Term Effects of Aβ42 Immunization in Alzheimer's Disease: Immune Response, Plaque Removal and Clinical Function," *Lancet* 372:216-223 (2008)). Therefore, an immunotherapeutic approach directed specifically to the β-sheet conformation that can effectively reduce the toxic oligomeric forms and amyloid burden of both Aβ and tau and overcome the aforementioned problems is warranted.

The present invention is directed to overcoming these and other deficiencies in the art.

SUMMARY OF THE INVENTION

A first aspect of the present disclosure is directed to an antibody or binding fragment thereof that binds β-sheet secondary structure of a pathological monomeric or oligomeric non-fibrillar protein. The antibody or binding fragment thereof comprises a heavy chain variable region that comprises a complementarity-determining region 1 (H-CDR1) having an amino acid sequence of any one of SEQ ID NOs: 23-26, and 50, or a modified amino acid sequence of any one of SEQ ID NOs: 23-26, and 50, said modified sequence containing 1, 2, or 3 amino acid residue modifications as compared to any one of SEQ ID NOs: 23-26, or 50. The heavy chain variable region also comprises a complementarity-determining region 2 (H-CDR2) having an amino acid sequence of any one of SEQ ID NOs: 27-30, and 51, or a modified amino acid sequence of any one of SEQ ID NOs: 27-30, and 51, said modified sequences containing 1, 2, 3, or 4 amino acid residue modifications as compared to any one of SEQ ID NOs: 27-30, or 51. The heavy chain variable region further comprises a complementarity-determining region 3 (H-CDR3) having an amino acid sequence of any one of SEQ ID NOs: 31-34, and 52, or a modified amino acid sequence of any one of SEQ ID NO:

31-34, and 52, said modified sequence containing 1, 2, or 3 amino acid residue modifications as compared to any one of SEQ ID NOs: 31-34, and 52.

The antibody or binding fragment thereof as described herein may further comprise a light chain variable region. The light chain variable region comprises a complementarity-determining region 1 (L-CDR1) having an amino acid sequence of any one of SEQ ID NOs: 35-39, and 53, or a modified amino acid sequence of any one of SEQ ID NO: 35-39, and 53, said modified sequence containing 1, 2, 3, or 4 amino acid residue modifications as compared to any one of SEQ ID NO: 35-39, or 53. The light chain variable region also comprises a complementarity-determining region 2 (L-CDR2) having an amino acid sequence of any one of SEQ ID NOs: 40-44, and 54, or a modified amino acid sequence of any one of SEQ ID NO: 40-44, and 54, said modified sequence containing 1 or 2 amino acid residue modifications as compared to SEQ ID NO: 40-44, or 54. The light chain variable region also comprises a complementarity-determining region 3 (L-CDR3) having an amino acid sequence of any one of SEQ ID NOs: 45-49, and 55, or a modified amino acid sequence of any one of SEQ ID NO: 45-49, and 55, said modified sequence containing 1 or 2 amino acid residue modifications as compared to SEQ ID NO: 45-49, or 55.

Another aspect of the present disclosure is directed to a method of inhibiting onset of one or more symptoms of a condition mediated by an amyloidogenic protein or peptide in a subject. This method involves administering to the subject a pharmaceutical composition comprising an antibody or binding fragment thereof as described herein, where the composition is administered in an amount effective to inhibit onset of one or more symptoms of the condition mediated by the amyloidogenic protein or peptide in the subject.

Another aspect of the present disclosure is directed to a method of treating a condition mediated by an amyloidogenic protein or peptide in a subject. This method involves administering to the subject a pharmaceutical composition comprising an antibody or binding fragment thereof as described herein, where the composition is administered in an amount effective to treat the or ameliorate the condition, or one or more symptoms thereof, mediated by the amyloidogenic protein or peptide in the subject.

Another aspect of the present disclosure is directed to a method of treating a subject having or at risk of having a condition mediated by a pathological protein having a β-sheet secondary structure. This method involves administering to the subject a pharmaceutical composition comprising an antibody or binding fragment thereof as described herein, where the composition is administered in an amount effective to treat or ameliorate the condition, or one or more symptoms thereof, mediated by the pathological protein having the β-sheet secondary structure.

Another aspect of the present disclosure is directed to a method of diagnosing an amyloid disease in a subject. This method involves detecting, in the subject, the presence of an amyloidogenic protein or peptide using a diagnostic reagent, wherein the diagnostic reagent comprises the antibody or binding fragment described herein and diagnosing the amyloid disease in the subject based on said detecting.

Another aspect of the present disclosure is directed to a method of identifying a subject's risk for developing a condition mediated by an amyloidogenic protein or peptide. This method involves detecting, in the subject, the presence of an amyloidogenic protein or peptide using a diagnostic reagent comprising the antibody or binding fragment thereof described herein, and identifying the subject's risk of developing the condition mediated by the amyloidogenic protein or peptide based on the results of the detecting step.

Another aspect of the present disclosure is directed to a diagnostic kit that comprises the antibody or binding fragment thereof as described herein and a detectable label.

Described herein is the development of a methodology to produce conformational anti-secondary structure β-sheet monoclonal antibodies. The β-sheet secondary structure of proteins can be derived from many different primary sequences, but generally is dominant in the production of any pathologic misfolded proteins or peptides. A small 13 amino acids peptide of the carboxyl terminus of the very rare British amyloidosis (ABri), which is derived from an intronic DNA sequence expressed by a missense mutation and has no sequence homology to any other mammalian protein was used as the immunogen (Wisniewski and Goñi, "Immunotherapeutic Approaches for Alzheimer's Disease" *Neuron* 85:1162-1176 (2015), Vidal et al., "A Stop-Codon Mutation in the BRI Gene Associated with Familial British Dementia" *Nature* 399:776-781 (1999), Rostagno et al., "Chromosome 13 Dementias" *Cell Mol. Life Sci* 62:1814-1825 (2005), and Goñi et al., "Immunomodulation Targeting Abnormal Protein Conformation Reduces Pathology in a Mouse Model of Alzheimer's Disease" *PLoS ONE* 5:e13391 (2010), each of which is hereby incorporated by reference in its entirety). The peptide was polymerized by an extensive glutaraldehyde reaction to form immunogenic, covalently bound 10-100 kDa soluble and stable oligomers with high β-sheet secondary structure content (p13Bri) (Goñi et al., "Immunomodulation Targeting Abnormal Protein Conformation Reduces Pathology in a Mouse Model of Alzheimer's Disease" *PLoS ONE* 5:e13391 (2010), and Goñi et al., "Immunomodulation Targeting both Aβ and tau Pathological Conformers Ameliorates Alzheimer's Disease Pathology in TgSwDI and 3×Tg Mouse Models" *Journal of Neuroinflammation* 10:150 (2013), both of which are hereby incorporated by reference in their entirety). Inoculation in mice with a suitable adjuvant p13Bri produced an array of antibodies to the non-self motif and the β-sheet secondary structure. Hybridomas were produced and monoclonals were selected by the novel approach of specifically using as selector compounds, oligomeric conformers from different neurodegenerative disease (NDD) with the only commonality being the shared β-sheet secondary structure. These new monoclonals to β-sheet conformation in oligomers more effectively detect, monitor and treat NDD in humans and other susceptible animals.

BRIEF DESCRIPTION OF THE DRAWINGS

This patent or application file contains at least one drawing executed in color. Copies of this patent or patent application publication with color drawing(s) will be provided by the Office upon request and payment of the necessary fee.

FIG. 1A shows color coded pathways to oligomeric forms and fibrillar deposits of self-antigenic protein/peptides associated with pathology on most common NDD: Aß (red) and tau (brown) for Alzheimer's Disease; α-synuclein (orange) for Lewy Body diseases, and PrP (grey) for prionoses. Black shape represents common to all ß-sheet secondary structure acquired during pathological conformational change. Electron microscopy (EM) of oligomers and fibrils on the left and immunoblots of oligomeric forms detected by specific antibodies on the right, all color coded (also in FIGS. 3A-3C, 6A-6D, and 7A-7D). FIG. 1B shows one letter code of the 13 amino acids sequence of the non-self ABri peptide (purple boxed). Bottom pathway shows the normal conversion of ABri peptides to oligomers and fibrils (purple). Top pathway shows the controlled polymerized reaction with glutaraldehyde (see Example 1) leading to p13Bri the immunogenic, non-self, soluble and stable ß-sheet oligomers of 10-100 kDa molecular weight (from purple to green frame). Black shapes represent common to all ß-sheet structure. On the left, EM of the oligomeric p13Bri (green frame) and the oligomer/fibrils of the aged ABri peptide (purple frame). On the right Immunoblot with rabbit polyclonal anti-Bri and circular dichroism analysis of both forms (color coded and also in FIGS. 4A-4C). FIG. 1C shows the p13Bri (green boxed) inoculated into mice to produce hybridomas (Methods and table 1); horizontal blue arrows show the selection process of monoclonals by the oligomeric β-sheet conformers of [A] antigens (thick black frame and arrow); framed in blue the selected anti-conformational monoclonal antibodies that recognize ß-sheet secondary structure common to [A] and [B] pathways. The thick blue arrows from the framed blue antibodies signal possible interactive sites with pathological conformers on NDD (also in FIGS. 6A-6D, 7A-7D, and 10A-10B).

FIG. 2A shows electron microscopy (EM) of the sequential fibrillization of the ABri peptide; 1) 24 hours incubation at room temperature (RT); 2) one week incubation at RT with associated fibrils; 3) and 4) two weeks incubation at RT, big clusters of precipitated long fibrils. Scale bars represent 200 µm. FIG. 2B shows EM images of 13-mer Bri peptide after controlled polymerization with glutaraldehyde (p13Bri) showing different oligomeric states; 5) two hours after preparation of the sample; 6) one week after incubation at RT and, 7) and 8) after two weeks of incubation at RT. Scale bars represent 200 µm. FIG. 2C shows nitrocellulose blot from 15% SDS-PAGE of the ABri (lane 1) and p13Bri (lane 2) peptides. Left panel, fast green protein reversible stain; right panel immunoblot with anti-Bri antibody. Bracket marks oligomeric state between 10-100 kDa. FIG. 2D shows circular dichroism of the p13Bri peptide all β structure (p13Bri) and ABri monomer (ABrim).

FIG. 3A shows similarities of plasma reactivity from 3×Tg mice successfully immunized with p13Bri (top) 22 and CD-1 M4 mouse (bottom) on cerebral cortex and Hippocampus of old 3×Tg AD mice with amyloid and tau pathology. Right panels show higher magnification of the boxed areas. All scale bars represent 50 µm. FIG. 3B shows the same plasma comparison as in FIG. 3A but in the cortex of human AD brains. Left panels show negative reactivity on human control brains. Right panels show magnification of the boxed areas. Arrowheads show glial-like cells; arrows show cytoplasmic punctuated staining in neurons. Scale bars represent 50 µm. FIG. 3C shows EM images of Aβ1-40 and Aβ1-42 peptides on 50 mM bicarbonate pH 9.6 used to coat ELISA plates. Arrows show oligomeric forms decorating amyloid fibrils in both cases. Scale bars represent 200 µm. Right panel shows ELISA differential IgM reactivity to Aβ1-40 and Aβ1-42 from plasma of the M4 CD-1 mouse at different bleeding times as per Table 10.

FIG. 4A shows ELISA data showing plasma reactivity to Aβ40 and Aβ42 from different bleedings of all CD-1 mice as per Table 11, using peroxidase-labelled goat anti-mouse IgM (µ chain). Samples were run on triplicate. FIG. 4B shows ELISA data showing plasma reactivity to Aβ40 and Aβ42 from different bleedings of all CD-1 mice using peroxidase-labelled goat anti-mouse IgG (H+L). Samples were run on triplicate. FIG. 4C shows plate coating control showing similar reactivity detected for Aβ40 and Aβ42 with commercial antibodies 4G8/6E10 and secondary anti-mouse IgG (H+L).

FIG. 5A shows representative images showing the co-localization on the cortex of human AD brains of IgM and IgG antibodies present in the plasma of CD-1 M4 mouse inoculated with p13Bri. A combined T6+Tf pool was used as per Table 10. FIG. 5B shows higher magnification of the boxed area in FIG. 5A.

FIG. 6A shows EM of purified PHF from a human AD brain and protein kinase A treated PHF. Arrowheads show fibrils and arrows show oligomers in different aggregation clusters. Left two panels show overall differences of fibrils and oligomers associated to fibrils or in independent clusters. All scale bars are 50 µm. FIG. 6B shows immunoblots of recombinant deer PrP (dPrP); Aβ1-42 freshly dissolved, fibrilized or polymerized (Aβ42, Aβ4f and Aβ42p respectively), and PHF and PKA PHF. Individual specificity of commercial antibodies PHF-1 for hyperphosphorylated tau; 4G8 and 6E10 for Aβ peptides and 7D9 and 6D11 for PrP protein is compared to the cross-reactivity of hybridomas 10E and 23B reactive to more than one conformer and oligomeric forms. FIGS. 6C and 6D show co-localization of hybridoma 23B with either 4G8/6E10 or PHF-1 antibodies on human AD brain tissue. Scale bars represent 100 µm.

FIG. 7A shows EM of Aβ1-40, Aβ1-42, PHF purified from a human AD brain, and oligomerized PrP; arrows show oligomeric forms decorating amyloid fibrils. The right panel shows the ELISA reactivity of original positive or irrelevant clones to four neuroconformers. FIG. 7B (top) shows EM of Aβ1-40 and Aβ1-42 polymerized with glutaraldehyde and Aβ1-42 fibrillized, and the corresponding immunoblots. FIG. 7B (bottom) shows molecular weight marker (MW) followed by Aβ1-40 polymerized (Aβ40p), Aβ1-42 freshly dissolved (Aβ42), Aβ1-42 fibrillized (Aβ42f) and Aβ1-42 polymerized (Aβ42p). The left panel shows reversible Fast Green (FG) protein stain to assess comparable protein load. The next panel shows the reactivity with commercial IgG monoclonals 4G8 and 6E10 specific for Aβ peptides sequence. The three right panels show positive original clones before subcloning with differential reactivity to oligomeric forms of Aβ. FIG. 7C (top) shows EM of α-synuclein monomer, fibrillized on PBS or oligomerized with glutaraldehyde, and PHF. Bottom panels corresponding immunoblots lanes: α-synuclein monomer (α-syn m), α-synuclein fibrillized (α-syn f), α-synuclein oligomerized (α-syn p) and PHF. Left panel FG, next panel commercial anti-α-synuclein antibody; third from left commercial PHF-1 and to the right five original clones. FIG. 7D (top) shows EM of different states of aggregation of aged recPrP molecules. Bottom, immunoblots lanes: human (Hu-PrP), sheep (ShPrP) and deer PrP (dPrP). All PrPs were incubated for at least two days to maximize aggregation. Left panel FG, second panel commercial IgG monoclonals 7D9 and 6D11 that recognize middle parts of PrP. Next five panels show the reactivity of 5 original clones, before subcloning, with differential oligomer size detection previously unseen.

FIG. 8A shows typical ELISA plates coated with (in order from left to right on the graph) Aβ1-40, Aβ1-42, or PHF as per FIGS. 6A-6D, showing the difference between a clone with potential conformational monoclonal antibody and an irrelevant clone to mark the background IgM reactivity on a cell supernatant that had comparable number of cells. FIG. 8B shows control of the coat in each ELISA plate with commercial mouse IgG anti-Aβ 4G8 and 6E10 and commercial IgG anti-PHF PHF-1 (bars with lines). Background anti-IgM reactivity is similar to the irrelevant clone (hatched bars).

FIG. 9A shows fast green of cell supernatants of original hybridomas 3D, 10E, 10F, 11F, 12E and 23B obtained from the fusion of spleen cells of p13Bri immunized M4 mouse and SP2/0-IL6 fusion partner. Large amount of bovine serum albumin (BSA) from the growth media supplementation is shown. FIGS. 9B-9D show western blot of the 40% saturated Ammonium Sulfate (SAS) purified antibodies from original clones 3D, 10E, 10F, 11F, 12E and 23B. FIG. 9B shows fast green stain with residual BSA. FIG. 9C shows anti-mouse IgM μ reactivity. FIG. 9D shows anti-mouse Kappa reactivity. Left part of the blots show untreated samples and right part 0.1M Dithiothreitol (DTT) disulfide bridges reduced samples. IgMk p: pentameric IgM; IgMk m: monomeric IgM; Hμ r: mu Heavy chain reduced; Kf: free kappa Light chains and Kr: reduced kappa light chains.

FIG. 10A shows immunolabeling of human AD brain cortex. FIG. 10B shows human control brain cortex without pathology. Left panel, reactivity of the plasma from p13Bri immunized M4 mouse, arrows show cytoplasmic staining that extends to processes. Next five panels ammonium sulfate semi-purified anti β-sheet secondary structure conformational monoclonals. 23B labels cytoplasm, processes and extracellular material; 3D labels the whole neuronal body; 12E shows preference for glial cells; 10E and 10F show similar lighter staining pattern of neuronal cytoplasm, processes and nucleus. Scale bars represent 50 μm.

FIGS. 26A-26C show electron microscopy images of purified human PHF and reactivity of the conformational monoclonal antibodies TF-10E8 and TF-10F7 against PHF and three different strains of pathogenic PrP.

FIGS. 30A-31E depict reactivity of the original hybridoma 23B selected clone against Aβ1-40, Aβ1-42 and PHF; and the partial purification of the sub-clone GW-23B7 with saturated ammonium sulfate (SAS). FIG. 30A shows electron microscopy images of Aβ40 and Aβ42 in ammonium bicarbonate pH 9.6, used to coat ELISA plates. Arrows show representative oligomeric forms around fibrils of Aβ40 and Aβ42 respectively; scattered and loose in Aβ40 and compact and bundled in Aβ42. Bars represent 100 μm. FIG. 30B shows ELISA assay showing cross-reactivity of the cell supernatant of hybridoma 23B clone to (from left to right on the graph) Aβ1-40, Aβ1-42 and PHF detected by an anti-mouse IgG+IgA+IgM (H+L) antisera. FIG. 30C shows Fast Green of the concentrated cell supernatant, unreduced and DTT reduced Lanes 1 and 2, obtained from the sub-cloned conformational mAb GW-23B7 before purification and dominated by Bovine serum albumin (BSA) from fetal calf serum. FIG. 30D shows Fast Green of the 30% SAS precipitate showing the intact IgM and the Heavy and Light chains before and after reduction respectively (Lanes 3 and 4), and a small amount of the remaining BSA. IgMk p: pentameric; IgMk m: monomeric; Heavy chain reduced (Hμ r); truncated Heavy chain reduced (Hμ t), and Kappa Light chain reduced (Kr) shown. FIG. 30E shows Immunoblot of the SAS partially purified conformational mAb GW-23B7. The anti-mouse IgM (μ chain specific) shows the intact pentamer and IgM monomer before reduction (Lane 3) and after reduction the Heavy chain intact around 76 kDa plus 10-15% of a truncated Heavy chain at 60 kDa (Lane 4). The anti-mouse kappa antibody shows its presence in the pentameric and slightly in the monomeric IgM before reduction (Lane 3') and only one band for the Kappa Light chain after reduction (Lane 4').

FIG. 31A shows ELISA data showing the reactivity from cell supernatant of sub-cloned GW-23B7 IgM and an irrelevant clone from the same fusion, to PHF and oligomers differential on Aβ1-40 and Aβ1-42 (see Example 6). The right panel shows the even coating of the selected peptides on the plate and the lack of unspecific reactivity to secondary anti-mouse IgM. FIG. 31B shows western blot to show the pentameric integrity of the purified aβComAb GW-23B7. Lane 1 unreduced sample, lane 2 reduced with 0.1M DTT. Left panel: Fast Green reversible protein stain; middle panel: anti-mouse IgM (μ specific) and right panel: anti-mouse Kappa Light chains. IgMp: pentameric immunoglobulin M; Hμr: μ heavy chain reduced; Kr: Kappa light chain reduced. FIG. 31C shows ELISA assay showing the reactivity of purified aβComAb GW-23B7 diluted 1:1000, to (from left to right on the graph) Aβ1-40, Aβ1-42 and human PHF. FIG. 31D shows Surface Plasmon Resonance showing the binding affinity of the purified aβComAb GW-23B7 to the oligomeric species of Aβ1-42 and the lack of binding affinity to the monomeric forms. The $K_D$ (14 nM) was determined from the raw data on the left.

FIG. 32A shows representative images of the immunohistochemistry showing reactivity of the aβComAb GW-23B7 on human AD brains (top panels) compared to aged-matched and young human brain controls (middle and bottom panels respectively). Right panels are magnifications of the boxed areas on the left. Scale bars represent 100 μm on the left panels and 50 μm on the right panels. FIG. 32B shows fluorescent immunohistochemistry on human AD brains (two top panels) and a GSS brain (bottom panels). Left panels: GW-23B7 (left channel); middle panels (middle channels) commercial antibodies 4G8/6E10, PHF-1 and anti-glial fibrillary acidic protein (GFAP) top to bottom respectively; and right panels showing the co-localization indicated by white arrows. Scale bars represent 50 μm. FIG. 32C shows EM of Aβ1-42 fibrilized or polymerized with glutaraldehyde, PHF and protein kinase A treated PHF used on SDS-PAGE for immunoblots. FIG. 32D shows immunoblots comparing reactivity of the aβComAb GW-23B7 with the specific anti-Aβ peptides antibodies 4G8/6E10 to Aβ1-40, Aβ1-40 polymerized, Aβ1-42 fibrilized and Aβ1-42 polymerized (Lanes 1 to 4 respectively); the PHF-1 specific antibody for hyperphosphorylated tau on PHF and PHF PKa treated (Lanes 5 and 6 respectively), and the 7D9/6D11 antibodies specific for PrP molecules to oligomerized PrP and CWD prions (Lanes 7 and 8 respectively).

FIG. 33A) and FIG. 33B) cortex and FIG. 33C) Hippocampus. The conformational mAb GW-23B7 was used as primary reagent detected by HRP-labeled anti-mouse IgM (μ specific) as a secondary antibody; color was developed using DAB. Right panels are magnifications of the boxed areas on the left. Bars represent 50 μm. FIGS. 33A-33C show various potential stages of extra- and intracellular pathology are apparently detected by GW-23B7. Dark stain is seen in the cytoplasm of many neurons with some of them extending punctuate stain inside the nucleus (white arrows). FIG. 33A shows extensive punctuated extra-cellular material (black arrows) coincidental within supposed plaque contours; many neurons seem to be dystrophic or degraded to a point that they lose membrane definition and integrity (black arrowheads). Neuronal processes are also detected (white arrowheads). Some in FIG. 33B apparently making contact through zones of defined or undefined intact structure; whereas in FIG. 33C all the length of the detected material is confined in either well-defined cellular structures as in the neuron on the bottom right (right panel) or in discontinuous structures "leaking" to the extracellular milieu from the dystrophic neuron on the upper left.

FIG. 43A shows immunoblot showing protein stain, μ and kappa reactivity around the 1,000 kDa position of an intact pentameric IgMk (Lane 1). FIG. 34B shows immunoblot of PHF and PHF PKa purified from a human AD brain (Lanes A and B) detected by PHF-1 commercial antibody specific for hyperphosphorylated tau or by the GW-23B7; right panel shows immunohistochemical recognition by GW-23B7 of intra- and extracellular pathology associated structures on a human AD brain section. FIG. 34C shows immunoblots comparing reactivity to Aβ1-42 and Aβ1-42 oligomerized (Lanes C and D) by the commercial anti-Aβ 4G8/6E10 antibodies or the GW-23B7; on the right panel co-localization on a human AD brain section of punctuated or strong precipitated material recognized by GW-23B7 (black stain) within amyloid plaques of Aβ amyloid detected by 4G8/6E10 specific antibodies (light grey stain).

FIG. 35A shows protocol of the intra-peritoneal infusion of GW-23B7 or vehicle alone on 3xTg AD mice, behavioral tests and sacrifice of the tested animals. FIG. 35B shows comparative kinetics of pentameric IgM distribution inside brains pooled from 18 m.o. 3xTg animals infused with either GW-23B7 or vehicle alone as per bottom part of protocol on FIG. 35A. Western blots of soluble supernatants from 20% brain homogenates were stained before and after reduction with reversible Fast Green to assess comparable protein loading (top panel) and detected by anti-mouse μH chain or anti-mouse kappa L chain on the middle and bottom panel respectively.

The relative concentrations determined by densitometry of the bands are plotted on the graph on the right. (c). Radial Arm Maze (RAM) behavioral test showing significant differences ($p<0.0001$ determined by two-way ANOVA) between animals infused with GW-23B7 (n=4) or vehicle alone (n=4). In the treated animal group there was also a significant days effect ($p<0.0001$).

Figures 36A, 36B:
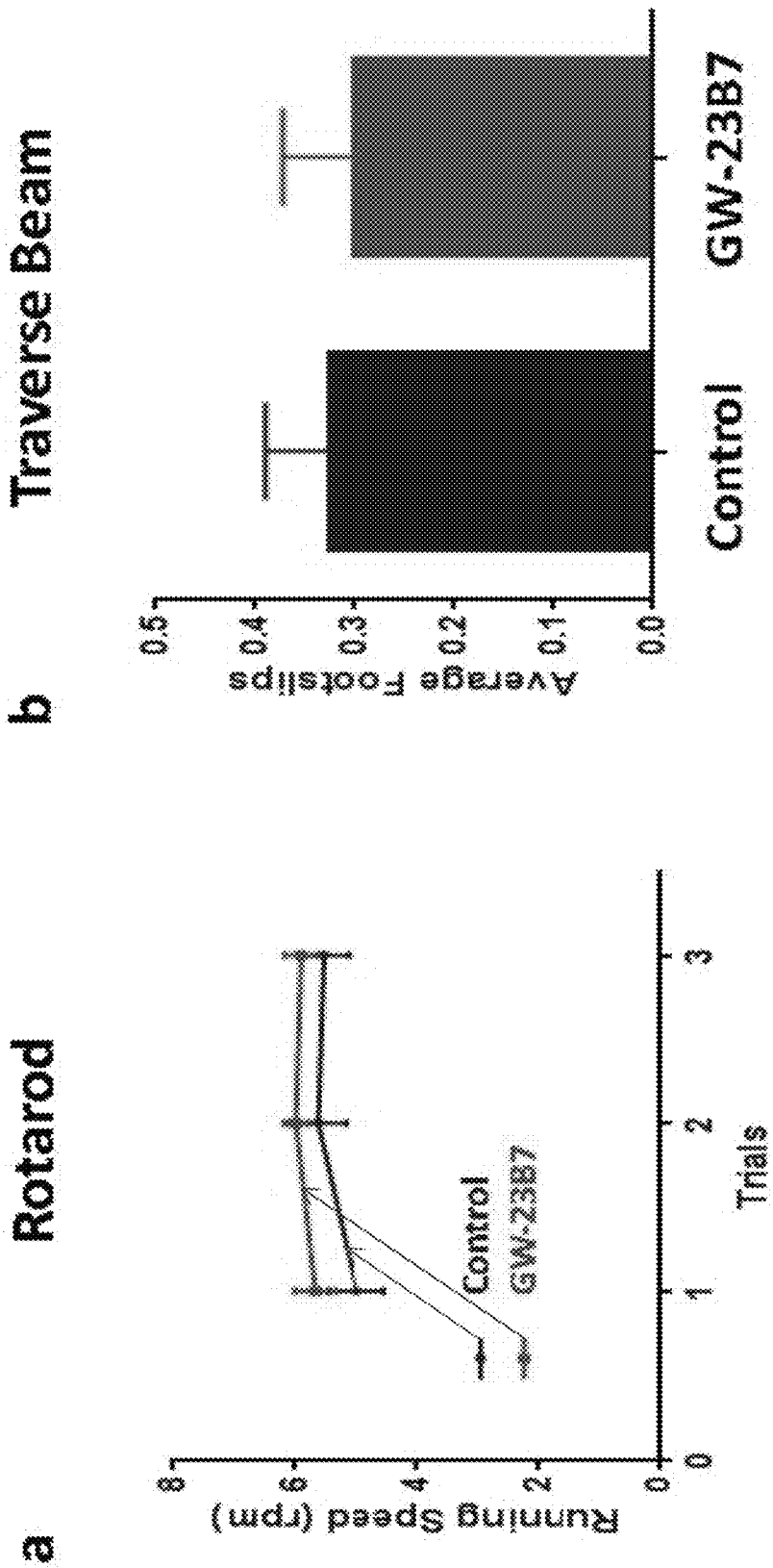

FIGS. 36A-36B depict locomotor tests on 18 m.o. 3×Tg AD mice infused with aβComAb GW-23B7 or with control vehicle alone. FIG. 36A shows Rotarod to determine balance and coordination; no differences were seen between the control and the GW-23B7 infused groups. FIG. 36B shows Traverse Beam to determine general motor coordination; no differences were seen between the control and the GW-23B7 infused groups.

Figures 37A, 37B, 37C:
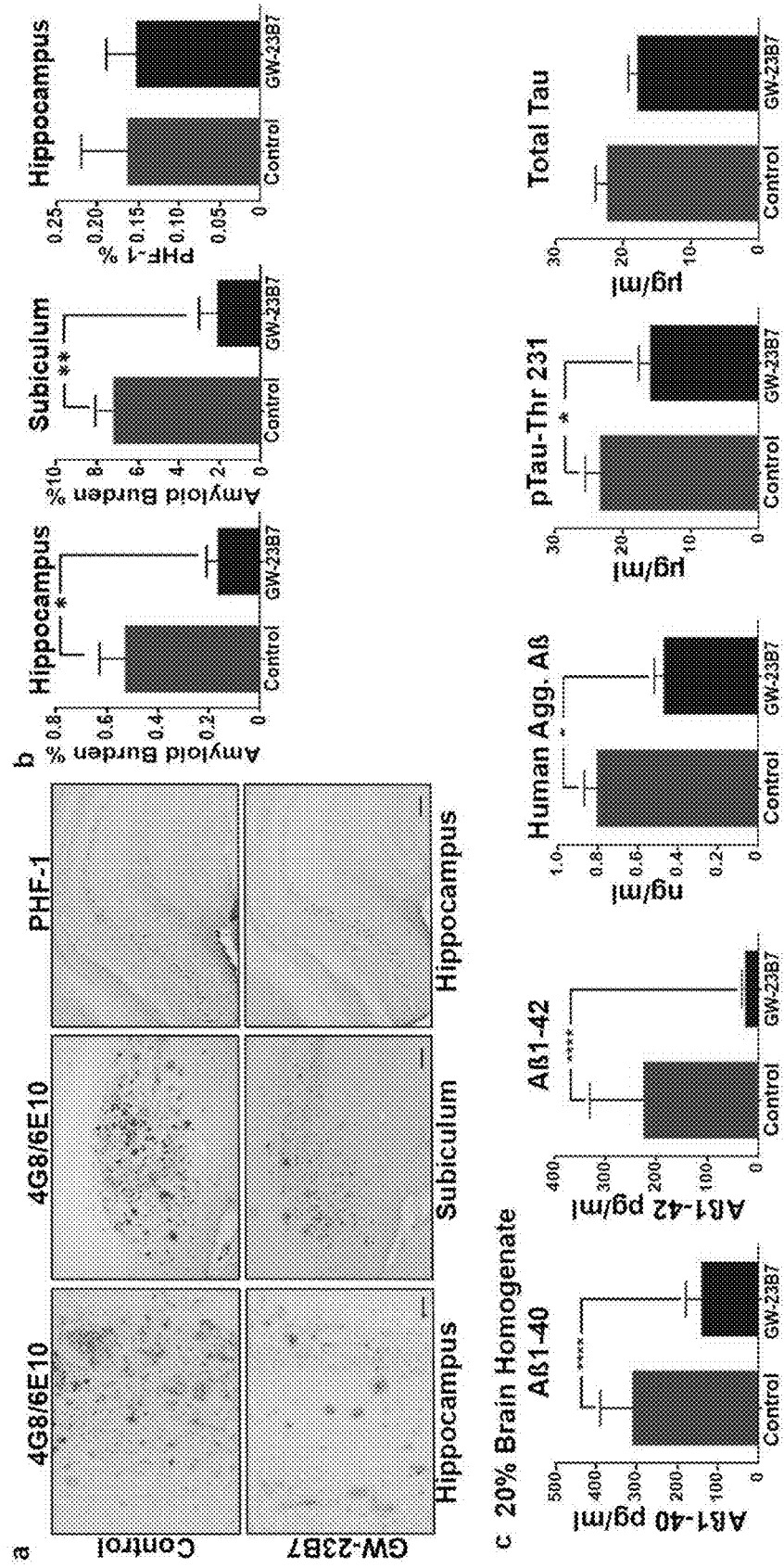

FIGS. 37A-37C depict levels of extracellular amyloid-β burden, intracellular PHF burden and soluble Aβ or ptau on brains from 19 months old 3×Tg mice infused with aβComAb GW-23B7 or control vehicle alone. FIG. 37A shows immunohistochemistry of representative GW-23B7 or vehicle control infused 3×Tg mouse brains showing on Hippocampus and Subiculum amyloid plaques detected by specific antibodies 4G8/6E10 or intraneuronal PHF as detected by commercial antibody PHF-1. Scale bars represent 200 µm. FIG. 37B shows quantitation of the amyloid and tau burden for each group of infused animals characterized on FIG. 37A; *: $p<0.05$ and : $p<0.01$. No significant differences for intracellular PHF-1 burden. FIG. 37C** shows levels of soluble Aβ1-40, Aβ1-42, human aggregated Aβ, threonine 231 phosphorylated tau and total tau on supernatants from 20% brain homogenates of the GW-23B7 and vehicle infused 3×Tg mice groups; *: $p<0.05$ and ****: $p<0.0001$.

Figures 38A, 38B:
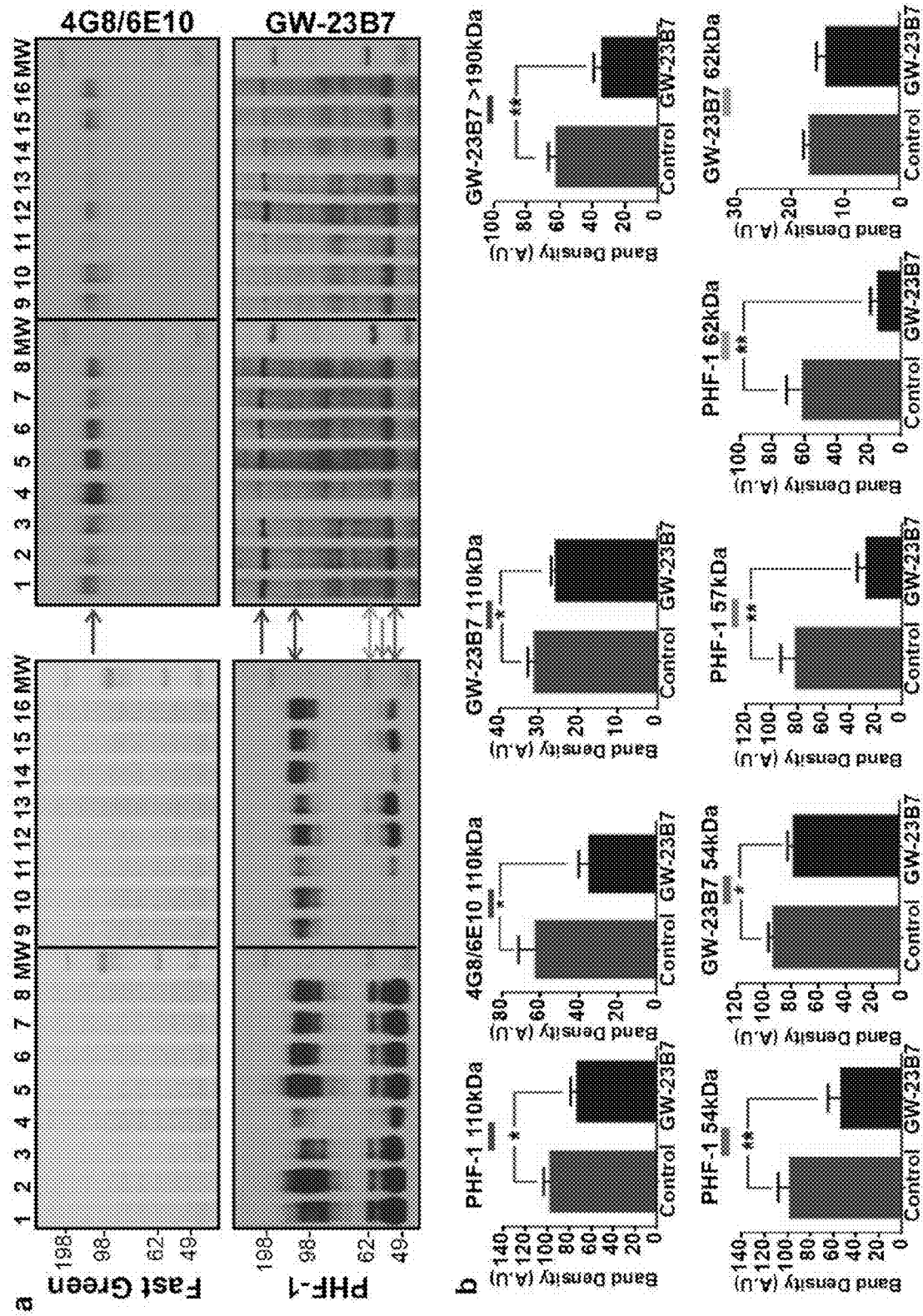

FIGS. 38A-38B depict immunoblots detecting oligomers on soluble supernatants from 20% brain homogenates of 19 m.o. 3×Tg mice infused with purified aβComAb GW-23B7 or vehicle alone. FIG. 38A shows SDS-PAGE blotted of individual soluble supernatants from 20% brain homogenates of control infused 19 m.o. 3×Tg mice (Lanes 1-8), and 19 m.o. 3×Tg mice infused with GW-23B7 (Lanes 9-16). Top left panel Fast Green protein reversible stain for comparable loading; top right panel immunoblot with 4G8/6E10 antibodies specific for Aβ peptides; bottom left panel immunoblot with PHF-1 antibody specific for hyperphosphorylated tau; and bottom right panel immunoblot with GW-23B7. Different molecular weight oligomeric forms analyzed are identified by color coded arrows, same color same molecular weight. FIG. 38B shows densitometric quantitation of the oligomer bands coded with color arrows in FIG. 38A. Statistical analysis by two-way ANOVA; *: $p<0.05$; **: $p<0.01$.

DETAILED DESCRIPTION OF THE INVENTION

Described is a novel approach to produce conformational monoclonal antibodies selected to specifically react with the β-sheet secondary structure of pathological proteins, including pathological oligomeric conformers that are characteristic of many neurodegenerative diseases. Contrary to past and current efforts, a mammalian non-self-antigen is utilized as an immunogen. The small, non-self peptide selected was covalently polymerized with glutaraldehyde until it reached a high β-sheet secondary structure content, and species between 10-100 kDa that are immunogenic, stable and soluble (p13Bri). Inoculation of p13Bri in mice elicited antibodies to the peptide and the β-sheet secondary structure conformation. Hybridomas were produced and clones selected for their reactivity with at least two different oligomeric conformers from Alzheimer's, Parkinson and/or Prion diseases. The resulting conformational monoclonals are able to detect pathological oligomeric forms in different human neurodegenerative diseases by ELISA, immunohistochemistry and immunoblots. This technological approach has resulted in the development of monoclonal antibodies as described herein that are useful tools for detection, monitoring and treatment of multiple misfolding disorders.

Figures 1A, 1B, 1C:
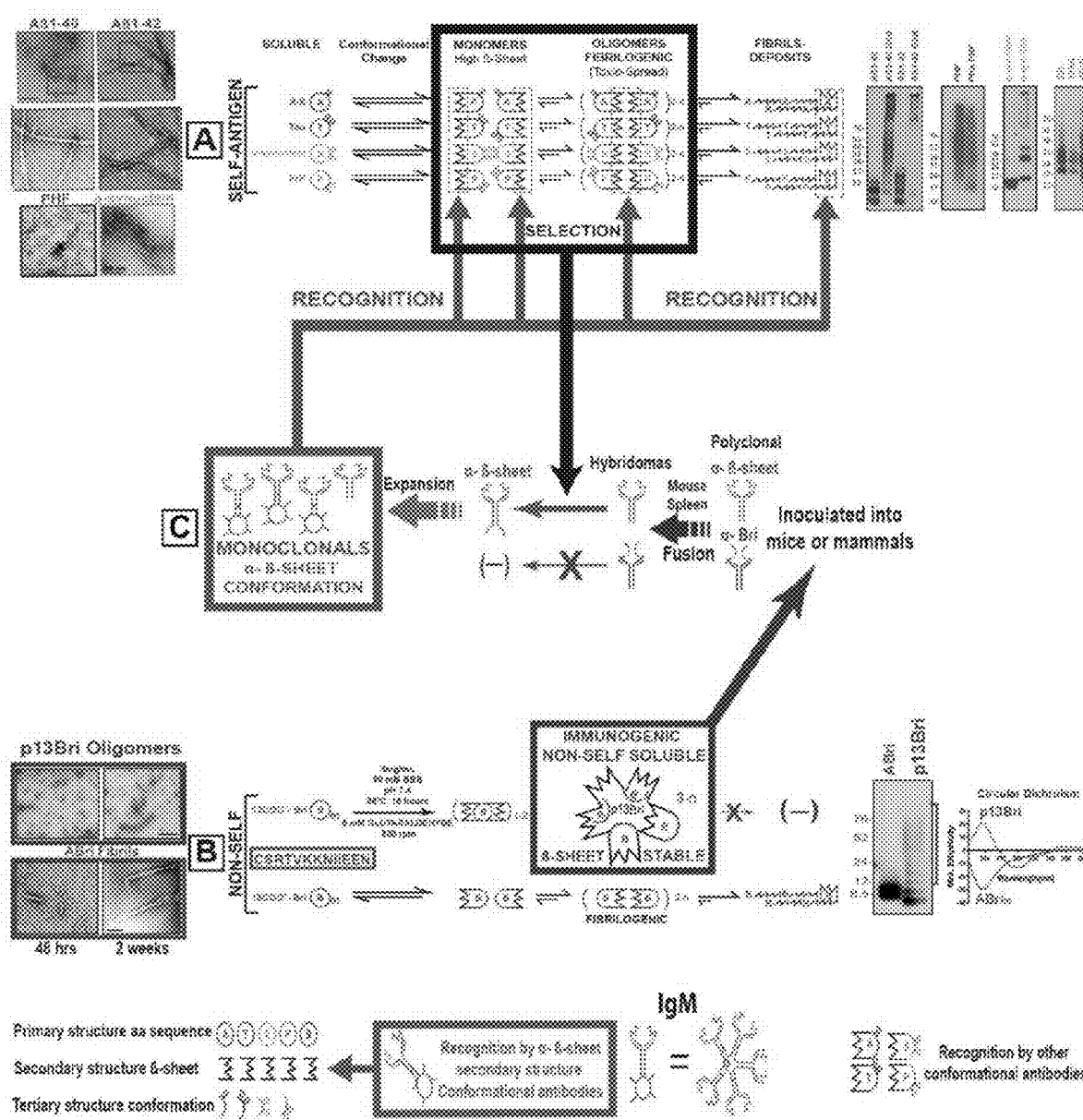
FIGS. 1A-1C depict the production of anti ß-sheet secondary structure conformational monoclonal antibodies with specificity to oligomeric toxic conformers present in neurodegenerative diseases (NDD).
Figures 2A, 2B, 2C, 2D:
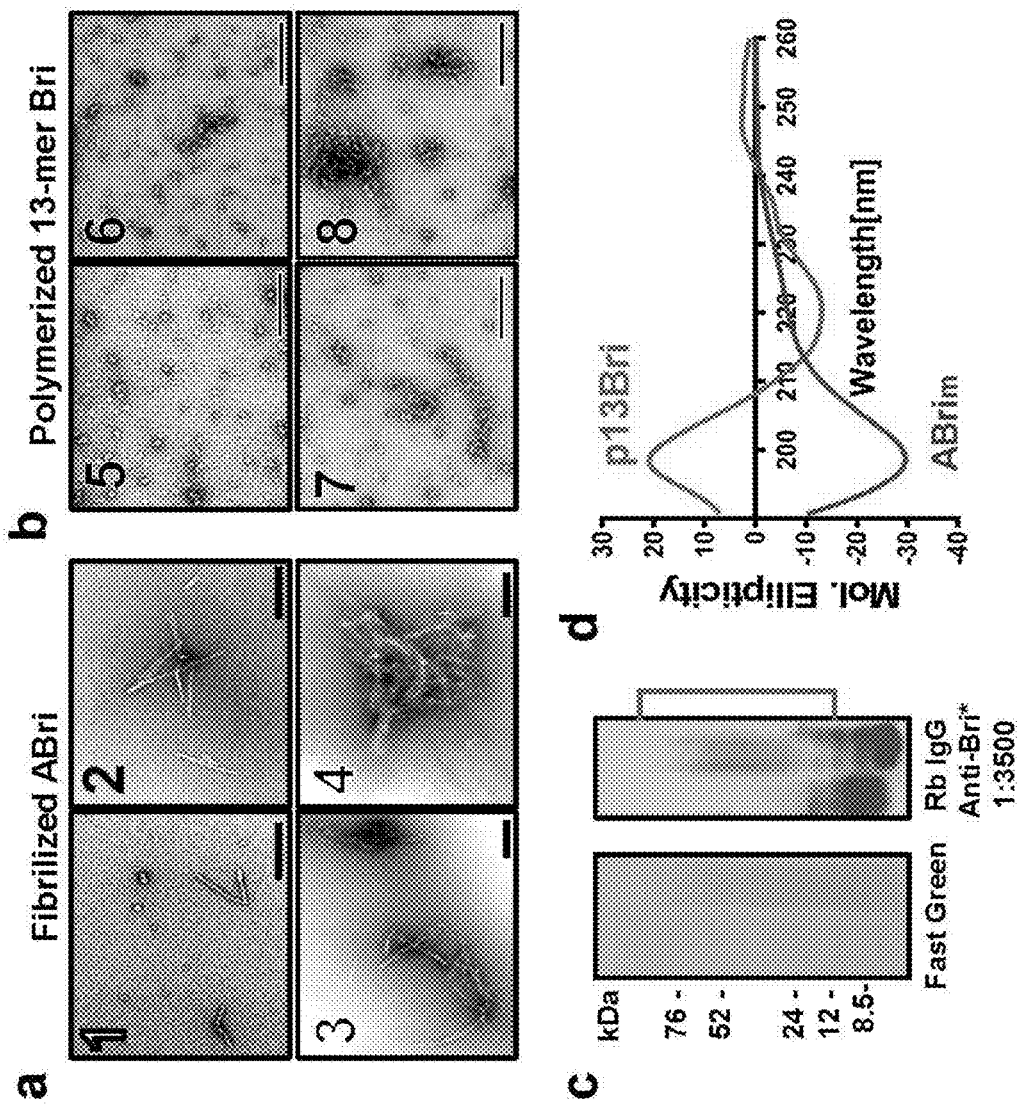
FIGS. 2A-2D depict the characterization of the ABri and Polymerized immunogenic 13-mer Bri (p13Bri) Peptides.

The antibodies and binding fragments thereof that are described herein selectively recognize and bind the toxic, pathological forms of amyloidogenic proteins, but not the non-toxic, non-pathological forms of these proteins or peptides. Toxic forms of the amyloidogenic proteins include soluble oligomeric forms and insoluble fibrous protein/peptide aggregates of amyloid proteins or peptides. FIG. 1A depicts the conformational equilibrium pathway of several exemplary proteins, i.e., Aβ, Tau, α-synuclein, and prion, as they progress from soluble, non-toxic proteins to insoluble, toxic proteins. The pathway involves an initial conformational transition from non-pathological soluble proteins to modified monomer forms containing high β-sheet secondary structure. Continued transition of the β-sheet containing monomers results in the formation of fibrillogenic β-sheet oligomers and finally insoluble fibril deposits. The oligomeric form of the amyloid proteins or peptides is a multimeric species formed from modified monomers, dimers, trimers, etc. of the protein or peptide. The various conformational forms of the amyloidogenic proteins (i.e., modified monomers→oligomers→fibrils) all contain a secondary structure that is predominately β-sheet, which is specifically recognized in the modified monomers and oligomers by the antibodies described herein. The final fibrils are compacted and the β-sheet secondary structure gets either buried or inaccessible to the hydrophilic solvent soluble antibodies described herein. This β-sheet secondary structure is absent or is present at a low percentage in the non-pathological forms of these proteins. Some β-sheet secondary structures of non-pathological forms of proteins are found within their interior; hence, these β-sheets are of difficult access and recognition by the antibodies described herein.

As used herein, "amyloidogenic protein" encompasses any insoluble fibrous protein/peptide aggregate that can be deposited intra- or extracellularly within the body. Amyloidogenic protein/peptide deposition may be organ-specific (e.g., central nervous system, pancreas, etc.) or systemic. As depicted in FIG. 1A, all amyloidogenic proteins in the oligomeric forms share in common a β-sheet secondary structure that can be recognized by certain anti-conformational antibodies and fragments thereof that are described in herein. Amyloidogenic proteins recognized by the antibodies described herein include, without limitation, amyloid precursor protein APP, amyloid β prion and prion proteins, α-synuclein, tau, insulin, ABri precursor protein, ADan precursor protein, amylin, huntingtin, TDP-43, Doppel, apolipoprotein AI, apolipoprotein AII, lysozyme, cystatin C, gelsolin, protein, atrial natriuretic factor, calcitonin, keratoepithelin, lactoferrin, immunoglobulin light chains, transthyretin, serum amyloid A (SAA) and derived amyloid A (AA), β2-microglobulin, immunoglobulin heavy chains, fibrinogen alpha chains, prolactin, keratin, amylin, and medin. Amyloid deposition may occur as its own entity or as a result of another illness (e.g., multiple myeloma, chronic infection, or chronic inflammatory disease).

The term "antibody" is used in the broadest sense and specifically covers monoclonal antibodies (including full length monoclonal antibodies), polyclonal antibodies, multispecific antibodies (e.g., bispecific antibodies), and antibody fragments so long as they exhibit the desired binding activity, i.e., binding to the toxic, pathological oligomeric forms of amyloidogenic proteins.

In one embodiment, the antibody of the disclosure is an immunoglobulin (Ig) molecule and comprises four polypeptide chains, i.e., two heavy (H) chains and two light (L) chains linked by disulfide bonds. Five types of mammalian Ig heavy chains are known: $\alpha$, $\delta$, $\epsilon$, $\gamma$, and $\mu$, wherein the type of heavy chain defines the class (isotype) of the antibody. Antibodies of the disclosure can be of any class (e.g., IgG, IgE, IgM, IgD, and IgA), and subclass (e.g., IgG1, IgG2, IgG3, IgG4, IgA1 and IgA2). In one embodiment, the antibody of the disclosure is an IgM antibody. In another embodiment, the antibody disclosed herein is not an IgG antibody.

The heavy chain may contain two regions, the constant region ($C_H$) and the variable region ($V_H$). The constant region shares high homology in all naturally occurring antibodies of the same isotype within the same species. Like the heavy chain, a light chain may also consist of one constant domain ($C_L$) and one variable domain ($V_L$). In mammals there are two types of immunoglobulin light chain, lambda ($\lambda$) and kappa ($\kappa$). The unique binding property or antigen binding specificity of a given antibody is determined by the variable (V) regions. In particular, three hyper-variable loops in each the light ($V_L$) and the heavy ($V_H$) chains, known as complementarity determining regions (CDR), are responsible for the antigen binding specificity. These regions are described in more detail infra.

An antibody fragment of the disclosure is a molecule containing an antigen binding region or antigen binding domain of a full antibody (e.g., the $V_H$ region, the $V_L$ region, or a combination of both regions). In one embodiment, the antibody fragment comprises a single-chain polypeptide containing one, two, or three of the CDRs of the light-chain variable domain, or one, two, or three of the CDRs of the heavy chain variable region. In another embodiment, the antibody fragment of the disclosure is a single domain antibody (also referred to as a nanobody), e.g., a peptide chain of about 110 amino acids long comprising one heavy chain variable region domain or one light chain variable region domain of a full antibody. In another embodiment, the antibody fragment is a fragment antigen-binding (F(ab)) fragment or a F(ab')$_2$ fragment.

Antibodies and antibody fragments of the present disclosure also encompass mutants, variants, or derivatives of the disclosed antibodies or fragments thereof which retain the essential epitope binding features of an Ig molecule. For example, the single domain antibodies can be derived from camelid ($V_{HH}$ domains) or cartilaginous fish (V-NAR) variable domains, alone or fused to an Fc domain. In another embodiment, the antibody fragment comprises the heavy chain and light chain variable regions fused together to form a single-chain variable domain antibody (scFv) or a single-chain variable domain with an Fc portion (i.e., a scFv-Fc, e.g., a minibody). In another embodiment, the antibody fragment is a divalent or bivalent single-chain variable fragment, engineered by linking two scFvs together either in tandem (i.e., tandem scFv), or such that they dimerize to form diabodies. In yet another embodiment, the antibody is a trivalent single chain variable fragment, engineered by linking three scFvs together, either in tandem or in a trimer formation to form triabodies. In another embodiment, the antibody is a tetrabody single chain variable fragment. In another embodiment, the antibody is a "linear antibody" which is an antibody comprising a pair of tandem Fd segments ($V_H$—$C_H1$-$V_H$-$C_H1$) that form a pair of antigen binding regions (see Zapata et al. *Protein Eng.* 8(10):1057-1062 (1995), which is hereby incorporated by reference in its entirety).

Antibody and antibody fragments disclosed herein can be mono-valent, bi-valent, or tri-valent with regard to binding domains, and the binding domains may be mono-specific, bi-specific, or tri-specific in binding specificity by design.

As noted above, the $V_H$ and $V_L$ regions of an antibody are subdivided into regions of hypervariability, termed complementarity determining regions (CDR). The CDRs are interspersed with regions that are more conserved in each family of V genes, termed framework regions (FR). These FR regions are specific to place in the proper spatial configuration the contact amino acid residues of the CDRs that are responsible for most of the binding capacity of the antibody. Each $V_H$ and $V_L$ is composed of three CDRs and four FRs, arranged from amino-terminus to carboxy-terminus in the following order: FR1, CDR1, FR2, CDR2, FR3, CDR3, FR4.

The three CDRs in each of the variable regions of the heavy chain and the light chain are designated CDR1, CDR2 and CDR3 for each of the variable regions (i.e., (L-CDR1, 2 and 3 of light chain and H-CDR1, 2, and 3 of heavy chain). The term "CDR set" refers to a group of three CDRs that occur in a single variable region capable of binding the antigen. The exact boundaries of these CDRs have been defined differently according to different systems. The system described by Kabat (Kabat et al., Sequences of Proteins of Immunological Interest (National Institutes of Health, Bethesda, Md. (1987) and (1991), which is hereby incorporated by reference in its entirety) not only provides an unambiguous residue numbering system applicable to any variable region of an antibody, but also provides precise residue boundaries defining the three CDRs. These CDRs may be referred to as Kabat CDRs. Chothia and coworkers (Chothia & Lesk, *J. Mol. Biol.* 196:901-917 (1987) and Chothia et al., *Nature* 342:877-883 (1989) which are hereby incorporated by reference in their entirety, describe certain sub-portions within Kabat CDRs that adopt nearly identical peptide backbone conformations, despite having great diversity at the level of amino acid sequence. These regions may be referred to as Chothia CDRs, which have boundaries that overlap with Kabat CDRs. Other boundaries defining CDRs overlapping with the Kabat CDRs have been described by Padlan, *FASEB J.* 9:133-139 (1995) and MacCallum, *J Mol Biol* 262(5):732-45 (1996), which are hereby incorporated by reference in their entirety.

In one embodiment, the CDRs and FRs of the heavy and light chain variable regions of the antibody or fragment thereof of the present disclosure are defined in accordance with Kabat et al., "Sequences of Proteins of Immunological interest" $5^{th}$ ed. (1991), which is hereby incorporated by reference in its entirety. In accordance with the Kabat system, an antibody of the present disclosure comprises a heavy chain variable region where FR1 encompasses residues 1-25 (after the leader sequences) and contains a conserved cysteine (Cys) residue at position 22. CDR1 region extends from residue 26 to about residue 35. The residue at position 35 is defined by the conserved tryptophan (Trp) residue at position 36, which is essential for antibody folding. The CDR1 may contain up to 2 residue insertions (i.e., 35A and 35B). FR2 of the heavy chain variable region begins at the tryptophan residue at about position 36 and extends up to the duplet Isoleucine-Glycine (Ile-Gly) at position 48-49 in some $V_H$ families or Leucine (Leu) at position 48 and Alanine (Ala), Serine (Ser) at position 49 in other $V_H$ families. CDR2 of the $V_H$ extends from residue 50 to residue 65 with 3 possible insertions or deletions in the middle of the CDR (typically 16-20 residues in length). The third framework of the $V_H$ extends from the conserved Arginine (Arg) or Lysine (Lys) residue at position 66 to position 94, which is two amino acid residues after the consensus Cys residue at position 92. FR3 may comprise 3 insertions, therefore ranging between 29-32 amino acid residues in total. CDR3 starts at residue 95, as defined by the conserved Cys at position 92, is between 3-25 amino acid residues in length, and is made by the recombination of three different genes, i.e. a VH gene of any family, a partial or complete DH gene, and a JH gene.

In accordance with the Kabat numbering system, the FR1 of the light chain variable region ($V_L$) of an antibody or fragment thereof as described herein extends from residue 1 (after the leader sequence) to the conserved Cys at residue 23. CDR1 begins after the conserved Cys residue, i.e., at position 24 and extends 10-17 residues to the amino acid residue before the conserved Trp residue at about position 35. The Trp residue is essential for antibody folding. The second framework of the $V_L$ begins at the conserved Trp residue and extends to the conserved Tyrosine (Tyr) at position 49. CDR2 of the $V_L$ extends from position 50 after the conserved Tyr residue to position 56, ending before the conserved Gly residue or equivalent at position 57. CDR2 typically has seven amino acid residues or less. The third framework begins at the consensus Gly at position 57 and extends to the Cys as position 88. The cysteine at position 88 forms the disulfide bridge with the conserved cysteine at position 23. CDR3 of the $V_L$ starts at position 89 (after the consensus Cys at position 88) and extends to position 97. Residues 97 and 98 are conserved threonine and phenylalanine. The length of CDR3 is made by the recombination of two different genes, i.e. a $V_L$ gene of any family and a $J_L$ gene. Thus, the length of CDR3 varies as it may contain up to six amino acid residue insertions. The fourth framework region begins at position 98 and extends through position 107.

In one embodiment, the antibody or binding fragment thereof described herein is a chimeric antibody. A chimeric antibody is an antibody where one portion of the amino acid sequence of each of the heavy and light chains is homologous to corresponding sequences in an antibody derived from a particular species or belonging to a particular class, while the remaining segment of each chain is homologous to corresponding sequences in another species or class. Typically the variable region of both light and heavy chains mimics the variable regions of antibodies derived from one species of mammals, while the constant portions are homologous to sequences of antibodies derived from another. For example, the variable region can be derived from presently known sources using readily available B-cells or hybridomas from non-human host organisms in combination with constant regions derived from, for example, human cell preparations. Methods of making chimeric antibodies are well known in the art, see e.g., U.S. Pat. No. 4,816,567; and Morrison et al., "Chimeric human antibody molecules: mouse antigen-binding domains with human constant region domains" *Proc. Natl. Acad. Sci. USA* 81:6851-6855 (1984), which are hereby incorporated by reference in their entirety).

In another embodiment, the antibody or binding fragment thereof is a CDR-grafted antibody. A "CDR-grafted antibody" is an antibody which comprises heavy and light chain variable region sequences of one species, where one or more of the CDR regions are replaced with CDR regions of another species. For example, in one embodiment the CDR grafted antibody comprises human or humanized heavy and light chain variable regions, where one or more of the CDRs within these regions is replaced with one or more CDRs from another species, e.g., murine CDRs as shown in Tables 1 and 2 herein.

In another embodiment, the antibody or binding fragment thereof is a humanized antibody. A humanized antibody is an antibody or a variant, derivative, analog or portion thereof which comprises a framework region having substantially the amino acid sequence of a human antibody and a complementary determining region having substantially the amino acid sequence of a non-human antibody. As used herein, the term "substantially" in the context of a CDR refers to a CDR having an amino acid sequence that is at least 65%, at least 70%, at least 75%, at least 80%, at least 85%, at least 90%, at least 95%, at least 98% or at least 99% identical to the amino acid sequence of a non-human antibody CDR. Likewise, the term "substantially" in the context of a FR refers to a FR having an amino acid sequence that is at least 65%, at least 70%, at least 75%, at least 80%, at least 85%, at least 90%, at least 95%, at least 98% or at least 99% identical to the amino acid sequence of a human FR. A humanized antibody comprises substantially all of at least one, and typically two, variable domains (Fab, Fab', F(ab')$_2$, Fv) in which all or substantially all of the CDR regions correspond to those of a non-human immunoglobulin (i.e., the donor antibody) and all or substantially all of the framework regions are those of a human or humanized immunoglobulin framework sequence (i.e., the acceptor antibody).

Methods of humanizing antibodies are well known in the art, see e.g., Almagro and Fransson, "Humanization of Antibodies," *Frontiers in Bioscience* 13:1619-1633 (2008), U.S. Pat. No. 6,054,297 to Carter et al., U.S. Pat. No. 8,343,489, and U.S. Patent Application Publication No. US20100261620 to Almagro et al., which are hereby incorporated by reference in their entirety. The human or humanized framework sequences can be chosen based on known structure, i.e., a fixed framework sequence, sequence homology to the framework sequences of the donor antibody (e.g., the antibody from which the CDRs are derived), i.e., a best-fit framework sequence, or a combination of both approaches. Regardless of the method chosen to select the human framework sequence, the sequences can be selected from mature framework sequences, germline gene sequences, or consensus framework sequences. Compatible human framework sequences are those that are similar in both length and sequence to the framework sequence of the donor antibody sequence (i.e., the antibody from which the CDRs are derived) to ensure proper folding of the antibody and binding domain formation.

In one embodiment, the humanized framework sequence of a humanized antibody of the disclosure comprises a consensus framework sequence. A consensus framework sequence is derived from a consensus immunoglobulin sequence, which is the sequence formed from the most frequently occurring amino acids (or nucleotides) in a family of related immunoglobulin sequences (see e.g., WINNAKER, "From Genes to Clones: Introduction to Gene Technology" (1987); Carter et al., *Proc. Natl. Acad. Sci. USA*, 89:4285 (1992); and Presta et al., *J. Immunol.*, 151:2623 (1993), which are hereby incorporated by reference in their entirety). In a family of immunoglobulins, each position in the consensus sequence is occupied by the amino acid residue occurring most frequently at that position in the family. If two amino acids occur equally frequently, either can be included in the consensus sequence.

In another embodiment, a humanized antibody or binding fragment thereof as disclosed herein comprises a fixed framework region. Human heavy chain and light chain FR sequences known in the art can be used as heavy chain and light chain "acceptor" framework sequences (or simply, "acceptor" sequences) to humanize a non-human antibody using techniques known in the art (see e.g., (Sims et al., *J. Immunol.*, 151:2296 (1993); Chothia et al., *J. Mol. Biol.*, 196:901 (1987), which are hereby incorporated by reference in their entirety). In one embodiment, human heavy chain and light chain acceptor sequences are selected from the framework sequences listed in publicly available databases such as V-base or in the international ImMunoGeneTics® (IMGT®) information system.

Humanized antibodies or binding fragments thereof as described herein may also comprise at least a portion of an immunoglobulin constant region (Fc), typically that of a human immunoglobulin. In one embodiment, the humanized antibody disclosed herein comprises the light chain as well as at least the variable domain of a heavy chain. The humanized antibody may further comprise the CH1, hinge, CH2, CH3, and CH4 regions of the heavy chain. In another embodiment, the humanized antibody comprises only a humanized light chain. In another embodiment, the humanized antibody comprises only a humanized heavy chain. In another embodiment, the humanized antibody comprises only a humanized variable domain of a light chain and/or a humanized variable domain of a heavy chain.

Humanized antibodies and binding fragments thereof as described herein may be selected from any class of immunoglobulins, including IgM, IgG, IgD, IgA and IgE, and any isotype, including without limitation IgG1, IgG2, IgG3, IgG4, IgA1, and IgA2. The humanized antibody or binding fragment thereof may comprise sequences from more than one class or isotype, and particular constant domains may be selected to optimize desired effector functions using techniques well-known in the art.

In one embodiment, the antibodies and binding fragments thereof as described herein are human antibodies. Methods of producing human antibodies that are known in the art are suitable for use in accordance with the present disclosure. For example, one can produce transgenic animals (e.g., mice) that are capable, upon immunization, of producing a full repertoire of human antibodies in the absence of endogenous immunoglobulin production. For example, it has been described that the homozygous deletion of the antibody heavy-chain joining region ($J_H$) gene in chimeric and germ-line mutant mice results in complete inhibition of endogenous antibody production. Transfer of the human germ-line immunoglobulin gene array into such germ-line mutant mice will result in the production of human antibodies upon antigen challenge. See, e.g., Jakobovits et al., *Proc. Natl Acad. Sci. USA* 90:2551 (1993); Jakobovits et al., *Nature* 362:255-258 (1993); U.S. Pat. No. 5,545,806 to Lonberg et al, U.S. Pat. No. 5,569,825 to Lonberg et al, and U.S. Pat. No. 5,545,807 to Surani et al, which are hereby incorporated by reference in their entirety.

Alternatively, phage display technology (McCafferty et al., *Nature* 348:552-553 (1990), which is hereby incorporated by reference in its entirety) can be used to produce human antibodies and antibody fragments in vitro, from immunoglobulin variable (V) domain gene repertoires from unimmunized donors. According to this technique, antibody V domain genes are cloned in-frame into either a major or minor coat protein gene of a filamentous bacteriophage and displayed as functional antibody fragments on the surface of the phage particle. Because the filamentous particle contains a single-stranded DNA copy of the phage genome, selections based on the functional properties of the antibody also result in selection of the gene encoding the antibody exhibiting those properties. Thus, the phage mimics some of the properties of the B-cell. Phage display can be performed in a variety of formats, see e.g., Johnson and Chiswell, *Current Opinion in Structural Biology* 3:564-571 (1993), which is hereby incorporated by reference in its entirety. A repertoire of V genes from unimmunized human donors can be constructed and antibodies to a diverse array of antigens (including self-antigens) can be isolated essentially following the techniques described by Marks et al., *J. Mol. Biol.* 222:581-597 (1991), Griffith et al., *EMBO J.* 12:725-734 (1993), see e.g., U.S. Pat. No. 5,565,332 to Hogenboom and U.S. Pat. No. 5,573,905 to Lerner et al., which are hereby incorporated by reference in their entirety.

The antibodies and binding fragments thereof described herein can be human antibodies or humanized antibodies (fully or partially humanized) as described supra. Alternatively, the antibodies and binding fragments thereof can be animal antibodies such as, but not limited to, a bird (for example, a duck, chicken, or a goose), a shark, a whale, or a mammal, including a non-primate (for example, a cow, a pig, a camel or all camelids, a llama, a horse, a goat, a rabbit, a sheep, a deer or other cervids, a hamster, a guinea pig, a cat, a dog, a rat, a mouse, etc.) or a non-human primate (for example, a monkey, a chimpanzee, etc.).

Methods of antibody production, in particular, monoclonal antibody production, may be carried out using the methods described herein and those well-known in the art (MONOCLONAL ANTIBODIES—PRODUCTION, ENGINEERING AND CLINICAL APPLICATIONS (Mary A. Ritter and Heather M. Ladyman eds., 1995), which is hereby incorporated by reference in its entirety). Generally, the process involves obtaining immune cells (lymphocytes) from the spleen of an animal which has been previously immunized with the antigen of interest (e.g., polymerized Bri peptide as described in the Examples herein) either in vivo or in vitro.

The antibody-secreting lymphocytes are then fused with myeloma cells or transformed cells, which are capable of replicating indefinitely in cell culture, thereby producing an immortal, immunoglobulin-secreting cell line. Fusion with mammalian myeloma cells or other fusion partners capable of replicating indefinitely in cell culture is achieved by standard and well-known techniques, for example, by using polyethylene glycol (PEG) or other fusing agents (Milstein and Kohler, "Derivation of Specific Antibody-Producing Tissue Culture and Tumor Lines by Cell Fusion," *Eur J Immunol* 6:511 (1976), which is hereby incorporated by reference in its entirety). The immortal cell line, which is preferably murine, but may also be derived from cells of other mammalian species, is selected to be deficient in enzymes necessary for the utilization of certain nutrients, to be capable of rapid growth, and have good fusion capability. The resulting fused cells, or hybridomas, are cultured, and the resulting colonies screened for the production of the desired monoclonal antibodies. Colonies producing such antibodies are cloned, and grown either in vivo or in vitro to produce large quantities of antibody.

In another embodiment, monoclonal antibodies can be isolated from antibody phage libraries generated using the techniques described in McCafferty et al., "Phage Antibodies: Filamentous Phage Displaying Antibody Variable Domains," *Nature* 348:552-554 (1990), which is hereby incorporated by reference in its entirety. Clackson et al., "Making Antibody Fragments using Phage Display Libraries," Nature 352:624-628 (1991); and Marks et al., "By-Passing Immunization. Human Antibodies from V-Gene Libraries Displayed on Phage," J. Mol. Biol. 222:581-597 (1991), which are hereby incorporated by reference in their entirety, describe the isolation of murine and human antibodies, respectively, using phage libraries. Subsequent publications describe the production of high affinity (nM range) human antibodies by chain shuffling (Marks et al., BioTechnology 10:779-783 (1992), which is hereby incorporated by reference in its entirety), as well as combinatorial infection and in vivo recombination as a strategy for constructing very large phage libraries (Waterhouse et al., Nuc. Acids. Res. 21:2265-2266 (1993), which is hereby incorporated by reference in its entirety). Thus, these techniques are viable alternatives to traditional monoclonal antibody hybridoma techniques for isolation of monoclonal antibodies.

Alternatively, monoclonal antibodies can be made using recombinant DNA methods as described in U.S. Pat. No. 4,816,567 to Cabilly et al, which is hereby incorporated by reference in its entirety. The polynucleotides encoding a monoclonal antibody are isolated from mature B-cells or hybridoma cells, for example, by RT-PCR using oligonucleotide primers that specifically amplify the genes encoding the heavy and light chains of the antibody. The isolated polynucleotides encoding the heavy and light chains are then cloned into suitable expression vectors, which when transfected into host cells such as E. coli cells, simian COS cells, Chinese hamster ovary (CHO) cells, or myeloma cells that do not otherwise produce immunoglobulin protein, generate monoclonal antibodies.

The polynucleotide(s) encoding a monoclonal antibody can further be modified using recombinant DNA technology to generate alternative antibodies. For example, the constant domains of the light and heavy chains of a mouse monoclonal antibody can be substituted for those regions of a human antibody to generate a chimeric antibody. Alternatively, the constant domains of the light and heavy chains of a mouse monoclonal antibody can be substituted for a non-immunoglobulin polypeptide to generate a fusion antibody. In other embodiments, the constant regions are truncated or removed to generate the desired antibody fragment of a monoclonal antibody. Furthermore, site-directed or high-density mutagenesis of the variable region can be used to optimize specificity and affinity of a monoclonal antibody.

FIG. 1B is a schematic depiction of an exemplary method for antigen preparation and monoclonal antibody production to generate the antibodies disclosed herein. As described in the Examples herein, a 13mer peptide of ABri, which is a non-self antigen lacking tertiary structure, is suitable for directional covalent polymerization to form an immunogenic, non-self, stable, and soluble antigen for antibody production. This antigen is produced by a controlled reaction with glutaraldehyde to form predominantly β-sheet oligomers. The oligomers do not progress to form fibrils as shown in the normal equilibrium pathway that the 13mer ABri peptide would undergo. The stable, soluble, non-self oligomer formed as a result of the controlled glutaraldehyde reaction is administered to mice or other mammals to induce a polyclonal antibody response (FIG. 1C). The polyclonal antibodies generated upon inoculation primarily recognize either ABri primary sequence or the secondary β-sheet structure. The spleen of an animal with a good response to β-sheet conformers is dislodged and the splenocytes are fused with the Sp2/0 supplemented Sp2/mIL6 partner to produce hybridomas. Hybridomas producing clones that bind to β-sheet conformational structure common to oligomeric forms of Aβ, Tau, α-synuclein, and PrP are positively selected for and expanded. As shown in FIG. 1C, the selectively expanded antibodies recognize the β-sheet secondary structure that is shared by various amyloidogenic proteins at various stages during their transition from non-toxic to toxic pathological forms. While the process in FIG. 1B depicts the utilization of a 13-mer ABri peptide, various other peptides and fusion peptides that are suitable for controlled glutaraldehyde polymerization to form an immunogenic, non-self, stable and soluble antigen with high β-sheet secondary structure suitable for antibody production are disclosed in U.S. Pat. No. 8,409,584 to Wisniewski et al., which is hereby incorporated by reference in its entirety.

In one embodiment, the antibody or binding fragment thereof as disclosed herein comprises a heavy chain variable region (HCVR) having a H-CDR1 with an amino acid sequence selected from SEQ ID NOs: 23-26, and 50, or a modified amino acid sequence thereof containing 1, 2, 3, 4, 5, 6, 7, 8, or 9 amino acid residue modifications as compared to SEQ ID NOs: 23-26, or 50 that maintain or enhance binding specificity of the H-CDR1. In one embodiment, the amino acid sequence of the H-CDR1 contains no more than 1, 2, or 3 amino acid modifications as compared to any one of SEQ ID NOs: 23-26, and 50. The HCVR further comprises a H-CDR2 with an amino acid sequence selected from SEQ ID NOs: 27-30, and 51, or a modified amino acid sequence thereof containing 1, 2, 3, 4, 5, 6, 7, 8, 9, 10, 11, 12, 13, 14, 15, 16 amino acid residue modifications as compared to SEQ ID NOs: 27-30, or 51 that maintain or enhance binding specificity of the H-CDR2. In one embodiment, the amino acid sequence of the H-CDR2 contains no more than 1, 2, 3, or 4 amino acid modifications as compared to any one of SEQ ID NOs: 27-30, and 51. The HCVR of the antibody or binding fragment thereof comprises a H-CDR3 with an amino acid sequence selected from SEQ ID NOs: 31-34, and 52, or a modified amino acid sequence thereof containing 1, 2, 3, 4, 5, or 6 amino acid residue modifications as compared to SEQ ID NOs: 31-34, or 52 that maintain or enhance binding specificity of the H-CDR3. In one embodiment, the amino acid sequence of the H-CDR3 contains no more than 1, 2, or 3 amino acid modifications as compared to any one of SEQ ID NOs: 31-34, and 52. The amino acid sequences of SEQ ID NOs: 23-34 and 50-52 are provided in Table 1 below.

TABLE 1

Exemplary Heavy Chain CDR Amino Acid Sequences

| Ab Name | HCVR CDR1 | SEQ ID NO | HCVR CDR2 | SEQ ID NO | HCVR CDR3 | SEQ ID NO |
|---|---|---|---|---|---|---|
| TF-10E8 | GYSFTSYYIH | 23 | WIYPGSGNTKYNEKFKG | 27 | SYGDYDY | 31 |
| FT-12E1 | GFSLTSYGVH | 24 | VIWSGGSTDYNAAFIS | 28 | NPSAYYSNYWFAY | 32 |

TABLE 1-continued

Exemplary Heavy Chain CDR Amino Acid Sequences

| Ab Name | HCVR CDR1 | SEQ ID NO | HCVR CDR2 | SEQ ID NO | HCVR CDR3 | SEQ ID NO |
|---|---|---|---|---|---|---|
| WG-3D7 | GYSFTGYYMH | 25 | EINPSTGGTSYNQKFKG | 29 | DYYSKAY | 33 |
| TF-10F7 | GYSFTSYYIH | 23 | WIYPGSGNTKYNEKFKG | 27 | SYGDYDY | 31 |
| GW-23B7 | GFNIKNTYMH | 26 | RIDPANGNTKYAPKFQG | 30 | FYAMDY | 34 |
| FT-11F2 | GFSLSTYGMGVG | 50 | NIWWNDDKYYNSALKS | 51 | IGWLLAWFAY | 52 |

In one embodiment, the antibody or binding fragment thereof as disclosed herein comprises a light chain variable region (LCVR) that has a complementarity-determining region 1 (L-CDR1) having an amino acid sequence of any one of SEQ ID NOs: 35-39, and 53, or a modified amino acid sequence thereof containing 1, 2, 3, 4, 5, 6, 7, 8, 9, or 10 amino acid residue modifications as compared to any one of SEQ ID NO: 35-39, or 53 that maintain or enhance binding specificity of the L-CDR1. In one embodiment, the amino acid sequence of the L-CDR1 contains no more than 1, 2, 3, or 4 amino acid modifications as compared to any one of SEQ ID NOs: 35-39, or 53. The LCVR further comprises a L-CDR2 having an amino acid sequence of any one of SEQ ID NOs: 40-44, 54, or 112 or a modified amino acid sequence thereof containing 1, 2, 3, or 4 amino acid residue modifications as compared to SEQ ID NO: 40-44, 54, or 112 that maintain or enhance binding specificity of the L-CDR2. In one embodiment, the amino acid sequence of the L-CDR2 contains no more than 1 or 2 amino acid modifications as compared to any one of SEQ ID NOs: 40-44, 54, or 112. The LCVR further comprises a L-CDR3 having an amino acid sequence of any one of SEQ ID NOs: 45-49, and 55 or a modified amino acid sequence thereof containing 1, 2, 3, 4, 5, 6, 7, or 8 amino acid residue modifications as compared to SEQ ID NO: 45-49, or 55 that maintain or enhance binding specificity of the L-CDR3. In one embodiment, the amino acid sequence of the L-CDR3 contains no more than 1 or 2 amino acid modifications as compared to any one of SEQ ID NOs: 45-49, or 55. The amino acid sequences of SEQ ID NOs: 35-49, 53-55, and 112 are provided in Table 2 below.

substitutions or functionally equivalent amino acid residue substitutions that result in variant CDR sequences having similar or enhanced binding characteristics to those of the CDR sequences of Table 1 and Table 2. Conservative substitutions are those that take place within a family of amino acids that are related in their side chains. Genetically encoded amino acids can be divided into four families: (1) acidic (aspartate, glutamate); (2) basic (lysine, arginine, histidine); (3) nonpolar (alanine, valine, leucine, isoleucine, proline, phenylalanine, methionine, tryptophan); and (4) uncharged polar (glycine, asparagine, glutamine, cysteine, serine, threonine, tyrosine). Phenylalanine, tryptophan, and tyrosine are sometimes classified jointly as aromatic amino acids. Alternatively, the amino acid repertoire can be grouped as (1) acidic (aspartate, glutamate); (2) basic (lysine, arginine histidine), (3) aliphatic (glycine, alanine, valine, leucine, isoleucine, serine, threonine), with serine and threonine optionally grouped separately as aliphatic-hydroxyl; (4) aromatic (phenylalanine, tyrosine, tryptophan); (5) amide (asparagine, glutamine); and (6) sulfur-containing (cysteine and methionine) (Stryer (ed.), Biochemistry, 2nd ed, WH Freeman and Co., 1981, which is hereby incorporated by reference in its entirety). Non-conservative substitutions can also be made to the heavy chain CDR sequences of Table 1 and the light chain CDR sequences of Table 2. Non-conservative substitutions involve substituting one or more amino acid residues of the CDR with one or more amino acid residues from a different class of amino acids to improve or enhance the binding properties of CDR.

TABLE 2

Exemplary Light Chain CDR Amino Acid Sequences

| Ab Name | LCVR CDR1 | SEQ ID NO | LCVR CDR2 | SEQ ID NO | LCVR CDR3 | SEQ ID NO |
|---|---|---|---|---|---|---|
| TF-10E8 | RSSQSLVHSNGNTYLH | 35 | KVSNRFS | 40 | SQSTHVPRT | 45 |
| FT-12E1 | KASQYVGTYVA | 36 | SASYRHT | 41 | QQYSSSPLT | 46 |
| WG-3D7 | KASQSVSNDVA | 37 | YASNRYT | 42 | QQDYSSPYT | 47 |
| TF-10F7 | RASKSVSTSGYSYMH | 38 | LVSNLES | 43 | SQSTHVPRT | 48 |
| GW-23B7 | RASKSINKYLA | 39 | SGSTLQS | 44 | QQHNEYPWT | 49 |
| FT-11F2(1) | KSSQSLLNSRTRKNYLA | 53 | WASTRES | 54 | KQSYNLLT | 55 |
| FT-11F2(1) | KSSQSLLNSRTRKNYLA | 53 | WGSTRYS | 112 | KQSYNLLT | 55 |

Suitable amino acid modifications to the heavy chain CDR sequences of Table 1 and/or the light chain CDR sequences of Table 2 include, for example, conservative The amino acid sequences of the heavy chain variable region CDRs of Table 1 and/or the light chain variable region CDRs of Table 2 may further comprise one or more internal neutral amino acid insertions or deletions that do not alter amyloidogenic protein binding. A neutral amino acid insertion or deletion encompasses the insertion or deletion of any amino acid as long as its insertion or deletion does not alter the binding specificity of the variable domain region. In one embodiment, the H-CDR3 having an amino acid sequence of any one of SEQ ID NOs: 31-34, or 52, further contains one or more internal neutral amino acid insertions or deletions that do not alter amyloidogenic protein binding. In another embodiment, the L-CDR1, having an amino acid sequence of any one of SEQ ID NOs: 35-39, and 53 further contains one or more internal neutral amino acid insertions or deletions that do not alter amyloidogenic protein binding.

In one embodiment, the antibody or binding fragment thereof has a heavy chain variable region with a H-CDR1 having the amino acid sequence of SEQ ID NO: 23, or a modified amino acid sequence thereof containing 1, 2, or more amino acid residue modifications as compared to SEQ ID NO: 23; a H-CDR2 having the amino acid sequence of SEQ ID NO: 27, or a modified amino acid sequence thereof containing 1, 2, 3, 4, or more amino acid residue modifications as compared to SEQ ID NO: 27; and a H-CDR3 comprising the amino acid sequence of SEQ ID NO: 31, or a modified amino acid sequence thereof, said modified amino acid sequence containing 1, 2, or more amino acid modifications as compared to SEQ ID NO: 31. In one embodiment, this antibody further comprises a light chain variable region that comprises a L-CDR1 having the amino acid sequence of SEQ ID NO: 35, or a modified amino acid sequence thereof containing 1, 2, 3, or 4 amino acid residue modifications as compared to SEQ ID NO: 35; a L-CDR2 comprising the amino acid sequence of SEQ ID NO: 40, or a modified amino acid sequence thereof containing 1 or 2 amino acid residue modifications as compared to said SEQ ID NO: 40; and a L-CDR3 comprising the amino acid sequence of SEQ ID NO: 45, or a modified amino acid sequence thereof containing 1 or 2 amino acid residue modifications as compared to SEQ ID NO: 45. An exemplary monoclonal antibody having these heavy chain and light chain variable regions is referred to herein as the TF-10E8 antibody.

The TF-10E8 antibody comprises a $V_H$ chain amino acid sequence of SEQ ID NO: 2 as shown below. The CDR regions of the $V_H$ chain are underlined, and the framework regions (i.e., FR1-FR4) flanking the CDRs are shown in bold typeface.

SEQ ID NO: 2
QVQLQQSGPELVKPGASVKISCKAS<u>GYSFTSYYIH</u>WVKQRPGQGLEWI

GWIYPGSGNTKYNEKFKGKATLTADTSSSTAYMQLSSLTSEDSAVYYC

AR<u>SYGDYDY</u>WGQGTTLTVSS

The TF-10E8 antibody comprises a $V_L$ chain amino acid sequence of SEQ ID NO: 4 as shown below. The CDR regions of the $V_L$ chain are underlined, and the framework regions (i.e., FR1-FR4) flanking the CDRs are shown in bold typeface.

SEQ ID NO: 4
DVVMTQTPLSLPVSLGDQASISC<u>RSSQSLVHSNGNTYLH</u>WYLQKPGQS

PKLLIY<u>KVSNRFS</u>GVPDRFSGSGSGTDFTLKISRVEAEDLGVYFC<u>SQS

THVPRT</u>FGGGTKLEIK

In one embodiment, the antibody or binding fragment thereof as described herein comprises a $V_H$ region having an amino acid sequence of SEQ ID NO: 2 and/or a $V_L$ region having an amino acid sequence of SEQ ID NO:4. In one embodiment the antibody is the monoclonal TF-10E8 antibody having a heavy chain amino acid sequence of SEQ ID NO: 57 and a light chain amino acid sequence of SEQ ID NO: 59 as shown in Table 6 infra.

In another embodiment, the antibody or binding fragment thereof comprises a $V_H$ region having an amino acid sequence that shares at least 60%, at least 65%, at least 70%, at least 75%, at least 80%, at least 85%, at least 90%, at least 91%, at least 92%, at least 93%, at least 94% at least 95%, at least 96%, at least 97%, at least 98%, at least 99% sequence identity to SEQ ID NO: 2, and/or a $V_L$ region having an amino acid sequence that shares at least 60%, at least 65%, at least 70%, at least 75%, at least 80%, at least 85%, at least 90%, at least 91%, at least 92%, at least 93%, at least 94% at least 95%, at least 96%, at least 97%, at least 98%, at least 99% sequence identity to SEQ ID NO: 4.

In one embodiment, the antibody or binding fragment thereof of the present disclosure comprises a humanized variant of the $V_H$ of SEQ ID NO:2 and/or a humanized variant of the $V_L$ of SEQ ID NO: 4, where the framework regions are humanized or replaced with human immunoglobulin framework sequences. As noted supra, suitable human or humanized framework sequences can be chosen based on their known structure, a consensus sequence, sequence homology to the framework sequences of donor antibody (e.g., the framework sequences of SEQ ID NOs: 2 and 4), or a combination of these approaches. The humanized framework regions are designed to be similar in length and sequence to the parental framework sequences of SEQ ID NO: 2 and SEQ ID NO: 4, respectively. In one embodiment, the humanized framework regions share 50%, 55%, 60%, 65%, 70%, 75%, 80%, 85%, 90%, 95% or more sequence identity to the framework regions of SEQ ID NO:2 and SEQ ID NO: 4, respectively. In another embodiment, the humanized framework regions are 60%, 65%, 70%, 75%, 80%, 85%, 90%, 95% or more similar in length to the framework regions of SEQ ID NO:2 and SEQ ID NO: 4, respectively. Humanized variants of the $V_H$ of SEQ ID NO: 2 and the $V_L$ of SEQ ID NO: 4 share at least 50%, at least 55%, at least 60%, at least 65%, at least 70%, at least 75%, at least 80%, at least 85%, at least 90%, at least 95% sequence identity along the entire length of SEQ ID NO: 2 and SEQ ID NO: 4, respectively.

Another aspect of the present disclosure relates to an antibody or binding portion thereof (e.g., a human antibody) that competes for binding to a toxic oligomeric form of an amyloidogenic protein with a monoclonal antibody, wherein said monoclonal antibody comprises a heavy chain variable region comprising an H-CDR1 of SEQ ID NO: 23, an H-CDR2 of SEQ ID NO: 27, and an H-CDR3 of SEQ ID NO: 31 and a light chain variable region comprising L-CDR1 of SEQ ID NO: 35, L-CDR2 of SEQ ID NO: 40, and L-CDR3 of SEQ ID NO: 45. In accordance with this aspect of the disclosure, a competitive binding assay, such as Bio-Layer Interferometry (BLI) can be utilized to identify an antibody or binding portion thereof that competes for binding to a toxic amyloidogenic protein with the enumerated monoclonal antibody. Other competitive binding assays known in the art can also be utilized to identify a competitive binding antibody in accordance with this aspect of the disclosure.

In another embodiment, the antibody or binding fragment thereof has a heavy chain variable region with a H-CDR1 having the amino acid sequence of SEQ ID NO: 24, or a modified amino acid sequence thereof containing 1, 2, or more amino acid residue modifications as compared to SEQ ID NO: 24; a H-CDR2 having the amino acid sequence of SEQ ID NO: 28, or a modified amino acid sequence thereof containing 1, 2, 3, 4, or more amino acid residue modifications as compared to SEQ ID NO: 28; and a H-CDR3 comprising the amino acid sequence of SEQ ID NO: 32, or a modified amino acid sequence thereof, said modified amino acid sequence containing 1, 2, 3, 4, 5, 6, or more amino acid modifications as compared to SEQ ID NO: 32. In one embodiment, this antibody or binding fragment thereof further comprises a light chain variable region. The light chain variable region comprises a L-CDR1 having the amino acid sequence of SEQ ID NO: 36, or a modified amino acid sequence thereof containing 1, 2, 3, or 4 amino acid residue modifications as compared to SEQ ID NO: 36; a L-CDR2 comprising the amino acid sequence of SEQ ID NO: 41, or a modified amino acid sequence thereof containing 1 or 2 amino acid residue modifications as compared to said SEQ ID NO: 41; and a L-CDR3 comprising the amino acid sequence of SEQ ID NO: 46, or a modified amino acid sequence thereof containing 1 or 2 amino acid residue modifications as compared to SEQ ID NO: 46. An exemplary monoclonal antibody having these heavy chain and light chain variable region CDRs is referred to herein as the FT-12E1 antibody.

The FT-12E1 antibody comprises a $V_H$ chain amino acid sequence of SEQ ID NO: 6 as shown below. The CDR regions of the $V_H$ chain are underlined, and the framework regions (i.e., FR1-FR4) flanking the CDRs are shown in bold typeface.

SEQ ID NO: 6
QVQLKQSGPGLVPPSQSLSITCTVSGFSLTSYGVHWVRQSPGKGLEWL

GVIWSGGSTDYNAAFISRLSISKDNSKSQVFFKMNSLQADDTAIYYCARN

PSAYYSNYWFAYWGQGTLVTVSA

The FT-12E1 antibody comprises a $V_L$ chain amino acid sequence of SEQ ID NO: 8 as shown below. The CDR regions of the $V_L$ chain are underlined, and the framework regions (i.e., FR1-FR4) flanking the CDRs are shown in bold typeface.

SEQ ID NO: 8
DIVMTQSQNFMSTSVGDRVSVTCKASQYVGTYVAWYQQKPGQSPKAL

IYSASYRHTGVPDRFTGSGSGTDFTLTISNVQSEDLADYFCQQYSSSPLT

FGSGTKLEIK

In one embodiment, the antibody or binding fragment thereof as described herein comprises a $V_H$ region amino acid sequence of SEQ ID NO: 6 and/or a $V_L$ region amino acid sequence of SEQ ID NO: 8. In one embodiment the antibody is the monoclonal FT-12E1 antibody having a heavy chain amino acid sequence of SEQ ID NO: 61 and a light chain amino acid sequence of SEQ ID NO: 63 as shown in Table 6 infra.

In another embodiment, the antibody or binding fragment thereof comprises a $V_H$ region having an amino acid sequence that shares at least 60%, at least 65%, at least 70%, at least 75%, at least 80%, at least 85%, at least 90%, at least 91%, at least 92%, at least 93%, at least 94% at least 95%, at least 96%, at least 97%, at least 98%, at least 99% sequence identity to SEQ ID NO: 6, and/or a $V_L$ region having an amino acid sequence that shares at least 70%, at least 75%, at least 80%, at least 85%, at least 90%, at least 91%, at least 92%, at least 93%, at least 94% at least 95%, at least 96%, at least 97%, at least 98%, at least 99% sequence identity to SEQ ID NO: 8.

In one embodiment, the antibody or binding fragment thereof of the present disclosure comprises a humanized variant of the $V_H$ of SEQ ID NO: 6 and/or a humanized variant of the $V_L$ of SEQ ID NO: 8, where the framework regions are humanized or replaced with human framework sequences. In one embodiment, the humanized framework regions share 50%, 55%, 60%, 65%, 70%, 75%, 80%, 85%, 90%, 95% or more sequence identity to the framework regions of SEQ ID NO:6 and SEQ ID NO: 8, respectively. In another embodiment, the humanized framework regions are 60%, 65%, 70%, 75%, 80%, 85%, 90%, 95% or more similar in length to the framework regions of SEQ ID NO:6 and SEQ ID NO: 8, respectively. Humanized variants of the $V_H$ of SEQ ID NO: 6 and the $V_L$ of SEQ ID NO: 8 share at least 50%, at least 55%, at least 60%, at least 65%, at least 70%, at least 75%, at least 80%, at least 85%, at least 90%, at least 95% sequence identify along the entire length of SEQ ID NO: 6 and SEQ ID NO: 8, respectively.

Another aspect of the present disclosure relates to an antibody or binding portion thereof (e.g., a human antibody) that competes for binding to a toxic oligomeric form of an amyloidogenic protein with a monoclonal antibody, wherein said monoclonal antibody comprises a heavy chain variable region comprising an H-CDR1 of SEQ ID NO: 24, an H-CDR2 of SEQ ID NO: 28, and an H-CDR3 of SEQ ID NO: 32 and a light chain variable region comprising L-CDR1 of SEQ ID NO: 36, L-CDR2 of SEQ ID NO: 41, and L-CDR3 of SEQ ID NO: 46. In accordance with this aspect of the disclosure, a competitive binding assay, such as Bio-Layer Interferometry (BLI) can be utilized to identify an antibody or binding portion thereof that competes for binding to a toxic amyloidogenic protein with the enumerated monoclonal antibody. Other competitive binding assays known in the art can also be utilized to identify a competitive binding antibody in accordance with this aspect of the disclosure.

In another embodiment, the antibody or binding fragment thereof has a heavy chain variable region with a H-CDR1 having the amino acid sequence of SEQ ID NO: 25, or a modified amino acid sequence thereof containing 1, 2, or more amino acid residue modifications as compared to SEQ ID NO: 25; a H-CDR2 having the amino acid sequence of SEQ ID NO: 29, or a modified amino acid sequence thereof containing 1, 2, 3, 4, or more amino acid residue modifications as compared to SEQ ID NO: 29; and a H-CDR3 comprising the amino acid sequence of SEQ ID NO: 33, or a modified amino acid sequence thereof, said modified amino acid sequence containing 1 or 2 more amino acid modifications as compared to SEQ ID NO: 33. In one embodiment, this antibody or binding fragment thereof further comprises a light chain variable region. The light chain variable region comprises a L-CDR1 having the amino acid sequence of SEQ ID NO: 37, or a modified amino acid sequence thereof containing 1, 2, 3, or 4 amino acid residue modifications as compared to SEQ ID NO: 37; a L-CDR2 comprising the amino acid sequence of SEQ ID NO: 42, or a modified amino acid sequence thereof containing 1 or 2 amino acid residue modifications as compared to said SEQ ID NO: 42; and a L-CDR3 comprising the amino acid sequence of SEQ ID NO: 47, or a modified amino acid sequence thereof containing 1 or 2 amino acid residue modifications as compared to SEQ ID NO: 47 An exemplary monoclonal antibody having these heavy chain and light chain variable region CDRs is referred to herein as the WG-3D7 antibody.

The WG-3D7 antibody comprises a $V_H$ chain amino acid sequence of SEQ ID NO: 10 as shown below. The CDR regions of the $V_H$ chain are underlined, and the framework regions (i.e., FR1-FR4) flanking the CDRs are shown in bold typeface.

SEQ ID NO: 10
EVKLQQSGPELVKPGASVKISCKAS<u>GYSFTGYYMH</u>WVKQSSEKSLEWI

G<u>EINPSTGGTSYNQKFKG</u>KATLTVDKSSSTAYMQLKSLTSEDSAVYYCAR

<u>DYYSKAY</u>WGQGTLVTVSA

The WG-3D7 antibody comprises a $V_L$ chain amino acid sequence of SEQ ID NO: 12 as shown below. The CDR regions of the $V_L$ chain are underlined, and the framework regions (i.e., FR1-FR4) flanking the CDRs are shown in bold typeface.

SEQ ID NO: 12
SIVMTQTPKFLLVSAGDRVTITC<u>KASQSVSNDVA</u>WYQQKPGQSPKLL

IY<u>YASNRYT</u>GVPDRFTGSGYGTDFTFTISTVQAEDLAVYFC<u>QQDYSSPY</u>

TFGGGTKLEIK

In one embodiment, the antibody or binding fragment thereof as described herein comprises a $V_H$ region having an amino acid sequence of SEQ ID NO: 10 and/or a $V_L$ region having an amino acid sequence of SEQ ID NO: 12. In one embodiment the antibody is the monoclonal WG-3D7 antibody having a heavy chain amino acid sequence of SEQ ID NO: 65 and a light chain amino acid sequence of SEQ ID NO: 67 as shown in Table 6 infra.

In another embodiment, the antibody or binding fragment thereof comprises a $V_H$ region having an amino acid sequence that shares at least 60%, at least 65%, at least 70%, at least 75%, at least 80%, at least 85%, at least 90%, at least 91%, at least 92%, at least 93%, at least 94% at least 95%, at least 96%, at least 97%, at least 98%, at least 99% sequence identity to SEQ ID NO: 10, and/or a $V_L$ region having an amino acid sequence that shares at least 60%, at least 65%, at least 70%, at least 75%, at least 80%, at least 85%, at least 90%, at least 91%, at least 92%, at least 93%, at least 94% at least 95%, at least 96%, at least 97%, at least 98%, at least 99% sequence identity to SEQ ID NO: 12.

In one embodiment, the antibody or binding fragment thereof of the present disclosure comprises a humanized variant of the $V_H$ of SEQ ID NO: 10 and/or a humanized variant of the $V_L$ of SEQ ID NO: 12, where the framework regions are humanized or replaced with human framework sequences. In one embodiment, the humanized framework regions share 50%, 55%, 60%, 65%, 70%, 75%, 80%, 85%, 90%, 95% or more sequence identity to the framework regions of SEQ ID NO:10 and SEQ ID NO: 12, respectively. In another embodiment, the humanized framework regions are 60%, 65%, 70%, 75%, 80%, 85%, 90%, 95% or more similar in length to the framework regions of SEQ ID NO: 10 and SEQ ID NO: 12, respectively. Humanized variants of the $V_H$ of SEQ ID NO: 10 and the $V_L$ of SEQ ID NO: 12 share at least 50%, at least 55%, at least 60%, at least 65%, at least 70%, at least 75%, at least 80%, at least 85%, at least 90%, at least 95% sequence identify along the entire length of SEQ ID NO: 10 and SEQ ID NO: 12, respectively.

Another aspect of the present disclosure relates to an antibody or binding portion thereof (e.g., a human antibody) that competes for binding to a toxic oligomeric form of an amyloidogenic protein with a monoclonal antibody, wherein said monoclonal antibody comprises a heavy chain variable region comprising an H-CDR1 of SEQ ID NO: 25, an H-CDR2 of SEQ ID NO: 29, and an H-CDR3 of SEQ ID NO: 33, and a light chain variable region comprising L-CDR1 of SEQ ID NO: 37, L-CDR2 of SEQ ID NO: 42, and L-CDR3 of SEQ ID NO: 47. In accordance with this aspect of the disclosure, a competitive binding assay, such as Bio-Layer Interferometry (BLI) can be utilized to identify an antibody or binding portion thereof that competes for binding to a toxic amyloidogenic protein with the enumerated monoclonal antibody. Other competitive binding assays known in the art can also be utilized to identify a competitive binding antibody in accordance with this aspect of the disclosure.

In another embodiment, the antibody or binding fragment thereof has a heavy chain variable region with a H-CDR1 having the amino acid sequence of SEQ ID NO: 23, or a modified amino acid sequence thereof containing 1, 2, or more amino acid residue modifications as compared to SEQ ID NO: 23; a H-CDR2 having the amino acid sequence of SEQ ID NO: 27, or a modified amino acid sequence thereof containing 1, 2, 3, 4, or more amino acid residue modifications as compared to SEQ ID NO:27; and a H-CDR3 comprising the amino acid sequence of SEQ ID NO: 31, or a modified amino acid sequence thereof, said modified amino acid sequence containing 1 or 2 more amino acid modifications as compared to SEQ ID NO: 31. In one embodiment, this antibody or binding fragment thereof further comprises a light chain variable region. The light chain variable region comprises a L-CDR1 having the amino acid sequence of SEQ ID NO: 38, or a modified amino acid sequence thereof containing 1, 2, 3, or 4 amino acid residue modifications as compared to SEQ ID NO: 38; a L-CDR2 comprising the amino acid sequence of SEQ ID NO: 43, or a modified amino acid sequence thereof containing 1 or 2 amino acid residue modifications as compared to said SEQ ID NO: 43; and a L-CDR3 comprising the amino acid sequence of SEQ ID NO: 48, or a modified amino acid sequence thereof containing 1 or 2 amino acid residue modifications as compared to SEQ ID NO: 48 An exemplary monoclonal antibody having these heavy chain and light chain variable region CDRs is referred to herein as the TF-10F7 antibody.

The TF-10F7 antibody comprises a $V_H$ chain amino acid sequence of SEQ ID NO: 2 as shown below. The CDR regions of the $V_H$ chain are underlined, and the framework regions (i.e., FR1-FR4) flanking the CDRs are shown in bold typeface.

SEQ ID NO: 2
QVQLQQSGPELVKPGASVKISCKAS<u>GYSFTSYYIH</u>WVKQRPGQGLEWI

G<u>WIYPGSGNTKYNEKFKG</u>KATLTADTSSSTAYMQLSSLTSEDSAVYYC

AR<u>SYGDYDY</u>WGQGTTLTVSS

The TF-10F7 antibody comprises a $V_L$ chain amino acid sequence of SEQ ID NO: 18 as shown below. The CDR regions of the $V_L$ chain are underlined, and the framework regions (i.e., FR1-FR4) flanking the CDRs are shown in bold typeface.

SEQ ID NO: 18
DIVLTQSPASLAVSLGQRATISYRASKSVSTSGYSYMHWNQQKPGQP

PRLLIYLVSNLESGVPARFSGSGSGTDFTLKISRVEAEDLGVYFCSQS

THVPRTFGGGTKLEIK

In one embodiment, the antibody or binding fragment thereof as described herein comprises a $V_H$ region having an amino acid sequence of SEQ ID NO: 2 and/or a $V_L$ region having an amino acid sequence of SEQ ID NO: 18. In one embodiment, the antibody is the monoclonal TF-10F7 antibody having a heavy chain amino acid sequence of SEQ ID NO: 69 and a light chain amino acid sequence of SEQ ID NO: 71 as shown in Table 6 infra.

In another embodiment, the antibody or binding fragment thereof comprises a $V_H$ region having an amino acid sequence that shares at least 60%, at least 65%, at least 70%, at least 75%, at least 80%, at least 85%, at least 90%, at least 91%, at least 92%, at least 93%, at least 94% at least 95%, at least 96%, at least 97%, at least 98%, at least 99% sequence identity to SEQ ID NO: 2, and/or a $V_L$ region having an amino acid sequence that shares at least 60%, at least 65%, at least 70%, at least 75%, at least 80%, at least 85%, at least 90%, at least 91%, at least 92%, at least 93%, at least 94% at least 95%, at least 96%, at least 97%, at least 98%, at least 99% sequence identity to SEQ ID NO: 18.

In one embodiment, the antibody or binding fragment thereof of the present disclosure comprises a humanized variant of the $V_H$ of SEQ ID NO: 2 and/or a humanized variant of the $V_L$ of SEQ ID NO: 18, where the framework regions are humanized or replaced with human framework sequences. In one embodiment, the humanized framework regions share 50%, 55%, 60%, 65%, 70%, 75%, 80%, 85%, 90%, 95% or more sequence identity to the framework regions of SEQ ID NO: 2 and SEQ ID NO: 18, respectively. In another embodiment, the humanized framework regions are 60%, 65%, 70%, 75%, 80%, 85%, 90%, 95% or more similar in length to the framework regions of SEQ ID NO: 2 and SEQ ID NO: 18, respectively. Humanized variants of the $V_H$ of SEQ ID NO: 2 and the $V_L$ of SEQ ID NO: 18 share at least 50%, at least 55%, at least 60%, at least 65%, at least 70%, at least 75%, at least 80%, at least 85%, at least 90%, at least 95% sequence identify along the entire length of SEQ ID NO: 2 and SEQ ID NO: 18, respectively.

Another aspect of the present disclosure relates to an antibody or binding portion thereof (e.g., a human antibody) that competes for binding to a toxic oligomeric form of an amyloidogenic protein with a monoclonal antibody, wherein said monoclonal antibody comprises a heavy chain variable region comprising an H-CDR1 of SEQ ID NO: 23, an H-CDR2 of SEQ ID NO: 27, and an H-CDR3 of SEQ ID NO: 31, and a light chain variable region comprising L-CDR1 of SEQ ID NO: 38, L-CDR2 of SEQ ID NO: 43, and L-CDR3 of SEQ ID NO: 48. In accordance with this aspect of the disclosure, a competitive binding assay, such as Bio-Layer Interferometry (BLI) can be utilized to identify an antibody or binding portion thereof that competes for binding to a toxic amyloidogenic protein with the enumerated monoclonal antibody. Other competitive binding assays known in the art can also be utilized to identify a competitive binding antibody in accordance with this aspect of the disclosure.

In another embodiment, the antibody or binding fragment thereof has a heavy chain variable region with a H-CDR1 having the amino acid sequence of SEQ ID NO: 26 or a modified amino acid sequence thereof containing 1, 2, or more amino acid residue modifications as compared to SEQ ID NO: 26; a H-CDR2 having the amino acid sequence of SEQ ID NO: 30, or a modified amino acid sequence thereof containing 1, 2, 3, 4, or more amino acid residue modifications as compared to SEQ ID NO:30; and a H-CDR3 comprising the amino acid sequence of SEQ ID NO: 34, or a modified amino acid sequence thereof, said modified amino acid sequence containing 1 or 2 more amino acid modifications as compared to SEQ ID NO: 34. In one embodiment, this antibody or binding fragment thereof further comprises a light chain variable region. The light chain variable region comprises a L-CDR1 having the amino acid sequence of SEQ ID NO: 39, or a modified amino acid sequence thereof containing 1, 2, 3, or 4 amino acid residue modifications as compared to SEQ ID NO: 39; a L-CDR2 comprising the amino acid sequence of SEQ ID NO: 44, or a modified amino acid sequence thereof containing 1 or 2 amino acid residue modifications as compared to said SEQ ID NO: 44; and a L-CDR3 comprising the amino acid sequence of SEQ ID NO: 49, or a modified amino acid sequence thereof containing 1 or 2 amino acid residue modifications as compared to SEQ ID NO: 49 An exemplary monoclonal antibody having these heavy chain and light chain variable region CDRs is referred to herein as the GW-23B7 antibody.

The GW-23B7 antibody comprises a $V_H$ chain amino acid sequence of SEQ ID NO: 20 as shown below. The CDR regions of the $V_H$ chain are underlined, and the framework regions (i.e., FR1-FR4) flanking the CDRs are shown in bold typeface.

SEQ ID NO: 20
EVQLQQSVAELVRPGASVKLSCTASGFNIKNTYMHWVKQRPEQGLEWI

GRIDPANGNTKYAPKFQGKATITADTSSNTAYLQLSSLTSEDTAIYYCAR

GSFYAMDYWGQGTSVTVSS

The GW-23B7 antibody comprises a $V_L$ chain amino acid sequence of SEQ ID NO: 22 as shown below. The CDR regions of the $V_L$ chain are underlined, and the framework regions (i.e., FR1-FR4) flanking the CDRs are shown in bold typeface.

SEQ ID NO: 22
DVQITQSPSYLAASPGETITINCRASKSINKYLAWYQEKPGKTNKLL

IYSGSTLQSGIPSRFSGSGSGTDFTLTISSLEPEDFAMYHCQQHNE

YPWTFGGGTKLEIK

In one embodiment, the antibody or binding fragment thereof as described herein comprises a $V_H$ region having an amino acid sequence of SEQ ID NO: 20 and/or a $V_L$ region having an amino acid sequence of SEQ ID NO: 22. In one embodiment, the antibody is the monoclonal GW-23B7 antibody having a heavy chain amino acid sequence of SEQ ID NO: 73 and a light chain amino acid sequence of SEQ ID NO: 75 as shown in Table 6 infra.

In another embodiment, the antibody or binding fragment thereof comprises a $V_H$ region having an amino acid sequence that shares at least 60%, at least 65%, at least 70%, at least 75%, at least 80%, at least 85%, at least 90%, at least 91%, at least 92%, at least 93%, at least 94% at least 95%, at least 96%, at least 97%, at least 98%, at least 99% sequence identity to SEQ ID NO: 20, and/or a $V_L$ region having an amino acid sequence that shares at least 60%, at least 65%, at least 70%, at least 75%, at least 80%, at least 85%, at least 90%, at least 91%, at least 92%, at least 93%, at least 94% at least 95%, at least 96%, at least 97%, at least 98%, at least 99% sequence identity to SEQ ID NO: 22.

In one embodiment, the antibody or binding fragment thereof of the present disclosure comprises a humanized variant of the $V_H$ of SEQ ID NO: 20 and/or a humanized variant of the $V_L$ of SEQ ID NO: 22, where the framework regions are humanized or replaced with human framework sequences. In one embodiment, the humanized framework regions share 50%, 55%, 60%, 65%, 70%, 75%, 80%, 85%, 90%, 95% or more sequence identity to the framework regions of SEQ ID NO: 20 and SEQ ID NO: 22, respectively. In another embodiment, the humanized framework regions are 60%, 65%, 70%, 75%, 80%, 85%, 90%, 95% or more similar in length to the framework regions of SEQ ID NO: 20 and SEQ ID NO: 22, respectively. Humanized variants of the $V_H$ of SEQ ID NO: 20 and the $V_L$ of SEQ ID NO: 22 share at least 50%, at least 55%, at least 60%, at least 65%, at least 70%, at least 75%, at least 80%, at least 85%, at least 90%, at least 95% sequence identify along the entire length of SEQ ID NO: 20 and SEQ ID NO: 22, respectively.

Another aspect of the present disclosure relates to an antibody or binding portion thereof (e.g., a human antibody) that competes for binding to a toxic oligomeric form of an amyloidogenic protein with a monoclonal antibody, wherein said monoclonal antibody comprises a heavy chain variable region comprising an H-CDR1 of SEQ ID NO: 26, an H-CDR2 of SEQ ID NO: 30, and an H-CDR3 of SEQ ID NO: 34, and a light chain variable region comprising L-CDR1 of SEQ ID NO: 39, L-CDR2 of SEQ ID NO: 44, and L-CDR3 of SEQ ID NO: 49. In accordance with this aspect of the disclosure, a competitive binding assay, such as Bio-Layer Interferometry (BLI) can be utilized to identify an antibody or binding portion thereof that competes for binding to a toxic amyloidogenic protein with the enumerated monoclonal antibody. Other competitive binding assays known in the art can also be utilized to identify a competitive binding antibody in accordance with this aspect of the disclosure.

In one embodiment, the antibody or binding fragment thereof has a heavy chain variable region with a H-CDR1 having the amino acid sequence of SEQ ID NO: 50, or a modified amino acid sequence thereof containing 1, 2, 3, or more amino acid residue modifications as compared to SEQ ID NO: 50; a H-CDR2 having the amino acid sequence of SEQ ID NO: 51, or a modified amino acid sequence thereof containing 1, 2, 3, 4, or more amino acid residue modifications as compared to SEQ ID NO: 51; and a H-CDR3 comprising the amino acid sequence of SEQ ID NO: 52, or a modified amino acid sequence thereof, said modified amino acid sequence containing 1, 2, or more amino acid modifications as compared to SEQ ID NO: 52. In one embodiment, this antibody further comprises a light chain variable region that comprises a L-CDR1 having the amino acid sequence of SEQ ID NO: 53, or a modified amino acid sequence thereof containing 1, 2, 3, or 4 amino acid residue modifications as compared to SEQ ID NO: 53; a L-CDR2 comprising the amino acid sequence of SEQ ID NO: 54, or a modified amino acid sequence thereof containing 1 or 2 amino acid residue modifications as compared to said SEQ ID NO: 54; and a L-CDR3 comprising the amino acid sequence of SEQ ID NO: 55, or a modified amino acid sequence thereof containing 1 or 2 amino acid residue modifications as compared to SEQ ID NO: 55. In another embodiment, this antibody comprises a light chain variable region that comprises a L-CDR1 having the amino acid sequence of SEQ ID NO: 53, or a modified amino acid sequence thereof containing 1, 2, 3, or 4 amino acid residue modifications as compared to SEQ ID NO: 53; a L-CDR2 comprising the amino acid sequence of SEQ ID NO: 112, or a modified amino acid sequence thereof containing 1 or 2 amino acid residue modifications as compared to said SEQ ID NO: 112; and a L-CDR3 comprising the amino acid sequence of SEQ ID NO: 55, or a modified amino acid sequence thereof containing 1 or 2 amino acid residue modifications as compared to SEQ ID NO: 55. An exemplary monoclonal antibody having these heavy chain and light chain variable regions is referred to herein as the FT-11F2 antibody.

The FT-11F2 antibody comprises a $V_H$ chain amino acid sequence of SEQ ID NO: 14 as shown below. The CDR regions of the $V_H$ chain are underlined, and the framework regions (i.e., FR1-FR4) flanking the CDRs are shown in bold typeface.

SEQ ID NO: 14
QVTLKESGPGILQPSQTLSLTCSFSGFSLSTYGMGVGWIRQPSGKGLEWL

ANIWWNDDKYYNSALKSRLTISKDTSNNQVFLKISSVDTADTATYYCAQI

GWLLAWFAYWGQGTLVTVSA

The FT-11F2 antibody comprises a $V_L$ chain amino acid sequence of SEQ ID NO: 16 as shown below. The CDR regions of the $V_L$ chain are underlined, and the framework regions (i.e., FR1-FR4) flanking the CDRs are shown in bold typeface.

SEQ ID NO: 16
DIVMSQSPSSLAVSAGEKVTMSCKSSQSLLNSRTKNYLAWYQQKPGQSP

KLLIYWASTRESGVPDRFTGSGSGTDFTLTISSVQAEDLAVYYCKQSYNLL

TFGAGTKLELK

In another embodiment, the FT-11F2 antibody comprises a VL chain amino acid sequence of SEQ ID NO: 109 as shown below. The CDR regions of the $V_L$ chain are underlined, and the framework regions (i.e., FR1-FR4) flanking the CDRs are shown in bold typeface.

SEQ ID NO: 109
DIVMSQSPSSLAVSAGDKVTMSCKSSQSLLNSRTKNYLAWYQQKPG

QSPKVLVYWGSTRYSGVPDRFTGSGSGTDYTLTVSSVQAEDLAVYFC

KQSYNLLTFGAGTKL

In one embodiment, the antibody or binding fragment thereof as described herein comprises a $V_H$ region having an amino acid sequence of SEQ ID NO: 14 and/or a $V_L$ region having an amino acid sequence of SEQ ID NO:16. In another embodiment, the antibody or binding fragment thereof as described herein comprises a $V_H$ region having an amino acid sequence of SEQ ID NO: 14 and/or a $V_L$ region having an amino acid sequence of SEQ ID NO:109.

In another embodiment, the antibody or binding fragment thereof comprises a $V_H$ region having an amino acid sequence that shares at least 60%, at least 65%, at least 70%, at least 75%, at least 80%, at least 85%, at least 90%, at least 91%, at least 92%, at least 93%, at least 94% at least 95%, at least 96%, at least 97%, at least 98%, at least 99% sequence identity to SEQ ID NO: 14, and/or a $V_L$ region having an amino acid sequence that shares at least 60%, at least 65%, at least 70%, at least 75%, at least 80%, at least 85%, at least 90%, at least 91%, at least 92%, at least 93%, at least 94% at least 95%, at least 96%, at least 97%, at least 98%, at least 99% sequence identity to SEQ ID NO: 16 or SEQ ID NO: 109.

In one embodiment, the antibody or binding fragment thereof of the present disclosure comprises a humanized variant of the $V_H$ of SEQ ID NO:14 and/or a humanized variant of the $V_L$ of SEQ ID NO: 16 or SEQ ID NO: 109, where the framework regions are humanized or replaced with human immunoglobulin framework sequences. As noted supra, suitable human or humanized framework sequences can be chosen based on their known structure, a consensus sequence, sequence homology to the framework sequences of donor antibody (e.g., the framework sequences of SEQ ID NOs: 14, 16, and 109), or a combination of these approaches. The humanized framework regions are designed to be similar in length and sequence to the parental framework sequences of SEQ ID NO: 14, SEQ ID NO: 16, and SEQ ID NO: 109, respectively. In one embodiment, the humanized framework regions share 50%, 55%, 60%, 65%, 70%, 75%, 80%, 85%, 90%, 95% or more sequence identity to the framework regions of SEQ ID NO:14, SEQ ID NO: 16, and SEQ ID NO: 109, respectively. In another embodiment, the humanized framework regions are 60%, 65%, 70%, 75%, 80%, 85%, 90%, 95% or more similar in length to the framework regions of SEQ ID NO:14, SEQ ID NO: 16, and SEQ ID NO: 109, respectively. Humanized variants of the $V_H$ of SEQ ID NO: 14 and the $V_L$ of SEQ ID NO: 16 or SEQ ID NO: 109 share at least 50%, at least 55%, at least 60%, at least 65%, at least 70%, at least 75%, at least 80%, at least 85%, at least 90%, at least 95% sequence identity along the entire length of SEQ ID NO: 14, SEQ ID NO: 16, and SEQ ID NO: 109, respectively.

Another aspect of the present disclosure relates to an antibody or binding portion thereof (e.g., a human antibody) that competes for binding to a toxic oligomeric form of an amyloidogenic protein with a monoclonal antibody, wherein said monoclonal antibody comprises a heavy chain variable region comprising an H-CDR1 of SEQ ID NO: 50, an H-CDR2 of SEQ ID NO: 51, and an H-CDR3 of SEQ ID NO: 52, and a light chain variable region comprising L-CDR1 of SEQ ID NO: 53, L-CDR2 of SEQ ID NO: 54, and L-CDR3 of SEQ ID NO: 55. In accordance with this aspect of the disclosure, a competitive binding assay, such as Bio-Layer Interferometry (BLI) can be utilized to identify an antibody or binding portion thereof that competes for binding to a toxic amyloidogenic protein with the enumerated monoclonal antibody. Other competitive binding assays known in the art can also be utilized to identify a competitive binding antibody in accordance with this aspect of the disclosure.

In one embodiment, the antibody or binding fragment thereof does not comprise or consist of the amino acid sequence of mAb 3D6 as disclosed in U.S. Pat. No. 8,409,584 to Wisniewski and Goni.

Another aspect of the present disclosure is directed to an antibody mimetic that binds toxic oligomeric forms of amyloidogenic proteins. An "antibody mimetic" as referred to herein encompasses any organic compound, e.g., a peptide or polypeptide, that can specifically bind an antigen like an antibody, and is about 3-20 kDa. In one embodiment, the antibody mimetic comprises a scaffold which binds its antigen via amino acids in exposed loops similar to the CDR loops of an antibody. These antibody mimetics include, without limitation, adnectins, lipocalins, Kunitz domain-based binders, avimers, knottins, fynomers, atrimers, and cytotoxic T-lymphocyte associated protein-4 (CTLA4)-based binders (reviewed in Weidle et al., "The Emerging Role of New Protein Scaffold-based Agents for the Treatment of Cancer," *Cancer Genomics & Proteomics* 10:155-168 (2013), which is hereby incorporated by reference in its entirety. In accordance with this aspect of the present disclosure, the loop binding regions of the antibody mimetic are adapted to comprise one or more of the heavy chain and/or light chain CDRs of the antibodies disclosed herein. For example, an antibody mimetic of the present disclosure may comprise a first loop region having an amino acid sequence of any one of SEQ ID NOs: 23-26, and 50, or a modified amino acid sequence of any one of SEQ ID NOs: 23-26, and 50, said modified sequence containing 1 or 2 amino acid residue modifications as compared to any one of SEQ ID NOs: 23-26, or 50. The antibody mimetic may comprise another loop region having an amino acid sequence of any one of SEQ ID NOs: 27-30, and 51, or a modified amino acid sequence of any one of SEQ ID NOs: 27-30, and 51, said modified sequences containing 1, 2, 3, or 4 amino acid residue modifications as compared to any one of SEQ ID NOs: 27-30, or 51. The antibody mimetic may comprise another loop region having an amino acid sequence of any one of SEQ ID NOs: 31-34, and 52, or a modified amino acid sequence of any one of SEQ ID NO: 31-34, and 52, said modified sequence containing 1, 2, or 3 amino acid residue modifications as compared to any one of SEQ ID NOs: 31-34, and 52. The antibody mimetic may further comprise another loop region having an amino acid sequence of any one of SEQ ID NOs: 35-39, and 53, or a modified amino acid sequence of any one of SEQ ID NO: 35-39, and 53, said modified sequence containing 1, 2, 3, or 4 amino acid residue modifications as compared to any one of SEQ ID NO: 35-39, or 53. The antibody mimetic may comprise another loop region having an amino acid sequence of any one of SEQ ID NOs: 40-44, and 54, or a modified amino acid sequence of any one of SEQ ID NO: 40-44, and 54, said modified sequence containing 1 or 2 amino acid residue modifications as compared to SEQ ID NO: 40-44, or 54. The antibody mimetic may comprise another loop region having an amino acid sequence of any one of SEQ ID NOs: 45-49, and 55, or a modified amino acid sequence of any one of SEQ ID NO: 45-49, and 55, said modified sequence containing 1 or 2 amino acid residue modifications as compared to SEQ ID NO: 45-49, or 55.

In one embodiment, the antibody mimetic comprises one or more modified fibronectin type III (FN3) domains (e.g., an adnectin or centyrin molecule), where each modified FN3 domain has one or more loop regions that comprise one or more CDR sequences or modified CDR sequences as disclosed herein (i.e., the sequences disclosed supra in Tables 1 and 2).

The FN3 domain is an evolutionary conserved protein domain that is about 100 amino acids in length and possesses a beta sandwich structure. The beta sandwich structure of human FN3 comprises seven beta-strands, referred to as strands A, B, C, D, E, F, G, with six connecting loops, referred to as loops AB, BC, CD, DE, EF, and FG that exhibit structural homology to immunoglobulin binding domains. Three of the six loops, i.e., loops DE, BC, and FG, correspond topologically to the complementarity determining regions of an antibody, i.e., CDR1, CDR2, and CDR3. The remaining three loops are surface exposed in a manner similar to antibody CDR3. In accordance with the present disclosure, one or more of the loop regions of each FN3 domain of the binding molecule are modified to comprise one or more CDR sequences disclosed herein.

The modified FN3 domain can be a FN3 domain derived from any of the wide variety of animal, yeast, plant, and bacterial extracellular proteins containing these domains. In one embodiment, the FN3 domain is derived from a mammalian FN3 domain. Exemplary FN3 domains include, for example and without limitation, any one of the 15 different FN3 domains present in human tenascin C, or the 15 different FN3 domains present in human fibronectin (FN) (e.g., the 10$^{th}$ fibronectin type III domain). Exemplary FN3 domains also include non-natural synthetic FN3 domains, such as those described in U.S. Pat. Publ. No. 2010/0216708 to Jacobs et al., which is hereby incorporated by reference in its entirety. Individual FN3 domains are referred to by domain number and protein name, e.g., the 3$^{rd}$ FN3 domain of tenascin (TN3), or the 10$^{th}$ FN3 domain of fibronectin (FN10).

Another aspect of the present disclosure is directed to isolated polynucleotides encoding the antibody or binding fragment thereof or antibody mimetic as described herein. The nucleic acid molecules described herein include isolated polynucleotides, portions of expression vectors or portions of linear DNA sequences, including linear DNA sequences used for in vitro transcription/translation, and vectors compatible with prokaryotic, eukaryotic or filamentous phage expression, secretion, and/or display of the antibodies or binding fragments thereof described herein.

In one embodiment, the isolated polynucleotide encodes the heavy chain variable region of the antibody or binding fragment disclosed herein. This isolated polynucleotide comprises a nucleotide sequence encoding the H-CDR1 that is selected from any one of the nucleotide sequences of SEQ ID NOs: 76-80, or a nucleotide sequence comprising 80% sequence similarity to any one of SEQ ID NOs: 76-80. The isolated polynucleotide further comprises a nucleotide sequence encoding the H-CDR2 that is selected from any one of the nucleotide sequences of SEQ ID NOs: 81-85, or a nucleotide sequence comprising 80% sequence similarity to any one of SEQ ID NOs: 81-85. The isolated polynucleotide further comprises a nucleotide sequence encoding the H-CDR3 that is selected from any one of the nucleotide sequences of SEQ ID NOs: 86-90, or a nucleotide sequence comprising 80% sequence similarity to any one of SEQ ID NOs: 86-90. The nucleotide sequences encoding the heavy chain CDRs of the antibodies and binding fragments thereof as described herein are provided in Table 3 below.

TABLE 3

Nucleotide Sequences Encoding Antibody Heavy Chain CDRs

| Ab Name | HCVR CDR1 | SEQ ID NO | HCVR CDR2 | SEQ ID NO | HCVR CDR3 | SEQ ID NO |
|---------|-----------|-----------|-----------|-----------|-----------|-----------|
| TF-10E8 | GGCTACAGCTTC ACAAGCTACTAT ATACACT | 76 | TGGATTTATCCTGG AAGTGGTAATACTA AGTACAATGAGAAG TTCAAGGGC | 81 | AGCTATGGTGACTAC GACTAC | 86 |
| FT-12E1 | GGTTTCTCATTA ACTAGCTATGGT GTACAC | 77 | GTGATATGGAGTGG TGGAAGCACAGACT ACAATGCAGCTTTC ATATCC | 82 | AATCCCTCCGCCTAC TATAGTAACTACTGG TTTGCTTAC | 87 |
| WG-3D7 | GGTTACTCATTC ACTGGCTACTAC ATGCAC | 78 | GAGATTAATCCTAG CACTGGTGGTACTA GCTACAACCAGAAG TTCAAGGGC | 83 | GACTACTATAGTAAG GCTTAC | 88 |
| TF-10F7 | GGCTACAGCTTC ACAAGCTACTAT ATACAC | 76 | TGGATTTATCCTGG AAGTGGTAATACTA AGTACAATGAGAAG TTCAAGGGC | 81 | AGCTATGGTGACTAC GACTAC | 86 |
| GW-23B7 | GGCTTCAACATT AAAAACACCTAT ATGCAC | 79 | AGGATTGATCCTGC GAATGGTAATACTA AATATGCCCCGAAG TTCCAGGGC | 84 | TTTTATGCTATGGAC TAC | 89 |
| FT-11F2 | ACTTATGGTATG GGTGTAGGT | 80 | AACATTTGGTGGAA TGATGATAAGTACT ATAACTCAGCCCTG AAGAGC | 85 | ATAGGGTGGTTACTA GCCTGGTTTGCTTAC | 90 |

In one embodiment, the isolated polynucleotide of the disclosure comprises the nucleotide sequences of SEQ ID NOs: 76, 81, and 86, or nucleotide sequences comprising at least 80%, at least 85%, at least 90%, at least 95%, at least 96%, 97%, 98%, or 99% sequence similarity to the nucleotide sequences of SEQ ID NOs: 76, 81, and 86. An exemplary polynucleotide comprising the nucleotide sequences of SEQ ID NOs: 76, 81, and 86 comprises the nucleotide sequence of SEQ ID NO: 1 (Table 5), which encodes the heavy chain variable region of the TF-10E8 antibody and the TF-10F7 antibody as disclosed herein. In one embodiment, the isolated polynucleotide encoding the heavy chain variable region of the antibody or fragment thereof of the present disclosure comprises a nucleotide sequence that has at least 80%, at least 85%, at least 90%, at least 95%, at least 96%, 97%, 98%, or 99% sequence similarity to the nucleotide sequence of SEQ ID NO: 1.

In another embodiment, the isolated polynucleotide of the disclosure comprises the nucleotide sequences of SEQ ID NOs: 77, 82, and 87, or nucleotide sequences comprising at least 80%, at least 85%, at least 90%, at least 95%, at least 96%, 97%, 98%, or 99% sequence similarity to the nucleotide sequences of SEQ ID NOs: 77, 82, and 87. An exemplary polynucleotide comprising the nucleotide sequences of SEQ ID NOs: 77, 82, and 87 comprises the nucleotide sequence of SEQ ID NO: 5 (Table 5), which encodes the heavy chain variable region of the FT-12E1 antibody as disclosed herein. In one embodiment, the isolated polynucleotide encoding the heavy chain variable region of the antibody or fragment thereof of the present disclosure comprises a nucleotide sequence that has at least 80%, at least 85%, at least 90%, at least 95%, at least 96%, 97%, 98%, or 99% sequence similarity to the nucleotide sequence of SEQ ID NO: 5.

In another embodiment, the isolated polynucleotide of the disclosure comprises the nucleotide sequences of SEQ ID NOs: 78, 83, and 88, or nucleotide sequences comprising at least 80%, at least 85%, at least 90%, at least 95%, at least 96%, 97%, 98%, or 99% sequence similarity to the nucleotide sequences of SEQ ID NOs: 78, 83, and 88. An exemplary polynucleotide comprising the nucleotide sequences of SEQ ID NOs: 78, 83, and 88 comprises the nucleotide sequence of SEQ ID NO: 9 (Table 5), which encodes the heavy chain variable region of the WG-3D7 antibody as disclosed herein. In one embodiment, the isolated polynucleotide encoding the heavy chain variable region of the antibody or fragment thereof of the present disclosure comprises a nucleotide sequence that has at least 80%, at least 85%, at least 90%, at least 95%, at least 96%, 97%, 98%, or 99% sequence similarity to the nucleotide sequence of SEQ ID NO: 9.

In another embodiment, the isolated polynucleotide of the disclosure comprises the nucleotide sequences of SEQ ID NOs: 79, 84, and 89, or nucleotide sequences comprising at least 80%, at least 85%, at least 90%, at least 95%, at least 96%, 97%, 98%, or 99% sequence similarity to the nucleotide sequences of SEQ ID NOs: 79, 84, and 89. An exemplary polynucleotide comprising the nucleotide sequences of SEQ ID NOs: 79, 84, and 89 comprises the nucleotide sequence of SEQ ID NO: 19 (Table 5), which encodes the heavy chain variable region of the GW-23B7 antibody as disclosed herein. In one embodiment, the isolated polynucleotide encoding the heavy chain variable region of the antibody or fragment thereof of the present disclosure comprises a nucleotide sequence that has at least 80%, at least 85%, at least 90%, at least 95%, at least 96%, 97%, 98%, or 99% sequence similarity to the nucleotide sequence of SEQ ID NO: 19.

In another embodiment, the isolated polynucleotide of the disclosure comprises the nucleotide sequences of SEQ ID NOs: 80, 85, and 90, or nucleotide sequences comprising at least 80%, at least 85%, at least 90%, at least 95%, at least 96%, 97%, 98%, or 99% sequence similarity to the nucleotide sequences of SEQ ID NOs: 80, 85, and 90. An exemplary polynucleotide comprising the nucleotide sequences of SEQ ID NOs: 80, 85, and 90 comprises the nucleotide sequence of SEQ ID NO: 13 (Table 5), which encodes the heavy chain variable region of the FT-11F2 antibody as disclosed herein. In one embodiment, the isolated polynucleotide encoding the heavy chain variable region of the antibody or fragment thereof of the present disclosure comprises a nucleotide sequence that has at least 80%, at least 85%, at least 90%, at least 95%, at least 96%, 97%, 98%, or 99% sequence similarity to the nucleotide sequence of SEQ ID NO: 13.

In one embodiment, the isolated polynucleotide encodes the light chain variable region of the antibody or binding fragment. This isolated polynucleotide comprises a nucleotide sequence encoding the L-CDR1 that is selected from any one of the nucleotide sequences of SEQ ID NOs: 91-96, or a nucleotide sequence comprising at least 80% sequence similarity to any one of SEQ ID NOs: 91-96. The isolated polynucleotide further comprises a nucleotide sequence encoding the L-CDR2 that is selected from any one of the nucleotide sequences of SEQ ID NOs: 97-102, or a nucleotide sequence comprising at least 80% sequence similarity to any one of SEQ ID NOs: 97-102. The isolated polynucleotide further comprises a nucleotide sequence encoding the L-CDR3 that is selected from any one of the nucleotide sequences of SEQ ID NOs: 103-108, or a nucleotide sequence comprising at least 80% sequence similarity to any one of SEQ ID NOs: 103-108. The nucleotide sequences encoding the light chain CDRs of the antibodies and binding fragments thereof as described herein are provided in Table 4 below.

TABLE 4

Nucleotide Sequences Encoding Antibody Light Chain CDRs

| Ab Name | LCVR CDR1 | SEQ ID NO | LCVR CDR2 | SEQ ID NO | LCVR CDR3 | SEQ ID NO |
|---|---|---|---|---|---|---|
| TF-10E8 | AGATCTAGTCAGAGCCTTGTACACAGTAATGGAAACACCTATTTACA | 91 | AAAGTTTCCAACCGATTTTCT | 97 | TCTCAAAGTACACATGTTCCTCGGACG | 103 |
| FT-12E1 | AAGGCCAGTCAGTATGTGGGTACTTATGTAGCC | 92 | TCGGCATCCTACCGGCATACT | 98 | CAGCAATATAGCAGCTCTCCTCTCACG | 104 |
| WG-3D7 | AAGGCCAGTCAGAGTGTGAGTAATGATGTAGCT | 93 | TATGCATCCAATCGCTACACT | 99 | CAGCAGGATTATAGCTCTCCGTACACG | 105 |
| TF-10F7 | AGGGCCAGCAAAAGTGTCAGTACATCTGGCTATAGTTATATGCAC | 94 | CTTGTATCCAACCTAGAATCT | 100 | TCTCAAAGTACACATGTTCCTCGGACG | 106 |
| GW-23B7 | AGGGCAAGTAAGAGCATTAACAAATATTTAGCC | 95 | TCTGGATCCACCTTGCAATCT | 101 | CAACAGCATAATGAATACCCGTGGACG | 107 |

TABLE 4-continued

Nucleotide Sequences Encoding Antibody Light Chain CDRs

| Ab Name | LCVR CDR1 | SEQ ID NO | LCVR CDR2 | SEQ ID NO | LCVR CDR3 | SEQ ID NO |
|---|---|---|---|---|---|---|
| FT-11F2 | AAATCCAGTCAGAGTCT GCTCAACAGTAGAACCC GAAAGAACTACTTGGCT | 96 | TGGGCATCCACT AGGGAATCT | 102 | AAGCAATCTTAT AATCTGCTCACG | 108 |

In one embodiment, the isolated polynucleotide of the disclosure comprises the nucleotide sequences of SEQ ID NOs: 91, 97, and 103, or nucleotide sequences comprising at least 80%, at least 85%, at least 90%, at least 95%, at least 96%, 97%, 98%, or 99% sequence similarity to the nucleotide sequences of SEQ ID NOs: 91, 97, and 103. An exemplary polynucleotide comprising the nucleotide sequences of SEQ ID NOs: 91, 97, and 103 comprises the nucleotide sequence of SEQ ID NO: 3 (Table 5), which encodes the light chain variable region of the TF-10E8 antibody as disclosed herein. In one embodiment, the isolated polynucleotide encoding the light chain variable region of the antibody or fragment thereof of the present disclosure comprises a nucleotide sequence that has at least 80%, at least 85%, at least 90%, at least 95%, at least 96%, 97%, 98%, or 99% sequence similarity to the nucleotide sequence of SEQ ID NO: 3.

In one embodiment, the isolated polynucleotide of the disclosure comprises the nucleotide sequences of SEQ ID NOs: 92, 98, and 104, or nucleotide sequences comprising at least 80%, at least 85%, at least 90%, at least 95%, at least 96%, 97%, 98%, or 99% sequence similarity to the nucleotide sequences of SEQ ID NOs: 92, 98, and 104. An exemplary polynucleotide comprising the nucleotide sequences of SEQ ID NOs: 92, 98, and 104 comprises the nucleotide sequence of SEQ ID NO: 7 (Table 5), which encodes the light chain variable region of the FT-12E1 antibody as disclosed herein. In one embodiment, the isolated polynucleotide encoding the light chain variable region of the antibody or fragment thereof of the present disclosure comprises a nucleotide sequence that has at least 80%, at least 85%, at least 90%, at least 95%, at least 96%, 97%, 98%, or 99% sequence similarity to the nucleotide sequence of SEQ ID NO: 7.

In one embodiment, the isolated polynucleotide of the disclosure comprises the nucleotide sequences of SEQ ID NOs: 93, 99, and 105, or nucleotide sequences comprising at least 80%, at least 85%, at least 90%, at least 95%, at least 96%, 97%, 98%, or 99% sequence similarity to the nucleotide sequences of SEQ ID NOs: 93, 99, and 105. An exemplary polynucleotide comprising the nucleotide sequences of SEQ ID NOs: 93, 99, and 105 comprises the nucleotide sequence of SEQ ID NO: 11 (Table 5), which encodes the light chain variable region of the WG-3D7 antibody as disclosed herein. In one embodiment, the isolated polynucleotide encoding the light chain variable region of the antibody or fragment thereof of the present disclosure comprises a nucleotide sequence that has at least 80%, at least 85%, at least 90%, at least 95%, at least 96%, 97%, 98%, or 99% sequence similarity to the nucleotide sequence of SEQ ID NO: 11.

In one embodiment, the isolated polynucleotide of the disclosure comprises the nucleotide sequences of SEQ ID NOs: 94, 100, and 106, or nucleotide sequences comprising at least 80%, at least 85%, at least 90%, at least 95%, at least 96%, 97%, 98%, or 99% sequence similarity to the nucleotide sequences of SEQ ID NOs: 94, 100, and 106. An exemplary polynucleotide comprising the nucleotide sequences of SEQ ID NOs: 94, 100, and 106 comprises the nucleotide sequence of SEQ ID NO: 17 (Table 5), which encodes the light chain variable region of the TF-10F7 antibody as disclosed herein. In one embodiment, the isolated polynucleotide encoding the light chain variable region of the antibody or fragment thereof of the present disclosure comprises a nucleotide sequence that has at least 80%, at least 85%, at least 90%, at least 95%, at least 96%, 97%, 98%, or 99% sequence similarity to the nucleotide sequence of SEQ ID NO: 17.

In one embodiment, the isolated polynucleotide of the disclosure comprises the nucleotide sequences of SEQ ID NOs: 95, 101, and 107, or nucleotide sequences comprising at least 80%, at least 85%, at least 90%, at least 95%, at least 96%, 97%, 98%, or 99% sequence similarity to the nucleotide sequences of SEQ ID NOs: 95, 101, and 107. An exemplary polynucleotide comprising the nucleotide sequences of SEQ ID NOs: 95, 101, and 107 comprises the nucleotide sequence of SEQ ID NO: 21 (Table 5), which encodes the light chain variable region of the GW-23B7 antibody as disclosed herein. In one embodiment, the isolated polynucleotide encoding the light chain variable region of the antibody or fragment thereof of the present disclosure comprises a nucleotide sequence that has at least 80%, at least 85%, at least 90%, at least 95%, at least 96%, 97%, 98%, or 99% sequence similarity to the nucleotide sequence of SEQ ID NO: 21.

In one embodiment, the isolated polynucleotide of the disclosure comprises the nucleotide sequences of SEQ ID NOs: 96, 102, and 108, or nucleotide sequences comprising at least 80%, at least 85%, at least 90%, at least 95%, at least 96%, 97%, 98%, or 99% sequence similarity to the nucleotide sequences of SEQ ID NOs: 96, 102, and 108. An exemplary polynucleotide comprising the nucleotide sequences of SEQ ID NOs: 96, 102, and 108 comprises the nucleotide sequence of SEQ ID NO: 15 (Table 5), which encodes the light chain variable region of the FT-11F2 antibody (encoding the amino acid sequence of SEQ ID NO: 16) as disclosed herein. In another embodiment, the isolated polynucleotide of the disclosure comprises the nucleotide sequence of SEQ ID NO: 110 (Table 5), which encodes an alternative light chain variable region of the FT-11F2 (encoding the amino acid sequence of SEQ ID NO: 109). In one embodiment, the isolated polynucleotide encoding the light chain variable region of the antibody or fragment thereof of the present disclosure comprises a nucleotide sequence that has at least 80%, at least 85%, at least 90%, at least 95%, at least 96%, 97%, 98%, or 99% sequence similarity to the nucleotide sequence of SEQ ID NO: 15 or SEQ ID NO: 110.

TABLE 5

Nucleotide Sequences Encoding $V_H$ and $V_L$ Antibody Regions

| Antibody | Region | SEQ ID NO | Sequence (FR1-CDR1-FR2-CDR2-FR3-CDR3-FR4) |
|---|---|---|---|
| TF-10E8 | $V_H$ | 1 | CAGGTCCAGCTGCAGCAGTCTGGACCTGAGCTGGTGAAGCC TGGGGCTTCAGTGAAGATATCCTGCAAGGCTTCT<u>GGCTACA GCTTCACAAGCTACTATATACACT</u>GGGTGAAGCAGAGGCCT GGACAGGGACTTGAGTGGATTGGA<u>ATGGATTTATCCTGGAAG TGGTAATACTAAGTACAATGAGAAGTTCAAGGGC</u>AAGGCCA CACTGACGGCAGACACATCCTCCAGCACTGCCTACATGCAG CTCAGCAGCCTAACATCTGAGGACTCTGCGGTCTATTACTG TGCAAGA<u>AGCTATGGTGACTACGACTAC</u>TGGGGCCAAGGCA CCACTCTCACAGTCTCCTCA |
| TF-10E8 | $V_L$ | 3 | GATGTTGTGATGACCCAAACTCCACTCTCCCTGCCTGTCAG TCTTGGAGATCAAGCCTCCATCTCTTGC<u>AGATCTAGTCAGA GCCTTGTACACAGTAATGGAAACACCTATTTACATTGGTAC</u> CTGCAGAAGCCAGGCCAGTCTCCAAAGCTCCTGATCTAC<u>AA AGTTTCCAACCGATTTTCT</u>GGGGTCCCAGACAGGTTCAGTG GCAGTGGATCAGGGACAGATTTCACACTCAAGATCAGCAGA GTGGAGGCTGAGGATCTGGGAGTTTATTTCTGC<u>TCTCAAAG TACACATGTTCCTCGGAC</u>GTTCGGTGGAGGCACCAAGCTGG AAATCAAA |
| FT-12E1 | $V_H$ | 5 | CAGGTGCAGCTGAAACAGTCAGGACCTGGCCTAGTGCCGCC CTCACAGAGCCTGTCCATCACCTGCACAGTTTCT<u>GGTTTCT CATTAACTAGCTATGGTGTACACT</u>GGGTTCGCCAGTCTCCA GGAAAGGGTCTGGAGTGGCTGGGA<u>GTGATATGGAGTGGTGG AAGCACAGACTACAATGCAGCTTTCATATCCAGACT</u>GAGCA TCAGCAAGGACAACTCCAAGAGCCAAGTTTTCTTTAAAATG AACAGTCTGCAAGCTGATGACACAGCCATATACTACTGTGC CAGA<u>AATCCCTCCGCCTACTATAGTAACTACTGGTTTGCTT ACT</u>GGGGCCAAGGGACTCTGGTCACTGTCTCTGCA |
| FT-12E1 | $V_L$ | 7 | GACATTGTGATGACCCAGTCTCAAAATTTCATGTCCACATC AGTAGGAGACAGGGTCAGCGTCACCTGC<u>AAGGCCAGTCAGT ATGTGGGTACTTATGTAGCC</u>TGGTATCAACAGAAACCAGGG CAATCTCCTAAAGCACTGATTTAC<u>TCGGCATCCTACCGGCA TACT</u>GGAGTCCCTGATCGCTTCACAGGCAGTGGATCTGGGA CAGATTTCACTCTCACCATCAGCAATGTGCAGTCTGAAGAC CTGGCAGATTATTTCTGT<u>CAGCAATATAGCAGCTCTCCTCT</u> CACGTTCGGCTCGGGGACAAAGTTGGAAATAAAA |
| WG-3D7 | $V_H$ | 9 | GAGGTCAAGCTGCAGCAGTCTGGACCTGAGCTGGTGAAGCC TGGGGCTTCAGTGAAGATATCCTGCAAGGCTTCT<u>GGTTACT CATTCACTGGCTACACATGCACT</u>GGGTGAAGCAAAGTTCT GAAAAGAGCCTTGAGTGGATTGGA<u>GAGATTAATCCTAGCAC TGGTGGTACTAGCTACAACCAGAAGTTCAAGGGC</u>AAGGCCA CATTAACTGTAGACAAGTCATCCAGCACAGCCTACATGCAG CTCAAGAGCCTGACATCTGAGGACTCTGCTGTCTATTACTG TGCAAGA<u>GACTACTATAGTAAGGCTTAC</u>TGGGGCCAAGGGA CTCTGGTCACTGTCTCTGCA |
| WG-3D7 | $V_L$ | 11 | AGTATTGTGATGACCCAGACTCCCAAATTCCTGCTTGTATC AGCAGGAGACAGGGTTACCATAACCTGC<u>AAGGCCAGTCAGA GTGTGAGTAATGATGTAGCT</u>TGGTACCAACAGAAGCCAGGG CAGTCTCCTAAAACTGCTGATATAC<u>TATGCATCCAATCGCTA CACT</u>GGAGTCCCTGATCGCTTCACTGGCAGTGGATATGGGA CGGATTTCACTTTCACCATCAGCACTGTGCAGGCTGAAGAC CTGGCAGTTTATTTCTGT<u>CAGCAGGATTATAGCTCTCCGTA CACG</u>TTCGGAGGGGGGACCAAGCTGGAAATAAAA |
| TF-10F7 | $V_H$ | 1 | CAGGTCCAGCTGCAGCAGTCTGGACCTGAGCTGGTGAAGCC TGGGGCTTCAGTGAAGATATCCTGCAAGGCTTCT<u>GGCTACA GCTTCACAAGCTACTATATACACT</u>GGGTGAAGCAGAGGCCT GGACAGGGACTTGAGTGGATTGGA<u>ATGGATTTATCCTGGAAG TGGTAATACTAAGTACAATGAGAAGTTCAAGGGC</u>AAGGCCA CACTGACGGCAGACACATCCTCCAGCACTGCCTACATGCAG CTCAGCAGCCTAACATCTGAGGACTCTGCGGTCTATTACTG TGCAAGA<u>AGCTATGGTGACTACGACTAC</u>TGGGGCCAAGGCA CCACTCTCACAGTCTCCTCA |
| TF-10F7 | $V_L$ | 17 | GACATTGTGCTGACACAGTCTCCTGCTTCCTTAGCTGTATC TCTGGGGCAGAGGGCCACCATCTCATAC<u>AGGGCCAGCAAAA GTGTCAGTACATCTGGCTATAGTTATATGCAC</u>TGGAACCAA CAGAAACCAGGACAGCCACCCAGACTCCTCATCTAT<u>CTTGT ATCCAACCTAGAATCT</u>GGGGTCCCTGCCAGGTTCAGTGGCA GTGGATCAGGGACAGATTTCACACTCAAGATCAGCAGAGTG |

TABLE 5-continued

Nucleotide Sequences Encoding V_H and V_L Antibody Regions

| Antibody | Region | SEQ ID NO | Sequence (FR1-CDR1-FR2-CDR2-FR3-CDR3-FR4) |
|---|---|---|---|
| | | | GAGGCTGAGGATCTGGGAGTTTATTTCTGC<u>TCTCAAAGTAC<br>ACATGTTCCTCGGACG</u>TTCGGTGGAGGCACCAAGCTGGAAA<br>TCAAA |
| GW-23B7 | V_H | 19 | GAGGTTCAGCTGCAGCAGTCTGTGGCAGAGCTTGTGAGGCC<br>AGGGGCCTCAGTCAAGTTGTCCTGCACAGCTTCT<u>GGCTTCA<br>ACATTAAAAACACCTATATGCAC</u>TGGGTGAAGCAGAGGCCT<br>GAACAGGGCCTGGAGTGGATTGGA<u>AGGATTGATCCTGCGAA<br>TGGTAATACTAAATATGCCCCGAAGTTCCAGGGCAAGGCCA<br>CTATAACTGCAGACACATCCTCCAACACAGCCTACCTGCAG<br>CTCAGCAGCCTGACATCTGAGGACACTGCCATCTATTACTG<br>TGCTAGAGGGAGT<u>TTTTTATGCTATGGACTAC</u>TGGGGTCAAG<br>GAACCTCAGTCACCGTCTCCTCA |
| GW-23B7 | V_L | 21 | GATGTCCAGATAACCCAGTCTCCATCTTATCTTGCTGCATC<br>TCCTGGAGAAACCATTACTATTAATTGC<u>AGGGCAAGTAAGA<br>GCATTAACAAATATTTAGCC</u>TGGTATCAAGAGAAACCTGGG<br>AAAACTAATAAGCTTCTTATCTAC<u>TCTGGATCCACCTTGCA<br>ATC</u>TGGAATTCCATCAAGGTTCAGTGGCAGTGGATCTGGTA<br>CAGATTTTACTCTCACCATCAGTAGCCTGGAGCCTGAAGAT<br>TTTGCAATGTATCACTGT<u>CAACAGCATAATGAATACCCGTG<br>GACG</u>TTCGGTGGAGGCACCAAGCTGGAAATCAAA |
| FT-11F2 | V_H | 13 | CAGGTCACTCTGAAAGAGTCTGGCCCTGGGATATTGCAGCC<br>CTCCCAGACCCTCAGTCTGACTTGTTCTTTCTCTGGGTTTT<br>CACTGAGC<u>ACTTATGGTATGGGTGTAGG</u>TTGGATTCGTCAG<br>CCTTCAGGGAAGGGTCTGGAGTGGCTGGCC<u>AACATTTGGTG<br>GAATGATGATAAGTACTATAACT</u>CAGCCCTGAAGAGCCGGC<br>TCACAATCTCCAAGGATACCTCCAACAACCAGGTATTCCTC<br>AAGATCTCCAGTGTGGACACTGCAGATACTGCCACATACTA<br>CTGTGCTCAA<u>ATAGGGTGGTTACTAGCCTGGTTTGCTTACT</u><br>GGGGCCAAGGGACTCTGGTCACTGTCTCTGCA |
| FT-11F2 (encoding the amino acid sequence of SEQ ID NO: 16) | V_L | 15 | GACATTGTGATGTCACAGTCTCCATCCTCCCTGGCTGTGTC<br>AGCAGGAGAGAAGGTCACTATGAGCTGC<u>AAATCCAGTCAGA<br>GTCTGCTCAACAGTAGAACCCGAAAGAAC</u>TACTTGGCTTGG<br>TACCAGCAGAAACCAGGGCAGTCTCCTAAACTGCTGATCTA<br>C<u>TGGGCATCCACTAGGGAATC</u>TGGGGTCCCTGATCGCTTCA<br>CAGGCAGTGGATCTGGGACAGATTTCACTCTCACCATCAGC<br>AGTGTGCAGGCTGAAGACCTGGCAGTTTATTACTGC<u>AAGCA<br>ATCTTATAATCTGCTCACG</u>TTCGGTGCTGGGACCAAGCTGG<br>AGCTGAAA |
| FT-11F2 (encoding the amino acid sequence of SEQ ID NO: 109) | V_L | 110 | GACATTGTGATGTCACAGTCTCCATCCTCCCTGGCTGTGTC<br>AGCAGGAGACAAGGTCACTATGAGCTGC<u>AAATCCAGTCAGA<br>GTCTGCTCAACAGTAGAACCCGAAAGAAC</u>TACTTGGCTTGG<br>TACCAGCAGAAACCAGGGCAGTCTCCTAAAGTGCTGGTCTA<br>C<u>TGGGGATCCACTAGGGACTC</u>TGGGGTCCCTGATCGCTTCA<br>CAGGCAGTGGATCTGGGACAGATTACACTCTCACCGTCAGC<br>AGTGTGCAGGCTGAAGACCTGGCAGTTTATTTCTGC<u>AAGCA<br>ATCTTATAATCTGCTCACG</u>TTCGGTGCTGGGACCAAGCTG |

In another embodiment, exemplary polynucleotides include those encoding humanized V_H and V_L regions as described supra. In another embodiment, exemplary polynucleotides include those encoding the heavy chain and light chain components of the various antibodies described herein, i.e., SEQ ID NOs: 56, 60, 64, 68, and 72, and SEQ ID NOs: 58, 62, 66, 70, and 74, respectively, as disclosed in Table 6 below.

The polynucleotides of the invention may be produced by chemical synthesis such as solid phase polynucleotide synthesis on an automated polynucleotide synthesizer and assembled into complete single or double stranded molecules. Alternatively, the polynucleotides of the invention may be produced by other techniques such a PCR followed by routine cloning. Techniques for producing or obtaining polynucleotides of a given known sequence are well known in the art.

The polynucleotides of the invention may comprise at least one non-coding sequence, such as a promoter or enhancer sequence, intron, polyadenylation signal, a cis sequence facilitating RepA binding, and the like. The polynucleotide sequences may also comprise additional sequences encoding additional amino acids that encode for example a marker or a tag sequence such as a histidine tag or an HA tag to facilitate purification or detection of the protein, a signal sequence, a fusion protein partner such as RepA, Fc or bacteriophage coat protein such as pIX or pIII.

Another embodiment of the disclosure is directed to a vector comprising at least one polynucleotide as described herein. Such vectors may be plasmid vectors, viral vectors, vectors for baculovirus expression, transposon based vectors or any other vector suitable for introduction of the polynucleotides described herein into a given organism or genetic background by any means.

Another embodiment of the disclosure is directed to one or more expression vectors comprising the polynucleotides encoding the antibody or binding fragment thereof or antibody mimetic as described herein. The polynucleotide sequences encoding the heavy and light chain variable domains, Fab fragments, or full-length chains of the antibodies disclosed herein are combined with sequences of promoter, translation initiation, 3' untranslated region, polyadenylation, and transcription termination to form one or more expression vector constructs.

In accordance with this embodiment, the expression vector construct encoding the antibodies or binding portions thereof as described herein can include the nucleic acid encoding the heavy chain polypeptide, a fragment thereof, a variant thereof, or combinations thereof. The heavy chain polypeptide can include a variable heavy chain (VH) region and/or at least one constant heavy chain (CH) region. The at least one constant heavy chain region can include a constant heavy chain region 1 (CH1), a constant heavy chain region 2 (CH2), a constant heavy chain region 3 (CH3), a constant heavy chain region 4 (CH4) in the immunoglobulin classes that it corresponds, and/or a hinge region. In some embodiments, the heavy chain polypeptide can include a VH region and a CH1 region. In other embodiments, the heavy chain polypeptide can include a VH region, a CH1 region, a hinge region, a CH2 region, a CH3 region, and a CH4 region.

The expression construct can also include a nucleic acid sequence encoding the light chain polypeptide, a fragment thereof, a variant thereof, or combinations thereof. The light chain polypeptide can include a variable light chain (VL) region and/or a constant light chain (CL) region.

The expression construct also typically comprises a promoter sequence suitable for driving expression of the antibody or binding fragment thereof. Suitable promoter sequences include, without limitation, the elongation factor 1-alpha promoter (EF1a) promoter, a phosphoglycerate kinase-1 promoter (PGK) promoter, a cytomegalovirus immediate early gene promoter (CMV), a chimeric liver-specific promoter (LSP) a cytomegalovirus enhancer/chicken beta-actin promoter (CAG), a tetracycline responsive promoter (TRE), a transthyretin promoter (TTR), a simian virus 40 promoter (SV40) and a CK6 promoter. Other promoters suitable for driving gene expression in mammalian cells that are known in the art are also suitable for incorporation into the expression constructs disclosed herein.

The expression construct can further encode a linker sequence. The linker sequence can encode an amino acid sequence that spatially separates and/or links the one or more components of the expression construct (heavy chain and light chain components of the encoded antibody).

Another embodiment of the invention is a host cell comprising the vectors described herein. The antibodies and binding fragments thereof described herein can be optionally produced by a cell line, a mixed cell line, an immortalized cell or clonal population of immortalized cells, as well known in the art (see e.g., Ausubel et al., ed., Current Protocols in Molecular Biology, John Wiley & Sons, Inc., NY, N.Y. (1987-2001); Sambrook et al., Molecular Cloning: A Laboratory Manual, $2^{nd}$ Edition, Cold Spring Harbor, N.Y. (1989); Harlow and Lane, Antibodies, a Laboratory Manual, Cold Spring Harbor, N.Y. (1989); Colligan et al., eds., Current Protocols in Immunology, John Wiley & Sons, Inc., NY (1994-2001); Colligan et al., Current Protocols in Protein Science, John Wiley & Sons, NY, N.Y., (1997-2001), which are hereby incorporated by reference in their entirety).

The host cell chosen for expression may be of mammalian origin or may be selected from COS-1, COS-7, HEK293, BHK21, CHO, BSC-1, He G2, SP2/0, HeLa, myeloma, lymphoma, yeast, insect, or plant cells, or any derivative, immortalized or transformed cell thereof. Alternatively, the host cell may be selected from a species or organism incapable of glycosylating polypeptides, e.g., a prokaryotic cell or organism, such as BL21, BL21(DE3), BL21-GOLD (DE3), XL1-Blue, JM109, HMS174, HMS174(DE3), and any of the natural or engineered *E. coli* spp, *Klebsiella* spp., or *Pseudomonas* spp strains.

The antibodies described herein can be prepared by any of a variety of techniques using the isolated polynucleotides, vectors, and host cells described supra. In general, antibodies can be produced by cell culture techniques, including the generation of monoclonal antibodies via conventional techniques, or via transfection of antibody genes, heavy chains and/or light chains into suitable bacterial or mammalian cell hosts, in order to allow for the production of antibodies, wherein the antibodies may be recombinant. Standard molecular biology techniques are used to prepare the recombinant expression vector, transfect the host cells, select for transformants, culture the host cells and recover the antibody from the culture medium. Transfecting the host cell can be carried out using a variety of techniques commonly used for the introduction of exogenous DNA into a prokaryotic or eukaryotic host cell, e.g., by electroporation, calcium-phosphate precipitation, DEAE-dextran transfection and the like. Although it is possible to express the antibodies described herein in either prokaryotic or eukaryotic host cells, expression of antibodies in eukaryotic cells is sometimes preferable, and sometimes preferable in mammalian host cells, because such eukaryotic cells (and in particular mammalian cells) are more likely than prokaryotic cells to assemble and secrete a properly folded and immunologically active antibody.

As noted above, exemplary mammalian host cells for expressing the recombinant antibodies of the invention include Chinese Hamster Ovary (CHO cells) (including dhfr-CHO cells, described in Urlaub and Chasin, *Proc. Natl. Acad. Sci. USA,* 77: 4216-4220 (1980), which is hereby incorporated by reference in its entirety). Other suitable mammalian host cells include, without limitation, NSO myeloma cells, COS cells, and SP2 cells. When recombinant expression vectors encoding antibody genes are introduced into mammalian host cells, the antibodies are produced by culturing the host cells for a period of time sufficient to allow for expression of the antibody in the host cells or, more preferably, secretion of the antibody into the culture medium in which the host cells are grown.

Host cells can also be used to produce functional antibody fragments, such as Fab fragments or scFv molecules. It is understood that variations on the above procedure are within the scope of the present disclosure. For example, it may be desirable to transfect a host cell with DNA encoding functional fragments of either the light chain and/or the heavy chain of an antibody described herein. Recombinant DNA technology may also be used to remove some or all the DNA encoding either or both of the light and heavy chains that is not necessary for binding to the antigens of interest. The molecules expressed from such truncated DNA molecules are also encompassed by the antibodies described herein.

In one embodiment, the sequence of the polynucleotide molecules encoding the antibodies and binding fragments described herein are modified using gene editing technology. Suitable gene editing technology and systems include, for example, zinc finger nucleases ("ZFNs") (Urnov et al., "Genome Editing with Engineered Zinc Finger Nucleases," *Nat. Rev. Genet.* 11: 636-646 (2010), which is hereby incorporated by reference in its entirety), transcription activator-like effector nucleases ("TALENs") (Joung & Sander, "TALENs: A Widely Applicable Technology for Targeted Genome Editing," *Nat. Rev. Mol. Cell Biol.* 14: 49-55 (2013), which is hereby incorporated by reference in its entirety), clustered regularly interspaced short palindromic repeat ("CRISPR")-associated endonucleases (e.g., CRISPR/CRISPR-associated ("Cas") 9 systems) (Wiedenheft et al., "RNA-Guided Genetic Silencing Systems in Bacteria and Archaea," *Nature* 482:331-338 (2012); Zhang et al., "Multiplex Genome Engineering Using CRISPR/Cas Systems," *Science* 339(6121): 819-23 (2013); and Gaj et al., "ZFN, TALEN, and CRISPR/Cas-based Methods for Genome Engineering," *Cell* 31(7):397-405 (2013), which are hereby incorporated by reference in their entirety). Gene editing modifications can be employed for humanization, class-switch recombination, and/or antibody fragment production (see e.g., Cheong et al., "Editing of Mouse and Human Immunoglobulin Genes by CRISPR-Cas9 System," *Nature Comm.* 7: 10934 (2016), and Flisikowska et al., "Efficient Immunoglobulin Gene Disruption and Targeted Replacement in Rabbit Using Zinc Finger Nucleases," *PLOS One* 6(6): e21045 (2011), which are hereby incorporated by reference in their entirety.

The antibodies and antibody binding fragments are recovered and purified from recombinant cell cultures by known methods including, but not limited to, protein A purification, ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. High performance liquid chromatography ("HPLC") can also be used for purification.

Table 6 below provides the heavy chain and light chain amino acid and corresponding nucleotide sequences of the exemplary antibodies that are described herein.

TABLE 6

Heavy Chain (HC) and Light Chain (LC) Nucleotide and Amino
Acid Sequences of Exemplary Antibodies of the Disclosure

| Antibody/Description | SEQ ID NO | SEQUENCE Leader sequence-FR1-CDR1-FR2-CDR2-FR3-CDR3-FR4-Constant region-Stop codon |
|---|---|---|
| TF-10E8 HC DNA | 56 | ATGGGATGGAGCTGGATCTTTCTCTTCCTCCTGTCAGGAACTGC AGGTGTCCATTGCCAGGTCCAGCTGCAGCAGTCTGGACCTGAGC TGGTGAAGCCTGGGGCTTCAGTGAAGATATCCTGCAAGGCTTCT GGCTACAGCTTCACAAGCTACTATATACACTGGGTGAAGCAGAG GCCTGGACAGGGACTTGAGTGGATTGGATGGATTTATCCTGGAA GTGGTAATACTAAGTACAATGAGAAGTTCAAGGGCAAGGCCACA CTGACGGCAGACACATCCTCCAGCACTGCCTACATGCAGCTCAG CAGCCTAACATCTGAGGACTCTGCGGTCTATTACTGTGCAAGGA GCTATGGTGACTACGACTACTGGGGCCAAGGCACCACTCTCACA GTCTCCTCAGAGAGTCAGTCCTTCCCAAATGTCTTTCCCCTCGT CTCCTGCGAGAGCCCCCTGTCTGATAAGAATCTGGTGGCCATGG GCTGCCTGGCCCGGGACTTCCTGCCCAGCACCATTTCCTTCACC TGGAACTACCAGAACAACACTGAAGTCATCCAGGGTATCAGAAC CTTCCCAACACTGAGGACAGGGGGCAAGTACCTAGCCACCTCGC AGGTGTTGCTGTCTCCCAAGAGCATCCTTGAAGGTTCAGATGAA TACCTGGTATGCAAAATCCACTACGGAGGCAAAAACAGAGATCT GCATGTGCCCATTCCAGCTGTCGCAGAGATGAACCCCAATGTAA ATGTGTTCGTCCCACCACGGGATGGCTTCTCTGGCCCTGCACCA CGCAAGTCTAAACTCATCTGCGAGGCCACGAACTTCACTCCAAA ACCGATCACAGTATCCTGGCTAAAGGATGGGAAGCTCGTGGAAT CTGGCTTCACCACAGATCCGGTGACCATCGAGAACAAAGGATCC ACACCCCAAACCTACAAGGTCATAAGCACACTTACCATCTCTGA AATCGACTGGCTGAACCTGAATGTGTACACCTGCCGTGTGGATC ACAGGGGTCTCACCTTCTTGAAGAACGTGTCCTCCACATGTGCT GCCAGTCCCTCCACAGACATCCTAACCTTCACCATCCCCCCCTC CTTTGCCGACATCTTCCTCAGCAAGTCCGCTAACCTGACCTGTC TGGTCTCAAACCTGGCAACCTATGAAACCCTGAATATCTCCTGG GCTTCTCAAAGTGGTGAACCACTGGAAACCAAAATTAAAATCAT GGAAAGTCATCCCAATGGCACCTTCAGTGCTAAGGGTGTGGCTA GTGTTTGTGTGGAAGACTGGAATAACAGGAAGGAATTTGTGTGT ACTGTGACTCACAGGGATCTGCCTTCACCACAGAAGAAATTCAT CTCAAAACCCAATGAGGTGCACAAACATCCACCTGCTGTGTACC TGCTGCCACCAGCTCGTGAGCAACTGAACCTGAGGGAGTCAGCC ACAGTCACCTGCCTGGTGAAGGGCTTCTCTCCTGCAGACATCAG TGTGCAGTGGCTTCAGAGAGGGCAACTCTTGCCCAAGAGAAGT ATGTGACCAGTGCCCCGATGCCAGAGCCTGGGGCCCCAGGCTTC TACTTTACCCACAGCATCCTGACTGTGACAGAGGAGGAATGGAA CTCCGGAGAGACCTATACCTGTGTTGTAGGCCACGAGGCCCTGC CACACCTGGTGACCGAGAGGACCGTGGACAAGTCCACTGGTAAA CCCACACTGTACAATGTCTCCCTGATCATGTCTGACACAGGCGG CACCTGCTATTGA |
| TF-10E8 HC Amino Acid | 57 | MGWSWIFLFLLSGTAGVHCQVQLQQSGPELVKPGASVKISCKAS GYSFTSYYIHWVKQRPGQGLEWIGWIYPGSGNTKYNEKFKGKAT LTADTSSSTAYMQLSSLTSEDSAVYYCARSYGDYDYWGQGTTLT VSS*ESQSFPNVFPLVSCESPLSDKNLVAMGCLARDFLPSTISFT WNYQNNTEVIQGIRTFPTLRTGGKYLATSQVLLSPKSILEGSDE YLVCKIHYGGKNRDLHVPIPAVAEMNPNVNVFVPPRDGFSGPAP* |

TABLE 6-continued

Heavy Chain (HC) and Light Chain (LC) Nucleotide and Amino Acid Sequences of Exemplary Antibodies of the Disclosure

| Antibody/Description | SEQ ID NO | SEQUENCE Leader sequence-FR1-CDR1-FR2-CDR2-FR3-CDR3-FR4-Constant region-Stop codon |
|---|---|---|
| | | *RKSKLICEATNFTPKPITVSWLKDGKLVESGFTTDPVTIENKGS* *TPQTYKVISTLTISEIDWLNLNVYTCRVDHRGLTFLKNVSSTCA* *ASPSTDILTFTIPPSFADIFLSKSANLTCLVSNLATYETLNISW* *ASQSGEPLETKIKIMESHPNGTFSAKGVASVCVEDWNNRKEFVC* *TVTHRDLPSPQKKFISKPNEVHKHPPAVYLLPPAREQLNLRESA* *TVTCLVKGFSPADISVQWLQRGQLLPQEKYVTSAPMPEPGAPGF* *YFTHSILTVTEEEWNSGETYTCVVGHEALPHLVTERTVDKSTGK* *PTLYNVSLIMSDTGGTCY* |
| TF-10E8 LC DNA | 58 | ATGAAGTTGCCTGTTAGGCTGTTGGTGCTGATGTTCTGGATTCC TGCTTCCAGCAGTGATGTTGTGATGACCCAAACTCCACTCTCCC TGCCTGTCAGTCTTGGAGATCAAGCCTCCATCTCTTGCAGATCT AGTCAGAGCCTTGTACACAGTAATGGAAACACCTATTTACATTG GTACCTGCAGAAGCCAGGCCAGTCTCCAAAGCTCCTGATCTACA AAGTTTCCAACCGATTTTCTGGGGTCCCAGACAGGTTCAGTGGC AGTGGATCAGGGACAGATTTCACACTCAAGATCAGCAGAGTGGA GGCTGAGGATCTGGGAGTTTATTTCTGCTCTCAAAGTACACATG TTCCTCGGACGTTCGGTGGAGGCACCAAGCTGGAAATCAAACGG GCTGATGCTGCACCAACTGTATCCATCTTCCCACCATCCAGTGA GCAGTTAACATCTGGAGGTGCCTCAGTCGTGTGCTTCTTGAACA ACTTCTACCCCAAAGACATCAATGTCAAGTGGAAGATTGATGGC AGTGAACGACAAAATGGCGTCCTGAACAGTTGGACTGATCAGGA CAGCAAAGACAGCACCTACAGCATGAGCAGCACCCTCACGTTGA CCAAGGACGAGTATGAACGACATAACAGCTATACCTGTGAGGCC ACTCACAAGACATCAACTTCACCCATTGTCAAGAGCTTCAACAG GAATGAGTGTTAG |
| TF-10E8 LC Amino Acid | 59 | MKLPVRLLVLMFWIPASSSDVVMTQTPLSLPVSLGDQASISCRS SQSLVHSNGNTYLHWYLQKPGQSPKLLIYKVSNRFSGVPDRFSG SGSGTDFTLKISRVEAEDLGVYFCSQSTHVPRT**FGGGTKLEIKR *ADAAPTVSIFPPSSEQLTSGGASVVCFLNNFYPKDINVKWKIDG* *SERQNGVLNSWTDQDSKDSTYSMSSTLTLTKDEYERHNSYTCEA* *THKTSTSPIVKSFNRNEC* |
| FT-12E1 HC DNA | 60 | ATGGCTGTCCTGGTGCTGCTCCTCTGCCTGGTGACATTCCCAAG CTGTGTCCTGTCCCAGGTGCAGCTGAAACAGTCAGGACCTGGCC TAGTGCCGCCCTCACAGAGCCTGTCCATCACCTGCACAGTTTCT GGTTTCTCATTAACTAGCTATGGTGTACACTGGGTTCGCCAGTC TCCAGGAAAGGGTCTGGAGTGGCTGGGAGTGATATGGAGTGGTG GAAGCACAGACTACAATGCAGCTTTCATATCCAGACTGAGCATC AGCAAGGACAACTCCAAGAGCCAAGTTTTCTTTAAAATGAACAG TCTGCAAGCTGATGACACAGCCATATACTACTGTGCCAGAAATC CCTCCGCCTACTATAGTAACTACTGGTTTGCTTACTGGGGCCAA GGGACTCTGGTCACTGTCTCTGCAGAGAGTCAGTCCTTCCCAAA TGTCTTTCCCCTCGTCTCCTGCGAGAGCCCCCTGTCTGATAAGA ATCTGGTGGCCATGGGCTGCCTGGCCCGGGACTTCCTGCCCAGC ACCATTTCCTTCACCTGGAACTACCAGAACAACACTGAAGTCAT CCAGGGTATCAGAACCTTCCCAACACTGAGGACAGGGGGCAAGT ACCTAGCCACCTCGCAGGTGTTGCTGTCTCCAAGAGCATCCTT GAAGGTTCAGATGAATACCTGGTATGCAAAATCCACTACGGAGG CAAAAACAGAGATCTGCATGTGCCCATTCCAGCTGTCGCAGAGA TGAACCCCAATGTAAATGTGTTCGTCCCACCACGGGATGGCTTC TCTGGCCCTGCACCACGCAAGTCTAAACTCATCTGCGAGGCCAC GAACTTCACTCCAAAACCGATCACAGTATCCTGGCTAAAGGATG GGAAGCTCGTGGAATCTGGCTTCACCACAGATCCGGTGACCATC GAGAACAAAGGATCCACACCCCAAACCTACAAGGTCATAAGCAC ACTTACCATCTCTGAAATCGACTGGCTGAACCTGAATGTGTACA CCTGCCGTGTGGATCACAGGGGTCTCACCTTCTTGAAGAACGTG TCCTCCACATGTGCTGCCAGTCCCTCCACAGACATCCTAACCTT CACCATCCCCCCCTCCTTTGCCGACATCTTCCTCAGCAAGTCCG CTAACCTGACCTGTCTGGTCTCAAACCTGGCAACCTATGAAACC CTGAATATCTCCTGGGCTTCTCAAAGTGGTGAACCACTGGAAAC CAAAATTAAAATCATGGAAAGTCATCCCAATGGCACCTTCAGTG CTAAGGGTGTGGCTAGTGTTTGTGTGGAAGACTGGAATAACAGG AAGGAATTTGTGTGTACTGTGACTCACAGGGATCTGCCTTCACC ACAGAAGAAATTCATCTCAAAACCCAATGAGGTGCACAAACATC CACCTGCTGTGTACCTGCTGCCACCAGCTCGTGAGCAACTGAAC CTGAGGGAGTCAGCCACAGTCACCTGCCTGGTGAAGGGCTTCTC TCCTGCAGACATCAGTGTGCAGTGGCTTCAGAGAGGGCAACTCT TGCCCCAAGAGAAGTATGTGACCAGTGCCCCGATGCCAGAGCCT GGGGCCCCAGGCTTCTACTTTACCCACAGCATCCTGACTGTGAC AGAGGAGGAATGGAACTCCGGAGAGACCTATACCTGTGTTGTAG GCCACGAGGCCCTGCCACACCTGGTGACCGAGAGGACCGTGGAC |

TABLE 6-continued

Heavy Chain (HC) and Light Chain (LC) Nucleotide and Amino
Acid Sequences of Exemplary Antibodies of the Disclosure

| Antibody/Description | SEQ ID NO | SEQUENCE Leader sequence-FR1-CDR1-FR2-CDR2-FR3-CDR3-FR4-Constant region-Stop codon |
|---|---|---|
| | | AAGTCCACTGGTAAACCCACACTGTACAATGTCTCCCTGATCAT GTCTGACACAGGCGGCACCTGCTATGA |
| FT-12E1 HC amino acid | 61 | MAVLVLLLCLVTFPSCVLSQVQLKQSGPGLVPPSQSLSITCTVS GFSLTSYGVHWVRQSPGKGLEWLGVIWSGGSTDYNAAFISRLSI SKDNSKSQVFFKMNSLQADDTAIYYCARNPSAYYSNYWFAYWGQ GTLVTVSA**ESQSFPNVFPLVSCESPLSDKNLVAMGCLARDFLPS TISFTWNYQNNTEVIQGIRTFPTLRTGGKYLATSQVLLSPKSIL EGSDEYLVCKIHYGGKNRDLHVPIPAVAEMNPNVNVFVPPRDGF SGPAPRKSKLICEATNFTPKPITVSWLKDGKLVESGFTTDPVTI ENKGSTPQTYKVISTLTISEIDWLNLNVYTCRVDHRGLTFLKNV SSTCAASPSTDILTFTIPPSFADIFLSKSANLTCLVSNLATYET LNISWASQSGEPLETKIKIMESHPNGTFSAKGVASVCVEDWNNR KEFVCTVTHRDLPSPQKKFISKPNEVHKHPPAVYLLPPAREQLN LRESATVTCLVKGFSPADISVQWLQRGQLLPQEKYVTSAPMPEP GAPGFYFTHSILTVTEEEWNSGETYTCVVGHEALPHLVTERTVD KSTGKPTLYNVSLIMSDTGGTCY |
| FT-12E1 LC DNA | 62 | ATGGAGACACATTCTCAGGTCTTTGTATACATGTTGCTGTGGTT GTCTGGTGTTGATGGAGACATTGTGATGACCCAGTCTCAAAATT TCATGTCCACATCAGTAGGAGACAGGGTCAGCGTCACCTGCAAG GCCAGTCAGTATGTGGGTACTTATGTAGCCTGGTATCAACAGAA ACCAGGGCAATCTCCTAAAGCACTGATTTACTCGGCATCCTACC GGCATACTGGAGTCCCTGATCGCTTCACAGGCAGTGGATCTGGG ACAGATTTCACTCTCACCATCAGCAATGTGCAGTCTGAAGACCT GGCAGATTATTTCTGTCAGCAATATAGCAGCTCTCCTCTCACGT TCGGCTCGGGGACAAAGTTGGAAATAAAACGGGCTGATGCTGCA CCAACTGTATCCATCTTCCCACCATCCAGTGAGCAGTTAACATC TGGAGGTGCCTCAGTCGTGTGCTTCTTGAACAACTTCTACCCCA GAGACATCAATGTCAAGTGGAAGATTGATGGCAGTGAACGACAA AATGGTGTCCTGAACAGTTGGACTGATCAGGACAGCAAAGACAG CACCTACAGCATGAGCAGCACCCTCACATTGACCAAGGACGAGT ATGAACGACATAACAGCTATACCTGTGAGGCCACTCACAAGACA TCAACTTCACCCATCGTCAAGAGCTTCAACAGGAATGAGTGTTA G** |
| FT-12E1 LC amino acid | 63 | METHSQVFVYMLLWLSGVDGDIVMTQSQNFMSTSVGDRVSVTCK ASQYVGTYVAWYQQKPGQSPKALIYSASYRHTGVPDRFTGSGSG TDFTLTISNVQSEDLADYFCQQYSSSPLTFGSGTKLEIK**RADAA PTVSIFPPSSEQLTSGGASVVCFLNNFYPRDINVKWKIDGSERQ NGVLNSWTDQDSKDSTYSMSSTLTLTKDEYERHNSYTCEATHKT STSPIVKSFNRNEC |
| WG-3D7 HC DNA | 64 | ATGGAATGGAGCTGGGTCTTTCTCTTCCTCCTGTCAGTAACTAC AGGTGTCCACTCTGAGGTCAAGCTGCAGCAGTCTGGACCTGAGC TGGTGAAGCCTGGGGCTTCAGTGAAGATATCCTGCAAGGCTTCT GGTTACTCATTCACTGGCTACTACATGCACTGGGTGAAGCAAAG TTCTGAAAAGAGCCTTGAGTGGATTGGAGAGATTAATCCTAGCA CTGGTGGTACTAGCTACAACCAGAAGTTCAAGGGCAAGGCCACA TTAACTGTAGACAAGTCATCCAGCACAGCCTACATGCAGCTCAA GAGCCTGACATCTGAGGACTCTGCTGTCTATTACTGTGCAAGAG ACTACTATAGTAAGGCTTACTGGGGCCAAGGGACTCTGGTCACT GTCTCTGCA**GAGAGTCAGTCCTTCCCAAATGTCTTTCCCCTCGT CTCCTGCGAGAGCCCCCTGTCTGATAAGAATCTGGTGGCCATGG GCTGCCTGGCCCGGGACTTCCTGCCCAGCACCATTTCCTTCACC TGGAACTACCAGAACAACACTGAAGTCATCCAGGGTATCAGAAC CTTCCCAACACTGAGGACAGGGGGCAAGTACCTAGCCACCTCGC AGGTGTTGCTGTCTCCCAAGAGCATCCTTGAAGGTTCAGATGAA TACCTGGTATGCAAAATCCACTACGGAGGCAAAAACAGAGATCT GCATGTGCCCATTCCAGCTGTCGCAGAGATGAACCCCAATGTAA ATGTGTTCGTCCCACCACGGGATGGCTTCTCTGGCCCTGCACCA CGCAAGTCTAAACTCATCTGCGAGGCCACGAACTTCACTCCAAA ACCGATCACAGTATCCTGGCTAAAGGATGGGAAGCTCGTGGAAT CTGGCTTCACCACAGATCCGGTGACCATCGAGAACAAGGATCC ACACCCCAAACCTACAAGGTCATAAGCACACTTACCATCTCTGA AATCGACTGGCTGAACCTGAATGTGTACACCTGCCGTGTGGATC ACAGGGGTCTCACCTTCTTGAAGAACGTGTCCTCCACATGTGCT GCCAGTCCCTCCACAGACATCCTAACCTTCACCATCCCCCCCTC CTTTGCCGACATCTTCCTCAGCAAGTCCGCTAACCTGACCTGTC TGGTCTCAAACCTGGCAACCTATGAAACCCTGAATATCTCCTGG GCTTCTCAAAGTGGTGAACCACTGGAAACCAAAATTAAAATCAT GGAAAGTCATCCCAATGGCACCTTCAGTGCTAAGGGTGTGGCTA GTGTTTGTGTGGAAGACTGGAATAACAGGAAGGAATTTGTGTGT |

TABLE 6-continued

Heavy Chain (HC) and Light Chain (LC) Nucleotide and Amino
Acid Sequences of Exemplary Antibodies of the Disclosure

| Antibody/Description | SEQ ID NO | SEQUENCE Leader sequence-FR1-CDR1-FR2-CDR2-FR3-CDR3-FR4-Constant region-Stop codon |
|---|---|---|
| | | ACTGTGACTCACAGGGATCTGCCTTCACCACAGAAGAAATTCAT CTCAAAACCCAATGAGGTGCACAAACATCCACCTGCTGTGTACC TGCTGCCACCAGCTCGTGAGCAACTGAACCTGAGGGAGTCAGCC ACAGTCACCTGCCTGGTGAAGGGCTTCTCTCCTGCAGACATCAG TGTGCAGTGGCTTCAGAGAGGGCAACTCTTGCCCCAAGAGAAGT ATGTGACCAGTGCCCCGATGCCAGAGCCTGGGGCCCCAGGCTTC TACTTTACCCACAGCATCCTGACTGTGACAGAGGAGGAATGGAA CTCCGGAGAGACCTATACCTGTGTTGTAGGCCACGAGGCCCTGC CACACCTGGTGACCGAGAGGACCGTGGACAAGTCCACTGGTAAA CCCACACTGTACAATGTCTCCCTGATCATGTCTGACACAGGCGG CACCTGCTATTGA |
| WG-3D7 HC amino acid | 65 | MEWSWVFLFLLSVTTGVHSEVKLQQSGPELVKPGASVKISCKAS GYSFTGYYMHWVKQSSEKSLEWIGEINPSTGGTSYNQKFKGKAT LTVDKSSSTAYMQLKSLTSEDSAVYYCARDYYSKAYWGQGTLVT VSA*ESQSFPNVFPLVSCESPLSDKNLVAMGCLARDFLPSTISFT WNYQNNTEVIQGIRTFPTLRTGGKYLATSQVLLSPKSILEGSDE YLVCKIHYGGKNRDLHVPIPAVAEMNPNVNVFVPPRDGFSGPAP RKSKLICEATNFTPKPITVSWLKDGKLVESGFTTDPVTIENKGS TPQTYKVISTLTISEIDWLNLNVYTCRVDHRGLTFLKNVSSTCA ASPSTDILTFTIPPSFADIFLSKSANLTCLVSNLATYETLNISW ASQSGEPLETKIKIMESHPNGTFSAKGVASVCVEDWNNRKEFVC TVTHRDLPSPQKKFISKPNEVHKHPPAVYLLPPAREQLNLRESA TVTCLVKGFSPADISVQWLQRGQLLPQEKYVTSAPMPEPGAPGF YFTHSILTVTEEEWNSGETYTCVVGHEALPHLVTERTVDKSTGK PTLYNVSLIMSDTGGTCY* |
| WG-3D7 LC DNA | 66 | ATGAAGTCACAGACCCAGGTCTTCGTATTTCTACTGCTCTGTGT GTCTGGTGCTCATGGGAGTATTGTGATGACCCAGACTCCCAAAT TCCTGCTTGTATCAGCAGGAGACAGGGTTACCATAACCTGCAAG GCCAGTCAGAGTGTGAGTAATGATGTAGCTTGGTACCAACAGAA GCCAGGGCAGTCTCCTAAACTGCTGATATACTATGCATCCAATC GCTACACTGGAGTCCCTGATCGCTTCACTGGCAGTGGATATGGG ACGGATTTCACTTTCACCATCAGCACTGTGCAGGCTGAAGACCT GGCAGTTTATTTCTGTCAGCAGGATTATAGCTCTCCGTACACGT TCGGAGGGGGGACCAAGCTGGAAATAAAA*CGGGCTGATGCTGCA CCAACTGTATCCATCTTCCCACCATCCAGTGAGCAGTTAACATC TGGAGGTGCCTCAGTCGTGTGCTTCTTGAACAACTTCTACCCCA AAGACATCAATGTCAAGTGGAAGATTGATGGCAGTGAACGACAA AATGGCGTCCTGAACAGTTGGACTGATCAGGACAGCAAAGACAG CACCTACAGCATGAGCAGCACCCTCACGTTGACCAAGGACGAGT ATGAACGACATAACAGCTATACCTGTGAGGCCACTCACAAGACA TCAACTTCACCCATTGTCAAGAGCTTCAACAGGAATGAGT*GTTA G* |
| WG-3D7 LC amino acid | 67 | MKSQTQVFVFLLLCVSGAHGSIVMTQTPKFLLVSAGDRVTITCK ASQSVSNDVAWYQQKPGQSPKLLIYYASNRYTGVPDRFTGSGYG TDFTFTISTVQAEDLAVYFCQQDYSSPYT**FGGGTKLEIK*RADAA PTVSIFPPSSEQLTSGGASVVCFLNNFYPKDINVKWKIDGSERQ NGVLNSWTDQDSKDSTYSMSSTLTLTKDEYERHNSYTCEATHKT STSPIVKSFNRNEC* |
| TF-10F7 HC DNA | 68 | ATGGGATGGAGCTGGATCTTTCTCTTCCTCCTGTCAGGAACTGC AGGTGTCCATTGCCAGGTCCAGCTGCAGCAGTCTGGACCTGAGC TGGTGAAGCCTGGGGCTTCAGTGAAGATATCCTGCAAGGCTTCT GGCTACAGCTTCACAAGCTACTATATACACTGGGTGAAGCAGAG GCCTGGACAGGGACTTGAGTGGATTGGATGGATTTATCCTGGAA GTGGTAATACTAAGTACAATGAGAAGTTCAAGGGCAAGGCCACA CTGACGGCAGACACATCCTCCAGCACTGCCTACATGCAGCTCAG CAGCCTAACATCTGAGGACTCTGCGGTCTATTACTGTGCAAGGA GCTATGGTGACTACGACTACTGGGGCCAAGGCACCACTCTCACA GTCTCCTCA*GAGAGTCAGTCCTTCCCAAATGTCTTTCCCCTCGT CTCCTGCGAGAGCCCCCTGTCTGATAAGAATCTGGTGGCCATGG GCTGCCTGGCCCGGGACTTCCTGCCCAGCACCATTTCCTTCACC TGGAACTACCAGAACAACACTGAAGTCATCCAGGGTATCAGAAC CTTCCCAACACTGAGGACAGGGGCAAGTACCTAGCCACCTCGC AGGTGTTGCTGTCTCCCAAGAGCATCCTTGAAGGTTCAGATGAA TACCTGGTATGCAAAATCCACTACGGAGGCAAAAACAGAGATCT GCATGTGCCCATTCCAGCTGTCGCAGAGATGAACCCCAATGTAA ATGTGTTCGTCCCACCACGGGATGGCTTCTCTGGCCCTGCACCA CGCAAGTCTAAAACTCATCTGCGAGGCCACGAACTTCACTCCAAA ACCGATCACAGTATCCTGGCTAAAGGATGGGAAGCTCGTGGAAT CTGGCTTCACCACAGATCCGGTGACCATCGAGAACAAAGGATCC* |

TABLE 6-continued

Heavy Chain (HC) and Light Chain (LC) Nucleotide and Amino Acid Sequences of Exemplary Antibodies of the Disclosure

| Antibody/Description | SEQ ID NO | SEQUENCE Leader sequence-FR1-CDR1-FR2-CDR2-FR3-CDR3-FR4-Constant region-Stop codon |
|---|---|---|
| | | ACACCCCAAACCTACAAGGTCATAAGCACACTTACCATCTCTGA AATCGACTGGCTGAACCTGAATGTGTACACCTGCCGTGTGGATC ACAGGGGTCTCACCTTCTTGAAGAACGTGTCCTCCACATGTGCT GCCAGTCCTCCACAGACATCCTAACCTTCACCATCCCCCCCTC CTTTGCCGACATCTTCCTCAGCAAGTCCGCTAACCTGACCTGTC TGGTCTCAAACCTGGCAACCTATGAAACCCTGAATATCTCCTGG GCTTCTCAAAGTGGTGAACCACTGGAAACCAAAATTAAAATCAT GGAAAGTCATCCCAATGGCACCTTCAGTGCTAAGGGTGTGG CTAGTGTTTGTGTGGAAGACTGGAATAACAGGAAGGAATTTGTG TGTACTGTGACTCACAGGGATCTGCCTTCACCACAGAAGAAATT CATCTCAAAACCCAATGAGGTGCACAAACATCCACCTGCTGTGT ACCTGCTGCCACCAGCTCGTGAGCAACTGAACCTGAGGGAGTCA GCCACAGTCACCTGCCTGGTGAAGGGCTTCTCTCCTGCAGACAT CAGTGTGCAGTGGCTTCAGAGAGGGCAACTCTTGCCCCAAGAGA AGTATGTGACCAGTGCCCCGATGCCAGAGCCTGGGGCCCCAGGC TTCTACTTTACCCACAGCATCCTGACTGTGACAGAGGAGGAATG GAACTCCGGAGAGACCTATACCTGTGTTGTAGGCCACGAGGCCC TGCCACACCTGGTGACCGAGAGGACCGTGGACAAGTCCACTGGT AAACCCACACTGTACAATGTCTCCCTGATCATGTCTGACACAGG CGGCACCTGCTATTGA |
| TF-10F7 HC amino acid | 69 | MGWSWIFLFLLSGTAGVHCQVQLQQSGPELVKPGASVKISCKAS GYSFTSYYIHWVKQRPGQGLEWIGWIYPGSGNTKYNEKFKGKAT LTADTSSSTAYMQLSSLTSEDSAVYYCARSYGDYDYWGQGTTLT VSS*ESQSFPNVFPLVSCESPLSDKNLVAMGCLARDFLPSTISFT WNYQNNTEVIQGIRTFPTLRTGGKYLATSQVLLSPKSILEGSDE YLVCKIHYGGKNRDLHVPIPAVAEMNPNVNVFVPPRDGFSGPAP RKSKLICEATNFTPKPITVSWLKDGKLVESGFTTDPVTIENKGS TPQTYKVISTLTISEIDWLNLNVYTCRVDHRGLTFLKNVSSTCA ASPSTDILTFTIPPSFADIFLSKSANLTCLVSNLATYETLNISW ASQSGEPLETKIKIMESHPNGTFSAKGVASVCVEDWNNRKEFVC TVTHRDLPSPQKKFISKPNEVHKHPPAVYLLPPAREQLNLRESA TVTCLVKGFSPADISVQWLQRGQLLPQEKYVTSAPMPEPGAPGF YFTHSILTVTEEEWNSGETYTCVVGHEALPHLVTERTVDKSTGK PTLYNVSLIMSDTGGTCY* |
| TF-10F7 LC DNA | 70 | ATGGAGACAGACACACTCCTGTTATGGGTACTGCTGCTCTGGGT TCCAGGTTCCACTGGTGACATTGTGCTGACACAGTCTCCTGCTT CCTTAGCTGTATCTCTGGGGCAGAGGGCCACCATCTCATACAGG GCCAGCAAAAGTGTCAGTACATCTGGCTATAGTTATATGCACTG GAACCAACAGAAACCAGGACAGCCACCCAGACTCCTCATCTATC TTGTATCCAACCTAGAATCTGGGGTCCCTGCCAGGTTCAGTGGC AGTGGATCAGGGACAGATTTCACACTCAAGATCAGCAGAGTGGA GGCTGAGGATCTGGGAGTTTATTTCTGCTCTCAAAGTACACATG TTCCTCGGACGTTCGGTGGAGGCACCAAGCTGGAAATCAAACGG GCTGATGCTGCACCAACTGTATCCATCTTCCCACCATCCAGTGA GCAGTTAACATCTGGAGGTGCCTCAGTCGTGTGCTTCTTGAACA ACTTCTACCCCAAAGACATCAATGTCAAGTGGAAGATTGATGGC AGTGAACGACAAAATGGCGTCCTGAACAGTTGGACTGATCAGGA CAGCAAAGACAGCACCTACAGCATGAGCAGCACCCTCACGTTGA CCAAGGACGAGTATGAACGACATAACAGCTATACCTGTGAGGCC ACTCACAAGACATCAACTTCACCCATTGTCAAGAGCTTCAACAG GAATGAGTGTTAG |
| TF-10F7 LC amino acid | 71 | METDTLLLWVLLLWVPGSTGDIVLTQSPASLAVSLGQRATISYR ASKSVSTSGYSYMHWNQQKPGQPPRLLIYLVSNLESGVPARFSG SGSGTDFTLKISRVEAEDLGVYFCSQSTHVPRTFGGGTKLEIKR *ADAAPTVSIFPPSSEQLTSGGASVVCFLNNFYPKDINVKWKIDG SERQNGVLNSWTDQDSKDSTYSMSSTLTLTKDEYERHNSYTCEA THKTSTSPIVKSFNRNEC* |
| GW-23B7 HC DNA | 72 | ATGAAATTCAGCTGGGTCATCTTCTTCCTGATGGCAGTGGTTAC AGGGGTCAATTCAGAGGTTCAGCTGCAGCAGTCTGTGGCAGAGC TTGTGAGGCCAGGGGCCTCAGTCAAGTTGTCCTGCACAGCTTCT GGCTTCAACATTAAAAACACCTATATGCACTGGGTGAAGCAGAG GCCTGAACAGGGCCTGGAGTGGATTGGAAGGATTGATCCTGCGA ATGGTAATACTAAATATGCCCCGAAGTTCCAGGGCAAGGCCACT ATAACTGCAGACACATCCTCAACACAGCCTACCTGCAGCTCAG CAGCCTGACATCTGAGGACACTGCCATCTATTACTGTGCTAGAG GGAGTTTTTATGCTATGGACTAC**TGGGGTCAAGGAACCTCAGTC ACCGTCTCCTCA*GAGAGTCAGTCCTTCCCAAATGTCTTTCCCCT CGTCTCCTGCGAGAGCCCCCTGTCTGATAAGAATCTGGTGGCCA TGGGCTGCCTGGCCCGGGACTTCCTGCCCAGCACCATTTCCTTC |

TABLE 6-continued

Heavy Chain (HC) and Light Chain (LC) Nucleotide and Amino Acid Sequences of Exemplary Antibodies of the Disclosure

| Antibody/Description | SEQ ID NO | SEQUENCE Leader sequence-FR1-CDR1-FR2-CDR2-FR3-CDR3-FR4-Constant region-Stop codon |
|---|---|---|
| | | ACCTGGAACTACCAGAACAACACTGAAGTCATCCAGGGTATCAG<br>AACCTTCCCAACACTGAGGACAGGGGGCAAGTACCTAGCCACCT<br>CGCAGGTGTTGCTGTCTCCCAAGAGCATCCTTGAAGGTTCAGAT<br>GAATACCTGGTATGCAAAATCCACTACGGAGGCAAAAACAGAGA<br>TCTGCATGTGCCCATTCCAGCTGTCGCAGAGATGAACCCCAATG<br>TAAATGTGTTCGTCCCACCACGGGATGGCTTCTCTGGCCCTGCA<br>CCACGCAAGTCTAAACTCATCTGCGAGGCCACGAACTTCACTCC<br>AAAACCGATCACAGTATCCTGGCTAAAGGATGGGAAGCTCGTGG<br>AATCTGGCTTCACCACAGATCCGGTGACCATCGAGAACAAAGGA<br>TCCACACCCCAAACCTACAAGGTCATAAGCACACTTACCATCTC<br>TGAAATCGACTGGCTGAACCTGAATGTGTACACCTGCCGTGTGG<br>ATCACAGGGGTCTCACCTTCTTGAAGAACGTGTCCTCCACATGT<br>GCTGCCAGTCCCTCCACAGACATCCTAACCTTCACCATCCCCCC<br>CTCCTTTGCCGACATCTTCCTCAGCAAGTCCGCTAACCTGACCT<br>GTCTGGTCTCAAACCTGGCAACCTATGAAACCCTGAATATCTCC<br>TGGGCTTCTCAAAGTGGTGAACCACTGGAAACCAAAATTAAAAT<br>CATGGAAAGTCATCCCAATGGCACCTTCAGTGCTAAGGGTGTGG<br>CTAGTGTTTGTGTGGAAGACTGGAATAACAGGAAGGAATTTGTG<br>TGTACTGTGACTCACAGGGATCTGCCTTCACCACAGAAGAAATT<br>CATCTCAAAACCCAATGAGGTGCACAAACATCCACCTGCTGTGT<br>ACCTGCTGCCACCAGCTCGTGAGCAACTGAACCTGAGGGAGTCA<br>GCCACAGTCACCTGCCTGGTGAAGGGCTTCTCTCCTGCAGACAT<br>CAGTGTGCAGTGGCTTCAGAGAGGGCAACTCTTGCCCCAAGAGA<br>AGTATGTGACCAGTGCCCCGATGCCAGAGCCTGGGGCCCCAGGC<br>TTCTACTTTACCCACAGCATCCTGACTGTGACAGAGGAGGAATG<br>GAACTCCGGAGAGACCTATACCTGTGTTGTAGGCCACGAGGCCC<br>TGCCACACCTGGTGACCGAGAGGACCGTGGACAAGTCCACTGGT<br>AAACCCACACTGTACAATGTCTCCCTGATCATGTCTGACACAGG<br>CGGCACCTGCTATTGA |
| GW-23B7<br>HC amino<br>acid | 73 | MKFSWVTFFLMAVVTGVNSEVQLQQSVAELVRPGASVKLSCTAS<br><u>GFNIKNTYMH</u>WVKQRPEQGLEWIG<u>RIDPANGNTKYAPKFQG</u>KAT<br>ITADTSSNTAYLQLSSLTSEDTAIYYCARGS<u>FYAMDY</u>WGQGTSV<br>TVSSESQSFPNVFPLVSCESPLSDKNLVAMGCLARDFLPSTISF<br>TWNYQNNTEVIQGIRTFPTLRTGGKYLATSQVLLSPKSILEGSD<br>EYLVCKIHYGGKNRDLHVPIPAVAEMNPNVNVFVPPRDGFSGPA<br>PRKSKLICEATNFTPKPITVSWLKDGKLVESGFTTDPVTIENKG<br>STPQTYKVISTLTISEIDWLNLNVYTCRVDHRGLTFLKNVSSTC<br>AASPSTDILTFTIPPSFADIFLSKSANLTCLVSNLATYETLNIS<br>WASQSGEPLETKIKIMESHPNGTFSAKGVASVCVEDWNNRKEFV<br>CTVTHRDLPSPQKKFISKPNEVHKHPPAVYLLPPAREQLNLRES<br>ATVTCLVKGFSPADISVQWLQRGQLLPQEKYVTSAPMPEPGAPG<br>FYFTHSILTVTEEEWNSGETYTCVVGHEALPHLVTERTVDKSTG<br>KPTLYNVSLIMSDTGGTCY |
| GW-23B7<br>LC DNA | 74 | ATGAGGTTCCAGGTTCAGGTTCTGGGGCTCCTTCTGCTCTGGAT<br>ACCAGGTGCCCAGTGTGATGTCCAGATAACCCAGTCTCCATCT<br>ATCTTGCTGCATCTCCTGGAGAAACCATTACTATTAATTGC<u>AGG</u><br><u>GCAAGTAAGAGCATTAACAAATATTTAGCC</u>TGGTATCAAGAGAA<br>ACCTGGGAAAACTAATAAGCTTCTTATCTAC<u>TCTGGATCCACCT</u><br><u>TGCAAT</u>CTGGAATTCCATCAAGGTTCAGTGGCAGTGGATCTGGT<br>ACAGATTTTACTCTCACCATCAGTAGCCTGGAGCCTGAAGATTT<br>TGCAATGTATCACTGT<u>CAACAGCATAATGAATACCCGTGGACGT</u><br>TCGGTGGAGGCACCAAGCTGGAAATCAAACGGGCTGATGCTGCA<br>CCAACTGTATCCATCTTCCCACCATCCAGTGAGCAGTTAACATC<br>TGGAGGTGCCTCAGTCGTGTGCTTCTTGAACAACTTCTACCCCA<br>GAGACATCAATGTCAAGTGGAAGATTGATGGCAGTGAACGACAA<br>AATGGTGTCCTGAACAGTTGGACTGATCAGGACAGCAAAGACAG<br>CACCTACAGCATGAGCAGCACCCTCACATTGACCAAGGACGAGT<br>ATGAACGACATAACAGCTATACCTGTGAGGCCACTCACAAGACA<br>TCAACTTCACCCATCGTCAAGAGCTTCAACAGGAATGAGTGTTA<br>G |
| GW-23B7<br>LC amino<br>acid | 75 | MRFQVQVLGLLLLWIPGAQCDVQITQSPSYLAASPGETITINC<u>R</u><br><u>ASKSINKYLA</u>WYQEKPGKTNKLLIY<u>SGSTLQS</u>GIPSRFSGSGSG<br>TDFTLTISSLEPEDFAMYHC<u>QQHNEYPWT</u>FGGGTKLEIKRADAA<br>PTVSIFPPSSEQLTSGGASVVCFLNNFYPRDINVKWKIDGSERQ<br>NGVLNSWTDQDSKDSTYSMSSTLTLTKDEYERHNSYTCEATHKT<br>STSPIVKSFNRNEC |

In another embodiment, the antibody or binding fragment thereof is a component of a pharmaceutical composition. In one embodiment, the pharmaceutical composition comprises a monoclonal antibody composition. In another embodiment, the pharmaceutical composition comprises one or more different antibodies as described herein. In another embodiment, the pharmaceutical composition comprises at least two different antibodies that bind to different epitopes of toxic oligomeric forms of amyloidogenic proteins or peptides as described herein. In another embodiment, the pharmaceutical composition comprises one or more antibodies as described herein and one or more prophylactic or therapeutic agents other than the antibodies described herein that are useful for preventing or treating a condition mediated by an amyloidogenic protein or peptide.

The therapeutically effective amount of antibody present in the pharmaceutical composition or formulation is determined by taking into account the desired dose volumes and mode(s) of administration. Exemplary antibody concentrations in the pharmaceutical compositions of the present disclosure include from about 0.1 mg/mL to about 50 mg/mL, from about 0.5 mg/mL to about 25 mg/mL, and from about 2 mg/mL to about 10 mg/mL.

An aqueous formulation is prepared comprising the antibody in a pH-buffered solution. The buffer has a pH in the range from about 4.5 to about 10, from about 5 to about 9, or from about 6 to about 8. Examples of buffers include phosphate buffers (e.g., phosphate buffered saline), acetate (e.g. sodium acetate), succinate (such as sodium succinate), gluconate, histidine, citrate and other organic acid buffers.

A polyol, which acts as a tonicifier and may stabilize the antibody, may be included in the formulation. In one embodiment, the tonicifying polyol is a salt such as sodium chloride. In another embodiment, the polyol is a nonreducing sugar, such as sucrose or trehalose. The polyol is added to the formulation in an amount which may vary with respect to the desired isotonicity of the formulation. Preferably the aqueous formulation is isotonic, in which case suitable concentrations of the polyol in the formulation are in the range from about 1% to about 15% w/v, or in the range from about 2% to about 10% w/v, for example. However, hypertonic or hypotonic formulations may also be suitable. The amount of polyol added may also alter with respect to the molecular weight of the polyol. For example, a lower amount of a monosaccharide (e.g. mannitol) may be added, compared to a disaccharide (such as trehalose).

A surfactant may also be added to the pharmaceutical composition containing the antibody. Exemplary surfactants include nonionic surfactants such as polysorbates (e.g. polysorbates 20, 80 etc), poloxamers (e.g. poloxamer 188), Pluronic F68, and PEG (polyethylene glycol). The amount of surfactant added is such that it reduces aggregation of the formulated antibody and/or minimizes the formation of particulates in the formulation and/or reduces adsorption. For example, the surfactant may be present in the formulation in an amount from about 0.001% to about 0.5%, from about 0.005% to about 0.2%, or from about 0.01% to about 0.1%.

In one embodiment, the pharmaceutical composition contains the above-identified agents (i.e. antibody, buffer, polyol and surfactant) and is essentially free of one or more preservatives, such as benzyl alcohol, phenol, m-cresol, chlorobutanol and benzethonium Cl. In another embodiment, a preservative may be included in the pharmaceutical composition, particularly where the formulation is a multi-dose formulation. Suitable preservatives include, without limitation phenol, m-cresol, p-cresol, o-cresol, chlorocresol, benzyl alcohol, phenylmercuric nitrite, phenoxyethanol, formaldehyde, chlorobutanol, magnesium chloride (e.g., hexahydrate), alkylparaben (methyl, ethyl, propyl, butyl and the like), benzalkonium chloride, benzethonium chloride, sodium dehydroacetate and thimerosal, or mixtures thereof in an aqueous diluent. The concentration of preservative may be in the range from about 0.01% to about 5%, from about 0.5% to about 2% and any range or value therein. Non-limiting examples include, no preservative, 0.1-2% m-cresol, 0.1-3% benzyl alcohol, 0.001-0.5% thimerosal, 0.001-2.0% phenol, 0.0005-1.0% alkylparaben(s), and the like. One or more other pharmaceutically acceptable carriers, excipients or stabilizers such as those described in Remington's Pharmaceutical Sciences 16th edition, Osol, A. Ed. (1980) may be included in the composition provided that they do not adversely affect the desired characteristics of the formulation. Acceptable carriers, excipients or stabilizers are nontoxic to recipients at the dosages and concentrations employed and include; additional buffering agents; co-solvents; antioxidants including ascorbic acid and methionine; chelating agents such as EDTA; metal complexes (e.g. Zn-protein complexes); biodegradable polymers such as polyesters; and/or salt-forming counterions such as sodium.

The pharmaceutical compositions to be used for in vivo administration must be sterile. This is readily accomplished by filtration through sterile filtration membranes, prior to, or following, preparation of the composition.

The pharmaceutical compositions comprising antibodies or binding fragments thereof are for use in, but not limited to, diagnosing, detecting, or monitoring a condition mediated by an amyloidogenic protein or peptide, and preventing, treating, managing, or ameliorating a condition, or one or more symptoms thereof, mediated by an amyloidogenic protein or peptide.

In one embodiment, the antibodies described herein, binding fragments thereof, or a pharmaceutical composition containing the same, are employed in a method of prophylactically inhibiting the onset of a condition mediated by an amyloidogenic protein or peptide in a subject. This method involves administering to the subject the pharmaceutical composition comprising an antibody or binding fragment thereof as described herein, where the composition is administered in an amount effective to prophylactically inhibit onset of the condition or one or more of the symptoms of the condition mediated by an amyloidogenic protein or peptide in the subject.

In another embodiment, the antibodies described herein, binding fragments thereof, or a pharmaceutical composition containing the same are employed in a method of treating a condition mediated by an amyloidogenic protein or peptide in a subject. This method involves administering to the subject a pharmaceutical composition comprising an antibody or binding fragment thereof as described herein, where the composition is administered in an amount effective to treat or ameliorate the condition, or one or more symptoms thereof, mediated by an amyloidogenic protein or peptide in the subject.

In accordance with these embodiments, a condition mediated by an amyloidogenic protein includes, without limitation, Alzheimer's disease (AD) and all its variations, preclinical AD (i.e., individuals having evidence of brain amyloid deposition with or without tau pathology (see Sperling et al., *Alzheimer's & Dementia* 7:280-92 (2011), which is hereby incorporated by reference in its entirety)), Rapid Progressive dementia, Down syndrome (DS), frontotemporal dementia (FTD), Lewy Body Dementia (LBD), Parkinson's disease (PD), hereditary cerebral hemorrhage with amyloidosis (HCHWA), kuru, Creutzfeldt-Jakob disease (CJD)-familial, sporadic or new variant (nV)-, chronic wasting disease (CWD) and its adapted forms in other mammals, Gerstmann-Straussler-Scheinker disease (GSS), Huntington's disease (HD) and all its glutamine expansion repeats, fatal familial insomnia, British familial dementia and all its variations, Danish familial dementia and all its variations, frontotemporal lobar degeneration associated with protein tau (FTLD-tau), frontotemporal lobar degeneration associated with protein FUS (FTLD-FUS), FTD-TDP-43, Amyotrophic lateral sclerosis (ALS), FTD and ALS with all repeat expansions due to mutations on C9orf72, Mild Cognitive Impairment (MCI), familial corneal amyloidosis, Familial corneal dystrophies, medullary thyroid carcinoma, insulinoma, type 2 diabetes, isolated atrial amyloidosis, pituitary amyloidosis, aortic amyloidosis, plasma cell disorders, familial amyloidosis, senile cardiac amyloidosis, inflammation-associated amyloidosis, familial Mediterranean fever (FMF), dialysis-associated amyloidosis, systemic amyloidosis, familial systemic amyloidosis, motor neuron disease, traumatic brain injury (TBI), and chronic traumatic encephalopathy, bovine spongiform encephalopathy (BSE) and its adapted forms in other mammals, ovine Scrapie (Sc) and its adapted forms in other mammals.

In another embodiment, the antibodies described herein, binding fragments thereof, or a pharmaceutical composition containing the same are employed in a method of treating a subject having or at risk of having a condition mediated by a pathological protein having a β-sheet secondary structure. This method involves administering to the subject a pharmaceutical composition comprising an antibody or binding fragment thereof as described herein, where the composition is administered in an amount effective to treat, inhibit, or ameliorate the condition, or one or more symptoms thereof, mediated by the pathological protein having the β-sheet secondary structure.

Conditions associated with one or more pathological proteins having a β-sheet secondary structure that are suitable for treatment with the antibodies and binding fragments described herein include, without limitation, certain cancers (i.e. cancer cells which produce proteins in high concentration that are prone to be misfolded and express a β-sheet secondary structure), septic or toxic shock and associated inflammation (i.e. where protein fragments in cells oligomerize to form pores and express a β-sheet secondary structure), acquired immunodeficiency syndrome (AIDS) (i.e., gp120), necrotic autoimmune reaction, and influenza (i.e. by targeting the hemagglutinin stalk structure (see Wilson et al., *Nature* 289:366-373 (1981), which is hereby incorporated by reference in its entirety)).

In accordance with these embodiments, the "subject" is typically a human, but in some diseases, such as prion protein related diseases, the subject can be a non-human mammal, such as a bovine. Other non-human mammals amenable to treatment in accordance with the methods described herein include, without limitation, primates, dogs, cats, rodents (e.g., mouse, rat, guinea pig), camelids, horses, deer, cervids, cattle and cows, sheep, all ungulates, and pigs.

In prophylactic applications, the pharmaceutical compositions of the present invention are administered to a subject that is susceptible to, or otherwise at risk of, a particular condition mediated by an amyloidogenic protein or peptide in an amount sufficient to eliminate or reduce the risk of the condition or to delay, inhibit, or prevent the onset of the condition. Prophylactic application also includes the administration of an antibody composition to prevent or delay the recurrence or relapse of a condition mediated by an amyloidogenic protein or peptide. In the case of Alzheimer's disease, for example, virtually anyone is at risk of suffering from Alzheimer's disease if he or she lives long enough.

Therefore, the compositions of the present invention can be administered prophylactically to the general population without the need for any assessment of the risk of the subject patient. The present methods and compositions are especially suitable for prophylactic treatment of individuals who have a known genetic risk of Alzheimer's disease or other condition related to an amyloidogenic protein. Genetic markers associated with a risk of Alzheimer's disease include mutations in the APP gene, particularly mutations at position 717 and positions 670 and 671 referred to as the Hardy and Swedish mutations respectively. Other markers of risk are mutations in the presenilin genes (PS1 or PS2), presence of the ApoE4 genotype, presence of TREM2 genotypes associated with AD (such as the R47H, D87N, or H157Y polymorphisms), family history of AD, hypercholesterolemia, or atherosclerosis.

In therapeutic applications, pharmaceutical compositions are administered to a subject suspected of, or already suffering from an amyloidogenic condition in an amount sufficient to cure, or at least partially arrest or alleviate, one or more symptoms of the condition and its complications. An amount adequate to accomplish this is defined as a therapeutically- or pharmaceutically-effective dose. In both prophylactic and therapeutic regimes, agents are usually administered in several dosages until a sufficient response has been achieved. An effective dose of the composition of the present invention, for the treatment of the above described conditions will vary depending upon many different factors, including means of administration, target site, physiological state of the patient, whether the patient is human or an animal, other medications administered, and whether treatment is prophylactic or therapeutic.

In accordance with the prophylactic and therapeutic methods described herein, compositions comprising the antibody or binding fragments thereof are administered in a dosage ranging from about 0.0001 to 100 mg/kg, and more usually 0.01 to 10 mg/kg of the recipient's body weight. For example, the antibody or binding fragment thereof is administered in a dosage of 1, 2, 3, 4, 5, 6, 7, 8, 9 or 10 mg/kg, or higher, for example 15, 20, 25, 30, 35, 40, 45, 50, 55, 60, 65, 70, 75, 80, 85, 90, 95, or 100 mg/kg. An exemplary treatment regime entails administration once per every two weeks or once a month or once every 3 to 6 months. In some methods, two or more antibodies with different binding specificities are administered simultaneously, in which case the dosage of each antibody administered falls within the ranges indicated. Intervals between single dosages can be weekly, monthly or yearly. Intervals can also be irregular as indicated by measuring blood levels of antibody in the patient. Alternatively, antibody can be administered as a sustained release formulation, in which case less frequent administration is required. Dosage and frequency vary depending on the half-life of the antibody in the patient. In general, human antibodies show the longest half life, followed by humanized antibodies, chimeric antibodies, and nonhuman antibodies. The dosage and frequency of administration can vary depending on whether the treatment is prophylactic or therapeutic. In prophylactic applications, a relatively low dosage is administered at relatively infrequent intervals over a long period of time. Some patients continue to receive treatment for the rest of their lives. In therapeutic applications, a relatively high dosage at relatively short intervals is sometimes required until progression of the disease is reduced or terminated, and preferably until the patient shows partial or complete amelioration of symptoms of disease. Thereafter, the patient can be administered a prophylactic regime.

The mode of administration of the antibody, binding fragment thereof, or pharmaceutical composition described herein may be any suitable route that delivers the compositions to the host, such as parenteral administration, e.g., intradermal, intramuscular, intraperitoneal, intravenous or subcutaneous, pulmonary; transmucosal (oral, intranasal, intravaginal, rectal); using a formulation in a tablet, capsule, solution, powder, gel, particle; and contained in a syringe, an implanted device, osmotic pump, cartridge, micropump; or other means appreciated by the skilled artisan, as well known in the art. Site specific administration may be achieved by, for example, intrarticular, intrabronchial, intraabdominal, intracapsular, intracartilaginous, intracavitary, intracelial, intracerebellar, intracerebroventricular, intracolic, intracervical, intragastric, intrahepatic, intracardial, intraosteal, intrapelvic, intrapericardiac, intraperitoneal, intrapleural, intraprostatic, intrapulmonary, intrarectal, intrarenal, intraretinal, intraspinal, intrasynovial, intrathoracic, intrauterine, intravascular, intravesical, intralesional, vaginal, rectal, buccal, sublingual, intranasal, or transdermal delivery.

Administration can be systemic or local. In one embodiment, it may be desirable to administer the antibodies of the invention locally to the area in need of treatment; this may be achieved by, for example, and not by way of limitation, local infusion, by injection, or by means of an implant, said implant being of a porous or non-porous material, including membranes and matrices, such as sialastic membranes, polymers, fibrous matrices (e.g., Tissuel®), or collagen matrices.

In another embodiment, compositions containing the antibody or binding fragment thereof are delivered in a controlled release or sustained release system. In one embodiment, a pump is used to achieve controlled or sustained release. In another embodiment, polymeric materials can be used to achieve controlled or sustained release of the antibody compositions described herein. Examples of polymers used in sustained release formulations include, but are not limited to, poly(2-hydroxy ethyl methacry-late), poly(methyl methacrylate), poly(acrylic acid), poly(ethylene-co-vinyl acetate), poly(methacrylic acid), polyglycolides (PLG), polyanhydrides, poly(N-vinyl pyrrolidone), poly(vinyl alcohol), polyacrylamide, poly(ethylene glycol), polylactides (PLA), poly(lactide-co-glycolides) (PLGA), and polyorthoesters. The polymer used in a sustained release formulation is preferably inert, free of leachable impurities, stable on storage, sterile, and biodegradable. Also, the use of liposomes, microcapsules or microspheres, inclusion complexes, or other types of carriers known in the art are also contemplated.

In yet another embodiment, a controlled or sustained release system can be placed in proximity of the prophylactic or therapeutic target, thus requiring only a fraction of the systemic dose. Controlled and/or release systems for delivery of antibodies known in the art are suitable for use and delivery of compositions containing the antibodies and binding fragments thereof as described herein, see e.g., Song et al, "Antibody Mediated Lung Targeting of Long-Circulating Emulsions," *PDA Journal of Pharmaceutical Science & Technology* 50:372-397 (1995); Cleek et al, "Biodegradable Polymeric Carriers for a bFGF Antibody for Cardiovascular Application," *Pro. Int'l. Symp. Control. Rel. Bioact. Mater.* 24:853-854 (1997); and Lam et al., "Microencapsulation of Recombinant Humanized Monoclonal Antibody for Local Delivery," *Proc. Int'l. Symp. Control Rel. Bioact. Mater.* 24:759-760 (1997), each of which is incorporated herein by reference in their entireties.

In embodiments where the pharmaceutical composition comprises polynucleotides encoding the antibody or binding fragment thereof as described herein, the nucleic acid can be administered in vivo to promote expression of its encoded antibody, by constructing it as part of an appropriate nucleic acid expression vector and administering it so that it becomes intracellular, e.g., by use of a retroviral vector (see e.g., U.S. Pat. No. 4,980,286 to Morgan et al., which is hereby incorporated by reference in its entirety), or by direct injection, or by use of microparticle bombardment (see e.g., a gene gun; Biolistic, Dupont), or coating with lipids or cell-surface receptors or transfecting agents, or by administering it in linkage to a homeobox-like peptide which is known to enter the nucleus (see e.g., Joliot et al, *Proc. Natl. Acad. Sci. USA* 88: 1864-1868 (1991), which is hereby incorporated by reference in its entirety). Alternatively, a nucleic acid can be introduced intracellularly and incorporated within host cell DNA for expression by homologous recombination.

The polynucleotide compositions can result in the generation of the antibody in the subject within at least about 1 hour, 2 hours, 3 hours, 4 hours, 5 hours, 6 hours, 7 hours, 8 hours, 9 hours, 10 hours, 11 hours, 12 hours, 13 hours, 14 hours, 15 hours, 20 hours, 25 hours, 30 hours, 35 hours, 40 hours, 45 hours, 50 hours, or 60 hours of administration of the composition to the subject. The composition can result in generation of the synthetic antibody in the subject within at least about 1 day, 2 days, 3 days, 4 days, 5 days, 6 days, 7 days, 8 days, 9 days, or 10 days of administration of the composition to the subject. The composition can result in generation of the antibody in the subject within about 1 hour to about 6 days, about 1 hour to about 5 days, about 1 hour to about 4 days, about 1 hour to about 3 days, about 1 hour to about 2 days, about 1 hour to about 1 day, about 1 hour to about 72 hours, about 1 hour to about 60 hours, about 1 hour to about 48 hours, about 1 hour to about 36 hours, about 1 hour to about 24 hours, about 1 hour to about 12 hours, or about 1 hour to about 6 hours of administration of the composition to the subject.

The composition, when administered to the subject in need thereof, can result in the persistent generation of the antibody in the subject. The composition can result in the generation of the antibody in the subject for at least about 1 day, 2 days, 3 days, 4 days, 5 days, 6 days, 7 days, 8 days, 9 days, 10 days, 11 days, 12 days, 13 days, 14 days, 15 days, 16 days, 17 days, 18 days, 19 days, 20 days, 21 days, 22 days, 23 days, 24 days, 25 days, 26 days, 27 days, 28 days, 29 days, 30 days, 31 days, 32 days, 33 days, 34 days, 35 days, 36 days, 37 days, 38 days, 39 days, 40 days, 41 days, 42 days, 43 days, 44 days, 45 days, 46 days, 47 days, 48 days, 49 days, 50 days, 51 days, 52 days, 53 days, 54 days, 55 days, 56 days, 57 days, 58 days, 59 days, or 60 days.

If the compositions of the invention are to be administered topically, the compositions can be formulated in the form of an ointment, cream, transdermal patch, lotion, gel, shampoo, spray, aerosol, solution, emulsion, or other form well-known to one of skill in the art. See, e.g., Remington's Pharmaceutical Sciences and Introduction to Pharmaceutical Dosage Forms, 19th ed., Mack Pub. Co., Easton, Pa. (1995), which is hereby incorporated by reference in its entirety. For non-sprayable topical dosage forms, viscous to semisolid or solid forms comprising a carrier or one or more excipients compatible with topical application and having a dynamic viscosity greater than water are typically employed. Suitable formulations include, without limitation, solutions, suspensions, emulsions, creams, ointments, powders, liniments, salves, and the like, which are, if desired, sterilized or mixed with auxiliary agents (e.g., preservatives, stabilizers, wetting agents, buffers, or salts) for influencing various properties, such as, for example, osmotic pressure. Other suitable topical dosage forms include sprayable aerosol preparations wherein the active ingredient, for example in combination with a solid or liquid inert carrier, is packaged in a mixture with a pressurized volatile (e.g., a gaseous propellant, such as freon) or in a squeeze bottle.

If the methods described herein involve intranasal administration of the antibody composition, the composition can be formulated in an aerosol form, spray, mist or in the form of drops. In particular, prophylactic or therapeutic agents for use according to the present invention can be conveniently delivered in the form of an aerosol spray presentation from pressurized packs or a nebulizer, with the use of a suitable propellant (e.g., dichlorodifluoromethane, trichloro-fluoromethane, dichlorotetrafluoroethane, carbon dioxide or other suitable gas). In the case of a pressurized aerosol the dosage unit may be determined by providing a valve to deliver a metered amount. Capsules and cartridges (composed of, e.g., gelatin) for use in an inhaler or insufflator may be formulated containing a powder mix of the compound and a suitable powder base such as lactose or starch.

If the methods described herein involve oral administration of the antibody compositions described herein, the compositions can be formulated orally in the form of tablets, capsules, cachets, gelcaps, solutions, suspensions, and the like. Tablets or capsules can be prepared by conventional means with pharmaceutically acceptable excipients such as binding agents (e.g., pregelatinised maize starch, polyvinylpyrrolidone, or hydroxypropyl methylcellulose); fillers (e.g., lactose, microcrystalline cellulose, or calcium hydrogen phosphate); lubricants (e.g., magnesium stearate, talc, or silica); disintegrants (e.g., potato starch or sodium starch glycolate); or wetting agents (e.g., sodium lauryl sulphate). The tablets may be coated by methods well-known in the art. Liquid preparations for oral administration may take the form of, but not limited to, solutions, syrups or suspensions, or they may be presented as a dry product for constitution with water or other suitable vehicle before use. Such liquid preparations may be prepared by conventional means with pharmaceutically acceptable additives such as suspending agents (e.g., sorbitol syrup, cellulose derivatives, or hydrogenated edible fats); emulsifying agents (e.g., lecithin or acacia); non-aqueous vehicles (e.g., almond oil, oily esters, ethyl alcohol, or fractionated vegetable oils); and preservatives (e.g., methyl or propyl-p-hydroxybenzoates or sorbic acid). The preparations may also contain buffer salts, flavoring, coloring, and sweetening agents as appropriate.

Formulations for injection may be presented in unit dosage form (e.g., in ampoules or in multi-dose containers) with an added preservative. The compositions may take such forms as suspensions, solutions or emulsions in oily or aqueous vehicles, and may contain formulatory agents such as suspending, stabilizing and/or dispersing agents. Alternatively, the active ingredient may be in powder form for constitution with a suitable vehicle (e.g., sterile pyrogen-free water) before use. The methods of the invention may additionally comprise of administration of compositions formulated as depot preparations. Such long acting formulations may be administered by implantation (e.g., subcutaneously or intramuscularly) or by intramuscular injection. Thus, for example, the compositions may be formulated with suitable polymeric or hydrophobic materials (e.g., as an emulsion in an acceptable oil) or ion exchange resins, or as sparingly soluble derivatives (e.g., as a sparingly soluble salt).

The methods of the invention encompass administration of compositions formulated as neutral or salt forms. Pharmaceutically acceptable salts include those formed with anions such as those derived from hydrochloric, phosphoric, acetic, oxalic, tartaric acids, etc., and those formed with cations such as those derived from sodium, potassium, ammonium, calcium, ferric hydroxides, isopropylamine, triethylamine, 2-ethylamino ethanol, histidine, procaine, etc.

Generally, the ingredients of compositions are supplied either separately or mixed together in unit dosage form, for example, as a dry lyophilized powder or water free concentrate in a hermetically sealed container such as an ampoule or sachette indicating the quantity of active agent. Where the mode of administration is infusion, composition can be dispensed with an infusion bottle containing sterile pharmaceutical grade water or saline. Where the mode of administration is by injection, an ampoule of sterile water for injection or saline can be provided so that the ingredients may be mixed prior to administration.

The antibodies, binding fragments thereof, or pharmaceutical compositions containing the same can be packaged in hermetically sealed containers such as an ampoule or sachette indicating the quantity of the antibody or binding fragment thereof. In one embodiment, one or more of the antibodies, or pharmaceutical compositions of the invention is supplied as a dry sterilized lyophilized powder or water free concentrate in a hermetically sealed container and can be reconstituted (e.g., with water or saline) to the appropriate concentration for administration to a subject. In one embodiment, one or more of the antibodies or pharmaceutical compositions of the invention is supplied as a dry sterile lyophilized powder in a hermetically sealed container at a unit dosage of at least 5 mg, for example at least 10 mg, at least 15 mg, at least 25 mg, at least 35 mg, at least 45 mg, at least 50 mg, at least 75 mg, or at least 100 mg. The lyophilized antibodies or pharmaceutical compositions of the invention should be stored at between 2° C. and 8° C. in its original container and the antibodies, or pharmaceutical compositions of the invention should be administered within 1 week, for example within 5 days, within 72 hours, within 48 hours, within 24 hours, within 12 hours, within 6 hours, within 5 hours, within 3 hours, or within 1 hour after being reconstituted. In an alternative embodiment, one or more of the antibodies or pharmaceutical compositions of the invention is supplied in liquid form in a hermetically sealed container indicating the quantity and concentration of the antibody. In a further embodiment, the liquid form of the administered composition is supplied in a hermetically sealed container at least 0.25 mg/ml, for example at least 0.5 mg/ml, at least 1 mg/ml, at least 2.5 mg/ml, at least 5 mg/ml, at least 8 mg/ml, at least 10 mg/ml, at least 15 mg/ml, at least 25 mg/ml, at least 50 mg/ml, at least 75 mg/ml or at least 100 mg/ml. The liquid form should be stored at between 2° C. and 8° C. in its original container.

The antibodies and binding fragments described herein can be incorporated into a pharmaceutical composition suitable for parenteral administration. In one aspect, antibodies will be prepared as an injectable solution containing 0.1-250 mg/ml antibody. The injectable solution can be composed of either a liquid or lyophilized dosage form in a flint or amber vial, ampule or pre-filled syringe. The buffer can be L-histidine (1-50 mM), optimally 5-10 mM, at pH 5.0 to 7.0 (optimally pH 6.0). Other suitable buffers include but are not limited to, sodium succinate, sodium citrate, sodium phosphate or potassium phosphate. Sodium chloride can be used to modify the tonicity of the solution at a concentration of 0-300 mM (optimally 150 mM for a liquid dosage form).

Cryoprotectants can be included for a lyophilized dosage form, principally 0-10% sucrose (optimally 0.5-1.0%). Other suitable cryoprotectants include trehalose and lactose. Bulking agents can be included for a lyophilized dosage form, principally 1-10% mannitol (optimally 2-4%). Stabilizers can be used in both liquid and lyophilized dosage forms, principally 1-50 mM L-Methionine (optimally 5-10 mM). Additional surfactants include but are not limited to polysorbate 20 and BRIJ surfactants. The pharmaceutical composition comprising the antibodies described herein prepared as an injectable solution for parenteral administration, can further comprise an agent useful as an adjuvant, such as those used to increase the absorption, or dispersion of the antibody. A particularly useful adjuvant is hyaluronidase, such as Hylenex® (recombinant human hyaluronidase). Addition of hyaluronidase in the injectable solution improves human bioavailability following parenteral administration, particularly subcutaneous administration. It also allows for greater injection site volumes (i.e. greater than 1 ml) with less pain and discomfort, and minimum incidence of injection site reactions (see WO 04/078140 to Bookbinder et al., and U.S. Patent Appl. Publication No. US2006104968 to Bookbinder et al., which are hereby incorporated herein by reference in their entirety).

In another embodiment, the antibodies and binding fragments thereof as described herein are immobilized on a solid support. In one embodiment, the antibodies and binding fragments thereof are immobilized on a column or membrane used in dialysis as described in U.S. Pat. No. 8,318,175 to Frangione et al., which is hereby incorporated by reference in its entirety. In accordance with this embodiment, a subject having a condition mediated by an amyloidogenic protein or peptide is treated by dialyzing the subject's blood through the column and/or membrane containing the bound antibodies or binding fragments thereof to remove amyloidogenic proteins from the subject's blood that are recognized by the bound antibodies or binding fragments. Such dialyzing blood treatments are used to reduce or eliminate the presence of specific toxic amyloidogenic proteins of peptides free flowing in a subject's plasma. Preferred methods of dialysis include, without limitation, hemodialysis, plasma exchange, plasma perfusion and hemofiltration. The dialysis treatment can take place over a period of 2-3 hours (or longer), and is repeated as necessary. Typically, dialysis is conducted every 1-7 days for as long as the concentration of free amyloidogenic protein or peptide in the subject's blood remains high, e.g., above 0.1-0.5 ng/ml (10-50% of mean plasma level).

Suitable solid support material for immobilization of the antibodies and binding fragments thereof includes, without limitation, nitrocellulose, cellulose, nylon, plastic, rubber, polyacrylamide, agarose, poly(vinylalcoholo-co-ethylene). The solid support material can be formed in a variety of shapes, including flat dialyzers, semi-permeable membranes, semi-permeable hollow fibers, coils, permeable spheres, dialysis membranes, and plasmapheresis filters, optionally using linker molecules such as PEG (polyethelene glycol) to attach the ligand (as disclosed in WO 00/74824 to Bristow, which is hereby incorporated by reference in its entirety). In a hemofiltration device, the solid supports may be, for example, beads, plates, hollow filters, hollow fibers, or any combination thereof.

The antibodies and binding fragments described herein can also be employed in a number of diagnostic, prognostic and research applications.

Another aspect of the present disclosure is directed to a method of diagnosing an amyloidogenic condition or disease in a subject. This method involves detecting, in the subject, the presence of an amyloidogenic protein or peptide using a diagnostic reagent, wherein the diagnostic reagent comprises an antibody or binding fragment described herein. The diagnosis of an amyloid disease in the subject is based on the detection of an amyloidogenic protein or peptide in the subject.

Detecting the presence of an amyloidogenic protein or peptide in a subject using the antibodies or antibody fragments thereof as described herein can be achieved by obtaining a biological sample from the subject (e.g., blood, urine, cerebral spinal fluid, ocular lacrimal secretion, saliva, feces, nasal brushings and tissue or organ biopsy), contacting the biological sample with the diagnostic antibody reagent, and detecting binding of the diagnostic antibody reagent to an amyloidogenic protein or peptide if present in the sample from the subject. Assays for carrying out the detection of an amyloidogenic protein/peptide in a biological sample using a diagnostic antibody are well known in the art and include, without limitation, ELISA, immunohistochemistry, SIMOA (single molecule array), and Western blot.

In accordance with this and other embodiments described herein, the antibody or binding fragments described herein are coupled to a detectable label. The label can be any detectable moiety known and used in the art. Suitable labels include, without limitation, radioisotopes or radionuclides (e.g., $^{3}$H, $^{14}$C, $^{35}$S, $^{90}$Y, $^{99}$Tc, $^{111}$In, $^{125}$I, $^{131}$I, $^{177}$Lu, $^{166}$Ho, or $^{153}$Sm); fluorescent labels (e.g., FITC, rhodamine, lanthanide phosphors), enzymatic labels (e.g., horseradish peroxidase, luciferase, alkaline phosphatase); chemiluminescent markers; biotinyl groups; predetermined polypeptide epitopes recognized by a secondary reporter (e.g., leucine zipper pair sequences, binding sites for secondary antibodies, metal binding domains, epitope tags); and magnetic agents, such as gadolinium chelates.

Detecting the presence of amyloidogenic proteins or peptides in a subject using the diagnostic antibody reagent of the present invention can also be achieved using in vivo imaging techniques. In vivo imaging involves administering to the subject the antibody or binding fragments thereof described herein, and detecting the binding of the antibody or binding fragment thereof to the amyloidogenic protein in vivo.

Diagnostic antibodies or similar reagents can be administered by intravenous injection into the body of the patient, or directly into the brain by intracranial injection or by drilling a hole through the skull. The dosage of antibody should be within the same ranges as for treatment methods. In accordance with this embodiment, the antibody or binding fragment is coupled to an imaging agent to facilitate in vivo imaging. The imaging agent can be any agent known to one of skill in the art to be useful for imaging, preferably being a medical imaging agent. Examples of medical imaging agents include, but are not limited to, single photon emission computed tomography (SPECT) agents, positron emission tomography (PET) agents, magnetic resonance imaging (MRI) agents, nuclear magnetic resonance imaging (NMR) agents, x-ray agents, optical agents (e.g., fluorophores, bioluminescent probes, near infrared dyes, quantum dots), ultrasound agents and neutron capture therapy agents, computer assisted tomography agents, two photon fluorescence microscopy imaging agents, and multi-photon microscopy imaging agents. Exemplary detectable markers include radioisotopes (e.g., $^{18}$F, $^{11}$C, $^{13}$N, $^{64}$Cu, $^{124}$I, $^{76}$Br, $^{82}$Rb, $^{68}$Ga, $^{99m}$Tc, $^{111}$In, $^{201}$Tl or $^{15}$O, which are suitable for PET and/or SPECT use) and ultra-small superparamagnetic particles of iron oxide (USPIO) which are suitable for MRI.

Diagnosis of an amyloidogenic condition is performed by comparing the number, size, and/or intensity of detected amyloidogenic proteins/peptides in a sample from the subject or in the subject, to corresponding baseline values. An appropriate baseline value can be the average level of amyloidogenic protein/peptide found in a population of undiseased individuals. Alternatively, an appropriate baseline value may be the level of amyloid protein deposition in the same subject determined at an earlier time.

The diagnostic methods described herein can also be used to monitor a subject's response to therapy. In this embodiment, detection of amyloidogenic proteins or peptides in the subject is determined prior to the commencement of treatment. The level of amyloidogenic protein or peptide in the subject at this timepoint is used as a baseline value. At various times during the course of treatment the detection of amyloidogenic protein/peptide is repeated, and the measured values thereafter compared with the baseline values. A decrease in values relative to baseline signals a positive response to treatment.

A related aspect of the disclosure is directed to a method of identifying a subject's risk for developing a condition mediated by an amyloidogenic protein or peptide. This method involves detecting, in the subject, the presence of an amyloidogenic protein or peptide using a diagnostic reagent comprising the antibody or binding fragment thereof described herein, and identifying the subject's risk of developing a condition mediated by the amyloidogenic protein or peptide based on the results of the detecting step.

Methods of detecting the presence of an amyloidogenic protein/peptide in the subject or in a sample from the subject include the in vitro and in vivo methods described supra. In one embodiment, the subject is not exhibiting any definitive signs or symptoms of an amyloidogenic condition, and employment of this method serves as an early diagnostic. In another embodiment, the subject is not exhibiting any signs or symptoms of an amyloidogenic conditions, but has a genetic predisposition to a condition and employment off this method serves to predict the likelihood that the individual will develop the amyloidogenic condition in the future. In either embodiment, appropriate therapeutic and/or prophylactic intervention can be employed, e.g., administration of a therapeutic compositions containing the antibodies or binding fragments thereof in an amount effective to slow or prevent the onset or progression of the amyloidogenic condition.

Another aspect of the present disclosure is directed to a diagnostic kit that comprises the antibody or binding fragment thereof as described herein and a detectable label.

A suitable detectable label is any moiety attached to an antibody or an analyte to render the reaction between the antibody and the analyte detectable. A label can produce a signal that is detectable by visual or instrumental means. Various labels include signal-producing substances, such as chromogens, fluorescent compounds, chemiluminescent compounds, radioactive compounds, and the like, Representative examples of detectable labels include moieties that produce light, e.g., acridinium compounds, and moieties that produce fluorescence, e.g., fluorescein. In this regard, the moiety itself may not be detectable, but becomes detectable upon reaction with yet another moiety.

Other suitable detectable labels include radioactive labels (e.g., H, I, S, C, P, and P), enzymatic labels (e.g., horseradish peroxidase, alkaline peroxidase, glucose 6-phosphate dehydrogenase, and the like), chemiluminescent labels (e.g., acridinium esters, thioesters, or sulfonamides; luminol, isoluminol, phenanthridinium esters, and the like), fluorescent labels (such as fluorescein (e.g., 5-fluorescein, 6-carboxyfluorescein, 3'6-carboxyfluorescein, 5(6)-carboxyfluorescein, 6-hexachloro-fluorescein, 6-tetrachlorofluorescein, fluorescein isothiocyanate, and the like)), rhodamine, phycobiliproteins, R-phycoerythrin, quantum dots (e.g., zinc sulfide-capped cadmium selenide), a thermometric label, or an immuno-polymerase chain reaction label.

EXAMPLES

Example 1—Production of Monoclonal Antibodies Against Conformational β-Sheet Secondary Structures Common to Oligomeric Forms of Different Pathological Peptides and Proteins of Various Neurodegenerative Diseases Synthesis and Polymerization of 13-Mer Bri Peptide (pBri).

The procedure was performed as previously published (Goñi et al, "Immunomodulation Targeting Abnormal Conformation Reduces Pathology in a Mouse Model of Alzheimer's Disease," PLoS One 5(10): e13391 (2010), which is hereby incorporated by reference in its entirety). Briefly, the 13 residue peptide that corresponds to the carboxyl terminus of ABri (Cys-Ser-Arg-Thr-Val-Lys-Lys-Asn-Ile-Ile-Glu-Glu-Asn; SEQ ID NO: 111) was synthesized on an ABI 430A peptide synthesizer (AME Bioscience, Chicago, Ill.) at the Keck peptide synthesis facility at Yale University, CT. Mass spectroscopy of the lyophilized end-product was used to verify the expected molecular weight.

To have a stable oligomeric conformation and make the 13mer Bri peptide immunogenic by itself, the synthetic peptide was subjected to controlled polymerization using the following protocol: The peptide was dissolved at 3 mg/ml, in 100 mM borate-150 mM NaCl (BBS), pH 7.4. Fresh 1% glutaraldehyde in BBS was added to the peptide to a final 5 mM glutaraldehyde concentration and incubated in an Eppendorf block shaker at 800 rpm and 56° C. for 16 hrs (Goñi et al., "Immunomodulation Targeting Abnormal Protein Conformation Reduces Pathology in a Mouse Model of Alzheimer's Disease" PLoS. ONE 5:e13391 (2010), and Goñi et al., "Immunomodulation Targeting both Aβ and tau Pathological Conformers Ameliorates Alzheimer's Disease Pathology in TgSwDI and 3xTg mouse models" *Journal of Neuroinflammation* 10:150 (2013), both of which are hereby incorporated by reference in their entirety). The solution was then quenched with 0.5 M glycine to make the solution 100 mM in glycine. After five minutes the solution was diluted 1:3 with BBS transferred to a dialysis membrane with a MWCO 2000 (Spectra Laboratories, Rockleigh, N.J.) and dialyzed extensively against 200 volumes and three changes of 2 mM BBS at 4° C., aliquoted and lyophilized. To determine the degree of aggregation the original monomeric ABri peptide and polymerized 13mer Bri peptide (p13Bri) were electrophoresed on 12.5% (SDS)-polyacrylamide Tris-tricine gels together with the low range Rainbow™ molecular weight markers (Amersham Biosciences, Piscataway, N.J.) under reducing conditions, then transferred onto nitrocellulose membranes and blotted against a specific rabbit polyclonal anti-Bri. For circular dichroism the ABri and p13Bri at 0.25 mg/ml in saline were analyzed as previously described (Goñi et al., "Immunomodulation Targeting Abnormal Protein Conformation Reduces Pathology in a Mouse Model of Alzheimer's Disease" *PLoS. ONE*

5:e13391 (2010), which is hereby incorporated by reference in its entirety). For electron microscopy studies, the original and polymerized Bri peptides were incubated at 1 mg/ml in 50 mM phosphate-150 mM NaCl (PBS) pH 7.4. Within 24 hours, 3 µl of each sample were placed onto carbon coated 400 mesh Cu/Rh grid (Ted Pella Inc., Redding, Calif.) and stained with 1% uranyl acetate in distilled water (Polysciences, Inc, Warrington, Pa.). Stained grids were examined under Philips CM-12 electron microscope and photographed with a Gatan (4 k×2.7 k) digital camera. The EMs were also repeated on the aged samples kept at room temperature (RT) for one, two and four weeks.

Immunization of CD-1 Mice. Immunization of the CD-1 mice and the subsequent hybridoma production were performed at the Bi-Institutional Antibody and BioResource Core Facility of Memorial Sloan Kettering Cancer Center and The Rockefeller University. All procedures were approved by the Institutional Animal Care and Use Committee protocol #97-03-009 and followed NIH standards. The p13Bri peptide was dissolved in sterile saline and mixed 4:1 for the first two inoculations and 9:1 for the remaining inoculations, with Aluminum Hydroxide (Alum) adjuvant (Brenntag Biosector, Denmark) or with the Ribi-like Sigma Adjuvant system (each vial containing 0.5 mg Monophosphoryl Lipid A from *Salmonella minnesota* and 0.5 mg synthetic Trehalose Dicorynomycolate in 2% oil [squalene]-Tween® 80-water) (Sigma-Aldrich, St. Louis, Mo.). Animals were immunized as shown in Table 10 and Table 11. Mice received bi-weekly subcutaneous inoculations of 50 µg of the p13Bri and subsequent inoculations were reduced to 20 µg of immunogen. Bleedings were done 7 days after each inoculation starting after the second injection. Differential antibody titers to Aβ1-40 and 1-42 were determined by enzyme-linked immunosorbent analysis (ELISA); the plasma for any bleeding was diluted 1:150 with 50 mM Tris-Saline pH 7.2, 0.1% Tween 20 (TBS-T) and incubated on Immulon 2HB 96-well (Thermo, Waltham, Mass.) microtiter ELISA plates pre-coated with either 50 ng/well of Aβ1-40 or Aβ1-42 in 50 mM ammonium bicarbonate solution pH 9.6 preincubated at RT for 6 and 24-48 hs respectively, as previously described (Goñi et al., "Immunomodulation Targeting Abnormal Protein Conformation Reduces Pathology in a Mouse Model of Alzheimer's Disease" *PLoS. ONE* 5:e13391 (2010), which is hereby incorporated by reference in its entirety). Bound antibodies were detected with horseradish peroxidase-labeled goat anti-mouse IgG (H+L) (GE Healthcare UK) or goat anti-mouse IgM(µ) (KPL Gaithersburg, Md., USA). The color developing substrate was Tetramethyl benzidine (TMB) (Pierce, Rockford, Ill.) and the readings were made at 450 nm. After the 7th inoculation, the M4 mouse was rested for 45 days before being injected intravenously (i.v.) with 10 µg of p13Bri without adjuvant; the terminal bleeding was performed 4 days later, before harvesting the spleen for fusion. The remaining animals were inoculated s.c. 5 more times, for a total of twelve inoculations, with 20 µg of p13Bri, rested for two and a half months at which time an i.v. injection of 10 µg of p13Bri with no adjuvant was given to all the animals. Terminal bleedings and spleen harvesting for fusion were performed 4 days later. The spleens of M1 and M2 and the spleens of M3 and M5 were combined for only two fusions.

TABLE 10

Protocol of Immunization of Mouse M4 with p13Bri for the Production of β-sheet Secondary Structure Conformational Antibodies Cross-Reacting to Oligomeric Forms of Proteins and Peptides Found in Neurodegenerative Diseases.

| Date of Inoculation (in days) | P13Bri Antigen Amount (µg/animal) | Antigen to Adjuvant Ratio* | Route of Inoculation | Identification of Bleed | Date of Bleed (in days) |
|---|---|---|---|---|---|
| — | NONE | n/a | NONE | Pre-Immune T0 | −7 |
| 0 | 50 | 4:1 | s.c. | — | — |
| 14 | 50 | 4:1 | s.c. | — | — |
| — | — | — | — | T1 | 21 |
| 28 | 20 | 9:1 | s.c. | — | — |
| — | — | — | — | T2 | 35 |
| 49 | 20 | 9:1 | s.c. | — | — |
| — | — | — | — | T3 | 56 |
| 69 | 20 | 9:1 | s.c. | — | — |
| — | — | — | — | T4 | 76 |
| 91 | 20 | 9:1 | s.c. | — | — |
| — | — | — | — | T5 | 98 |
| 119 | 20 | 9:1 | s.c. | — | — |
| — | — | — | — | T6 | 126 |
| 165 | 10 | no adjuvant | i.v. | — | — |
| 169 | Splenocytes fused to SP2/0-166** | — | — | TTB M4 | 169 |

*Sigma adjuvant system
SC: Subcutaneous;
IV: Intravenous;
**Fusion Partner;
TTB: Terminal bleeding.

TABLE 11

Protocol for the Immunization of CD-1 Mice (M1 to M5) with p13Bri for the Production of β-sheet Secondary Structure Anti-Conformational Antibodies

| Date of Inoculation (in days) | P13Bri Antigen (μg/animal)* | Antigen to Adjuvant Ratio** | Route of Inoculation | Identification of Bleed | Date of Bleed (in days) |
|---|---|---|---|---|---|
| — | — | — | — | Pre-Immune T0 | −7 |
| 0 | 50 | 4:1 | s.c. | — | — |
| 14 | 50 | 4:1 | s.c. | — | — |
| — | — | — | — | T1 | 21 |
| 28 | 20 | 9:1 | s.c. | — | — |
| — | — | — | — | T2 | 35 |
| 49 | 20 | 9:1 | s.c. | — | — |
| — | — | — | — | T3 | 56 |
| 69 | 20 | 9:1 | s.c. | — | — |
| — | — | — | — | T4 | 76 |
| 91 | 20 | 9:1 | s.c. | — | — |
| — | — | — | — | T5 | 98 |
| 119 | 20 | 9:1 | s.c. | — | — |
| — | — | — | — | T6 | 126 |
| 140 | 20 (no M4) | 9:1 | s.c. | — | — |
| — | — | — | — | T7 | 147 |
| 161 | 20 (no M4) | 9:1 | s.c. | — | — |
| — | — | — | — | T8 | 168 |
| 165 | 10 (only M4) | no adjuvant | i.v. | — | — |
| 169 | M4 Fusion to SP2/0-166*** | — | — | terminal bleeding M4 | 169 |
| 181 | 20 | 9:1 | s.c. | — | — |
| — | — | — | — | T9 | 189 |
| 201 | 20 | 9:1 | s.c. | — | — |
| — | — | — | — | T10 | 208 |
| 258 | 20 | 9:1 | s.c. | — | — |
| — | — | — | — | T11 | 265 |
| 332 | 10 (M1, M2, M3, M5) | no adjuvant | i.v. | — | — |
| 336 | M1 + M2 Fused SP2/0-IL6*** | — | — | TTB M1, M2, M3, M5 | 336 |
| 338 | M1 + M5 Fused SP2/0-IL6*** | — | — | TTB M1, M2, M3, M5 | 336 |
| — | — | — | — | M1 + M2 Frozen | 341 |
| — | — | — | — | M3 + M5 Frozen | 341 |

*All animals inoculated unless indicated.
**Alum M1, M2;
Sigma adjuvant system: M3, M4, M5.
s.c.: subcutaneous.
i.v.: intravenous.
TTB: Terminal bleeding.
***Fusion partner Monoclonal Production.

Mouse M4 was sacrificed 169 days after the first inoculation. The spleen was taken and splenocytes were gently dislodged and fused to SP2/0-IL6 cells (ATCC® CRL2016™) using Polyethylene Glycol 1500 (Sigma-Aldrich St. Louis, Mo.). Fusion mixture was recovered overnight at 3 million pre-fusion viable cells per ml. Half of the fusion was cryopreserved and from the other half cells were plated the following day in a 96-well plate at 75,000 pre-fusion viable nucleated splenocytes per well at a final volume of 200 μl/well. Cells were cultured for 7 days, then the cells were fed and after 3 days screenings began. The media used was Gibco® Hybridoma-SFM (Fisher Scientific, USA); 15% Fetal Bovine Serum, Hybridoma Fusion and Cloning supplement (HFCS) (Sigma-Aldrich, St. Louis, Mo.) −2× for the fusion and selection in HAT and 1× during the screening-; 1× Gibco® HT Supplement (Fisher Scientific, Waltham, Mass.), 10 μg Gentamicin sulfate/nil (Fisher Scientific, Waltham, Mass.). The cloning protocol was a serial dilution done in a 96-well plate, and screening of wells with only one colony. To assess for the presence of possible conformational antibodies in any step of the screening and cloning, approximately 125 μL of cell supernatants were diluted 1:1 with TBS-T and 50 μL/well applied to Immulon 2HB 96-well (Thermo, Waltham, Mass.) microtiter ELISA plates pre-coated with either Aβ1-40, Aβ1-42, PrPRes or purified human paired helical filaments (PHF) from an AD subject, in a 50 mM ammonium bicarbonate solution pH 9.6 as previously described (Goñi et al., "Immunomodulation Targeting Abnormal Protein Conformation Reduces Pathology in a Mouse Model of Alzheimer's Disease" *PLoS. ONE* 5:e13391 (2010), and Goñi et al., "Immunomodulation Targeting both Aβ and tau Pathological Conformers Ameliorates Alzheimer's Disease Pathology in TgSwD1 and 3×Tg mouse models" *Journal of Neuroinflammalion* 10:150 (2013), both of which are hereby incorporated by reference in their entirety). Bound antibodies were detected with horseradish peroxidase-labeled goat anti-mouse IgG+IgA+IgM(H+L) (KPL, Gaithersburg, Md., USA). The color developing substrate was Tetramethyl benzidine (TMB) (Pierce, Rockford, Ill.) and the readings were made at 450 nm.

Samples that were positive for more than one antigen (positivity being defined as a titer more than three times over the background) were cloned again using the same procedure, followed by testing after three days growth. All clones positive for more than one antigen three times were cultured in 5 ml tubes until saturation. The tubes were centrifuged at 3,000×g for 10 minutes at 4° C.; supernatants were kept and the pelleted cells were divided into at least four vials containing 2×10⁶ cells in 0.5 mL of media diluted in half in DMSO, and cryopreserved in liquid nitrogen for storage and future expansion.

Mice M1, 2, 3 and 5 were sacrificed 332 days after the first inoculation. The splenocytes of mice M1 and M2 and the splenocytes of mice M3 and M5 were combined in equal ratios for two fusions as above described and cryopreserved for future use.

Partial Purification of Monoclonal Antibodies.

Monoclonal antibodies present in the supernatants obtained after the fusion of the splenocytes of M4 CD-1 mouse and partner cells SP2/0-IL6, with cloning by serial dilutions, were partially purified by precipitation with Saturated Ammonium Sulfate (SAS) −761.5 g/Lt at 21° C. (Berasain et al., "*Fasciola Hepatica*: Parasite-Secreted Proteinases Degrade All Human IgG Subclasses: Determination of the Specific Cleavage Sites and Identification of the Immunoglobulin Fragments Produced" *Exp Parasitol* 94:99-110 (2000), which is hereby incorporated by reference in its entirety). Samples were made 40% in the SAS, incubated at RT for at least 4 hours, centrifuged at 14,000×g for 15 minutes, the supernatant separated and the precipitate washed with a comparable volume of 40% SAS, centrifuged again and the supernatant pooled with the initial supernatant. The precipitate was fractionated and kept at 4° C. until further use. To assess the partial purification of the monoclonals and the specific reactivity, aliquots were dissolved directly into tricine sample buffer (BioRad, Hercules Calif.) and electrophoresed at ~1-2 μg/lane. The samples for antibody activity were dissolved in distilled deionized water (DDW) to half the original volume and subsequently brought to the desired dilution with the appropriate buffers for the technique.

Oligomerization of Neurodegenerative Antigens.

Human tissue related studies were performed under a protocol approved by the Institutional Review Board at New York University School of Medicine. In all cases, written informed consent for research was obtained from the patient or legal guardian, and the material used had appropriate ethical approval for use in this project. All patients' data and samples were coded and handled according to NIH guidelines to protect patients' identities.

Antigens known to be relevant in different neurodegenerative diseases, i.e. Aβ1-40 and Aβ1-42 (amyloidogenic in Alzheimer's Disease [AD] and other dementia), α-synuclein (Parkinson disease [PD] and Lewy Body Dementia), prion protein (PrPRes) (in prion disease) were polymerized to stable oligomeric states by the same glutaraldehyde methodology used to produce the p13Bri (Goñi et al., "Immunomodulation Targeting Abnormal Protein Conformation Reduces Pathology in a Mouse Model of Alzheimer's Disease" *PLoS. ONE* 5:e13391 (2010), and Goñi et al., "Immunomodulation Targeting both Aβ and tau Pathological Conformers Ameliorates Alzheimer's Disease Pathology in TgSwDI and 3×Tg mouse models" *Journal of Neuroinflammation* 10:150 (2013), both of which are hereby incorporated by reference in their entirety). To produce stable fibrils 1 mg/ml of either synthetic Aβ1-40, Aβ1-42 and α-synuclein peptides were incubated in PBS pH 7.2 at 37° C. for at least 72 hours, until most of the peptide produced fibrils as determined by EM. Recombinant deer PrP was incubated in 50 mM Tris buffer pH 7.4 to obtain aggregated species. Oligomeric/aggregated tau was obtained by purifying PHF from known cases of human Alzheimer's disease, who fulfilled the National Institute of Aging-Reagan criteria for AD, obtained from the Alzheimer Brain Bank of the Alzheimer's Disease Center at NYU, as previously described (Goñi et al., "Immunomodulation Targeting Abnormal Protein Conformation Reduces Pathology in a Mouse Model of Alzheimer's Disease" *PLoS. ONE* 5:e13391 (2010), and Wrzolek et al., "Immune Electron Microscopic Characterization of Monoclonal Antibodies to Alzheimer Neurofibrillary Tangles" *Am J Pathol* 141:343-355 (1992), which are both hereby incorporated by reference in their entirety). Briefly, 30 gm of frontal cortex was homogenized in 75 ml of 50 mM Tris-buffered saline (TBS), pH 7.4 using an Ultra Turrox T25 tissue homogenizer (IKA Works, Inc; Staufen, Germany). 75 ml of 20% sarcosyl in H2O was added to the sample and it was homogenized again. The homogenized material was centrifuged at 3,500 rpm in a Beckman GPR centrifuge and 6 ml aliquots of the supernatant were each layered over 1 ml TBS/0.1% sulfobetaine 3-14 (SB3-14) (Sigma-Aldrich, St Louis, Mo.) and centrifuged in an Optima Max ultracentrifuge at 75,000 rpm for 2 hours at 20° C. Each pellet was resuspended by sonication in 1 ml of 10% NaCl in TBS/0.1% SB3-14 followed by the addition of 6 ml of 10% NaCl in TBS/0.1% SB3-14, layered over 1 ml of 20% sucrose in 10% NaCl TBS/0.1%5B3-14 and centrifuged at 75,000 rpm for 1.5 hours at 20° C. The final pellets were resuspended in TBS by sonication prior to use. Purified PHF was also treated with proteinase K (Sigma-Aldrich, USA) to release oligomers from fibrils, at 1:100 in PBS pH 7.2 for 30 minutes at 37° C., immediately quenched with phenylmethanesuphonyl fluoride (PMSF) and either immediately dissolved in sample buffer for use in blots or frozen at −80° C. for future use.

Electron Microscopy.

Electron microscopy images, using negative staining, to assess the conformational states of monomeric, oligomeric or fibrillar forms of the aggregated and polymerized ABri, p13Bri, Aβ1-40 and Aβ1-42, α-synuclein, PHF and PrP were done as previously described and were taken at the NYULMC OCS Microscopy Core (Goñi et al., "Immunomodulation Targeting both Aβ and tau Pathological Conformers Ameliorates Alzheimer's Disease Pathology in TgSwDI and 3×Tg Mouse Models" *Journal of Neuroinflammation* 10:150 (2013), which is hereby incorporated by reference in its entirety). Samples were diluted 1 mg/ml in PBS pH 7.4 and vortexed before 3 μl of each one were placed onto carbon coated 400 mesh Cu/Rh grid (Ted Pella Inc., Redding, Calif.). Negative staining was performed using 1% uranyl acetate diluted in distilled water (Polysciences, Inc, Warrington, Pa.). Stained grids were examined under Philips CM-12 electron microscope and photographed with a Gatan (4 k×2.7 k) digital camera. In most cases samples were kept for weeks or months to repeat the EMs at different times to follow the fibrillization or the stability of the oligomers.

Immunohistochemistry.

Histology was performed on aged (>16 months old) 3×Tg (Odo et al., "Triple-Transgenic Model of Alzheimer's Disease with Plaques and Tangles: Intracellular Abeta and Synaptic Dysfunction" *Neuron* 39:409-421 (2003), which is hereby incorporated by reference in its entirety) mouse brain sections with extensive Aβ and tau pathology; or formalin fixed paraffin embedded brain cortex sections of human AD, human age-matched controls and human young controls obtained from the Alzheimer Brain Bank of the Alzheimer's Disease Center at NYU. 40 μm mouse brains sections fixed with periodate-lysine-paraformaldehyde (PLP), kept in DMSO cryoprotectant, were washed three times for 5 minutes with PBS pH 7.2 and twice for 15 min with 0.3% hydrogen peroxide to quench endogenous peroxidase activity. Sections were then blocked with MOM kit Blocking solution (Vector Laboratories, Burlingame, Calif.) following the manufacture's protocol and incubated overnight with conformational hyperimmune 3×Tg or CD-1 (M4) mouse plasma diluted 1:300 in MOM kit Diluent Solution. The following day, sections were washed three times with PBS and incubated 1 hour with biotinylated anti-mouse IgG (H+L) or anti-mouse IgM (µ specific chain) antibodies (Vector Laboratories, Burlingame, Calif.) diluted in PBS 1:1000 followed by 1 hour incubation of Vectastain® Aβ solution (Vector Laboratories, Burlingame, Calif.) as indicated by the manufacturer's protocol. Slides were developed with 3,3-diaminobenzidine tetrahydrochloride with 2.5% nickel ammonium sulfate (Acros Organics, NJ) diluted in 0.2M sodium acetate (NaAc) pH 6. The reaction was stopped by removal of the nickel solution and extensively rinsing with 0.2M NaAc before stabilizing with PBS and further mounting on glass slides with Depex® Mounting Media (Electron Microscopy Sciences, Hatfield, Pa.).

Paraffin embedded human brain sections were dewaxed and rehydrated with successive washes of xylene (2×5 minutes), 100% ethanol (2×5 minutes), 95% ethanol (5 minutes), 70% ethanol (5 minutes) and PBS (5 minutes). Next, slides underwent antigen retrieval by boiling for 20 minutes in 10 mM sodium citrate-0.05%-Tween20 pH 6.0. Sections were then washed with PBS (3×5 minutes), followed by 0.3% hydrogen peroxide washing, twice 15 minutes each. Next slides were washed with PBS (3×5 minutes) and blocked 1 hour at RT with 10% normal goat serum [NGS] (Thermo Scientific)-0.2% Triton X-100 (Sigma-Aldrich, St Louis, Mo.) in PBS. Slides were incubated overnight with the plasmas of hyperimmune 3×Tg or CD-1 (M4) mice diluted 1:300 in 3% NGS-0.2% Triton X-100. Slides were then washed three times with PBS and incubated for 1 hour with biotinylated anti-mouse IgM (µ specific chain) antibody diluted 1:1000 in PBS followed by 1 hour incubation of Vectastain® Aβ solution. Slides were further developed with 3,3-diaminobenzidine tetrahydrochloride with nickel ammonium sulfate as described above.

To assess the reactivity of the hybridoma derived monoclonal antibodies obtained after the fusion, Human brain sections were treated as above described but no antigen retrieval was performed. Monoclonal antibodies 23B7, 12E9, 10E8 and 10F7 were used with a dilution of 1:2500 and monoclonal antibody 3D7 was used at 1:3000.

For immunofluorescence, paraffin embedded human AD brain slides were dewaxed and rehydrated as described above, then blocked for 1 hour at RT with 10% NGS-0.2% Triton X-100 in PBS and then incubated overnight at 4° C. with plasma of a CD-1 (M4) mouse hyperimmunized with p13pBri, diluted 1:300 in PBS-T. Slides were then washed with PBS (3×5 minutes) and incubated 2 hours with Alexa Fluor® 488-conjugated goat anti-mouse IgM and Alexa Fluor® 647-conjugated goat anti-mouse IgG (Jackson ImmunoResearch, West Groove, Pa.) both diluted 1:500 in PBS, followed by 10 minutes incubation with bisBenzimide H 33342 trihydrochloride (Sigma-Aldrich, St. Louis, Mo.) diluted 1 µl/ml. Slides were then washed in PBS (3×5 minutes) and coverslipped with PermaFluor™ Aqueous Mounting Medium (Thermo Scientific, Waltham, Mass.).

All slides were first screened on a Leica DM LB 100T microscope, than scanned using a Hamamatsu Nanozoomer 2.0HT Digital Slide Scanner (Hamamatsu, Shizuoka Prefecture, Japan) at the NYU OCS Experimental Pathology Histology Core. The images were viewed using the Slidepath software (Leica, Wetzlar, Germany).

Electrophoresis and Western Blot.

To characterize the monoclonal antibodies obtained after the fusion and cloning, 1 µg of each antibody were mixed with an equal volume of tricine sample buffer, electrophoresed on Bolt™ 4-12% Bis-Tris gels and buffer (Thermo, Waltham, Mass.) under non-reducing conditions and transferred onto nitrocellulose membranes for 1 hour at 386 mA in 0.1% 3-(Cyclohexylamino)-1-propanesulfonic acid (CAPS) (Sigma-Aldrich, St. Louis, Mo.)-10% methanol. To assess equal protein loading in each lane, membranes were stained for 1 min with reversible 0.1% Fast Green FCF (Sigma-Aldrich CO, USA), as per the manufacturer's instructions, in 25% methanol-10% Acetic Acid. The background was de-stained with rapid changes of 25% methanol, followed by transfer to distilled water before scanning on a Canon F916900 scanner Canon Inc, China). Membranes were then washed in TBS-T for at least 15 minutes (until the reversible stain was removed from the proteins on the membrane), blocked with 5% non-fat dry milk in TBS-T pH 8.3, for 1 h at RT, washed three times with TBS-T, and then incubated 45 minutes with anti-mouse µ chain specific diluted 1:8000 (KPL, Gaithersburg, Md.) or anti-mouse Kappa diluted 1:5000 (Southern Biotech, Birmingham, Ala.). Bound antibodies were detected with the ECL detection system (Pierce, Rockford, Ill.) on autoradiography films (MIDSCI, St Louis, Mo.).

To determine the reactivity of the anti-conformational monoclonal antibodies to Aβ1-40, Aβ1-42, α-synuclein, PHF, PrP$^{Res}$, 22 L, sheep scrapie and deer PrP, each peptide or protein was loaded 1-2 µg/lane and electrophoresed on Bolt™ 4-12% Bis-Tris gels (Thermo, Waltham, Mass.) under non-reducing conditions using 3 µl of High range Rainbow™ molecular weight marker (Amersham Biosciences, Piscataway, N.J.) and later transferred onto nitrocellulose membranes for 1 hour at 386 mA in 0.1% CAPS-10% methanol. To assess the protein loading in each lane, the membranes were first stained with reversible 0.1% Fast Green FCF as described above. Membranes were scanned before being blocked with 5% non-fat dry milk in TBS-T pH 8.3, for 1 h at RT and washed three times with TBS-T. Membranes were then incubated with each monoclonal antibody, diluted 1:750 in TBS-T, or monoclonal anti-Aβ antibodies 4G8/6E10 (1:4000) (BioLegend, San Diego, Calif.), monoclonal anti-α-synuclein Ab-2 (1:3000) (Thermo, Waltham, Mass.), PHF-1 (1:2000) (which recognizes phosphorylated serine in positions 396 and 404, kindly provided by Dr. Peter Davies from the Feinstein Institute for Medical Research, Manhasset, N.Y.) or anti-PrP antibodies 7D9/6D11 (1:8000) (BioLegend, San Diego, Calif.).

Membranes were incubated later with peroxidase-linked anti-mouse IgG (GE Healthcare UK) (1:4000) for anti-α-synuclein, PHF-1 and 7D9/6D11. To detect bound monoclonal antibodies anti-mouse µ chain specific was used diluted at 1:8000 (KPL, Gaithersburg, Md.).

Results.

The ABri peptide selected as an immunogen is only 13 amino acids long with no sequence homology to any known mammalian protein. It can adopt a ß-sheet secondary structure and, by aggregation, form protofibrils evolving into an amyloid fibrillar form (FIG. 1B, lower pathway and FIGS. 2A-2D). To avoid fibril formation that previously complicated the immune response in humans, glutaraldehyde was selected for cross-linking polymerization. The ABri has two preferential Lysyl residues at positions 6 and 7 amenable to the covalent linkage of more than one unit through a glutaraldehyde bridge (Goñi et al., "Immunomodulation Targeting Abnormal Protein Conformation Reduces Pathology in a Mouse Model of Alzheimer's Disease" *PLoS. ONE* 5:e13391 (2010), and Goñi et al., "Immunomodulation Targeting both Aβ and tau Pathological Conformers Ameliorates Alzheimer's Disease Pathology in TgSwDI and 3×Tg Mouse Models" *Journal of Neuroinflammation* 10:150

(2013), which are both hereby incorporated by reference in their entirety). However, the free $NH_2$ group from the amino-terminus of a very small peptide, or the two adjacent Lysyl residues could be prone to form a Schiff base with the glutaraldehyde preventing further association (Moore et al., "Biophysical Analyses of Synthetic Amyloid-Beta(1-42) Aggregates Before and After Covalent Cross-Linking. Implications for Deducing the Structure of Endogenous Amyloid-Beta Oligomers" *Biochemistry* 48:11796-11806 (2009), and Migneault et al., "Glutaraldehyde: Behavior in Aqueous Solution, Reaction with Proteins, and Application to Enzyme Crosslinking" *Biotechniques* 37:790-796, 798-802 (2004), which are both hereby incorporated by reference in their entirety). Thus, a mild alkaline pH was selected for the reaction to stabilize the lysines net charge and maximize separation by charge repulsion, a high temperature and high rpm shaking was utilized to avoid stabilizing a blocked monomeric structure during the chemical reaction, a buffer with no phosphate or Tris groups that could interfere with the progression of oligomerization was selected, and a glutaraldehyde concentration to equalize the ratio of long self-polymerized glutaraldehyde chains versus the joining of two or more ABri peptides was selected (Goñi et al., "Immunomodulation Targeting Abnormal Protein Conformation Reduces Pathology in a Mouse Model of Alzheimer's Disease" *PLoS. ONE* 5:e13391 (2010), Goñi et al., "Immunomodulation Targeting both Aβ and tau Pathological Conformers Ameliorates Alzheimer's Disease Pathology in TgSwDI and 3×Tg Mouse Models" *Journal of Neuroinflammation* 10:150 (2013), and Migneault et al., "Glutaraldehyde: Behavior in Aqueous Solution, Reaction with Proteins, and Application to Enzyme Crosslinking" *Biotechniques* 37:790-796, 798-802 (2004), which are each hereby incorporated by reference in their entirety). Nevertheless, some monomers, dimers and trimers were formed as detected in gels by protein stain or specific antisera (FIG. 1B, green pathway, EM, CD and blot of FIGS. 2A-2D). These lower molecular weight forms still consisted of a predominant β-sheet secondary structure, but never aggregate into fibrils. The rest of the covalently linked oligomers distributed between 10 and 100 kDa, remained stable for very long periods of time, never forming potentially cross-seeding fibrils. This resulting p13Bri immunogen is composed from many intermediate size covalently linked oligomers with a high number of repetitions of the small 13mer motif in a predominant ß-sheet secondary structure (FIGS. 1A-1C and FIGS. 2A-2D).

The previously published p13Bri vaccine inoculated with Aluminum Hydroxide (Alum) as an adjuvant produced a mild polyclonal response to pathologic oligomeric forms present in three mouse models of AD; i.e., Tg APP/PS1 (with mainly amyloid plaques), Tg SwDI (with extensive vascular amyloid), and 3×Tg APP/PS1 P301L (with combined Aβ and tau pathologies) (Wisniewski et al. "Immunotherapeutic Approaches for Alzheimer's Disease" *Neuron* 85:1162-1176 (2015), Goñi et al., "Immunomodulation Targeting Abnormal Protein Conformation Reduces Pathology in a Mouse Model of Alzheimer's Disease" *PLoS. ONE* 5:e13391 (2010), and Goñi et al., "Immunomodulation Targeting both Aβ and tau Pathological Conformers Ameliorates Alzheimer's Disease Pathology in TgSwDI and 3×Tg Mouse Models" *Journal of Neuroinflammation* 10:150 (2013), which are each hereby incorporated by reference in their entirety) that most probably was not enough to obtain sufficient B-cells with the desired paratopes of the monoclonal antibodies obtained herein. Nevertheless, for the prevention therapy the small polyclonal response was sufficient as proved in all three AD mouse models, where AD pathology was greatly reduced and cognitive rescue was achieved by early vaccination (Wisniewski et al. "Immunotherapeutic Approaches for Alzheimer's Disease" *Neuron* 85:1162-1176 (2015), Goñi et al., "Immunomodulation Targeting Abnormal Protein Conformation Reduces Pathology in a Mouse Model of Alzheimer's Disease" *PLoS. ONE* 5:e13391 (2010), and Goñi et al., "Immunomodulation Targeting both Aβ and tau Pathological Conformers Ameliorates Alzheimer's Disease Pathology in TgSwDI and 3×Tg Mouse Models" *Journal of Neuroinflammation* 10:150 (2013), which are each hereby incorporated by reference in their entirety). To reproduce the successful immune response, increase the sustainable antibody concentration for monoclonal production purposes, and avoid possible interference from the transgenes of the AD mouse models, 5 wild type CD-1 mice were inoculated with a modified protocol, including some with a RiBi-like Sigma adjuvant to enhance the antibody immune response (See Table 11).

Figures 3A, 3B, 3C:
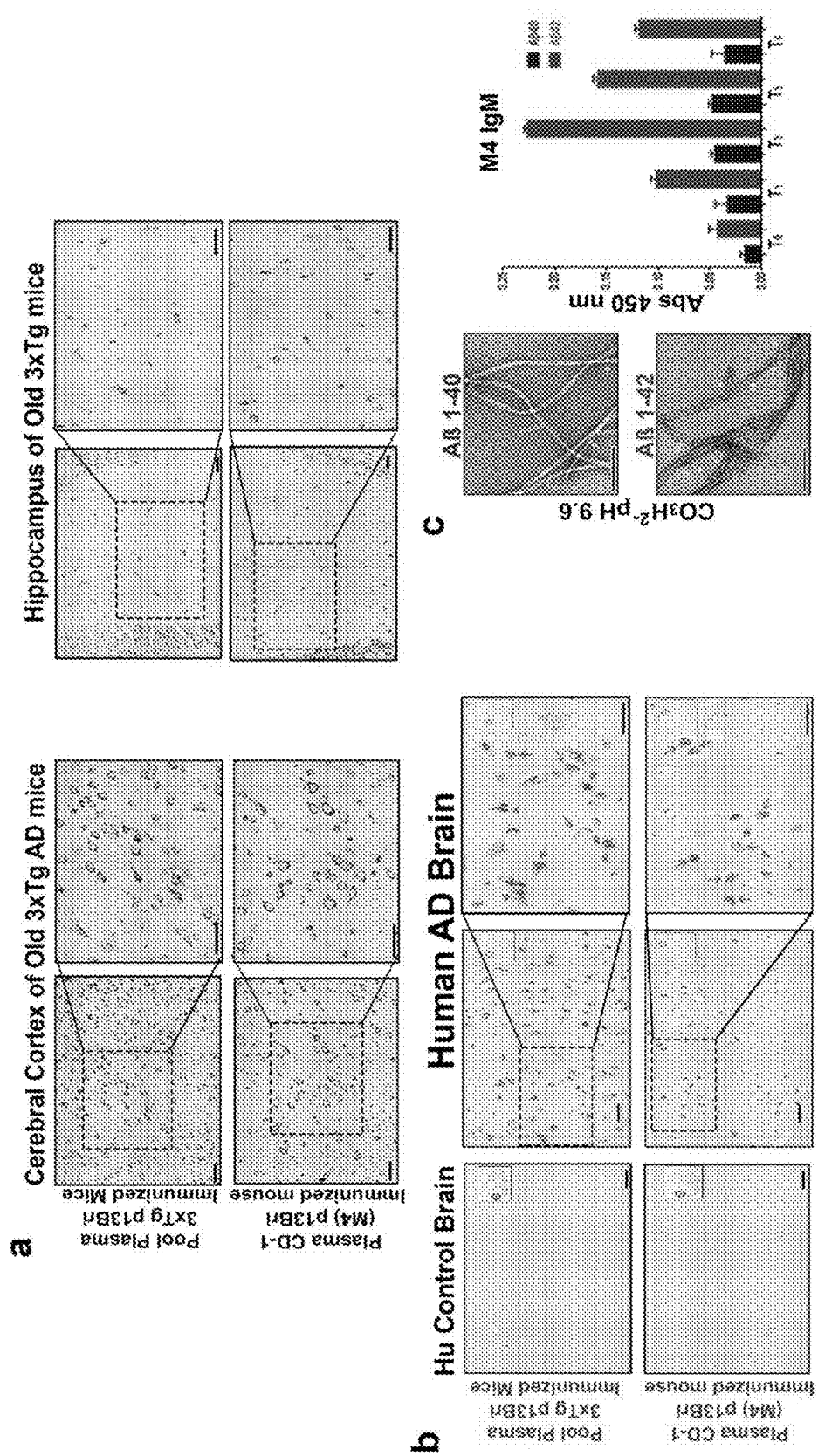
FIGS. 3A-3C depicts immunochemistry of plasma from p13Bri immunized 3×Tg AD mice and CD-1 M4 mouse on old 3×Tg AD mouse model brains, human AD and control brains; and immunoreactivity of M4 plasma on Aβ40/42 ELISA.
Figures 4A, 4B, 4C:
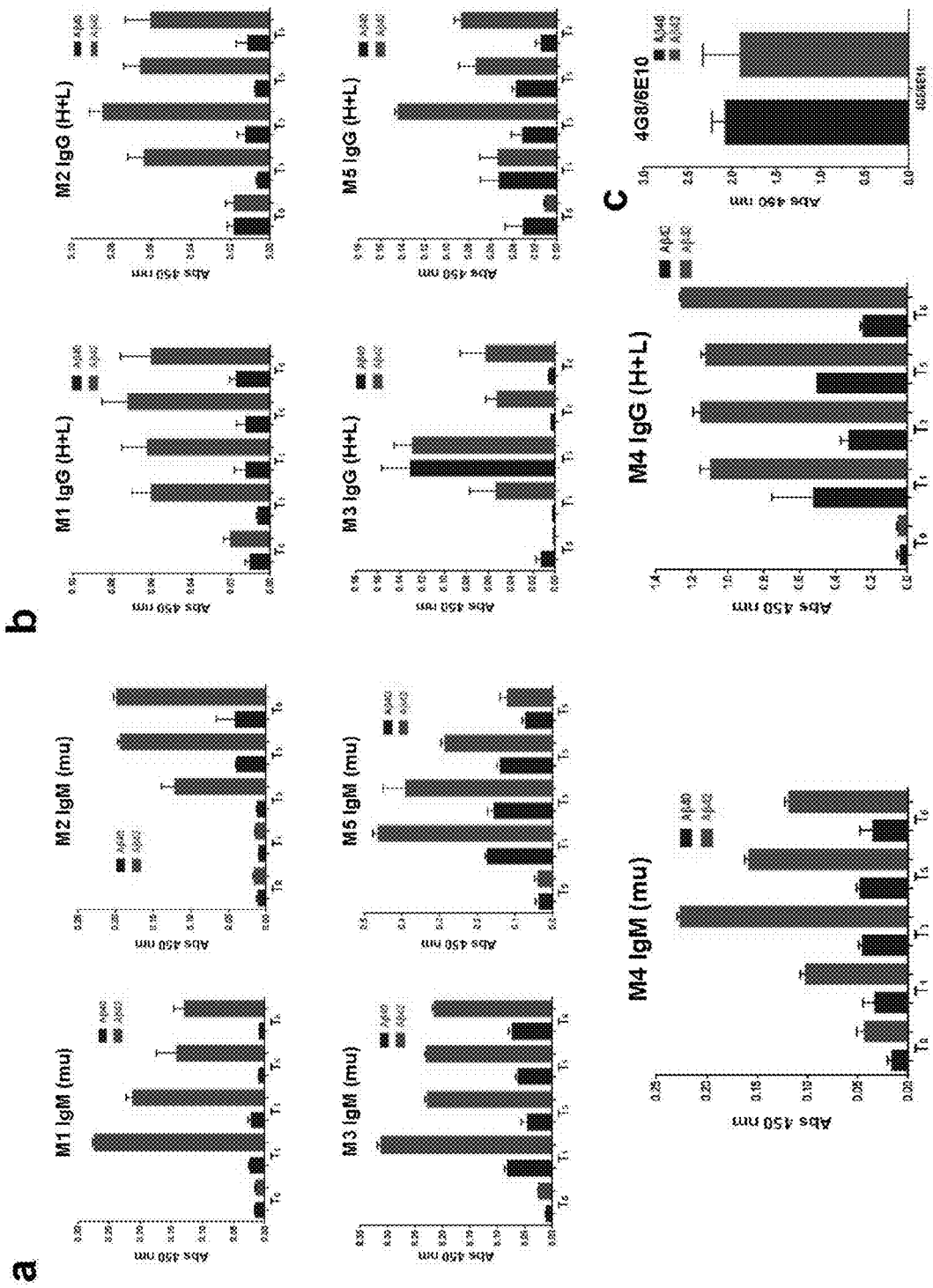
FIGS. 4A-4C depict plasma levels of Anti-Aβ 1-40 and Anti-Aβ 1-42 from p13Bri inoculated CD-1 mice.

The elicited polyclonal antibody response was analyzed by ELISA with differential Aβ1-40 and Aβ1-42 coats known to develop β-sheet aggregation (Goñi et al., "Immunomodulation Targeting Abnormal Protein Conformation Reduces Pathology in a Mouse Model of Alzheimer's Disease" *PLoS. ONE* 5:e13391 (2010), and Goñi et al., "Immunomodulation Targeting both Aβ and tau Pathological Conformers Ameliorates Alzheimer's Disease Pathology in TgSwDI and 3×Tg Mouse Models" *Journal of Neuroinflammation* 10:150 (2013), which are both hereby incorporated by reference in their entirety). Each Aβ peptide was dissolved in bicarbonate buffer pH 9.6 and left at RT to age; the Aβ1-40 for a few hours before coating and the Aβ1-42 for at least two days before coating; enough in both cases to establish aggregation and fibrillization. EM analysis of both Aβ peptides after aging, documented fibril formation; however, because of the high pH, a significant number of stable oligomeric forms surrounded the fibrils of Aβ1-42 at a higher concentration per area than with the Aβ1-40 fibrils (FIG. 3C). Even after using a completely different adjuvant and a strong regime of inoculations (shown on Table 10 and 11) the antibody quality of the polyclonal IgM and IgG responses obtained in CD-1 animals were similar to the ones reported in the 3×Tg inoculated animals but more robust, raising the possibility of having enough B-cells with the desired paratopes that could be derived into stable hybridoma cells (Goñi et al., "Immunomodulation Targeting both Aβ and tau Pathological Conformers Ameliorates Alzheimer's Disease Pathology in TgSwDI and 3×Tg Mouse Models" *Journal of Neuroinflammation* 10:150 (2013), which is hereby incorporated by reference in its entirety), and could distinguish the misfolded peptides and the differential concentration of oligomeric forms in both of them, with a much higher titer against Aβ1-42 versus Aβ1-40 (FIG. 3C and FIGS. 4A-4B). The control to assess for equal coating of both Aβ peptides was determined with two commercial IgG anti-Aβ primary structure monoclonal antibodies (mAbs) 4G8 and 6E10, that have similar reactivity for both Aβ1-40 and Aβ1-42 (FIG. 4C), demonstrating the differential data obtained from p13Bri immunized animals depended on the recognition of misfolded oligomeric forms (present at a higher concentration in the Aβ1-42 preparation) rather than an unspecific cross-reaction to the primary structure of the peptides used for plate coating.

Figures 5A, 5B:
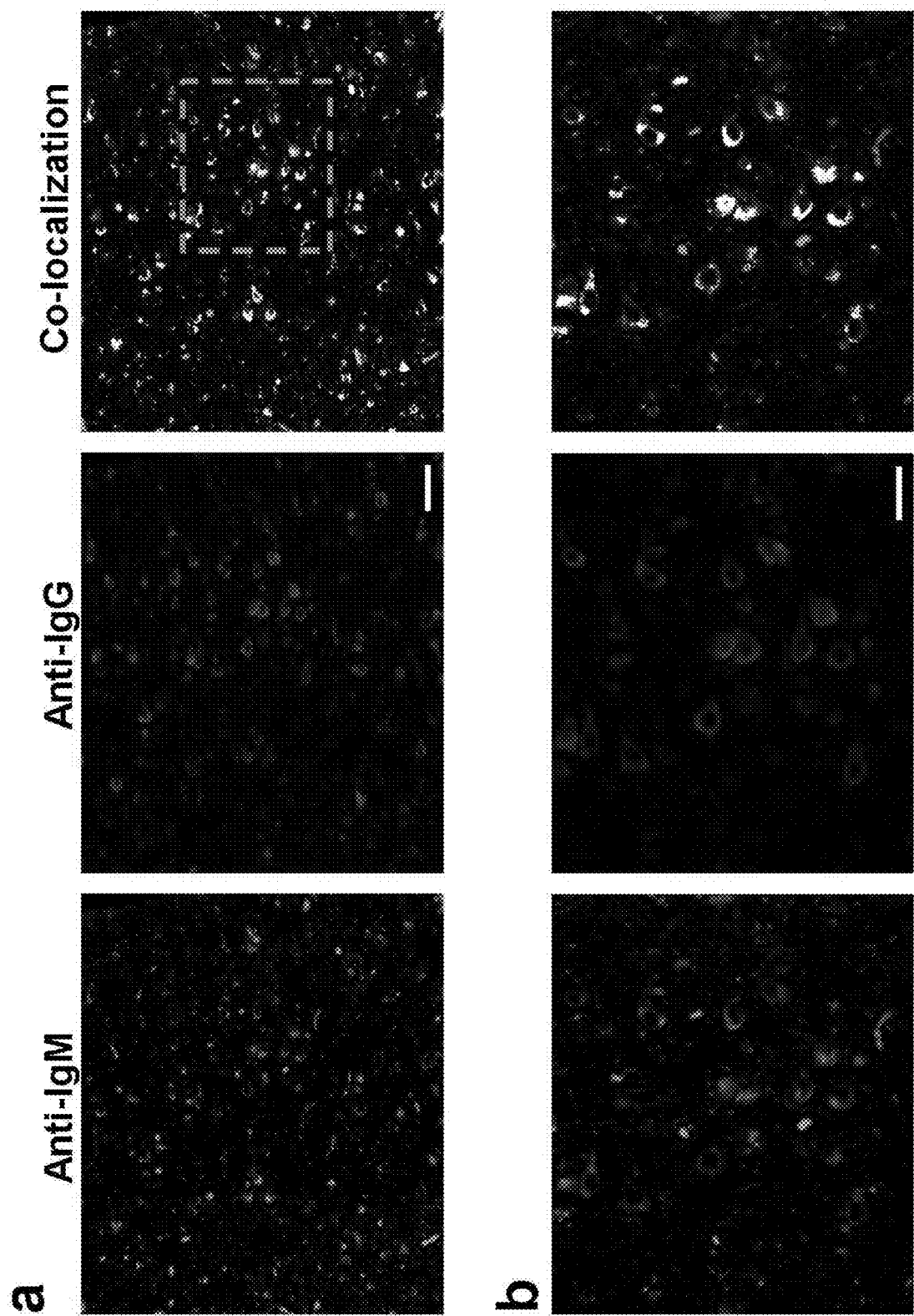
FIGS. 5A-5B depict co-localization on human AD brains of IgM and IgG antibodies present in the plasma of the p13Bri inoculated CD-1 M4 mouse.

By immunohistochemistry the plasma of the CD-1 inoculated animals as well as the previously reported pooled plasma from successfully vaccinated animals recognized similar neuronal cytoplasmic and extracellular material in the cerebral cortex and hippocampus of untreated old 3xTg mice with extensive amyloid-β and tau pathologies (FIG. 3A) (Goñi et al., "Immunomodulation Targeting Abnormal Protein Conformation Reduces Pathology in a Mouse Model of Alzheimer's Disease" *PLoS. ONE* 5:e13391 (2010), and Goñi et al., "Immunomodulation Targeting both Aβ and tau Pathological Conformers Ameliorates Alzheimer's Disease Pathology in TgSwDI and 3xTg Mouse Models" *Journal of Neuroinflammation* 10:150 (2013), which are both hereby incorporated by reference in their entirety). The same plasma samples were used to immunolabel the temporal cortex of human AD brains. Both the plasma of previously vaccinated animals (Goñi et al., "Immunomodulation Targeting Abnormal Protein Conformation Reduces Pathology in a Mouse Model of Alzheimer's Disease" *PLoS. ONE* 5:e13391 (2010), and Goñi et al., "Immunomodulation Targeting both Aβ and tau Pathological Conformers Ameliorates Alzheimer's Disease Pathology in TgSwDI and 3xTg Mouse Models" *Journal of Neuroinflammation* 10:150 (2013), which are both hereby incorporated by reference in their entirety) and the plasma from p13Bri immunized CD-1 mice recognized comparable intracellular and extracellular pathologic features in human AD sections but showed no significant immunolabeling in the cerebral cortex of human control brains with no AD pathology (FIG. 3B). Both IgM and IgG antibodies from the CD-1 animals co-localized with the same pathological structures in human AD brains (FIG. 5A-5B).

To test the feasibility of producing hybridomas with specific anti-β-sheet secondary structure, the CD-1 animal M4 that had the best IgM and IgG polyclonal response to β-sheet oligomers was selected (FIGS. 3A-3C and FIGS. 4A-4C). The protocol of the M4 p13Bri inoculations and fusion used for subsequent hybridoma production is shown in Table 10 and is described in herein.

After fusion of the M4 mouse spleen cells to the SP2/0-IL6 partner cells, the fused cells and the viable hybridomas were selected by incubation and serial dilution as per Table 10 and the Monoclonal Production method described herein.

The anti-β-sheet secondary structure selection process was novel for monoclonal production and involved the simultaneous detection of reactivity of plated viable hybridomas with four different NDD conformers. The small availability, in each round, of cell supernatant from three days growth of a limited number of hybridoma cells in 96 well plates required a sensitive ELISA differential analysis. The concentration of Aβ oligomers around fibrils of Aβ1-40 and Aβ1-42 samples was described above (FIG. 3C) and required two separate ELISA plates for analysis. Two additional ELISA plates were added, one plated with PHF extracted from a human AD brain and treated to maximize the number of clusters of β-sheet oligomeric conformers around fibrils (FIGS. 6A and 7A) that are expected to be associated with β-sheet steric zippers characteristic of toxic oligomerization before they become buried in fibril structures (Sawaya et al., "Atomic Structures of Amyloid Cross-Beta Spines Reveal Varied Steric Zippers" *Nature* 447:453-457 (2007), and Avila et al., "Tau Structures" *Front Aging Neurosci* 8:262 (2016), which are both hereby incorporated by reference in their entirety). The other ELISA was plated with aged elk recombinant PrP produced in *E. coli*, which has properties resembling PrP$^{Res}$ with oligomerization and exposed β-sheet motifs, without the extended β-sheet structure characteristic of amyloidogenic and infectious PrP$^{Sc}$ (FIGS. 6B, 7A, and 7D) (Cobb et al., "Conformational Stability of Mammalian Prion Protein Amyloid Fibrils is Dictated by a Packing Polymorphism Within the Core Region" *J Biol Chem* 289:2643-2650 (2014), Ostapchenko et al., "Two Amyloid States of the Prion Protein Display Significantly Different Folding Patterns" *J Mol Biol* 400:908-921 (2010), Lauren et al., "Cellular Prion Protein Mediates Impairment of Synaptic Plasticity by Amyloid-Beta Oligomers" *Nature* 457:1128-1132 (2009), and Wiltzius et al., "Molecular Mechanisms for Protein-Encoded Inheritance" *Nat Struct Mol Biol* 16:973-978 (2009), each of which is hereby incorporated by reference in its entirety).

Figures 7A, 7B, 7C, 7D:
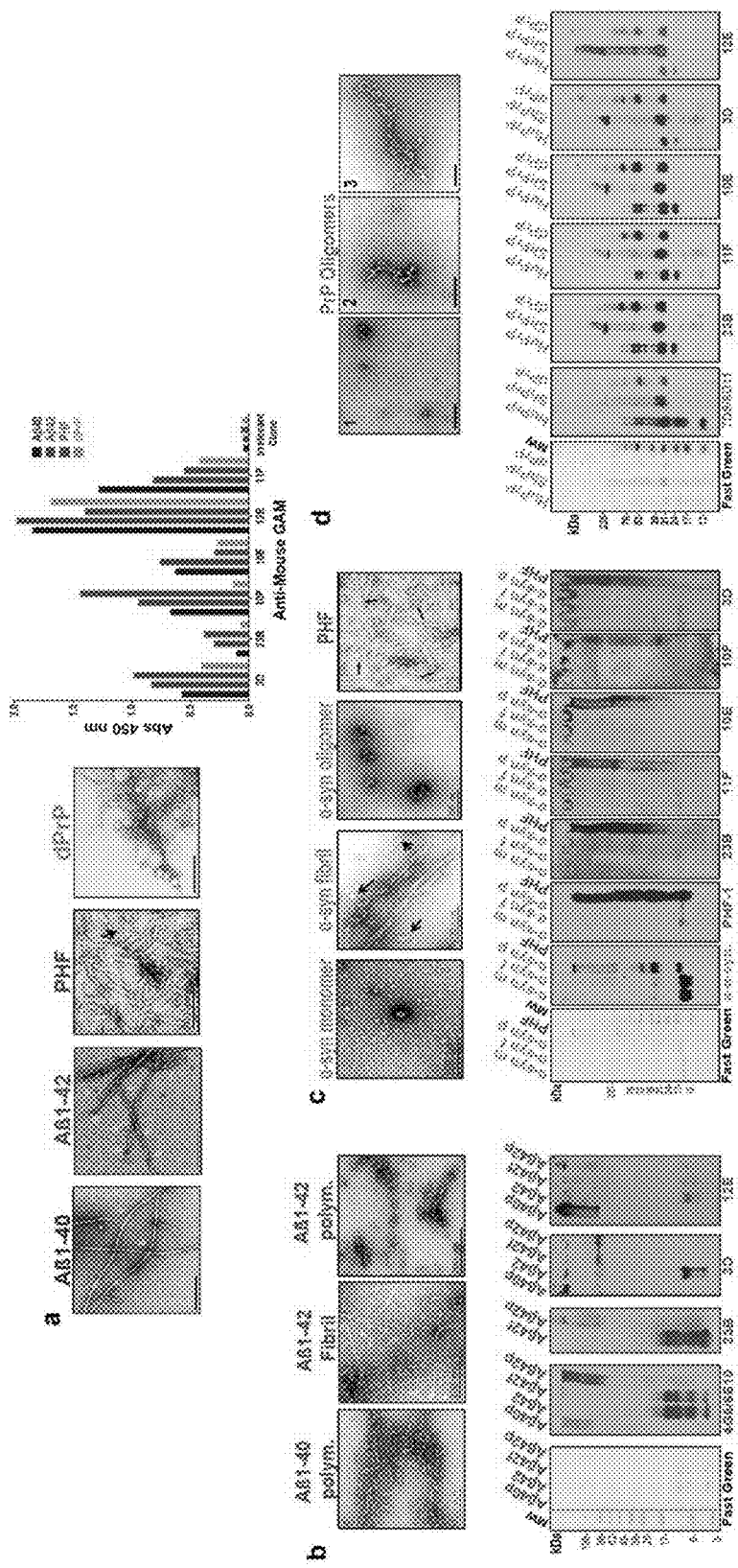
FIGS. 7A-7D depict electron microscopy of fibrillar and oligomeric forms of misfolded protein/peptides from NDDs and the recognition in ELISA and immunoblots by the original hybridomas, before subcloning, 3D, 23B, 10E, 11F, 10F, and 12E.
Figures 8A, 8B:
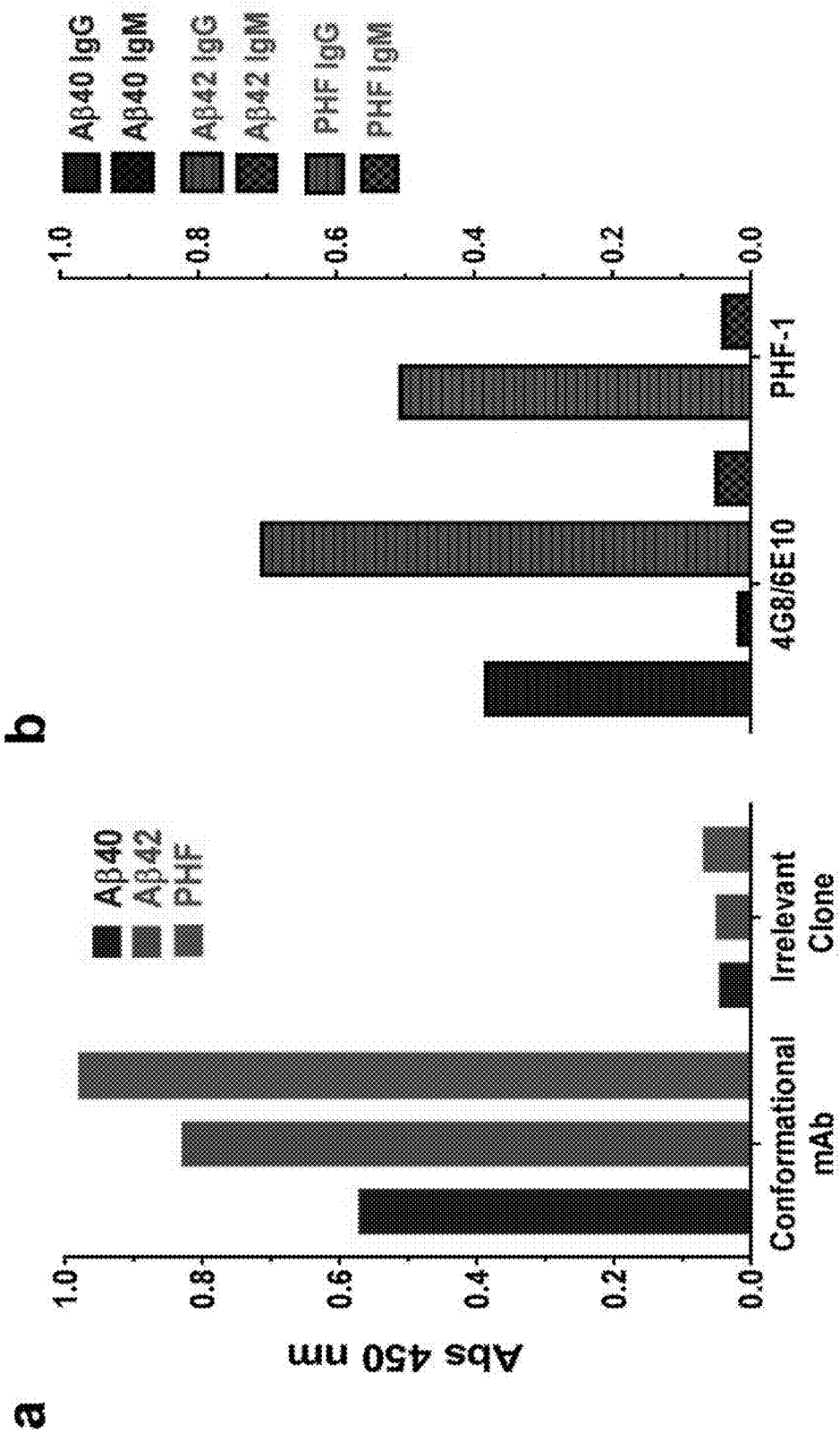
FIGS. 8A-8B depict control of protein/peptide coat and IgM reactivity in ELISA plates of Aβ1-40, Aβ1-42 and PHF.
Figures 9A, 9B, 9C, 9D:
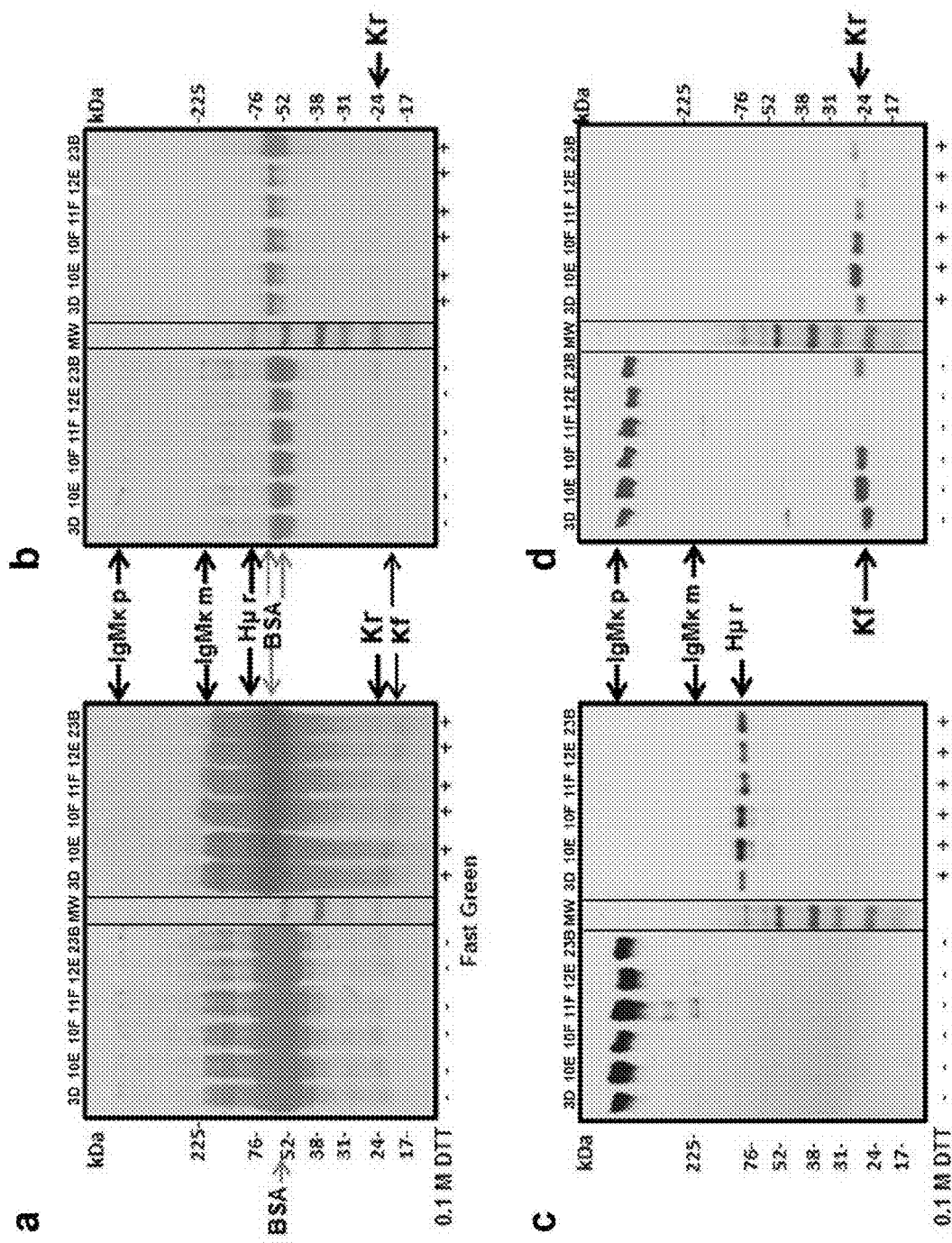
FIGS. 9A-9D depict purification and characterization of potential anti β-sheet secondary structure conformational monoclonal antibodies obtained from the fusion of p13Bri hyper-immunized M4 CD-1 mouse spleen cells with SP2/mIL-6 fusion partner.

In the first round of selection, more than fifty limited volume supernatants from samples of wells containing a few cells were analyzed at the same time precluding a further dilution for duplicates or for individual plates to assess IgG and IgM classes, separately. A polyclonal anti-mouse GAM, at a suitable dilution, was used to maximize detection. As a positive control, commercial antibodies to each specific sequence conformer on the corresponding plates were used, assuring the homogeneity of the coating. At the same time the anti-mouse GAM was able to recognize IgM or IgG hybridomas producing readings of at least three times over the background as shown by comparison to irrelevant clones (FIGS. 7A, 8A, and 8B). Cells from all supernatants that were positive with at least two of the four conformational selectors were subcloned as described supra. The clones that were positive for at least two conformers and maintained the reactivity for three rounds of subcloning were deemed potential anti-β-sheet monoclonals, separated and expanded (FIG. 1C, blue pathway).

Figures 6A, 6B, 6C, 6D:
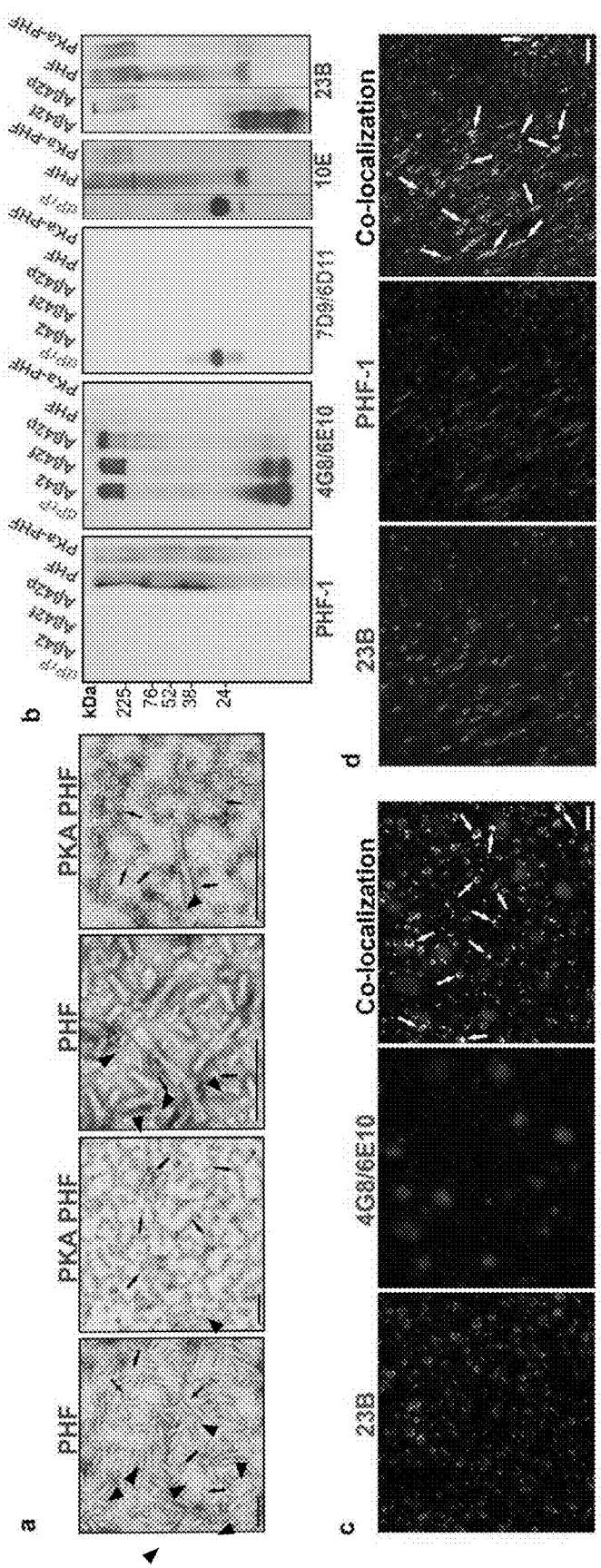
FIGS. 6A-6D depict electron microscopy of paired helical filaments (PHF) and PKA treated PHF, and comparative detection of specific NDD conformers.

Thirty five potential clones were obtained using the above criteria, which could be divided into six families of similarly reacting monoclonals from which the best representatives were 23B7; 10E8; 3D7; 12E1; 11F2 and 10F7 (FIGS. 6B; 7A-7D, and 10A). All clones that were stable with a sustained production of an anti-β-sheet monoclonal were later shown to be IgM-kappa in pentameric form (FIGS. 9A-9D), whereas unexpectedly, no stable IgG producing hybridomas survived the three rounds of selection.

After initial expansion of the potential anti-β-sheet secondary structure clones, enough cell supernatant was available to corroborate the ELISA reactivity in duplicate and was used as a source of primary antibody in specific immunoblots that showed the poly-reactivity to the same antigens that shared only a dominant β-sheet secondary structure, as well as to oligomerized α-synuclein. The immunoblots also showed specific detection of low abundance oligomeric structures from every NDD conformer that were typically detected less well or not at all by the anti-primary structure dependent commercial antisera specific for only one type of protein or peptide (FIG. 6B).

To assure the anti-β-sheet conformation reactivity was due only to IgM monoclonals; all six representative monoclonals were partially purified by ammonium sulfate precipitation (SAS) to remove more than 90% of the BSA and other contaminating proteins. The integrity of the IgMκ pentamer was maintained as well as the antibody specificity (FIGS. 9A-9D).

Each one of the representative monoclonals reacted in gels in a specific way with the different NDD oligomeric conformers (FIGS. 7B-7D), including reactivity to polymerized recombinant α-synuclein aggregated at the top of the gels, that has similarities to the toxic α-synuclein oligomers that are found in PD and LBD (FIG. 7C). Each selected monoclonal shows evidence of cross reactivity, with reactivity to at least two oligomeric conformers with differing primary sequence (FIGS. 7B-7D).

Figures 10A, 10B:
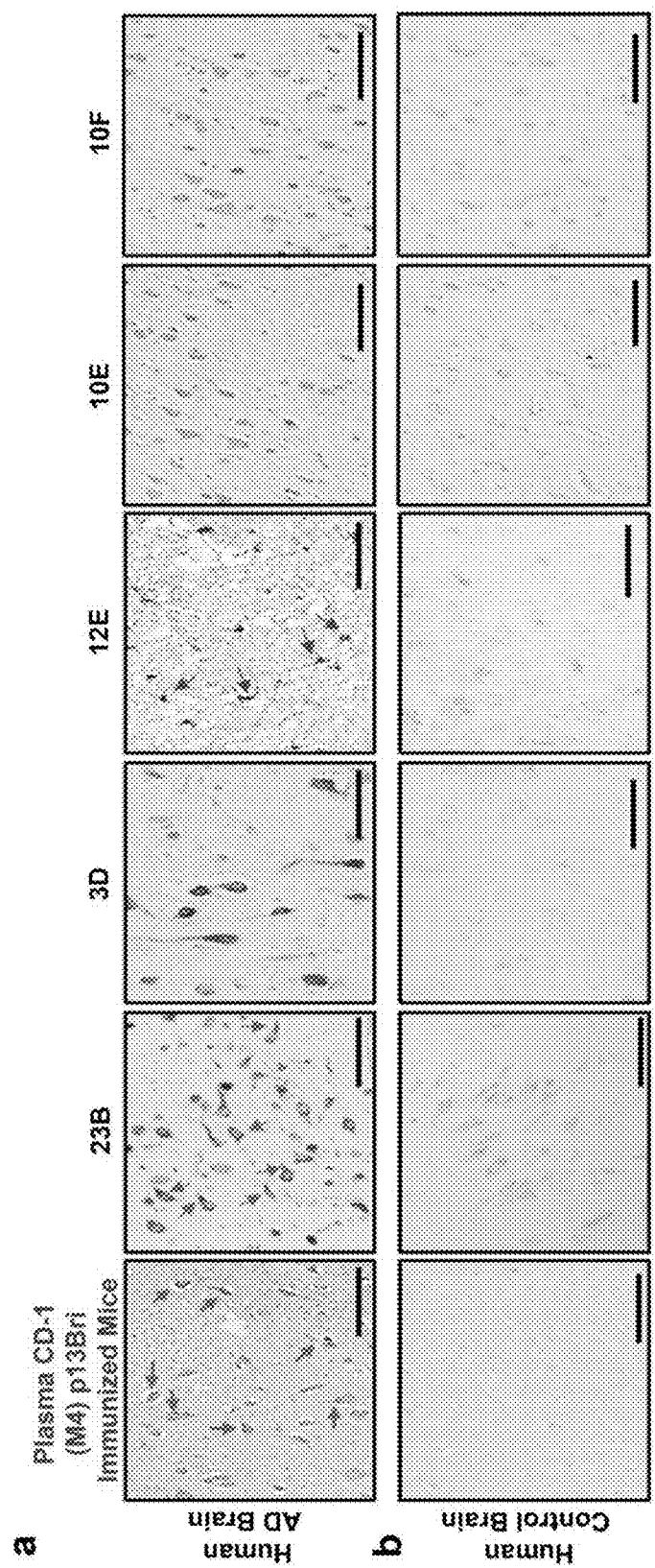
FIGS. 10A-10B depict immunohistochemistry of plasma from p13Bri immunized M4 mouse and five partially purified potential anti β-sheet secondary structure conformational monoclonal antibodies on human AD and control brains.

The SAS semi-purified monoclonals were used to immunolabel the cortex of human AD brains. Each monoclonal differentially labelled extracellular and cytoplasmic material: 23B7 strongly labels neuronal cytoplasm including processes and the nucleus; 3D7 labels the whole neuronal cell body; with both labeling some extracellular material. 12E1 preferentially labelled glial cells. 10E8 and 10F7 showed a lighter immunolabeling of all neuronal cytoplasmic components (FIG. 10A). No appreciable labelling was detectable with monoclonals using cortex tissue of human control brains with no NDD pathology (FIG. 10B). All reactivities can be traced as derived from the polyclonal response of the M4 mouse before fusion (FIGS. 3A, 3C, and FIG. 10A), demonstrating the monoclonals were originally elicited by the p13Bri immunization and selected by using the different NDD conformers.

Discussion.

As described herein, using a novel methodology, anti-β-sheet secondary structure monoclonal antibodies that recognize a dominant β-sheet structure present in pathology associated oligomers of misfolded protein/peptides of different NDD have been developed.

The production of anti-β-sheet monoclonal antibodies to a particular secondary structure present in oligomers of misfolded protein/peptides can be achieved in a sequential manner that involves first production of a stable oligomer preparation using a small non-self peptide polymerized to itself. This polymerized peptide, referred to as p13Bri, is derived from only the last 13 amino acids of the carboxyl terminus of the ABri peptide, oligomerized using glutaraldehyde as a cross linker to form a stable population of sequence homogeneous oligomers, as previously described (Vidal et al., "A Stop-Codon Mutation in the BRI Gene Associated with Familial British Dementia" Nature 399: 776-781 (1999), and Rostagno et al., "Chromosome 13 Dementias" Cell Mol. Life Sci 62:1814-1825 (2005), both of which are hereby incorporated by reference in their entirety) (FIGS. 1A-1C and 2A-2D). The carboxyl 13 residue end of ABri lacks any sequence homology to Aβ, tau or any other native human proteins, since it is derived from an intronic transcript (Wisniewski et al., "Immunotherapeutic Approaches for Alzheimer's Disease" Expert Rev Vaccines 15:401-415 (2016), Vidal et al., "A Stop-Codon Mutation in the BRI Gene Associated with Familial British Dementia" Nature 399:776-781 (1999), Rostagno et al., "Chromosome 13 Dementias" Cell Mol. Life Sci 62:1814-1825 (2005), and Goñi et al., "Immunomodulation Targeting Abnormal Protein Conformation Reduces Pathology in a Mouse Model of Alzheimer's Disease" PLoS. One 5:e13391 (2010), each of which is hereby incorporated by reference in its entirety). The length of this specific sequence allows it to gain a dominant β-sheet secondary structure, but is too short for significant folding to a tertiary structure, which would introduce unwanted competing conformations in the resulting immunogen. Thus, the polymerization process stabilized repeating motifs with only β-sheet secondary structure, increasing the oligomer size so that it would be immunogenic by itself.

Prior work using 3 different AD transgenic (Tg) mouse models, has shown that active immunization based on this approach produces a therapeutic polyclonal response that reduces all three key neuropathological features of AD, namely amyloid plaques, congophilic amyloid angiopathy (CAA), and tau related pathology, in association with significant cognitive benefits (Wisniewski et al., "Immunotherapeutic Approaches for Alzheimer's Disease" Neuron 85:1162-1176 (2015), Wisniewski et al., "Developing Therapeutic Vaccines Against Alzheimer's Disease" Expert Rev Vaccines 15:401-415 (2016), Goñi et al., "Immunomodulation Targeting Abnormal Protein Conformation Reduces Pathology in a Mouse Model of Alzheimer's Disease" PLoS. ONE 5:e13391 (2010), Goñi et al., "Immunomodulation Targeting Both Aβ and tau Pathological Conformers Ameliorates Alzheimer's Disease Pathology in TgSwDI and 3×Tg Mouse Models" Journal of Neuroinflammation 10:150 (2013), and Wisniewski and Goñi, "Immunotherapy for Alzheimer's Disease" Biochemical Pharmacology 88:499-507 (2014), each of which is hereby incorporated by reference in its entirety). Amyloid plaques and CAA were shown to be reduced in APP/PS1 (amyloid plaque model) and TgSwDI (CAA Tg model) model mice, respectively, while in 3×Tg mice (amyloid plaque and tau pathology model), p13Bri immunization led to reductions of both tau and Aβ pathology (Wisniewski et al., "Immunotherapeutic Approaches for Alzheimer's Disease" Neuron 85:1162-1176 (2015), Wisniewski et al., "Developing Therapeutic Vaccines Against Alzheimer's Disease" Expert Rev Vaccines 15:401-415 (2016), Goñi et al., "Immunomodulation Targeting Abnormal Protein Conformation Reduces Pathology in a Mouse Model of Alzheimer's Disease" PLoS. ONE 5:e13391 (2010), Goñi et al., "Immunomodulation Targeting Both Aβ and tau Pathological Conformers Ameliorates Alzheimer's Disease Pathology in TgSwDI and 3×Tg Mouse Models" Journal of Neuroinflammation 10:150 (2013), and Wisniewski and Goñi, "Immunotherapy for Alzheimer's Disease" Biochemical Pharmacology 88:499-507 (2014), each of which is hereby incorporated by reference in its entirety). Inoculation of p13Bri with Alum as an adjuvant in these three AD Tg models produced a systemic polyclonal response to pathologic/oligomeric forms of both Aβ and tau, with demonstrated cross-specificity to AD, prion disease, and LBD human brain tissue (FIGS. 3A-3C). These unusual results led to the production of hybridomas from which monoclonal antibodies with potential diagnostic or therapeutic value were selected by their specific reactivity to β-sheet secondary structures found in unrelated primary sequences of pathologic oligomeric conformers of diverse NDD.

In comparison to the previously reported successful active vaccination using p13Bri with Alum as an adjuvant in AD Tg mice, a longer and more intense immunization protocol along with a RiBi-like adjuvant (FIGS. 2A-2D) was employed herein to expand the antibody response to the dominant β-sheet secondary structure in oligomers and generate a greater number of spleen B-cells with anti-β-sheet receptors. Thus, the chance of transforming these B-cells into antibody producing stable hybridomas was increased. Thus, the polyclonal response was analyzed by ELISA tests as described herein with the understanding that detecting a differential in Aβ oligomers concentration per area around fibrils may reflect more accurately the real biochemical dynamic around plaques in AD (Riek et al., "The Activities of Amyloids From a Structural Perspective" Nature 539:227-235 (2016), which is hereby incorporated by reference in its entirety). Plasma from the p13Bri immunized CD-1 animals after 6 inoculations clearly showed a persistent IgM response to the oligomeric forms of Aβ (FIG. 3C and FIGS. 4A-4C). These persistent polyclonal IgMs, similar to what was previously reported (Goñi et al., "Immunomodulation Targeting Abnormal Protein Conformation Reduces Pathology in a Mouse Model of Alzheimer's Disease" PLoS. ONE 5:e13391 (2010), Goñi et al., "Immunomodulation Targeting Both Aβ and tau Pathological Conformers Ameliorates Alzheimer's Disease Pathology in TgSwDI and 3×Tg Mouse Models" Journal of Neuroinflammation 10:150 (2013), and Sigurdsson et al., "An Attenuated Immune Response is Sufficient to Enhance Cognition in an Alzheimer's Disease Mouse Model Immunized with Amyloid-β derivatives" *J. Neurosci* 24:6277-6282 (2004), each of which is hereby incorporated by reference in its entirety), were later shown to be consistent and their IgM producing B-cells able to be transformed into stable monoclonals (FIGS. 6-10).

In order to assure detection and separation of only the clones with specificity to a β-sheet secondary structure conformation, monoclonal clones were selected by testing reactivity to a number of different oligomer preparations from various NDD that only share a common β-sheet secondary structure, but no primary sequence or tertiary structure homology. Clones were selected that had strong reactivity to at least two distinct β-sheet secondary structure conformations, with a differing primary sequence. The aged or oligomerized Aβ peptides used in ELISA and blots (FIGS. 6 and 7) reflect the known structures of bend parallel or anti-parallel ß-sheet secondary structure, which will convert to oligomers and eventually fibrils (Sawaya et al, "Atomic Structures of Amyloid Cross-Beta Spines Reveal Varied Steric Zippers" *Nature* 447:453-457 (2007), Wiltzius et al., "Molecular Mechanisms for Protein-Encoded Inheritance" *Nat Struct Mol Biol* 16:973-978 (2009), and Barrow et al., "Solution Conformations and Aggregational Properties of Synthetic Amyloid Beta-Peptides of Alzheimer's Disease. Analysis of Circular Dichroism Spectra" *J. Mol. Biol* 225: 1075-1093 (1992), each of which is hereby incorporated by reference in its entirety). The PHF purified from AD subjects and the PHF digested with proteinase K were specific selectors of the dominant ß-sheet secondary structure associated with ptau toxic oligomers (FIGS. 6 and 7) (Walker et al., "Mechanisms of Protein Seeding in Neurodegenerative Diseases" *JAMA Neurol* 70:304-310 (2013), Sawaya et al., "Atomic Structures of Amyloid Cross-Beta Spines Reveal Varied Steric Zippers" *Nature* 447:453-457 (2007), Avila et al, "Tau Structures" *Front Aging Neurosci* 8:262 (2016), Wiltzius et al., "Molecular Mechanisms for Protein-Encoded Inheritance" *Nat Struct Mol Biol* 16:973-978 (2009), Daebel et al., "Beta-Sheet Core of tau Paired Helical Filaments Revealed by Solid-State NMR" *J Am Chem Soc* 134:13982-13989 (2012), and von Bergen et al., "Assembly of tau Protein into Alzheimer Paired Helical Filaments Depends on a Local Sequence Motif ((306)VQIVYK(311)) Forming Beta Structure" *Proc Natl Acad Sci USA* 97:5129-5134 (2000), which are each hereby incorporated by reference in their entirety), while the deer recombinant PrP served as an example of aggregation through ß-sheet dominant motifs similar to those found in oligomeric PrP$^{Res}$ (Sawaya et al, "Atomic Structures of Amyloid Cross-Beta Spines Reveal Varied Steric Zippers" *Nature* 447:453-457 (2007), and Wiltzius et al, "Molecular Mechanisms for Protein-Encoded Inheritance" *Nat Struct Mol Biol* 16:973-978 (2009), which are both hereby incorporated by reference in their entirety). In all cases, these new monoclonals recognized novel oligomeric structures that are not evident using conventional anti-primary structure antibodies (FIG. 6). These monoclonals are NDD pathology specific; however, each clone shows preferential binding to different oligomer species (FIGS. 7 and 10).

Many oligomer specific antibodies have been reported (Viola et al., "Amyloid Beta Oligomers in Alzheimer's Disease Pathogenesis, Treatment, and Diagnosis" *Acta Neuropathol* 129:183-206 (2015), Kayed et al., "Common Structure of Soluble Amyloid Oligomers Implies Common Mechanism of Pathogenesis" *Science* 300:486-489 (2003), Lee et al., "Targeting Amyloid-Beta Peptide (Abeta) Oligomers by Passive Immunization with a Conformation-Selective Monoclonal Antibody Improves Learning and Memory in Abeta Precursor Protein (APP) Transgenic Mice" *J Biol Chem* 281:4292-4299 (2006), Tucker et al., "The Murine Version of BAN2401 (mAb158) Selectively Reduces Amyloid-Beta Protofibrils in Brain and Cerebrospinal Fluid of tg-ArcSwe Mice" *J Alzheimers Dis* 43:575-588 (2015), Lambert et al., "Monoclonal Antibodies that Target Pathological Assemblies of Abeta" *J Neurochem* 100:23-35 (2007), Hillen et al., "Generation and Therapeutic Efficiency of Highly Oligomer-Specific Beta-Amyloid Antibodies" *J Neurosci* 30:10369-10379 (2010), Rasool et al., "Systemic Vaccination with Anti-Oligomeric Monoclonal Antibodies Improves Cognitive Function by Reducing Abeta Deposition and tau Pathology in 3xTg-AD mice" *J Neurochem* 126:473-482 (2013), Dorostkar et al., "Immunotherapy Alleviates Amyloid-Associated Synaptic Pathology in an Alzheimer's Disease Mouse Model" *Brain* 137: 3319-3326 (2014), Castillo-Carranza et al., "Tau Immunotherapy Modulates Both Pathological Tau and Upstream Amyloid Pathology in an Alzheimer's Disease Mouse Model" *J Neurosci* 35:4857-4868 (2015), and O'Nuallain et al., "Conformational Abs Recognizing a Generic Amyloid Fibril Epitope" *Proc Natl Acad Sci USA* 99:1485-1490 (2002), which are each hereby incorporated by reference in their entirety). However, none of these mAbs are specific for secondary structure or were raised to a non-self-antigen, and none have been shown to bind both Aβ oligomers, as well as pathological tau (PHF). All is a rabbit polyclonal antibody raised to Aβ1-40 bound to gold colloid particles (Kayed et al., "Conformation-Dependent Anti-Amyloid Oligomer Antibodies" *Methods Enzymol* 413:326-344 (2006), and Kayed et al., "Common Structure of Soluble Amyloid Oligomers Implies Common Mechanisms of Pathogenesis" *Science* 300:486-489 (2003), which are both hereby incorporated by reference in their entirety). NAB61 was generated using Aβ1-40 crosslinked with peroxynitrile (Lee et al., "Targeting Amyloid-Beta Peptide (Abeta) Oligomers by Passive Immunization with a Conformation-Selective Monoclonal Antibody Improves Learning and Memory in Abeta precursor Protein (APP) Transgenic Mice" *J Biol. Chem* 281:4292-4299 (2006), which is hereby incorporated by reference in its entirety). BAN2401 was raised to protofibrils of Aβ1-42 with the Arctic mutation (Tucker at al., "The Murine Version of BAN2401 (mAb158) Selectively Reduce Amyloid-Beta Protofibrils in Brain and Cerebrospinal Fluid of tg-ArcSwe Mice" *J Alzheimers Dis* 43:575-588 (2015), which is hereby incorporated by reference in its entirety). NU-1 was raised to amyloid β-derived diffusible ligands (ADDLs) of Aβ1-42 (Lambert et al., "Monoclonal Antibodies That Target Pathological Assemblies of Abeta"*J Neurochem* 100:23-35 (2007), which is hereby incorporated by reference in its entirety). A-887755 was raised to globulomers of Aβ20-42 (Hillen at al., "Generation and Therapeutic Efficacy of Highly Oligomer-Specific Beta-Amyloid Antibodies" *J Neurosci* 30: 10369-10379 (2010), and Dorostkar et al., "Immunotherapy Alleviates Amyloid-Associated Synaptic Pathology in an Alzheimer's Disease Mouse Model" *Brain* 137:3319-3326 (2014), which are both hereby incorporated by reference in their entirety). ACU-193 was raised to aggregated Aβ (Goure et al., "Targeting the Proper Amyloid-Beta Neuronal Toxins: a Path Forward for Alzheimer's Disease Immunotherapeutics" *Alzheimers Res Ther* 6:42 (2014), which is hereby incorporated by reference in its entirety). B10 is an antibody binding domain selected for stabilizing Aβ protofibrils (Habicht et al., "Directed Selection of a Conformational Antibody Domain that Prevents Mature Amyloid Fibril Formation by Stabilizing Abeta Protofibrils" *Proc Natl Acad Sci USA* 104:19232-19237 (2007), which is hereby incorporated by reference in its entirety). The two IgMs W01 and W02, both raised against Aβ, only recognize generic amyloid fibrils and protofibrillar Aβ but not soluble oligomeric forms (O'Nuallain et al., "Conformational Abs Recognizing a Generic Amyloid Fibril Epitope" *Proc Natl Acad Sci USA* 99:1485-14900 (2002), which is hereby incorporated by reference in its entirety). The same group, that produced A11, has also produced OC, a polyclonal, which was raised to Aβ1-42 fibrils (Kayed et al., "Fibril Specific, Conformation Dependent Antibodies Recognize a Generic Epitope Common to Amyloid Fibrils and Fibrillar Oligomers That is Absent in Prefibrillar Oligomers" *Mol. Neurodegener* 2:18 (2007), which is hereby incorporated by reference in its entirety) and developed the rabbit IgG mAbs 204 and 205 generated using Aβ1-40 coupled to colloidal gold particles (Rasool et al., "Systemic Vaccination with Anti-Oligomeric Monoclonal Antibodies Improves Cognitive Function by Reducing Abeta Deposition and Tau Pathology in 3xTg-AD Mice" *J Neurochem* 126:473-482 (2013), which is hereby incorporated by reference in its entirety). None of these aforementioned antibodies directly recognize tau oligomers/tau related pathology. Furthermore, the majority of these mAbs have been characterized with unspecific chemical methods such as dot blots. Hence, although they likely have high affinity for certain specific oligomer species, they might also bind to appropriately folded monomers at a lower affinity. In potential therapeutic settings the concentration of physiological monomeric species is much higher, hampering the effectiveness of such antibodies. Furthermore, all of these mAbs were raised and selected by variations of the same Aβ self-antigen, having the potential issue of late autoimmune toxicity. On the other hand, the anti-tau oligomer specific mAbs (TOMA) have also been raised, using the aggregated tau self-antigen, and shown to reduce tau pathology (Castillo-Carranza et al., "Tau Immunotherapy Modulates Both Pathological Tau and Upstream Amyloid Pathology in an Alzheimer's Disease Mouse Model" *J Neurosci* 35:4857-4868 (2015), which is hereby incorporated by reference in its entirety); however, these do not cross-immunoreact with Aβ oligomers.

Due to the novel method by which the anti-β-sheet conformational mAbs were generated and their poly-reactivity to toxic conformers found in most common NDD, the approach described herein is innovative and more likely to have therapeutic success in humans than any of the other existing oligomer targeting mAbs. The potential advantages of the anti-β sheet mAbs described herein are: 1) a diminished risk of inducing auto-immune complications since the immunogen used has no sequence homology to any human peptide/protein (except to the protein expressed in the very rare patients with British amyloidosis); 2) selective targeting of the β-sheet secondary structure found in toxic oligomers, thus avoiding interference with the multiple physiological functions of soluble Aβ, tau and α-synuclein; 3) reduced risk of inducing vasogenic edema/encephalitis related to direct clearance of fibrillar Aβ vascular deposits, since mainly oligomeric forms of Aβ and tau are being targeted; 4) concurrently targeting Aβ, tau and α-syn related pathologic conformers, addressing the mixed pathologies found in the majority of NDD patients (Hamilton et al., "Lewy Bodies in Alzheimer's Disease: A Neuropathological Review of 145 Cases Using Alpha-Synuclein Immunohistochemistry" *Brain Pathol* 10:378-384 (2000), White et al., "Neuropathologic Comorbidity and Cognitive Impairment in the Nun and Honolulu-Asia Aging Studies" *Neurology* 86:1000-1008 (2016), Schneider et al., "Mixed Brian Pathologies Account for Most Dementia Cases in Community-Dwelling Older Persons" *Neurology* 69:2197-2204 (2007), and James et al., "TDP-43 Stage, Mixed Pathologies, and Clinical Alzheimer's-Type Dementia" *Brain* (2016), each of which is hereby incorporated by reference in its entirety); 5) minimal risk of increasing toxic oligomer species as shown in some vaccination methods (Hara et al., "An Oral Abeta Vaccine Using a Recombinant Adeno-Associated Virus Vector in Aged Monkeys: Reduction in Plaque Amyloid and Increase in Abeta Oligomers" *J Alzheimers Dis* 54:1047-1059 (2016), which is hereby incorporated by reference in its entirety); 6) the possible use in prion diseases with the potential to interfere with the spread of PrP$^{Res}$. No other reported methodologies to produce mAbs to oligomers published thus far have this unique combination of properties. Hence, the technological approach described herein has the potential to develop tools for the detection, monitoring and treatment of multiple NDDs.

Example 2—Characterization of Anti-β-Sheet Conformational mAb aβComAb WG-3D7

Figures 11A, 11B:
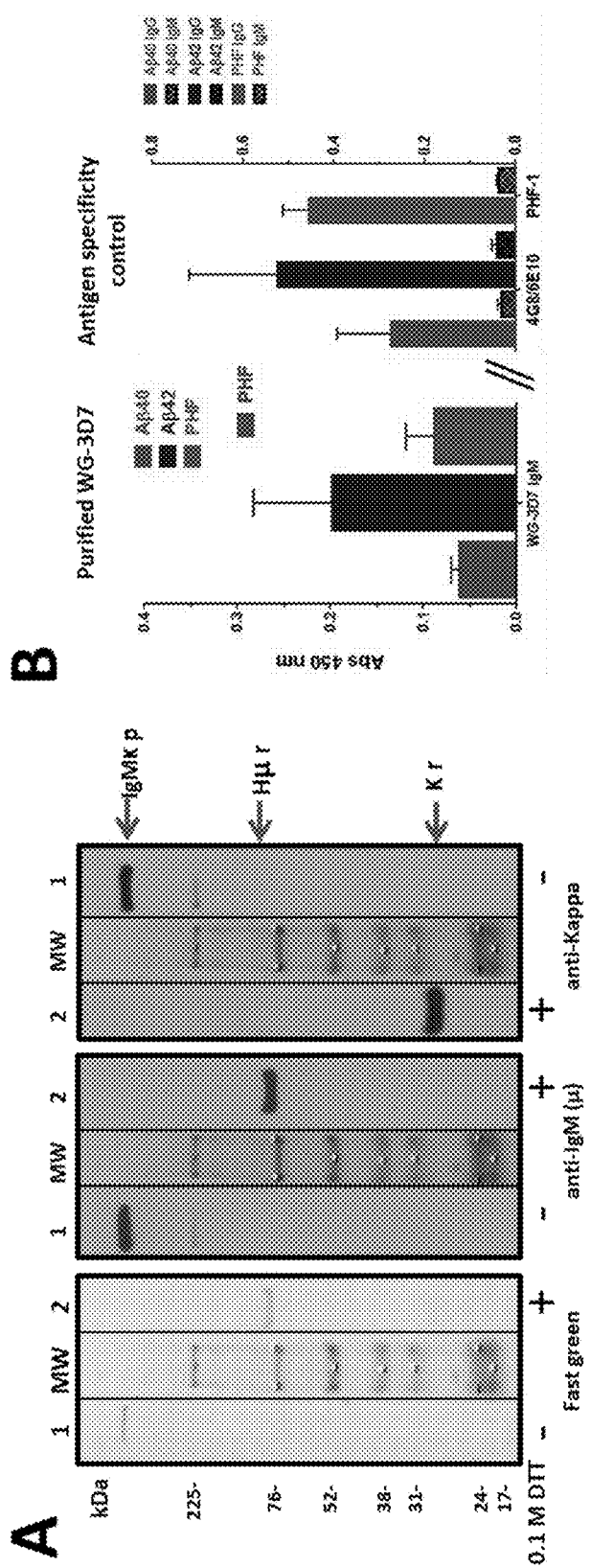
FIGS. 11A-11B depict purification of the conformational monoclonal antibody WG-3D7.

The purification of the anti-β-sheet conformational monoclonal antibody aβComAb WG-3D7 is depicted in FIGS. 11A-11B. FIG. 11A shows western blots of the conformational monoclonal antibody WG-3D7 purified with a llama anti-μ, column. The far left panel shows Fast Green staining for protein loading control, the middle panel shows anti-mouse IgM μ specific reactivity, and the right panel shows anti-mouse Kappa reactivity. Lanes 1 and 2 of each panel contain un-reduced and DTT reduced proteins, respectively (IgMk p=pentamer, Hμ r=reduced heavy chain, and Kr=Kappa light chain reduced). FIG. 11B contains graphs of ELISA data showing the reactivity of the purified conformational monoclonal antibody WG-3D7 against (in order from left to right on the graphs) Aβ40, oligomerized Aβ42, and PHF (left graph), and positive and negative controls showing that the antigen specificity of the WG-3D7 antibody (solid bars) is not an artifact of the secondary anti-IgM (hatched bars) (right graph).

Figures 12A, 12B, 12C, 12D, 12E:
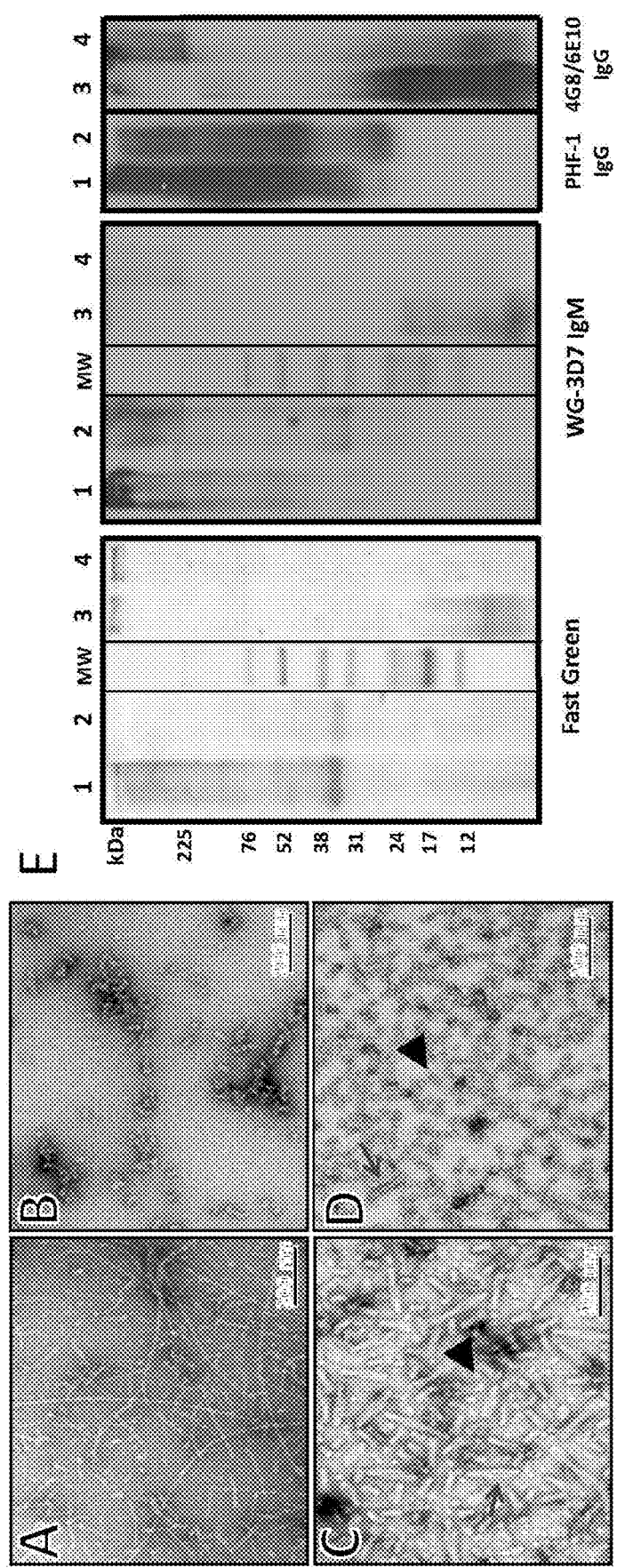
FIGS. 12A-12E show electron microscopy images of aggregated/oligomeric Amyloid β and PHF, and reactivity of the conformational monoclonal antibody WG-3D7 against these same pathogenic peptides.

The reactivity of the anti-β-sheet conformational monoclonal antibody aβComAb WG-3D7 against aggregated/oligomeric amyloid 13 and PHF is shown by electron microscopy in FIGS. 12A-12E FIGS. 12A and 12B show fibrilized and polymerized Aβ1-42, respectively. FIGS. 12C and 12D show PHF and Protein Kinase A (PKa) digested PHF (arrow fibril; arrowhead oligomer). FIG. 12E, middle panel, is a Western blot showing the reactivity of the conformational antibody WG-3D7 against PHF and PKa digested PHF (lanes 1 and 2), and Aβ42 fibrilized and polymerized forms (lanes 3 and 4). FIG. 12E, right panel, is a Western blot showing reactivity of PHF-1 IgG against PHF and PKa digested PHF (lanes 1 and 2), and reactivity of 468/6E10 IgG against AB42 fibrilized and polymerized forms (lanes 3 and 4). FIG. 12E, left panel shows the same blot as in middle and right panels, but stained with Fast Green to show protein loading.

Figures 13A, 13B:
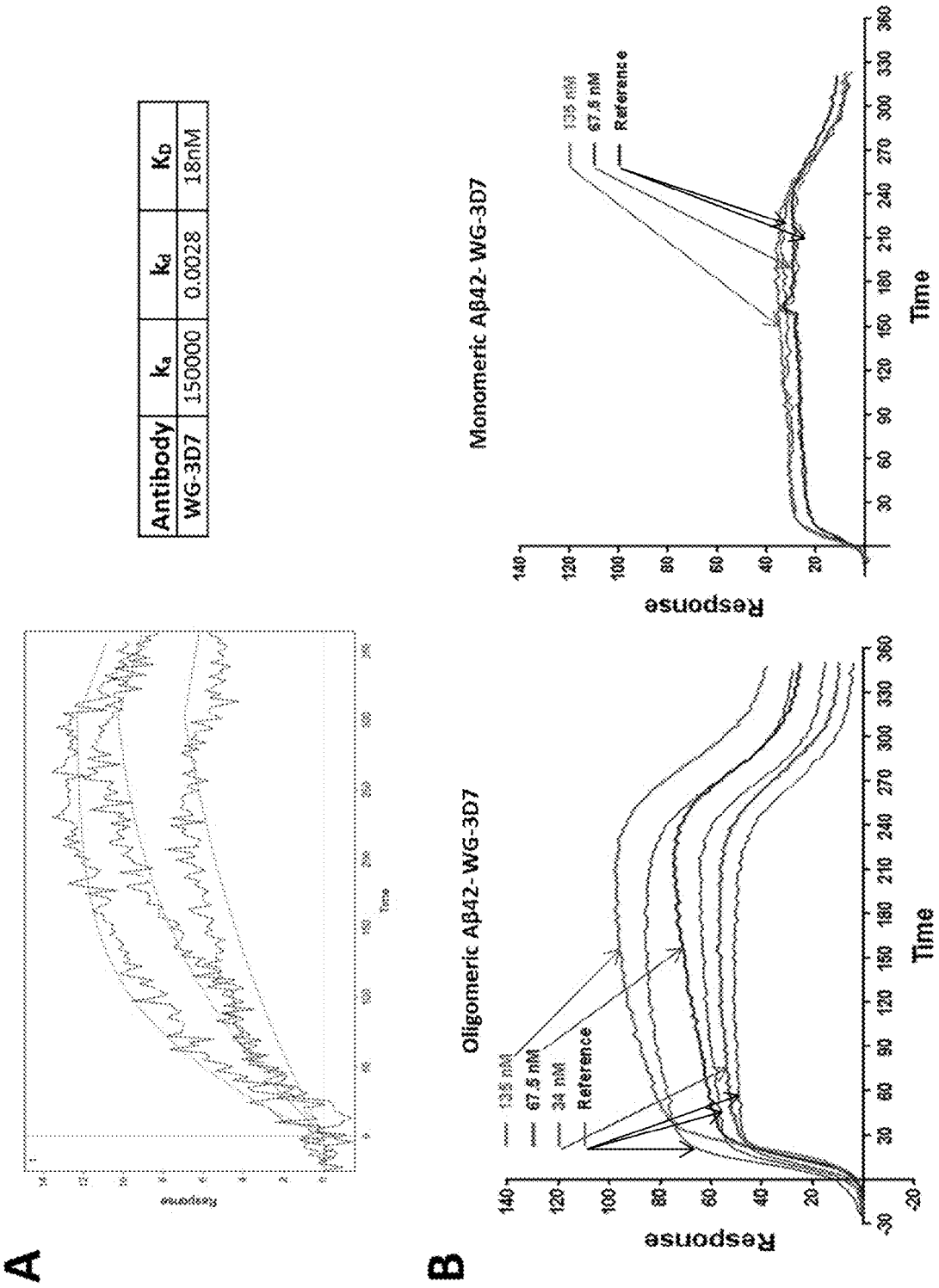
FIGS. 13A-13B demonstrate binding of the conformational monoclonal antibody WG-3D7 to oligomeric Aβ42 by surface plasmon resonance.

Binding of aβComAb WG-3D7 to oligomeric Aβ42 is shown in FIGS. 13A-13B. Surface plasmon resonance indicates binding affinity of the conformational antibody WG-3D7 to the oligomeric species of Aβ42 (FIG. 13B, left graph). In contrast there is no detectable binding to the monomeric form of Aβ42 (FIG. 13B, right graph). The normalized data of binding oligomer Aβ42 (FIG. 13A) was used to determine the association and dissociation rate constants also shown in FIG. 13A (right-hand table).

Figures 14A, 14B:
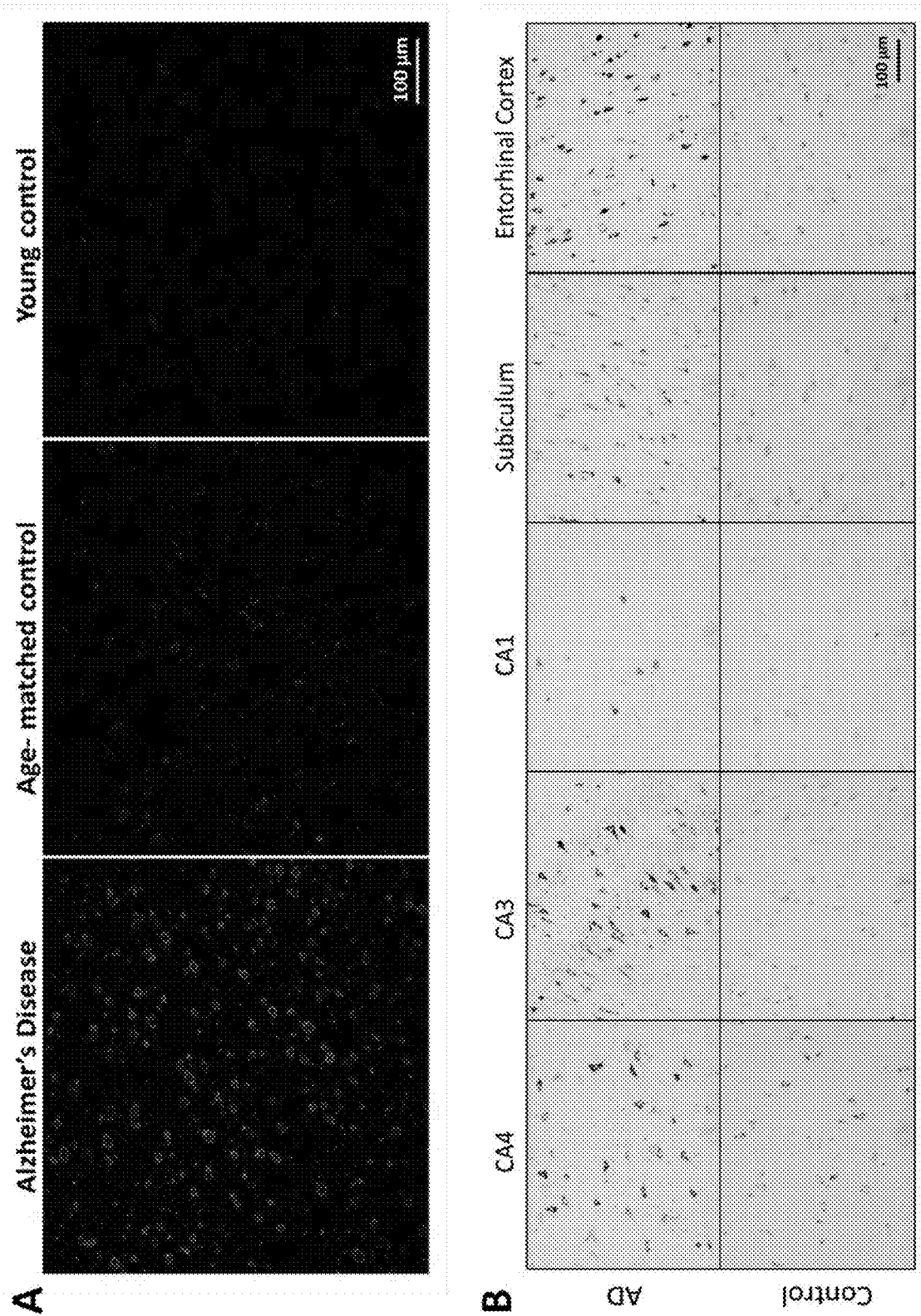
FIGS. 14A-14B depict immunohistochemistry on AD, age-matched, and young control human brains sections using conformational monoclonal antibody WG-3D7.

Immunohistochemical reactivity of αβComAb WG-3D7 on AD, age-matched, and young control human brains sections is shown in FIGS. 14A-14B. FIG. 14A shows representative images of WG-3D7 immunoreactivity in the entorhinal cortex of AD (left image), age-matched control (middle image), and young control (right image) brain sections. FIG. 14B are representative images showing WG-3D7 immunoreactivity in AD vulnerable brain regions (i.e., CA4, CA3, CA1, subiculum and entorhinal cortex) (top panel of images) versus control brain (bottom panel of images). For both immunofluorescent and DAB immunohistochemistry experiments, brains were stained in parallel in one experimental run. Brain slides were also treated and imaged at the same settings. Scale bar indicates 100 μm.

Figure 15A:
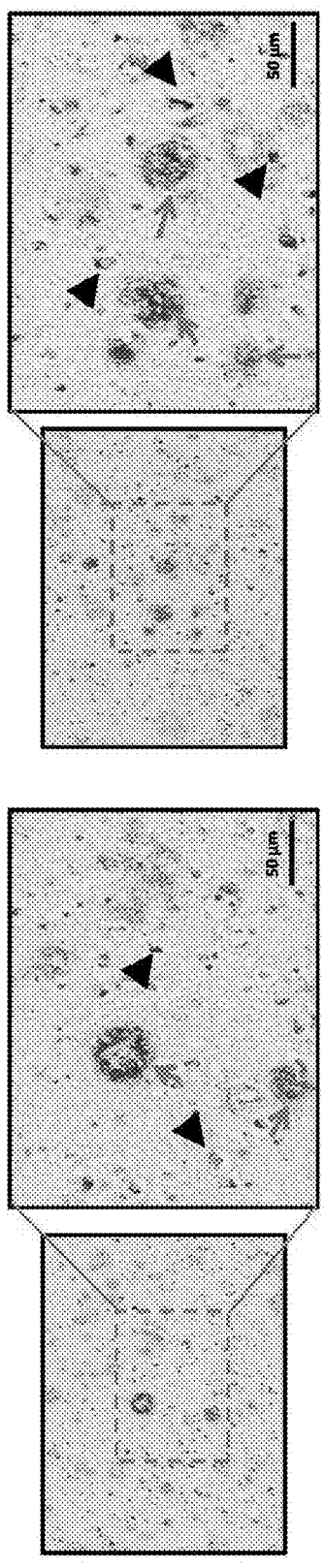
FIGS. 15A-15B depict immunohistochemistry of conformational monoclonal antibody WG-3D7 on human AD brains sections.
Figure 15B:
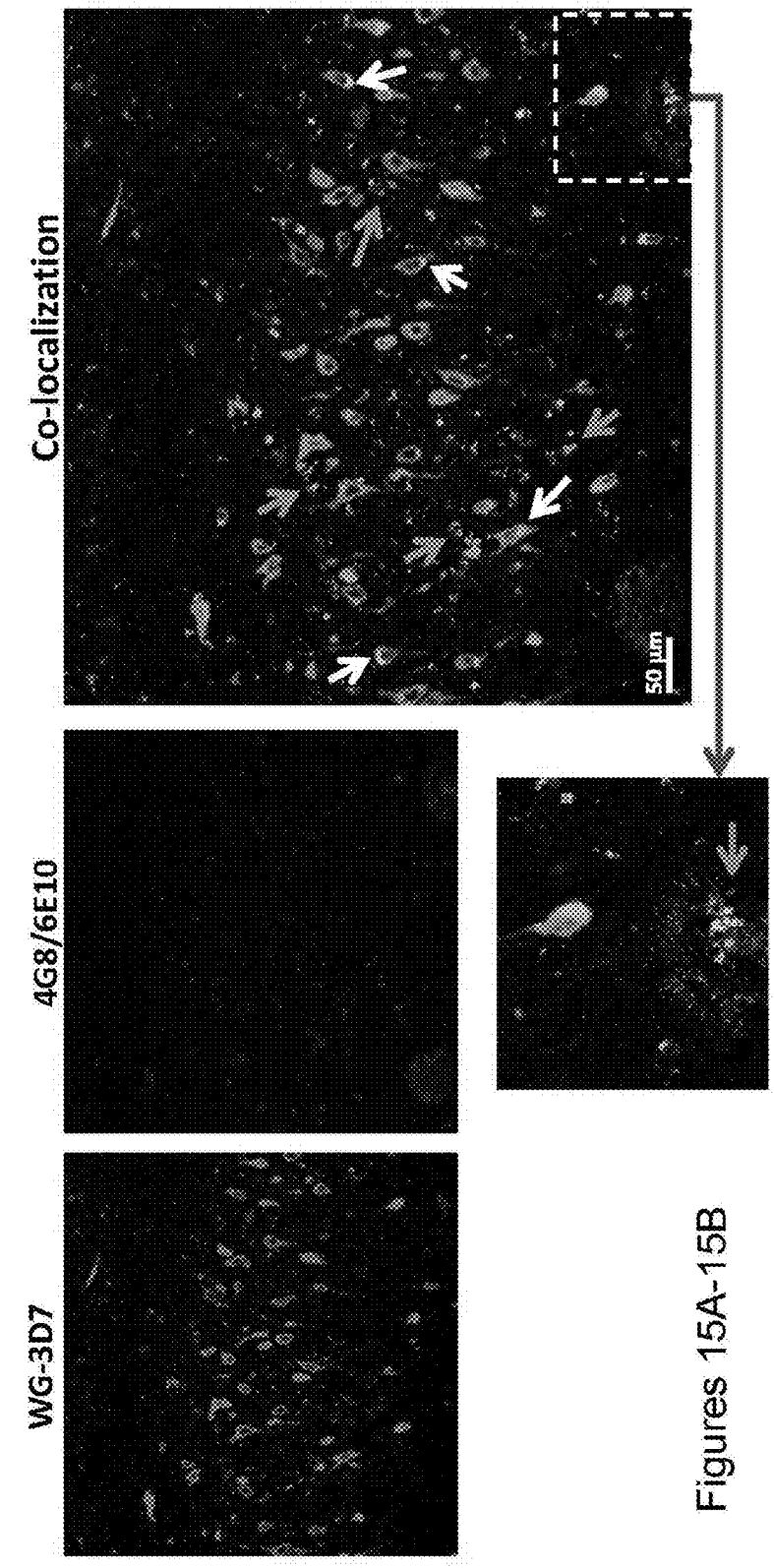

Immunohistochemistry of anti-β-sheet conformational monoclonal antibody αβComAb WG-3D7 on human AD brains sections is depicted in FIGS. 15A-15B. FIG. 15A shows representative images of co-staining of intraneuronal (arrowhead) and amyloid plaques (arrows) with commercial anti-Aβ specific 4G8/6E10 antibodies (black stain) and conformational antibody WG-3D7 (red-gray stain) in AD human brain tissue. FIG. 15B shows immunofluorescence of conformational monoclonal antibody WG-3D7 on human AD brain tissue alone (far left image), localization of Aβ using 4G8/6E10 antibody (FIG. 15B, top middle image), and co-localization of WG-3D7 and 4G8/6E10 staining (far right image). Lower middle image of FIG. 15B shows magnification of the area boxed in the co-localization image (i.e., FIG. 15B, right image). Scale bar indicates 50 μm. White arrows show intracellular co-staining of WG-3D7 antibody and amyloid β, grey arrows show extracellular material and plaques co-labeling with WG-3D7 and 4G8/6E10. Red staining appears to indicate WG-3D7 staining of oligomeric forms of Aβ within the plaques and the surroundings.

Figures 16A, 16B:
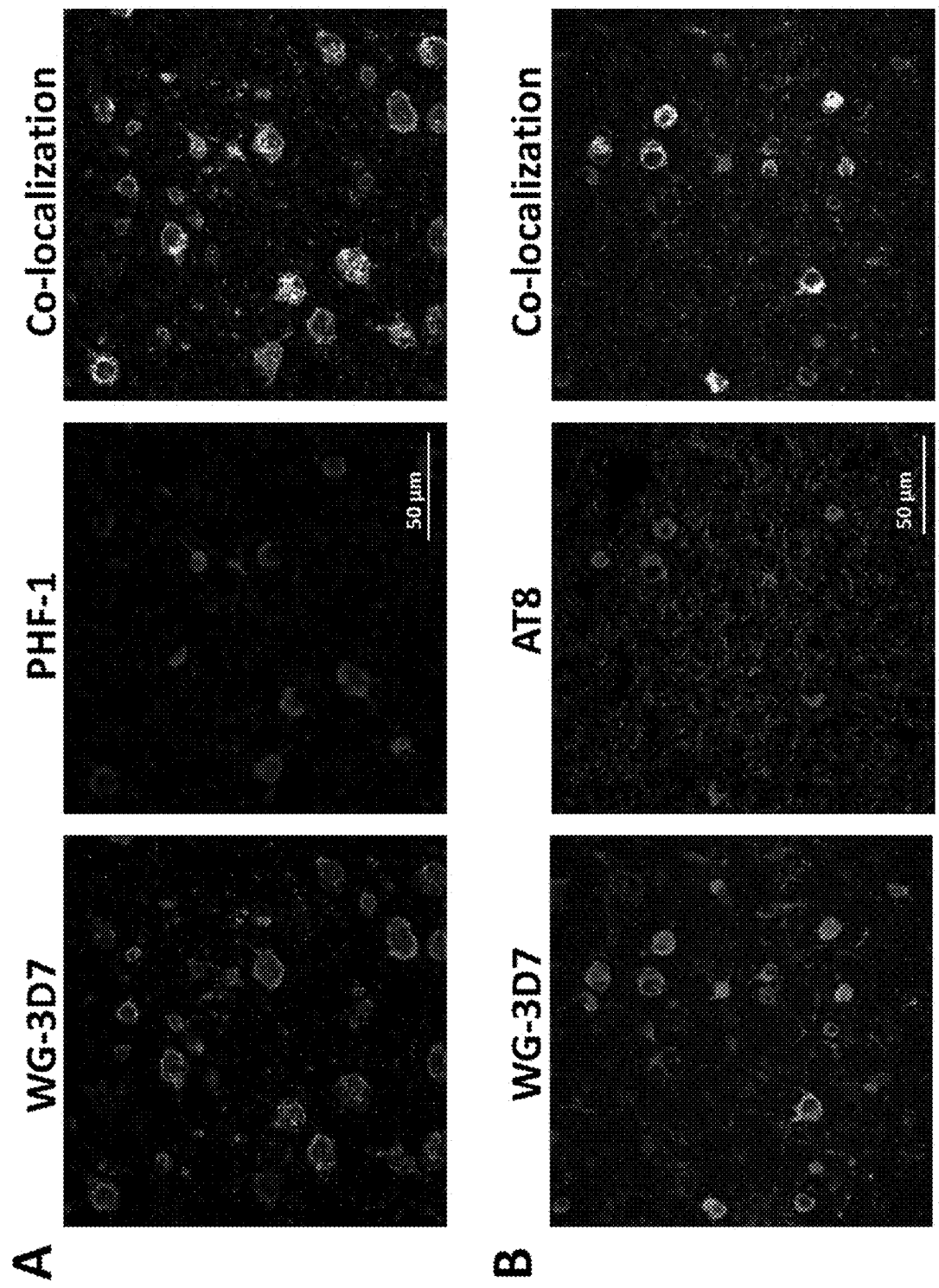
FIGS. 16A-16B demonstrate co-localization of conformational monoclonal antibody WG-3D7 and pathological Tau species in human AD brain sections.

The co-localization of αβComAb WG-3D7 and pathological Tau species in human AD brain sections is demonstrated in FIGS. 16A-16B. FIG. 16A shows immunofluorescence of conformational monoclonal antibody WG-3D7 (left image) and PHF-1 IgG (middle image) on human AD brain tissue. Co-localization of WG-3D7 and PHF-1 antibody (in white) staining is shown in FIG. 16A (right side image). FIG. 16B shows immunofluorescence of the conformational monoclonal antibody WG-3D7 (left side image) and antibody AT8 (middle image). Co-localization of WG-3D7 and AT8 staining (in white) is shown in FIG. 16B, right side image. Scale bars indicate 50 μm.

Example 3—Characterization of Anti-β-Sheet Conformational mAb αβComAb FT-11F2

Figures 17A, 17B:
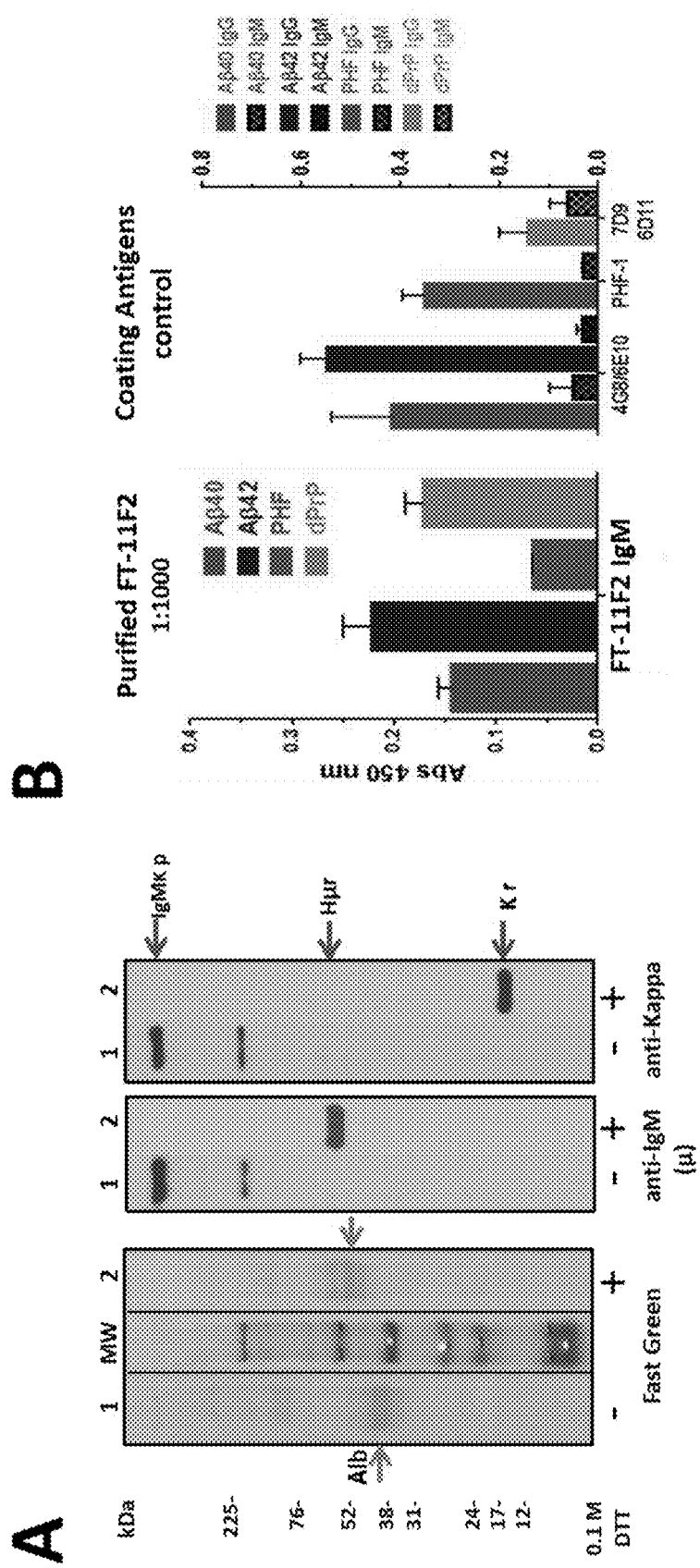
FIGS. 17A-17B depict purification of the conformational monoclonal antibody FT-11F2 with SAS and quantification of the antibody binding levels to pathological conformers.

The purification of the anti-β-sheet conformational monoclonal antibody FT-11F2 with SAS and quantification of the antibody binding levels to pathological conformers is depicted in FIGS. 17A-17B. FIG. 17A shows Western blots of the conformational monoclonal antibody FT-11F2, which was initially purified using 50% SAS. The left panel shows Fast Green staining for protein loading, the middle panel shows anti-mouse IgM μ specific reactivity, and the right panel shows anti-mouse Kappa specific reactivity. Lane 1 contains un-reduced sample (IgMk p=pentamer) and lane 2 contains 0.1 M dithiothreitol (DTT) reduced sample (Hμ r=reduced heavy chain and Kr=Kappa light chain reduced). FIG. 17B are graphs of ELISA data showing the reactivity of the purified conformational monoclonal antibody FT-11F2 against (in order from left to right on the graph) Aβ40, oligomerized Aβ42, PHF, and PrP (left graph). The right graph of FIG. 17B shows plate coating antigen controls. Immobilized antigen (i.e., Aβ40, oligomerized Aβ42, PHF, and PrP, in order from left to right on the graph) were bound by primary antibodies anti-Aβ 4G8/6E10 (IgG) antibody, PHF-1 (IgG) antibody, and anti-PrP 7D9/6D11 (IgG) antibody, and detected by a secondary antibody anti-mouse IgG. This reaction served as a positive control of the even distribution of the antigens seeded on the plates. Incubation with the same primary antibodies (solid bars) and secondary anti-IgM (hatched bars) served as a control for possible non-specific binding of the secondary anti-IgM. This data corroborates the specific binding of the IgM monoclonals to the respective antigens in the left graph.

Figures 18A, 18B:
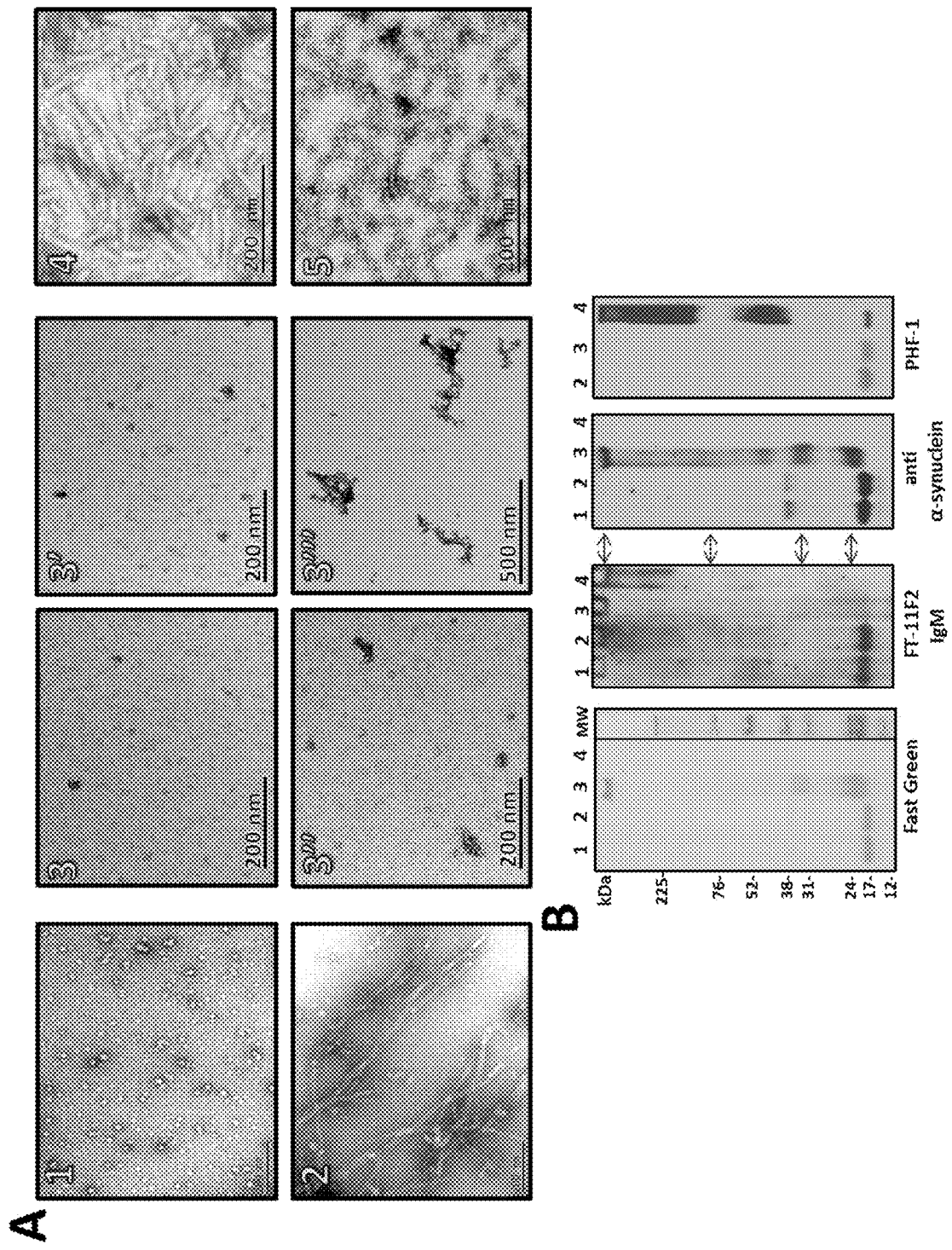
FIGS. 18A-18B demonstrate the reactivity of the conformational monoclonal antibody FT-11F2 against normal, fibrilized, and oligomeric α-synuclein and fibrils of purified human PHF.

The reactivity of anti-β-sheet conformational mAb FT-11F2 against normal, fibrilized, and oligomeric α-synuclein and fibrils of purified human PHF is shown in FIGS. 18A-18B. FIG. 18A shows electron microscopy images of normal α-synuclein (1), fibrilized α-synuclein (2) and oligomeric forms of α-synuclein after polymerization with glutaraldehyde β-3'''). There are different oligomeric states where size and aggregation varies, from small individual oligomers (3), gradually increasing its size (3' and 3'') and finally bigger oligomer aggregates (3''). Far right panels of FIG. 18A show PHF (4) and PKa digested PHF (5). FIG. 18B shows Western blots of the reactivity of the conformational antibody FT-11F2 (second blot) against normal α-synuclein (lane 1), fibrilized α-synuclein (lane 2), and oligomeric α-synuclein (lane 3) at different states (as shown in the EM images), and PHF (lane 4). The third and fourth blots of FIG. 18B show reactivity of anti α-synuclein and PHF-1 specific antibodies, respectively, which also cross-react with fibrilized and oligomeric α-synuclein. Arrows depict different oligomers of α-synuclein (as shown in FIG. 18A) that are recognized also by the FT-11F2 clone (lane 3).

Figure 19:
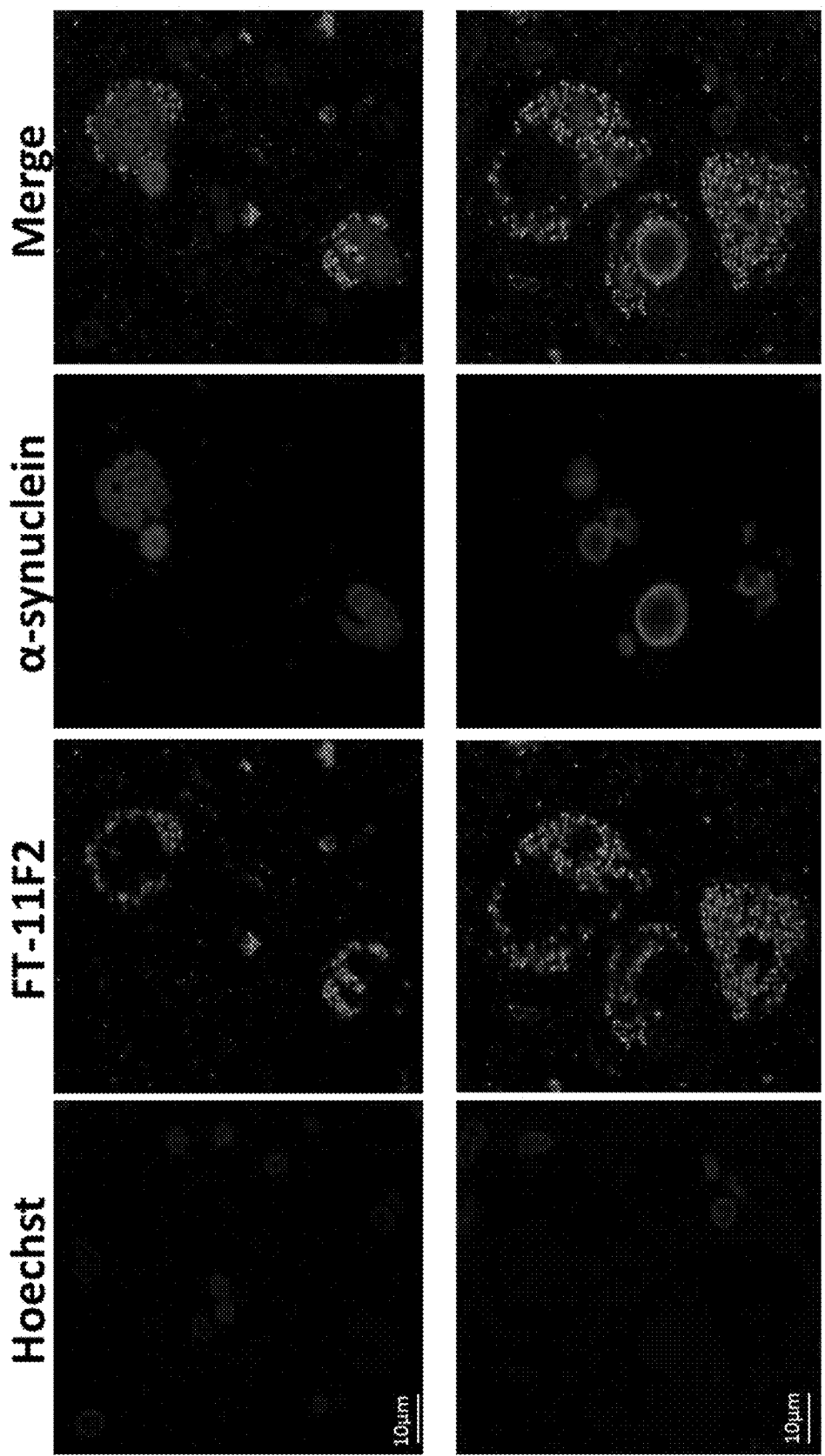
FIG. 19 depicts immunoreactivity of the conformational monoclonal antibody FT-11F2 against oligomeric α-synuclein forms surrounding Lewy bodies in Parkinson's disease in human brains.

The immunoreactivity of anti-β-sheet conformational mAb αβComAb FT-11F2 against oligomeric α-synuclein forms surrounding Lewy bodies in Parkinson's disease in human brains is shown in FIG. 19. Representative images showing immunoreactivity of the conformational monoclonal antibody FT-11F2 (second panel of images) and anti α-synuclein antibody (third panel of images) on human brain sections affected by Parkinson's disease in the substantia nigra. As shown in the fourth panel of images, conformational antibody FT-11F2 does not co-localize directly with the fibrillar α-synuclein that is found within Lewy bodies, but in the cytoplasm of substantia nigra neurons in the vicinity of the Lewy bodies. FT-11F2 does not immunolabel substantia nigra neurons from control, non-Parkinson's disease patients.

Figure 20:
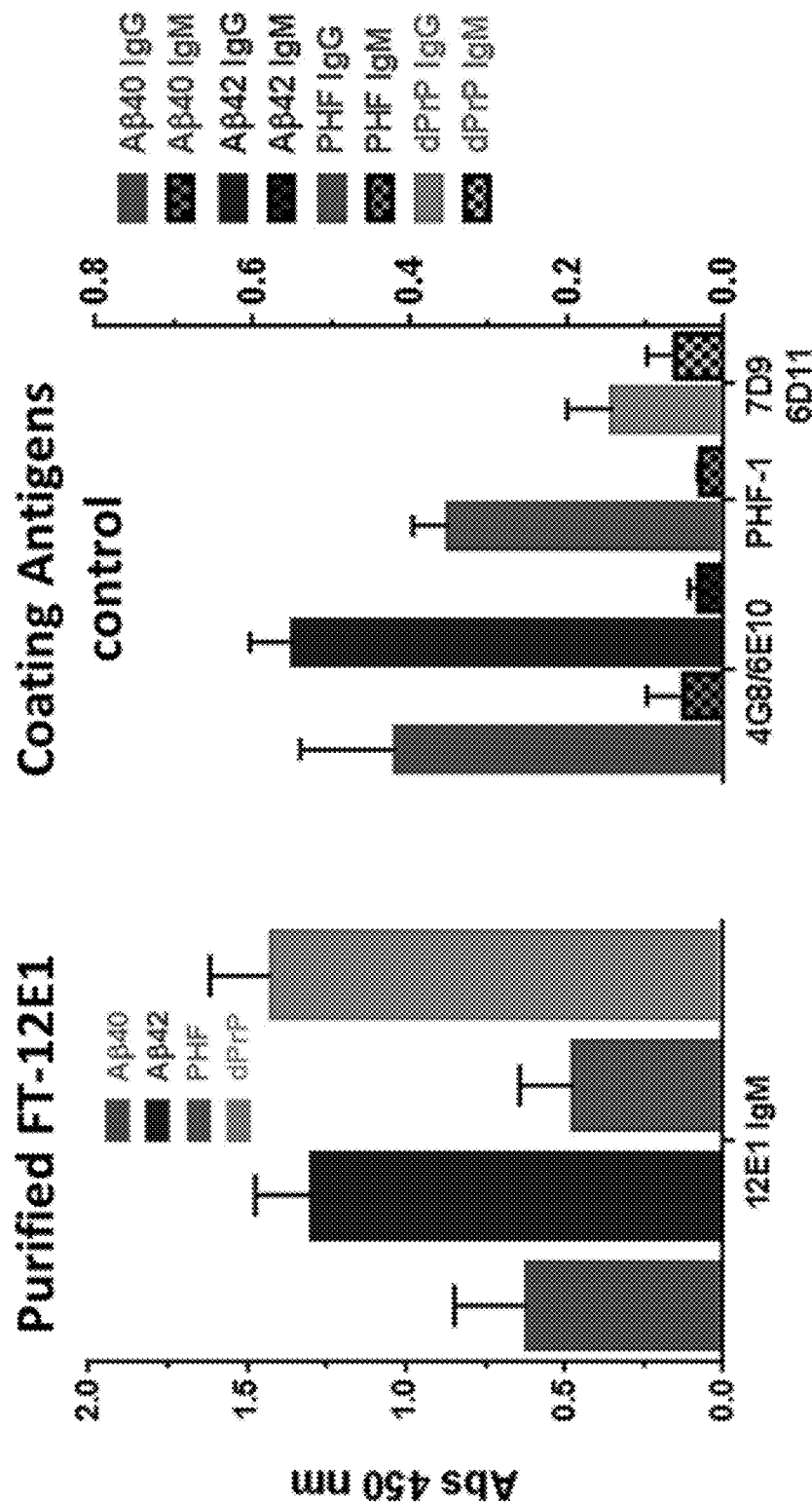
FIG. 20 depicts FT-12E1 reactivity against (from left to right on graph) Aβ 1-40, oligomerized Aβ 1-42, human purified PHF, and oligomerized, recombinant deer Prion protein (dPrP) (left graph).

Example 4—Characterization of Anti-β-Sheet Conformational mAb αβComAb FT-12E1

αβComAb FT-12E1 reactivity against Aβ 1-40, oligomerized Aβ 1-42, human purified PHF, and oligomerized, recombinant deer Prion protein (dPrP) is shown in FIG. 20. The right graph of FIG. 20 shows plate coating antigen control. Incubation of the immobilized antigen (i.e., from left to right, Aβ40, oligomerized Aβ42, PHF, and oligomerized dPrP) with primary antibodies (i.e., anti-Aβ 4G8/6E10 (IgG) antibody, PHF-1 (IgG) antibody, and anti-PrP 7D9/6D11 (IgG) antibody) and a secondary anti-mouse IgG antibody, served as a positive control for the even distribution of the antigens seeded on the plates. Incubation with the same primary antibodies (solid bars) and secondary anti- IgM (hatched bars) (right graph) served as a control for possible non-specific binding of the secondary anti-IgM. This data corroborates the specific binding of IgM monoclonals to the respective antigens in the left histogram.

Figures 21A, 21B:
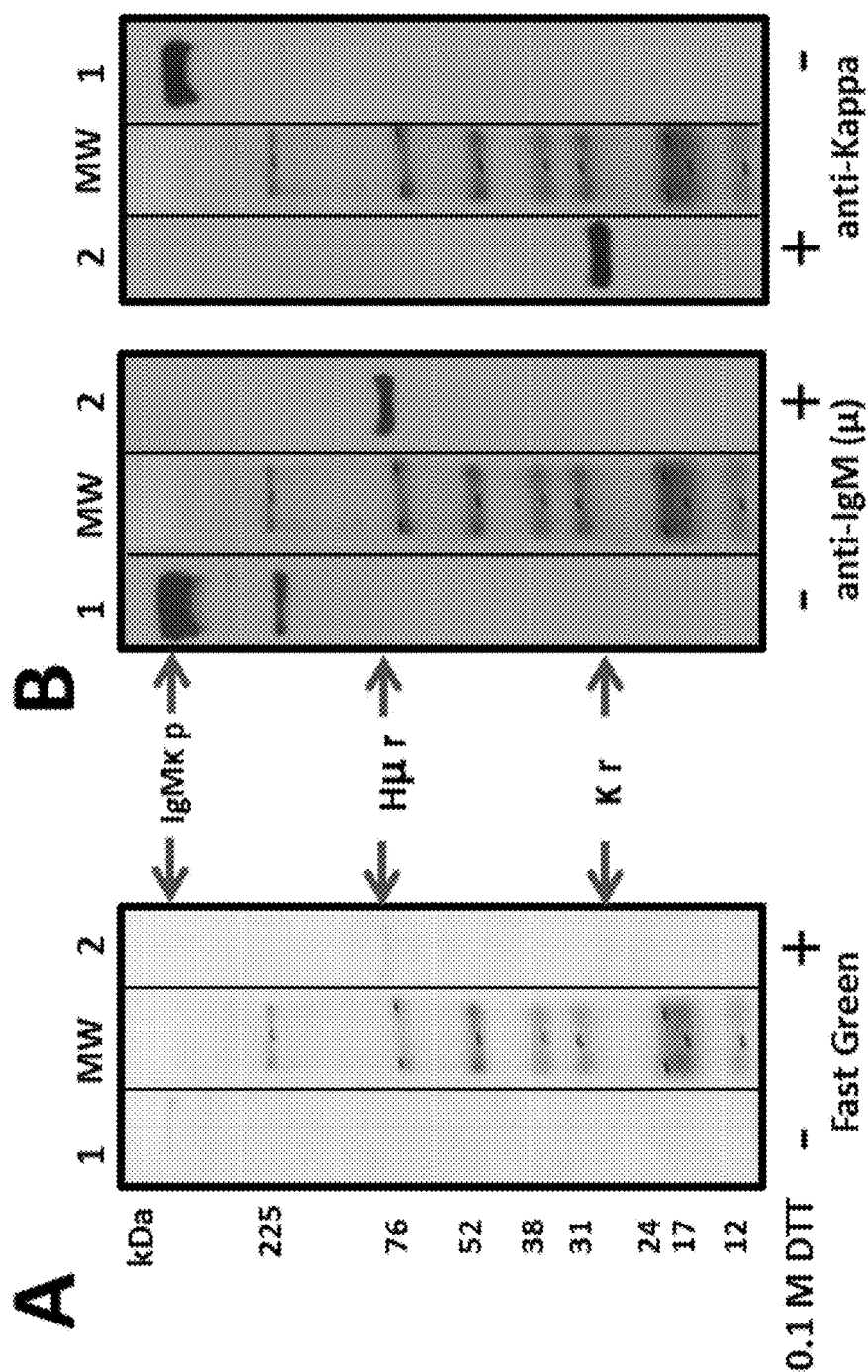
FIGS. 21A-21B depict purification of the conformational monoclonal antibody FT-12E1.

Purification of the anti-β-sheet conformational monoclonal antibody FT-12E1 is depicted in FIGS. 21A-21B. FIGS. 21A and 21B are western blots of the conformational monoclonal antibody FT-12E1 purified with a llama anti-μ column. FIG. 21A shows Fast Green staining as a protein loading control. FIG. 21B shows anti-mouse IgM μ specific (left panel) and anti-mouse Kappa reactivity (right panel). Lane 1 of each panel contains un-reduced sample and lane 2 contains DTT reduced protein (IgMk p=pentamer, Hμ r=reduced heavy chain, and Kr=Kappa light chain reduced).

Figures 22A, 22B, 22C:
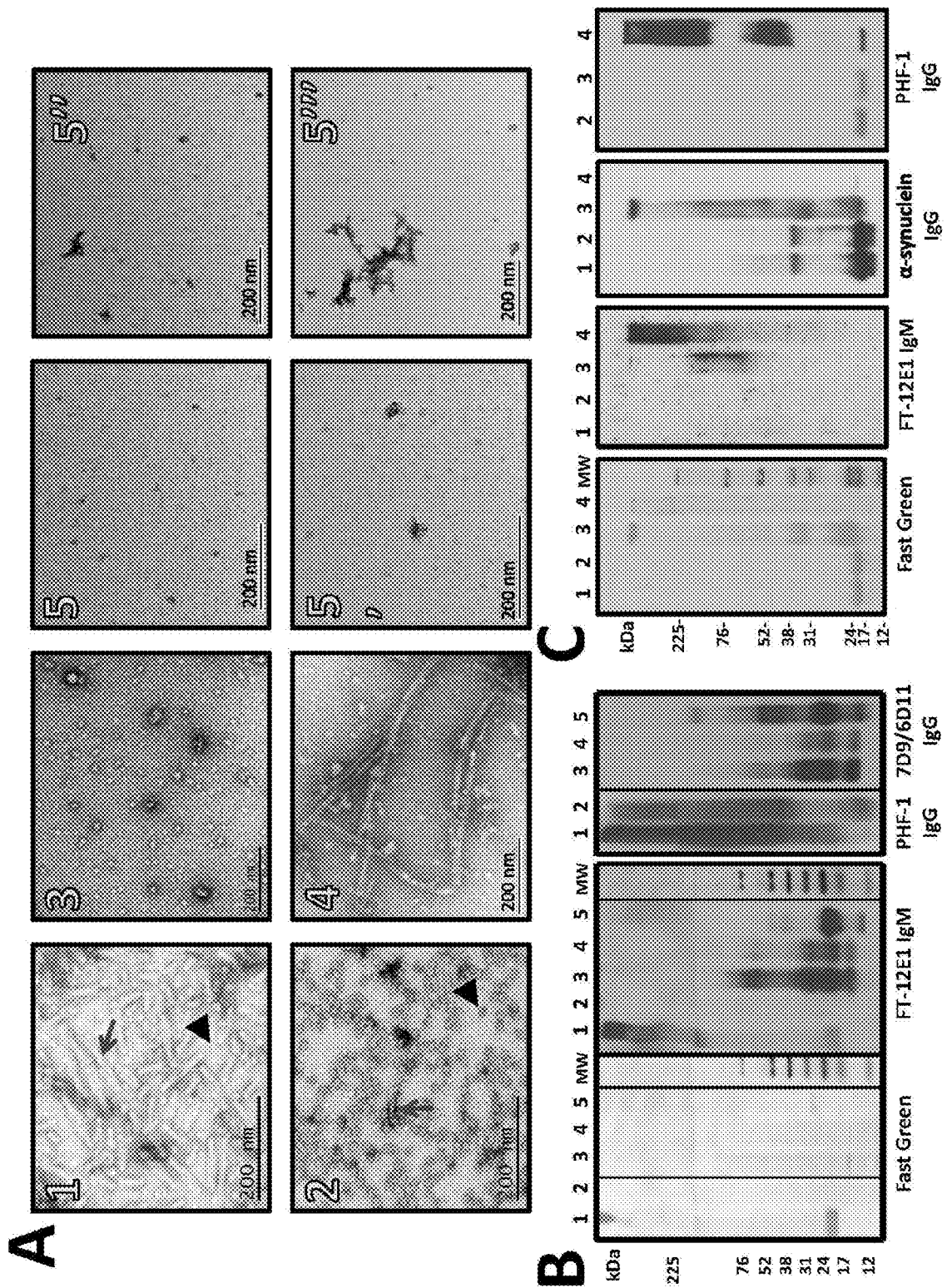
FIGS. 22A-22C show the reactivity of the conformational monoclonal antibody FT-12E1 against purified human PHF, three different strains of pathogenic PrP$^{Res}$, and α-synuclein.

The reactivity of anti-β-sheet conformational mAb aβComAb FT-12E1 against purified human PHF, three different strains of pathogenic PrP$^{Res}$, and α-synuclein is shown in FIGS. 22A-22C. FIG. 22A shows electron microscopy images of PHF (1) and PKa digested PHF (2) (grey arrow fibril; black arrowhead oligomer), normal α-synuclein (3), fibrilized α-synuclein (4), and oligomeric forms of α-synuclein after polymerization with glutaraldehyde (5-5′′′). Different oligomeric states of α-synuclein having a variety of sizes and aggregation states are depicted, from small single oligomers (5), to those incrementally increasing its size (5′ and 5″), and finally bigger oligomer clusters (5′′′). FIG. 22B (middle panel) is a Western blot showing the reactivity of the conformational monoclonal antibody FT-12E1 against PHF and PKa digested PHF (lanes 1 and 2), two different prion scrapie strains 22L, 139A and recombinant deer PrP (lanes 3, 4 and 5 respectively). The right-hand blot shows reactivity of PHF-1 IgG, and PrP specific antibodies 7D9/6D11 against the aforementioned protein samples as positive controls. The left-hand blot of FIG. 22B shows Fast Green staining of the middle and right blots as a protein loading control. FIG. 22C shows a series of four Western blots. The second blot in the series shows reactivity of the conformational antibody FT-12E1 against normal (lane 1), fibrilized (lane 2), and oligomeric (lane 3) α-synuclein, where FT-12E1 recognizes α-synuclein oligomers. The third and fourth blots of FIG. 22C show anti α-synuclein IgG and PHF-1 IgG reactivity against fibrilized and oligomeric α-synuclein samples loaded in the same lanes as described above. The first blot of FIG. 22C is a Fast Green protein loading control.

Figures 23A, 23B:
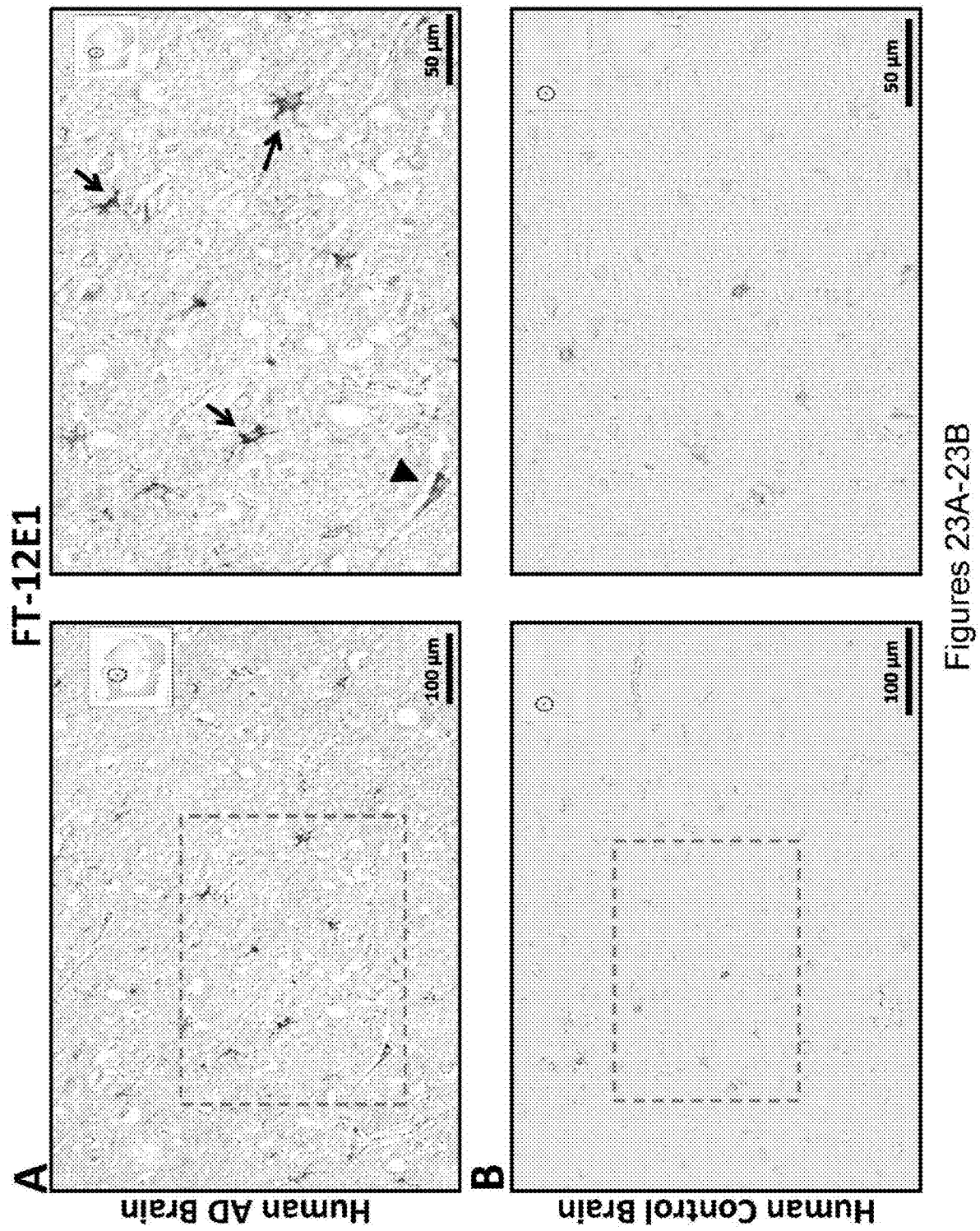
FIGS. 23A-23B demonstrate conformational monoclonal antibody FT-12E1 reactivity in AD human brain sections.
Figures 24A, 24B, 24C:
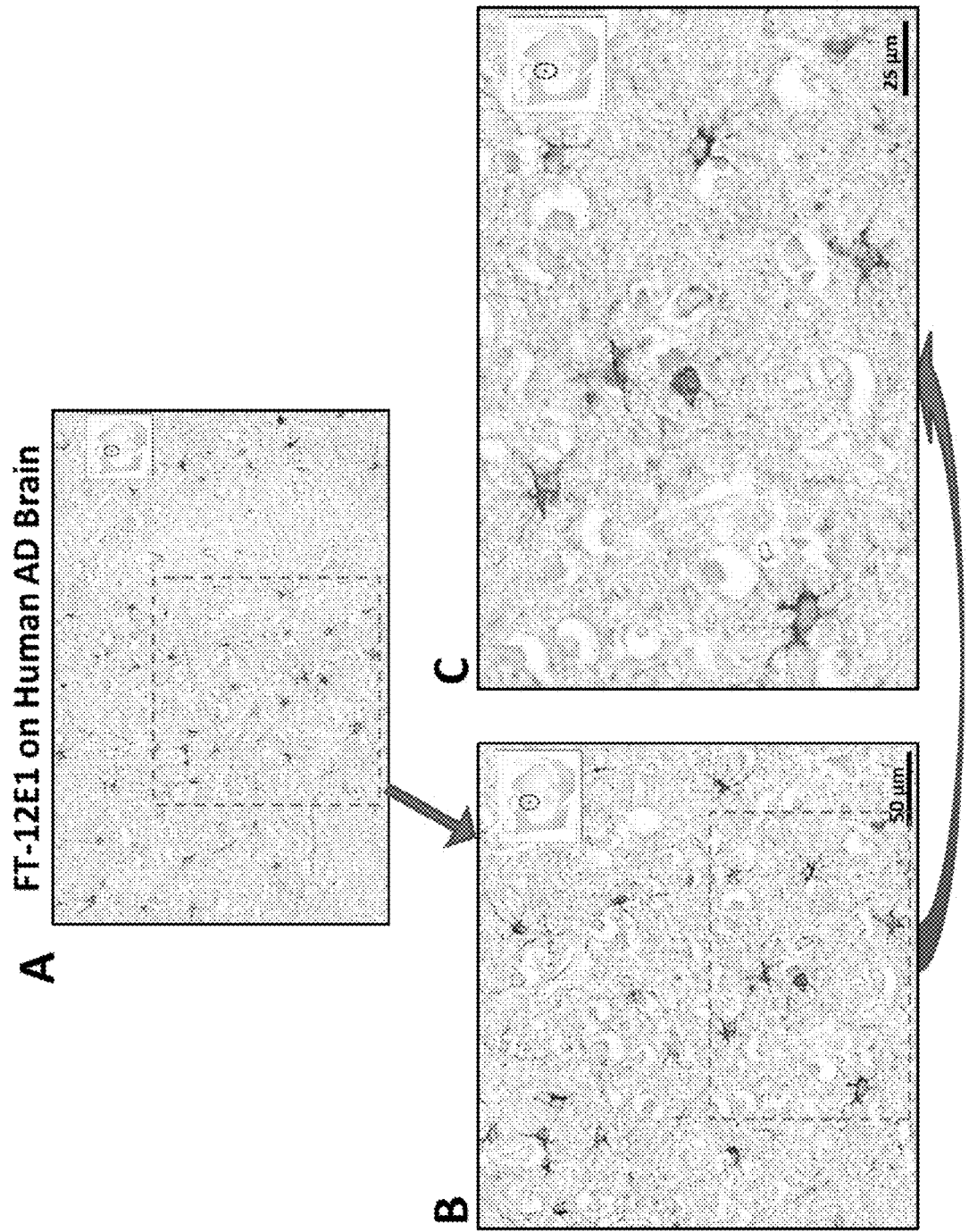
FIGS. 24A-24C demonstrate conformational monoclonal antibody FT-12E1 immunoreactivity in AD human brain sections.

The reactivity of anti-β-sheet conformational mAb FT-12E1 in AD human brain sections is depicted in FIGS. 23A-23B and FIGS. 24A-24C. FIG. 23A shows immunoreactivity of the conformational monoclonal antibody FT-12E1 is preferential to glial cells (black arrows) rather than neurons (black arrowhead). FIG. 23B (control) shows there is no staining in non-AD, control brain sections. The right images of FIGS. 23A and 23B are magnifications of the boxed areas shown in the left images of each figure. 24A is a representative image showing the staining pattern of the conformational monoclonal antibody FT-12E1 in a human AD brain section. FIGS. 24B and 24C are magnified views of the boxed areas, showing characteristic cytoplasmic staining in glial-like cells and along processes.

Example 5—Characterization of Anti-β-Sheet Conformational mAbs aβComAbs TF-10E8 and TF10F7

Figures 25A, 25B:
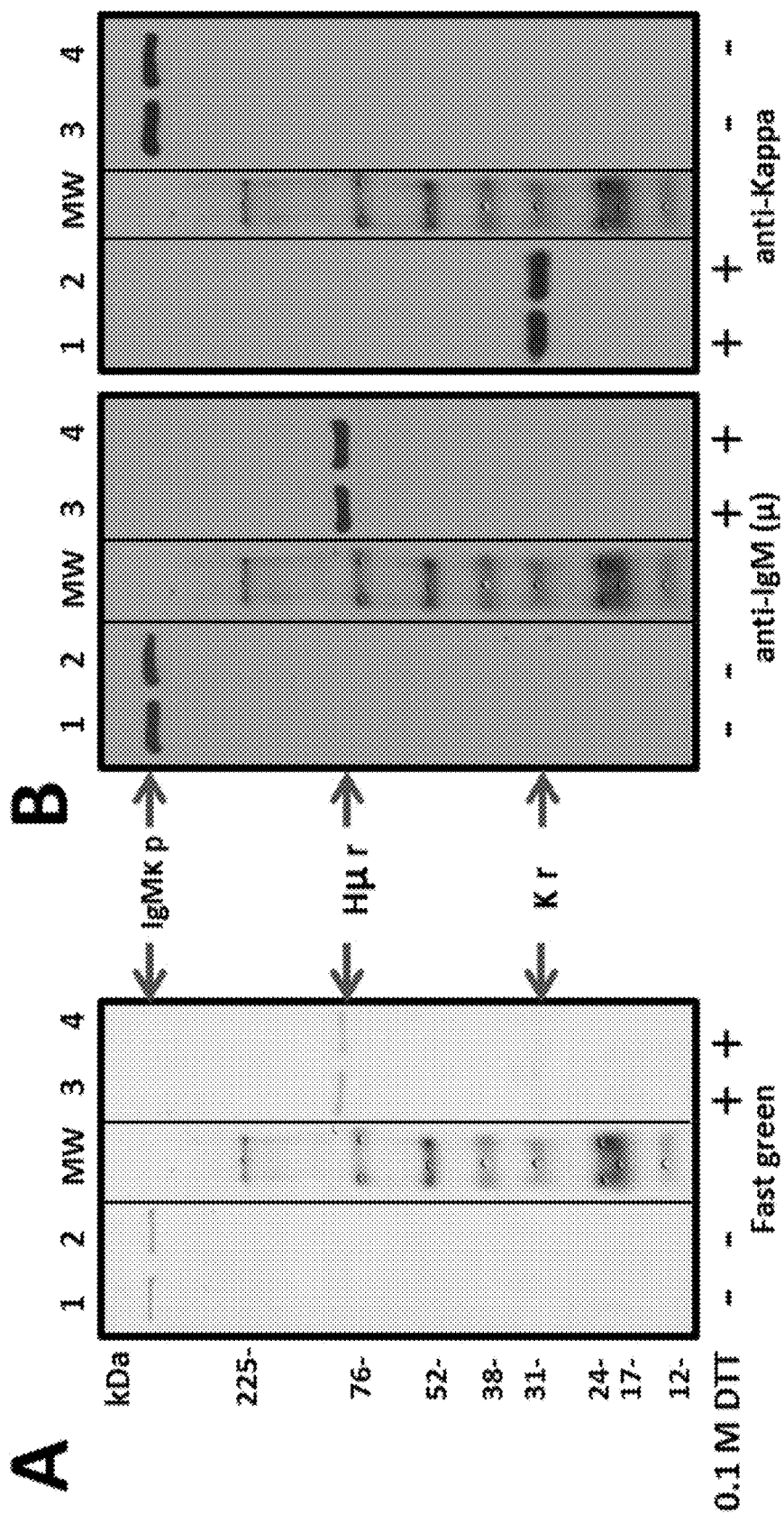
FIGS. 25A-25B show western blots of the conformational monoclonal antibodies TF-10E8 and TF-10F7 purified with a llama anti-μ column.

Purification of the anti-β-sheet conformational monoclonal antibodies TF-10E8 and TF-10F7 with a llama anti-μ column is depicted in FIGS. 25A-25B. FIG. 25A shows Fast green staining as a protein loading control. FIG. 25B shows anti-mouse IgM μ specific reactivity (left blot) and anti-mouse Kappa reactivity (right blot). Lanes 1 and 2 of each panel contain un-reduced TF-10E8 and TF-10F7 antibodies, respectively, and lanes 3 and 4 of each panel contain DTT reduced TF-10E8 and TF-10F7 antibodies, respectively. IgMk p=pentamer, r=reduced heavy chain, and Kr=Kappa light chain reduced.

The reactivity of mAbs TF-10E8 and TF-10F7 against PHF and three different strains of pathogenic PrP is demonstrated in FIGS. 26A-26C. FIG. 26A shows electron microscopy images of PHF (1) and PHF digested with PKa (2) (grey arrow fibril; black arrowhead oligomer). Typical oligomerized PrP from single oligomers (3) that start aggregating (4 and 5) to form bigger clusters of oligomers (6). FIGS. 26B and 26C are Western blots showing the reactivity of the conformational monoclonal antibodies TF-10E8 (FIG. 26B, middle) and TF-10F7 (FIG. 26C, middle) against PHF (lane 1) PKa digested PHF (lane 2), prion scrapie strains 22L (lane 3) and 139A (lane 4), and recombinant deer PrP (lane 5). Protein loading of the aforementioned blots was visualized using Fast Green staining (left most blots shown in FIGS. 26B and 26C). Positive control staining was carried out using PHF-1 IgG and 7D9/6D11 (Prp) IgG as shown in the right-most blots of FIGS. 26B and 26C.

Figures 27A, 27B:
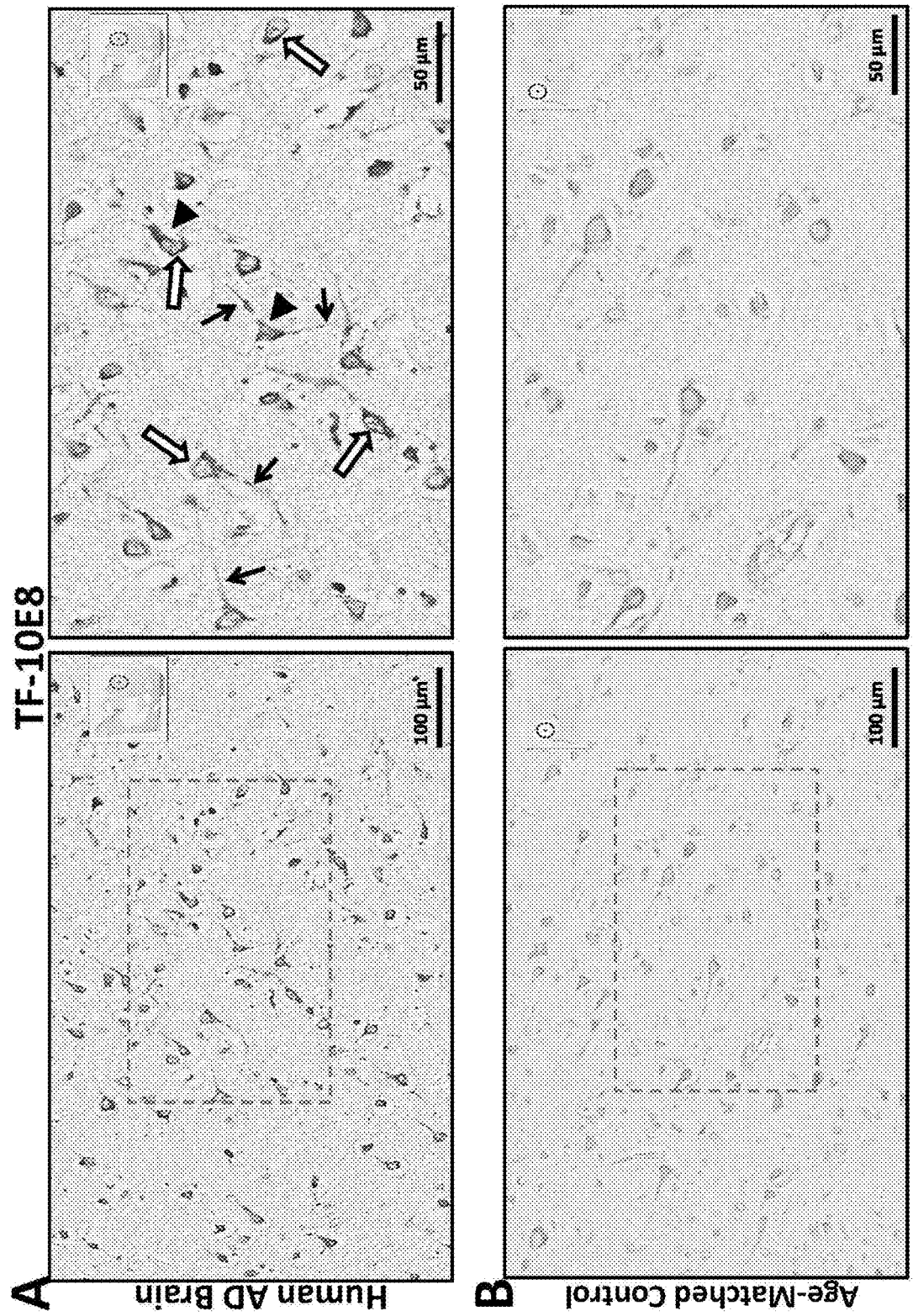
FIGS. 27A-27B depict immunoreactivity of the conformational monoclonal antibody TF-10E8 in AD affected human brain hippocampus tissue.

The immunoreactivity of anti-β-sheet conformational mAb TF-10E8 in AD affected human brain hippocampus tissue is shown in FIGS. 27A-27B. FIG. 27A shows representative images of the specificity of the conformational monoclonal antibody TF-10E8 for neuronal cytoplasm (black arrowhead), neuronal processes (black arrows) and with less intensity nuclei (white arrows) of neurons. FIG. 27B shows no TF-10E8 immunoreactivity in age-matched control brain sections. The right-hand images of FIGS. 27A and 27B, respectively, are higher magnification views of the boxed areas identified in left-hand images of each respective figure.

Figures 28A, 28B:
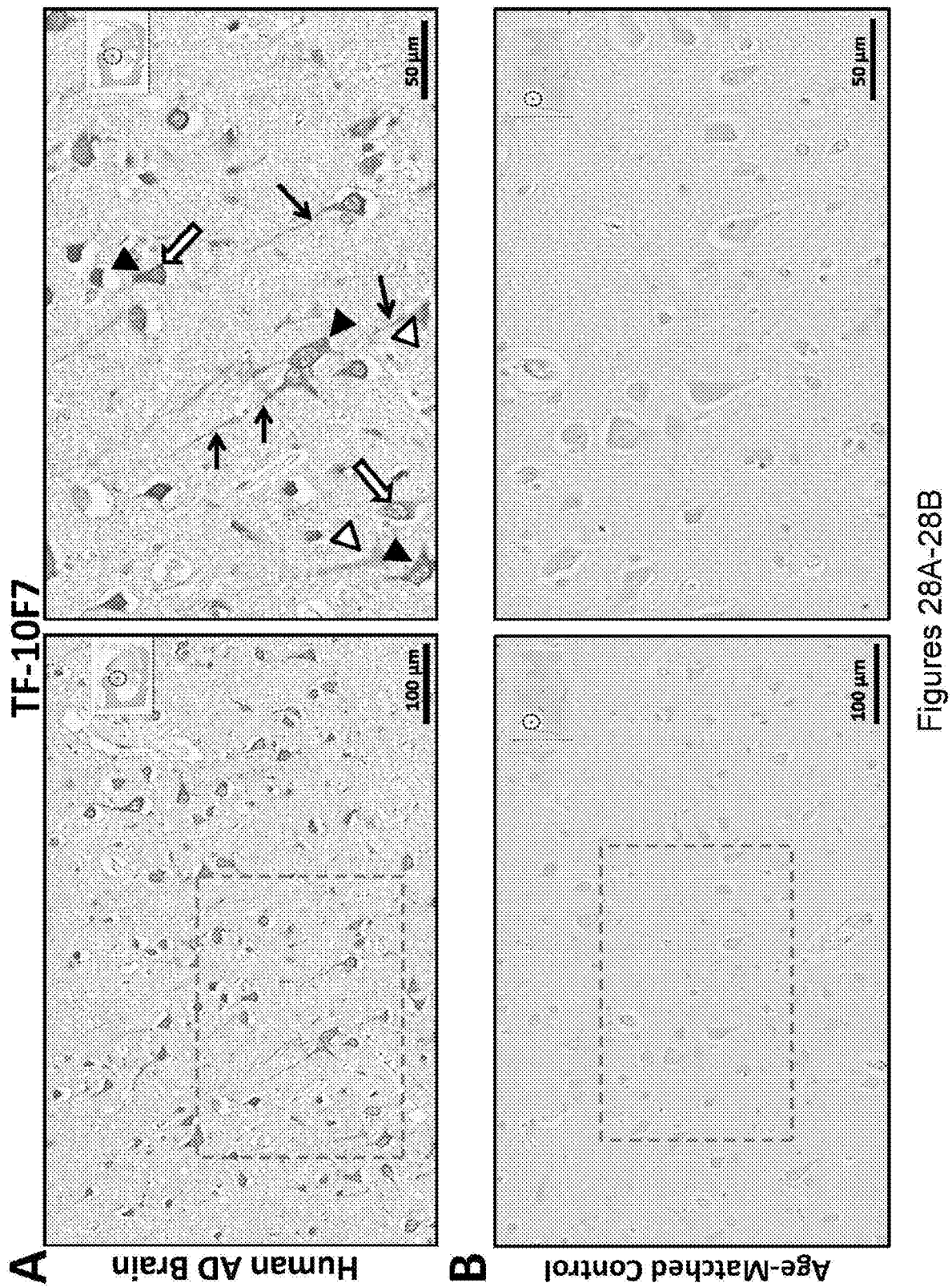
FIGS. 28A-28B depict immunoreactivity of the conformational monoclonal antibody TF-10F7 in AD affected human brain sections.

The immunoreactivity of anti-β-sheet conformational mAb TF-10F7 in AD affected human brain sections is shown in FIGS. 28A-28B. FIG. 28A shows representative images of the specificity of the conformational monoclonal antibody TF-10F7 for neuronal cytoplasm (black arrowhead), neuronal processes (black arrows), and nuclei (white arrows) of neurons. Some stained neurons are in close proximity to each other (consistent with the hypothesis that pathological oligomeric conformers can spread from neuron to neuron). It is possible to detect dystrophic neurons (white arrowheads). FIG. 28B are images showing no TF-10F7 immunoreactivity in age-matched control brain sections. The right-hand images of FIGS. 28A and 28B, respectively, are higher magnification views of the boxed areas identified in the left-hand images of each respective Figure.

Figures 29A, 29B:
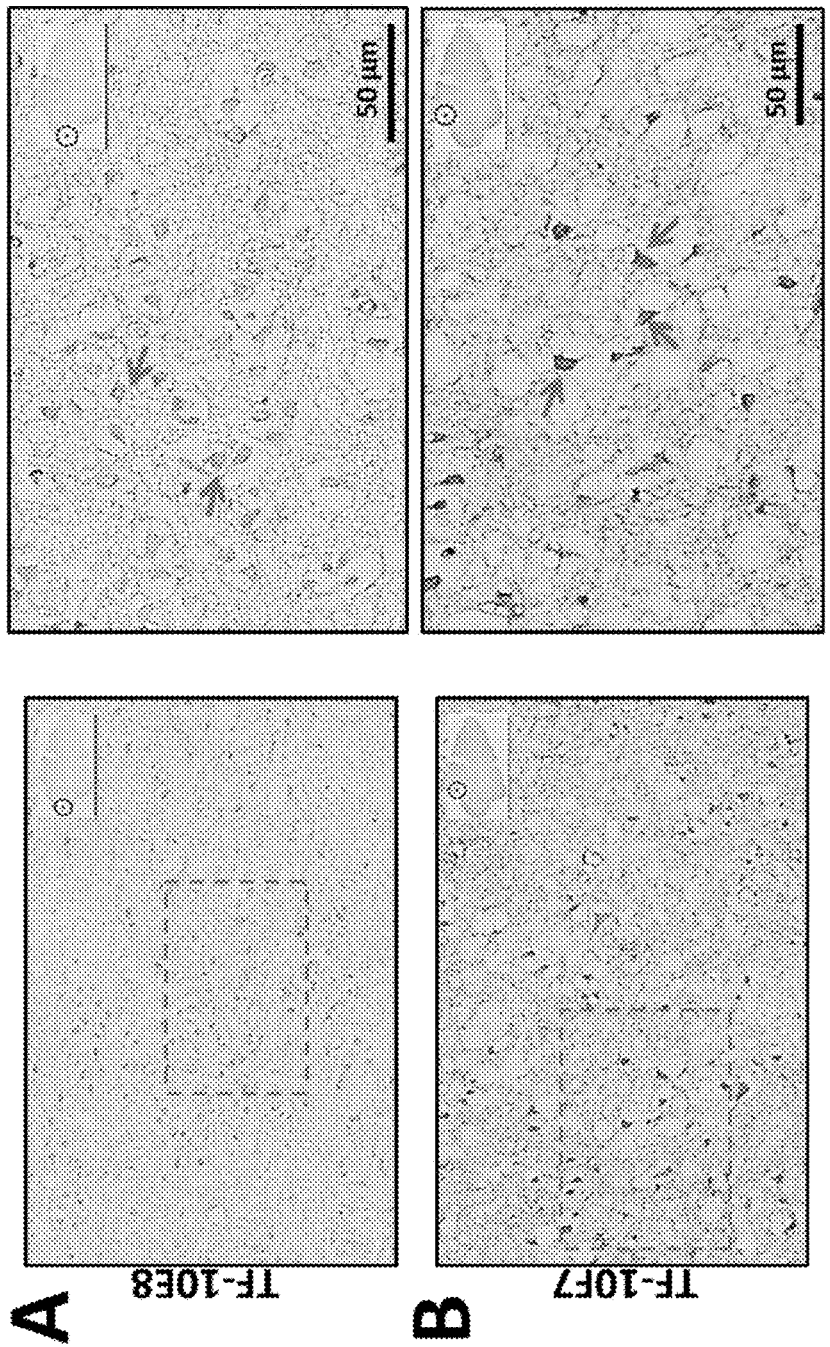
FIGS. 29A-29B depict immunoreactivity of the conformational monoclonal antibodies TF-10E8 and TF-10F7 in human brain sections of a subject having Gerstmann-Sträussler-Scheinker syndrome (GSS), a genetic, autosomal dominant prion disease.

The immunoreactivity of anti-β-sheet conformational mAbs aβComAbs TF-10E8 and TF-10F7 in human brain sections of a subject having Gerstmann-Sträussler-Scheinker syndrome (GSS), a genetic, autosomal dominant prion disease is shown in FIGS. 29A-29B. FIGS. 29A and 29B are representative images showing specificity of the conformational monoclonal antibodies TF-10E8 and TF-10F7 for neuronal cytoplasm, neuronal processes, and the nucleus of neurons in the GSS human brain sections (arrows). The right-hand images of FIGS. 29A and 29B show magnified views of the boxed areas identified in the left-hand images.

Example 6—Anti-β-Sheet Conformation Monoclonal Ameliorates Aβ and Tau Oligomer Pathology in an Alzheimer's Mode Production and Selection of the Anti-β-Sheet Conformational Monoclonal Antibody GW-23B7.

Anti-β-sheet conformational monoclonal antibody (aβComAb) GW-23B7 was obtained after immunization of a CD-1 mouse with the p13Bri immunogen and subsequent hybridoma production performed at the Bi-Institutional Antibody and BioResource Core Facility of Memorial Sloan Kettering Cancer Center and The Rockefeller University as described in Example 1. All procedures were approved by the Institutional Animal Care and Use Committee protocol #97-03-009 and followed NIH standards.

Selection of a conformational monoclonal with reactivity to oligomers presenting dominant β-sheet secondary structure was done by enzyme-linked immunosorbent analysis (ELISA) as previously described (Goñi et al., "Immunomodulation Targeting of Both Abeta and Tau Pathological Conformeres Ameliorates Alzheimer's Disease Pathology in TgSwDI and 3×Tg Mouse Models" *J Neuroinflammation* 10:150 (2013), and Goñi et al., "Immunomodulation Targeting Abnormal Protein Conformation Reduces Pathology in a Mouse Model of Alzheimer's Disease" *PLoS. ONE* 5(10):e13391 (2010), which are both hereby incorporated by reference in their entirety). Plates were coated overnight at 4° C. with either Aβ1-40 or Aβ1-42 in 50 mM ammonium sulfate pH 9.6 maximizing the oligomeric content difference between both Aβ peptides (FIGS. 30A-30E), paired helical filaments (PHF) purified from a human brain of Alzheimer's disease (AD) or PrP$^{res}$ as previously described in Example 1 (Goñi et al., Immunomodulation Targeting Abnormal Protein Conformation Reduces Pathology in a Mouse Model of Alzheimer's Disease" *PLoS ONE* 5(10):e13391 (2010), which is hereby incorporated by reference in its entirety. Approximately 125 µL of cell supernatant was diluted 1:1 with 50 mM Tris-buffered saline pH 7.2, 0.1% Tween 20 (TBS-T) and 50 µl/well were applied to each one of the four Immulon 2HB (Thermo, Waltham, Mass.) 96-well microtiter pre-coated plates. Bound antibodies were detected in the original cloning with horseradish peroxidase-labeled (HRP) goat anti-mouse IgG+IgM+IgA (H+L) (KPL, Gaithersburg, Md., USA). Color developing substrate was Tetramethyl benzidine (TMB; Pierce, Rockford, Ill.) and readings were made at 450 nm. aβComAb GW-23B7 was further subcloned and levels of reactivity tested as above in duplicates diluted 1:1000 in TBS-T and detected with HRP-goat anti-mouse IgM(µ) (KPL, Gaithersburg, Md., USA) or HRP-goat anti-mouse Kappa chain (Southern Biotech, US). Control coating was assessed with commercial 4G8/6E10 antibodies specific for Aβ peptides, PHF-1 for PHF and 7D9/6D11 antibodies for PrP; all detected with HRP-goat anti-mouse IgG (H+L) (GE Healthcare UK). Duplicates of the controls were used to determine the lack of cross-reactivity of the secondary anti-µ with the IgGs or the coating protein/peptides Purification of aβComAb GW-23B7.

The aβComAb GW-23B7 present in the subcloned hybridomas was precipitated with Saturated Ammonium Sulfate (SAS) 761.5 g/Lt at 21° C. Samples were made 30% in SAS, incubated at Room temperature (RT) for at least 4 hours, centrifuged at 14,000×g for 15 min and the precipitate washed with a comparable volume of 30% SAS and stored at 4° C. until further use.

Partially purified aβComAb GW-23B7 IgM was further purified through CaptureSelect (Thermo-Life Technologies, Waltham, Mass.) IgM affinity matrix containing a 14 kDa Llama antibody fragment recognizing specifically human or mouse IgM but none other immunoglobulins (IgG, IgA) from any animal. The ligand coupled to NHS-activated Sepharose 4 Fast Flow has a binding capacity of 2.5 mg of IgM per ml of matrix. Briefly, 1 ml of matrix in 20% ethanol was poured at RT into a 3 ml plastic column, equilibrated and washed with at least 20 bed volumes of PBS pH 7.2. The column was drained to the top before adding the sample diluted in PBS. The flow rate was established at 1 ml/min and the collected flow was passed again at least three times through the column to maximize binding. The column was then washed with 5 bed volumes of PBS before eluting the IgM with 1.5 bed volumes of 0.1 M Glycine pH 3.0; the eluates were immediately neutralized with 1N NaOH. A second 1.5 bed volume of 0.1M glycine pH 3.0 was added to release all the bound IgM and the column was regenerated with 10 bed volumes of PBS to start the process again as needed. The eluted IgM was aliquoted and kept at −80° C. until use. Each batch of IgM aβComAb GW-23B7 was assessed for purity on blots with specific antisera and protein stain, and for antibody activity against oligomers run on gels or ELISA as described above.

Surface Plasmon Resonance.

Measurements of the affinity of aβComAb GW-23B7 to Aβ oligomeric conformers were determined using surface plasmon resonance. Briefly, a carboxymethyl dextran gold sensor slide was activated with a 10 mg/ml N-hydroxysuccinimide/40 mg/ml N-ethyl-N'-(dimethylaminopropyl) carbodiimide aqueous solution injected over both channels of a Reichert SR 7000DC surface plasmon resonance system (Reichert Technologies, Depew, N.Y.) for 7 minutes at 20 uL/min. Then a 50 ug/mL solution of either glutaraldehyde polymerized Aβ1-42 or HFIP monomeric Aβ1-42 in 10 mM sodium acetate pH 5.0 buffer was injected over only one channel for 20 minutes at 20 µL/min, followed by blockage of excess activated groups by injection over both channels of 1M ethanolamine HCl pH 8.5 for 10 minutes. Kinetic measurements were performed at 25° C. with a flow rate of 25 µL/min using serial dilutions of the monoclonal antibody in PBS-T buffer pH 7.4. After each binding cycle the surface was regenerated by a short and fast injection of 10 mM hydrochloric acid. The plots and the KD were determined using the advanced biosensor data processing and analyzing Scrubber software 2.0a (Biologic Software).

Electron Microscopy.

Samples of Aβ1-40 and Aβ1-42 dissolved in ammonium bicarbonate pH 9.6 as used for ELISA assay coating, or samples of fibrilized and polymerized AO 1-42, Paired Helical Filament (PHF) and Protein Kinase A digested PHF diluted 1 mg/ml in PBS pH 7.4 were all applied, 3 µl of each, onto carbon coated 400 mesh Cu/Rh grids (Ted Pella Inc., Redding, Calif.) and stained with 1% uranyl acetate in distilled water (Polysciences, Inc, Warrington, Pa.). Stained grids were examined under Philips CM-12 electron microscope and photographed with a Gatan (4 k×2.7 k) digital camera.

Infusion of 3×Tg Mice with aβComAb GW-23B7 or Vehicle Control.

Figures 35A, 35B, 35C:
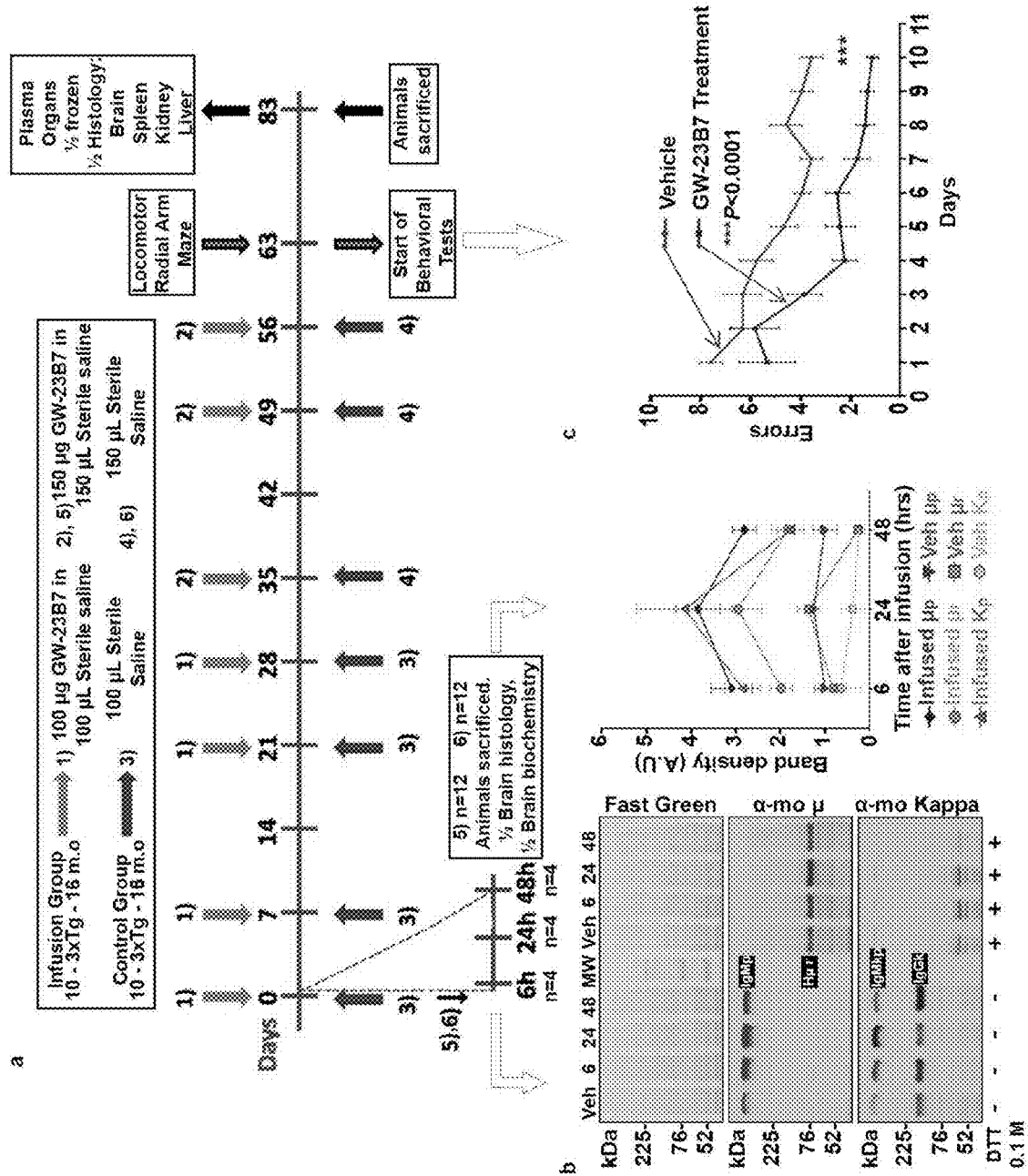
FIGS. 35A-35C depict a protocol of infusion of aβComAb GW-23B7 or vehicle control on 3xTg mice and the ensuing behavioral and kinetics tests.

A schematic of the protocol for infusion is shown in FIG. 35A. All procedures were approved by the NYU Institutional Animal Care and Use Committee protocol #170202-01 and followed NIH standards. Two groups (n=10) of 16 month old triple transgenic Alzheimer's Disease Mouse model APP KM670/671NL (Swedish), MAPT P301L, PSEN1 M146V (Oddo et al., "Triple-Transgenic Model of Alzheimer's Disease with Plaques and Tangles: Intracellular Abeta and Synaptic Dysfunction" *Neuron* 39(3):409-21 (2003), which is hereby incorporated by reference in its entirety) (3×Tg) with amyloid and tau pathologies, received a weekly intraperitoneal injection of either 100 µL of 1 µg/µL aβComAb GW-23B7 in sterile saline or 100 µL of sterile saline for the initial two weeks. Animals were rested for one week and received the same type of weekly injections for the following 3 weeks. After two weeks rest, both groups were inoculated weekly with either 150 μL of 1 μg/μL GW-23B7 or 150 μL of sterile saline control for two more weeks. One week after the last injection, locomotor and behavioral cognitive tests were performed for both groups spanning for three weeks of tests after which the animals were bled from the heart, thoroughly perfused with PBS pH 7.2 and sacrificed. The brains were harvested immediately, the cerebellum was removed, and the remainder split in half, one half flash frozen over dry ice for future biochemical studies and the other half fixed in periodate-lysine-paraformaldehyde (PLP) for histochemistry. Intraperitoneal cavity was visually checked for anomalies and kidneys, spleen and liver were collected for eventual controls.

Two additional groups of 18 m.o. 3×Tg mice (n=12 each group) were used to assess the kinetics of the IgM monoclonal penetration in the brain after a peripheral injection. The animals in each group received an intraperitoneal injection of either 150 μL of 1 μg/μL of mAb GW-23B7 in sterile saline or 150 μL sterile saline vehicle alone. Four animals of each group were euthanized at 6, 24 and 48 hours; extensively perfused with PBS (Goñi et al., "Immunomodulation Targeting of Both Abeta and Tau Pathological Conformers Ameliorates Alzheimer's Disease Pathology in TgSwDI and 3×Tg Mouse Models" *J. Neuroinflammation* 10:150 (2013), and Scholtzova et al., "Amyloid β and Tau Alzheimer's Disease Related Pathology is Reduced by Toll-like Receptor 9 Stimulation" *Acta Neuropathol. Comm.* 2:101 (2014), which are both hereby incorporated by reference in their entirety) and the brains harvested for biochemical and histochemical assays as above described.

Locomotor and Behavioral Testing.

Locomotor and behavioral cognitive tests were performed as previously described (Goñi et al., "Immunomodulation Targeting of Both Abeta and Tau Pathological Conformers Ameliorates Alzheimer's Disease Pathology in TgSwDI and 3×Tg Mouse Models" *J. Neuroinflammation* 10:150 (2013), and Scholtzova et al., "Amyloid β and Tau Alzheimer's Disease Related Pathology is Reduced by Toll-like Receptor 9 Stimulation" *Acta Neuropathol. Comm.* 2:101 (2014), which are both hereby incorporated by reference in their entirety). Prior to each test mice were adapted for 15 min to the room lights. Locomotor tasks were performed to verify that any treatment-related effects were not explained by sensorimotor abilities.

Traverse Beam.

Traverse beam test was used to determine general motor coordination and balance. Each mouse was placed on a beam 1.1 cm wide and 50.8 cm long supported 30 cm above a padded surface, with a black box attached to the end of the beam. Mice were monitored for a maximum time of 60 sec, recording the number of footslips before falling or reaching the goal box. When an animal fell, it was placed back at the position it was prior to the fall. The average number of footslips as per four successive trials was calculated. A footslip was defined as an error and recorded numerically.

Rotarod.

Each animal was placed on a Rotarod 7650 accelerating model apparatus with a diameter of 3.6 cm (Ugo Basile, Biological Research Apparatus, Varese, Italy) to assess differences in balance and forelimb and hindlimb motor coordination. The animals were adapted to the apparatus for two training sessions and tested three times with increasing speed. The rotor rod was initially set at 1 rpm and speed gradually increased every 30 sec. Latency to fall or invert from the top of the rotating barrel was recorded. The rod was cleaned with water and 30% ethanol after each session.

Radial Arm Maze.

Spatial learning was evaluated using an 8 arm radial arm maze (arms 35 cm length and 7 cm wide) with a cup of 1 cm diameter at the end of each arm. The central octagonal area had 14 cm diameter with Plexiglas guillotine doors operated remotely by a pulley system. Each cup at the end of the arms was baited with saccharine-flavored water. The behavioral test consisted of 5 adaptation days followed by 10 trial days. All the animals subjected to the test were deprived of water (only given access to water 2 hours per day). Trial time was set to a maximum of 15 minutes for each animal and the time the animals spent to visit all arms as well as the number of errors, defined as entries to previously visited arms, were recorded.

Brain Homogenization.

Flash frozen brain hemispheres from each animal were weighted and made 20% w/v on tissue homogenization buffer (THB) containing 20 mM Tris pH 7.4, 250 mM sucrose, 1 mM Ethylenediaminetetraacetic acid (EDTA), 2.5 mM Ethylene glycol-bis(β-aminoethyl ether)-N,N,N',N'-tetraacetic acid (EGTA) filtered through 0.2 μm mesh. Before use, freshly made 1.46 nM pepstatin, 1 mM phenylmethanesulfonyl-fluoride (PMSF), 1 mM sodium fluoride (NaF) and 0.96 mM sodium orthovanadate were added to obtain the working THB. Each half brain in THB was placed on ice and homogenized using a PRO 200 Hand-held homogenizer and a 5 mm×75 mm flat bottom generator probe (Pro Scientific, Monroe, Conn.) for 3 cycles of 30 seconds each at 30,000 rpm, pausing for 30 seconds between each homogenization cycle. The obtained 20% brain homogenates (BH) were aliquoted (200 μL/each) and stored at −80° C. until use.

Half brains of two additional groups of 3×Tg mice infused with aβComAb GW-23B7 or sterile saline and sacrificed at 6, 24 and 48 hrs were homogenized as above described. Half of the samples of each group were pooled, aliquoted (200 μL/each) and stored at −80° C. until use.

Electrophoresis and Western Blot.

For electrophoresis to confirm the identity of aβComAb GW-23B7, 1 μg of antibody with or without dithiothreitol (DTT) 0.1 M was mixed with an equal volume of tricine sample buffer (BioRad, Hercules Calif.), electrophoresed on Bolt™ 4-12% Bis-Tris (Thermo, Waltham, Mass.) polyacrylamide gels and system and transferred onto nitrocellulose membranes (NC) for 1 hour at 386 mA in 0.1% 3-(Cyclohexylamino)-1-propanesulfonic acid (CAPS) (Sigma-Aldrich, St. Louis, Mo.)-10% methanol. Equal protein loading was assessed on the membranes using protein reversible stain Fast Green (FG) FCF 0.1% (Fisher Scientific, Waltham, Mass.) in 25% methanol-10% Acetic acid for 1 minute, distained with 25% methanol, transferred to distilled water and scanned for records on a Canon F916900 scanner (Canon Inc, China). Membranes were then washed several times in TBS-T until all reversible stain was eliminated, blocked 1 hour at RT with 5% non-fat dry milk in TBS-T pH 8.3, and incubated with HRP-Rat anti-mouse IgM(μ) Heavy chain specific 1:6000 (Life Technologies, Waltham, Mass.) or HRP goat anti-mouse Kappa 1:6000 (Southern Biotech, Birmingham, Ala.). Bound antibodies were detected with ECL detection system (Pierce, Rockford, Ill.) on autoradiography films (MIDSCI, St Louis, Mo.); all films were scanned for records.

To evaluate the reactivity of aβComAb GW-23B7 against Aβ1-40, Aβ1-42 (fibrilized and polymerized) and Paired Helical Filaments (PHF) (Fibrillar and Proteinkinase A digested), 1-2 μg of each sample was electrophoresed, transfer to NC and blotted as indicated above. aβComAb GW-23B7 diluted 1:1000 in TBS-T was incubated with the blots for 1 hour at RT, and bound immunoglobulin detected with HRP anti-mouse IgM 1:2000. Commercial monoclonal anti-Aβ antibodies 4G8/6E10 (BioLegend, San Diego, Calif.) and anti-abnormally phosphorylated tau monoclonal PHF-1 (which recognizes phosphorylated serines at positions 396 and 404) were diluted 1:4000 and 1:2000 respectively and used as controls for the identity of peptides Aβ1-40, Aβ1-42 and PHF.

To test the presence of IgM in the brain of 3xTg mice treated with aβComAb GW-23B7 or with control sterile saline alone; pools of four 20% BH corresponding to either 6, 24 or 48 hrs. were treated with SAS as follows: 165 µL of each pool was mixed with 135 µL of SAS, incubated for 30 mins at RT in a tube rotator and tubes centrifuged for 6 mins at 14,000xg. Pellets were re-suspended in 100 µL of 45% SAS, vortexed repeatedly and centrifuged. Washed pellets were re-suspended sequentially in 75 µL of distilled deionized water and 75 µL of tricine sample buffer, centrifuged for 5 mins at 14,000xg at RT. 4 µL of the clear supernatant was mixed with 6 µL of tricine sample buffer with and without DTT 0.1 M and electrophoresed on Bolt™ 4-12% Bis-Tris polyacrylamide gels and system. The western blot was performed as described above. Each sample loaded into the gels represented the concentrated protein of approximately 1/150 of the whole brain to assure that minimal representation or differences in IgM immunoglobulin could be detected. aβComAb GW-23B7 infused animals were analyzed in pools and individually.

Quantitation of Aggregated/Oligomeric Aβ and Phosphorylated Tau on 3xTg Mice.

Aggregated/oligomeric Aβ levels were determined using the Human Aggregated Aβ ELISA kit (Invitrogen, Camarillo, Calif.), following the manufacturer's instructions. Briefly, 20% BH were thawed and made 1:4 in the diluents buffer. Samples were applied to the ELISA plates, incubated for 2 hs at RT, followed by extensive washing and incubation for 1 h at RT with biotin conjugated detection antibodies which bind only to the immobilized aggregated AP. After removal of excess antibody, HRP-labelled streptavidin was added. Samples were incubated for 30 min, washed and incubated with TMB substrate for color. Intensity of the colored product is directly proportional to the concentration of aggregated/oligomeric Aβ in the sample. The standards produced a linear curve and the best-fit lines determined by linear regression were used to calculate aggregated Aβ concentrations in the samples.

For the quantification of total tau and phosphorylated tau (Thr 231) the Meso Scale Discovery (MSD) assay (Rockville, Md.) was used as previously described (Goñi et al., "Immunomodulation Targeting of Both Abeta and Tau Pathological Conformers Ameliorates Alzheimer's Disease Pathology in TgSwDI and 3xTg Mouse Models" *J Neuroinflammation* 10:150 (2013), which is hereby incorporated by reference in its entirety). Soluble supernatants of 20% BH from 3xTg treated and control mice were diluted 1:125 with the provided standard diluent buffer and 100 µl aliquots seeded in each well on the MULTI-SPOT® 96-well 4-spot plate. The plates were incubated for 2 hs at RT, washed four times for 25 sec each and incubated for 1 hour with the SULFO-TAG™ anti-total tau antibody. The plates were then washed four times, covered to block the light, and incubated for 25 minutes with HRP-Streptavidin working solution. The reaction was stopped with stop solution and the plates read on the MSD system at 450 nm. All data were recorded and calculations made using the software provided with the MSD system.

Immunohistochemistry.

Immunohistochemistry to assess the reactivity of aβComAb GW-23B7 was performed on old 3xTg mice (>19 months old) with extensive amyloid-β and tau pathology; or formalin fixed paraffin embedded human cortex sections of Alzheimer's disease (AD), age-matched controls, young control brains and Gerstmann-Sträussler-Scheinker (GSS) brains with prion pathology obtained from the Alzheimer Brain Bank of the Alzheimer's Disease Center at NYU. All human tissue related studies were done with appropriate ethical standards under a protocol approved by the Institutional Review Board at NYU School of Medicine. Written informed consent for research was obtained from the patients or legal guardians. All data and samples were coded and handled according to NIH guidelines to protect patients' identities.

Sections were dewaxed followed by rehydration with successive washes of xylene (2x5 min), 100% ethanol (2x5 min), 95% ethanol (5 min), 70% ethanol (5 min) and phosphate-buffered solution (PBS) (5 min). Next, slides were washed with 0.3% hydrogen peroxide (2x15 min) to quench endogenous peroxidases, PBS (3x5 min) and 1 hour blocking at RT with 10% normal goat serum [NGS]-0.2% Triton X-100 in PBS. Slides were incubated overnight at 4° C. with aβComAb GW-23B7 diluted 1:2000 in 3% NGS-0.2% Triton X-100. Slides were washed three times with PBS and incubated with biotinylated anti-mouse IgM (µ specific chain) antibody (Vector Laboratories, Burlingame, Calif.) diluted 1:1000 in PBS for 1 hour followed by 1 hour incubation of Vectastain® Aβ solution (Vector Laboratories, Burlingame, Calif.). Slides were developed with 3,3-diaminobenzidine tetrahydrochloride with 2.5% nickel ammonium sulfate (Acros Organics, NJ) diluted in 0.2M sodium acetate (NaAc) pH 6. Reaction was stopped by removal of nickel solution and extensively rinsing with 0.2 M NaAc, then stabilized with PBS and mounted on glass slides with Depex® Mounting Media (Electron Microscopy Sciences, Hatfield, Pa.).

For immunofluorescence, paraffin embedded human AD or GSS brain sections were dewaxed and rehydrated as above described, then blocked 1 hour at RT with 3% NGS-0.2% Triton X-100. Antibodies to be used for co-localization were diluted in the same tube containing PBS, at the following concentrations: aβComAb GW-23B7 1:8000, anti-Aβ antibodies 4G8/6E10 1:3000, PHF-1 1:1500 and anti-GFAP 1:1500. Primary antibodies were incubated overnight at 4° C. Slides were washed with PBS (3x5 min) and incubated 2 hours with Alexa Fluor® 488-conjugated goat anti-mouse IgM (for GW-23B7) and Alexa Fluor® 647-conjugated goat anti-mouse IgG (for commercial antibodies against proteins present in NDDs) (Jackson ImmunoResearch, West Groove, Pa.) both diluted 1:500 in PBS. Slides were washed (3x5 min) and the coverslip was performed with PermaFluor™ Aqueous Mounting Medium (Thermo, Waltham, Mass.).

Black and red staining was performed using DAB for aβComAb GW-23B7 1:8500 as mentioned above. Slides were then washed with PBS (3x15 min), blocked 10 min at room temperature with 3% NGS-0.2%, incubated overnight with anti-Aβ antibodies 4G8/6E10 diluted 1:3000, washed with PBS (3x5 min), incubated with alkaline phosphatase anti-mouse IgG (Sigma-Aldrich St. Louis, Mo.) for 1 hour and color was developed with Vector Red Substrate (Vector Laboratories, Burlingame, Calif.). Slides were washed with PBS and mounted on glass slides as described above.

All mouse brains sections fixed with PLP, 40 µm/each, were stained as previously reported (Goñi et al., "Immunomodulation Targeting of Both Abeta and Tau Pathological Conformers Ameliorates Alzheimer's Disease Pathology in TgSwDI and 3×Tg Mouse Models" *J Neuroinflammation* 10:150 (2013), which is hereby incorporated by reference in its entirety), incubating overnight with monoclonal antibodies 4G8/6E10 1:3000, PHF-1 1:1500 or aβComAb GW-23B7 1:3000. Secondary antibodies used were biotinylated anti-mouse IgG (H+L) or anti-mouse IgM (Vector Laboratories, Burlingame, Calif.) diluted 1:1000 in PBS. Slides were developed with DAB in 2.5% nickel ammonium sulfate and mounted on glass slides with Depex® Mounting Media.

Statistical Analysis.

Statistical analyses were performed in the software GraphPad Prism v.7. For the behavioral testing, two-way ANOVA were used and two-tailed t tests for biochemistry assays.

Results.

Figures 30A, 30B, 30C, 30D, 30E:
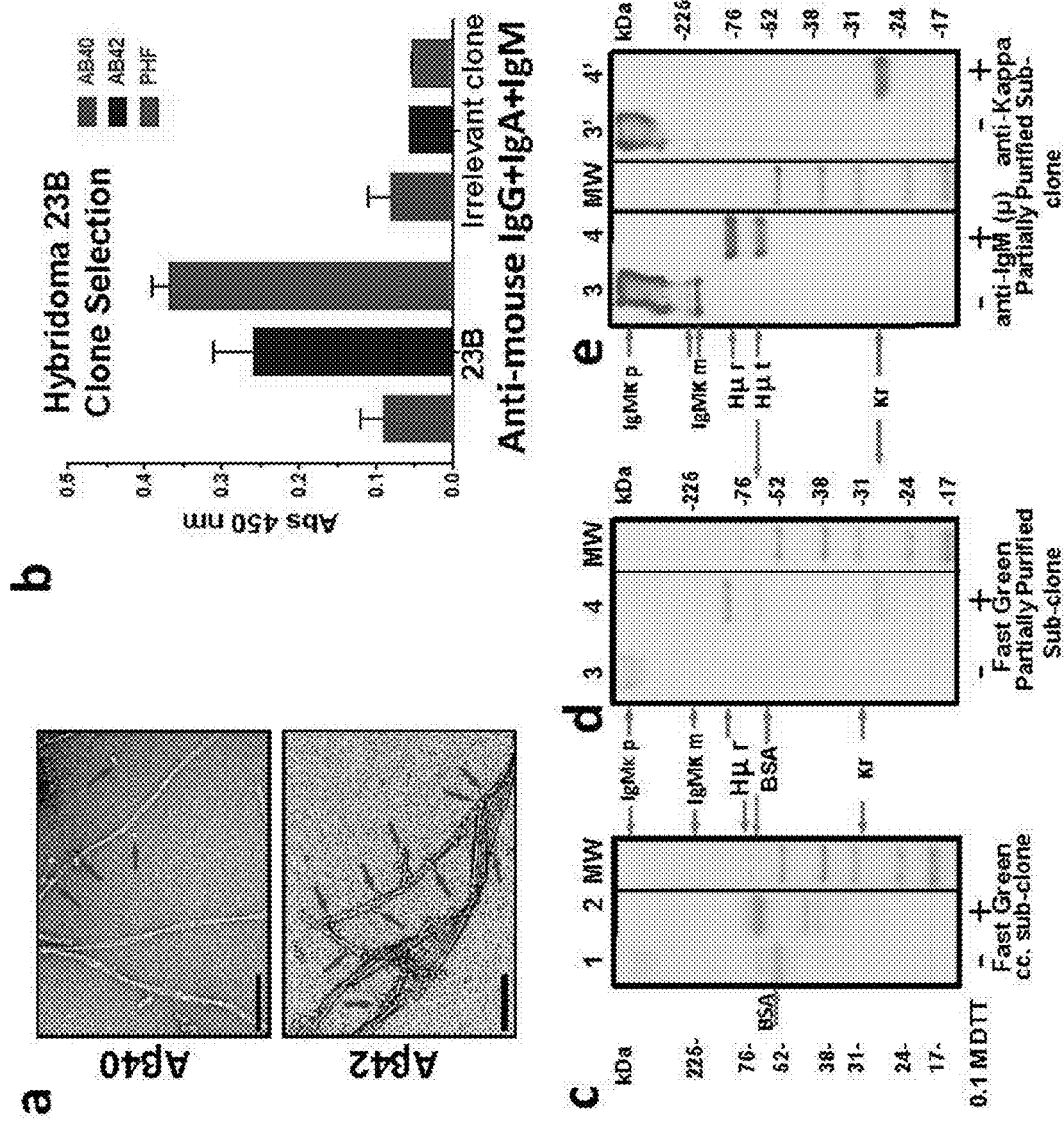

Original clone 23B obtained after the inoculation of a CD-1 mouse with β-sheet dominant p13Bri antigen and subsequent hybridoma production was assessed by an ELISA assay designed to detect the differential concentration of Aβ oligomers between Aβ1-40 and Aβ1-42 samples aged in alkaline buffer, and the most oligomer laced form of paired helical filaments (PHF) extracted from the brain of a confirmed typical human AD case (FIGS. 30A and 30B). Both misfolded proteins only have in common the β-sheet secondary structure of the abnormal conformers.

Small availability of cell supernatant from the initially viable hybridoma cells allowed only one determination per sample per antigen and detection of all the main classes of immunoglobulins together with total anti-mouse GAM antisera. The selection process was explained elsewhere and involved the measurement of the differential reactivity to Aβ40, Aβ42 and PHF of at least three times over the background O.D. readings compared to an irrelevant hybridoma clone from the same fusion (FIG. 30B). The 23B passed three rounds of selection before being classified as GW-23B7 anti-β-sheet conformational monoclonal antibody (aβComAb). The GW-23B7 was later grown in a 5 ml tube and the supernatant showed two main proteins consistent with the albumin from the bovine fetal serum supplement (BSA) and a potential immunoglobulin with a high molecular weight of around 1,000 kDa (FIG. 30C). The BSA was removed by partial purification on SAS precipitation, and the ensuing blot showed a high molecular weight band on top of the gel before reduction and three bands of approximately 76 kDa, 56 kDa and 27 kDa after reduction with DTT (FIG. 30D). The high molecular weight band reacted with both specific anti-mouse µ chain and anti-mouse kappa chain as expected for a pentameric IgMk; a small percentage of a monomeric form at around 180 kDa was also seen. The reduced material showed the intact Hµ at 76 kDa and a small fraction of truncated Hµ chain at 56 kDa not an uncommon find in some IgM preparations. The 27 kDa band was identified as the reduced kappa L chain (FIG. 30E).

Figures 31A, 31B, 31C, 31D:
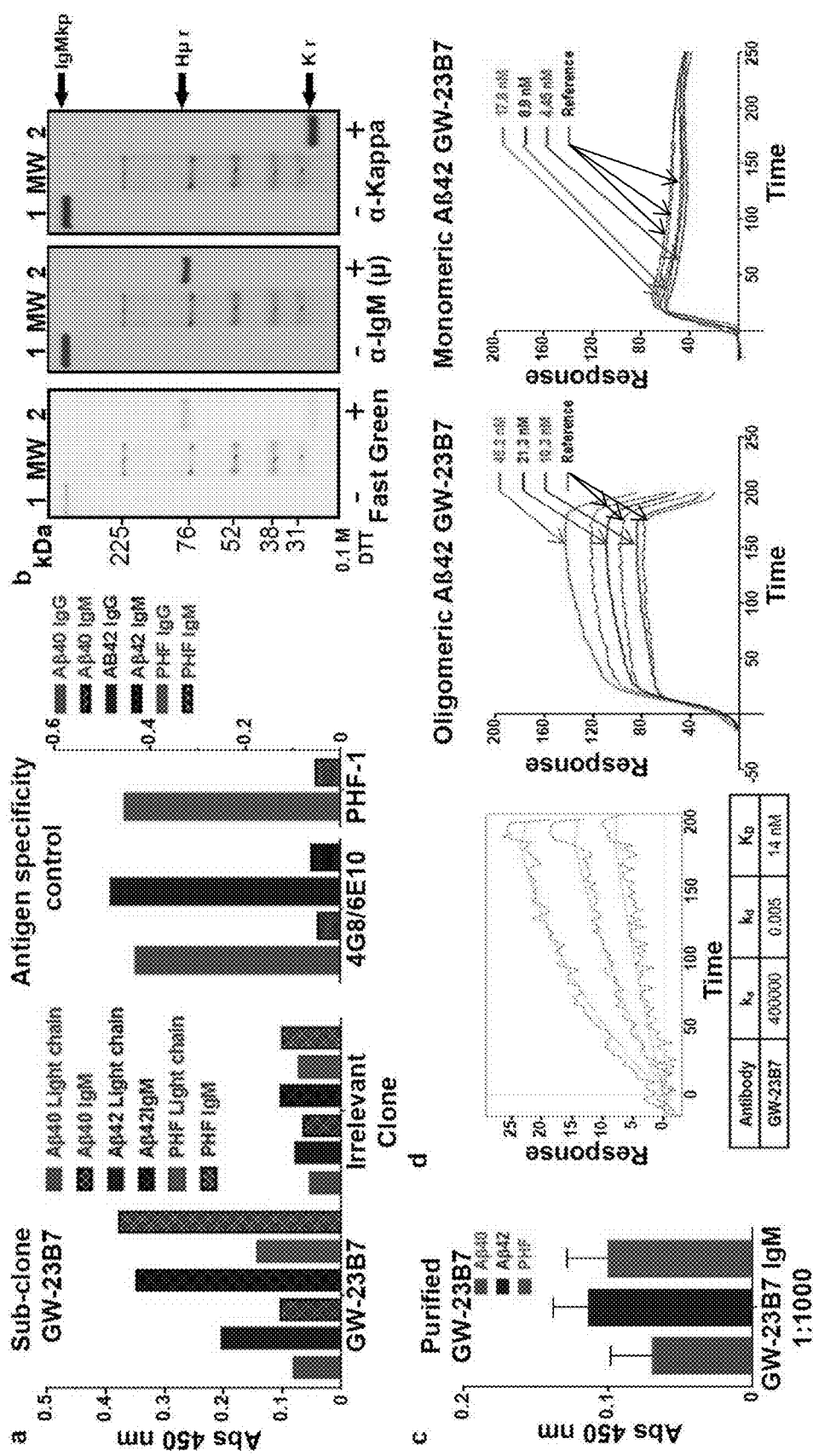
FIGS. 31A-31D depict sub-cloned and purified anti-β-sheet conformational monoclonal antibody (aβComAb) GW-23B7 specific reactivity to human paired helical filaments (PHF) and oligomeric Aβ.

The sub-clone aβComAb GW-23B7 showed by ELISA test significant cross-reactivity with both the differential Aβ oligomers and the oligomeric/fibrilar PHF; both reactivities were present in the same intact IgM molecule (FIG. 31A left panel). The control of the antigens coating the plates was done with commercial mouse IgG antibodies for Aβ 4G8/ 6E10, that recognized only the specific primary sequence of Aβ40 and Aβ42 and both in the same amount, and the commercial mouse IgG antibody PHF-1 specific for hyperphosphorylated tau that only reacted to the human PHF coating. Neither one of the bound IgG specific antibodies was detected by the secondary antibody to µ chain, a necessary control to discard unspecific cross-recognition of the coating antigens by the labeled secondary antisera (FIG. 31A right panel).

Further purified through a llama $V_{HH}$ anti-mouse IgM column, the aβComAb GW-23B7 was recovered as >99% pure IgMk pentameric with intact heavy and light chains (FIG. 31B) retaining the same cross-reactivity to differential Aβ oligomers and PHF in ELISA plates after a 1:1000 dilution to the original supernatant (FIG. 31C). To corroborate the GW-23B7 binding to oligomeric forms of Aβ42, the purified IgMk was run on surface plasmon resonance (SPR) with gold sensor slides immobilizing either oligomeric Aβ42 or the HFIP treated monomeric form. The GW-23B7 only showed binding affinity for the oligomeric form with a $K_D$ in the nanomolar range (FIG. 31D).

Figures 32A, 32B, 32C, 32D:
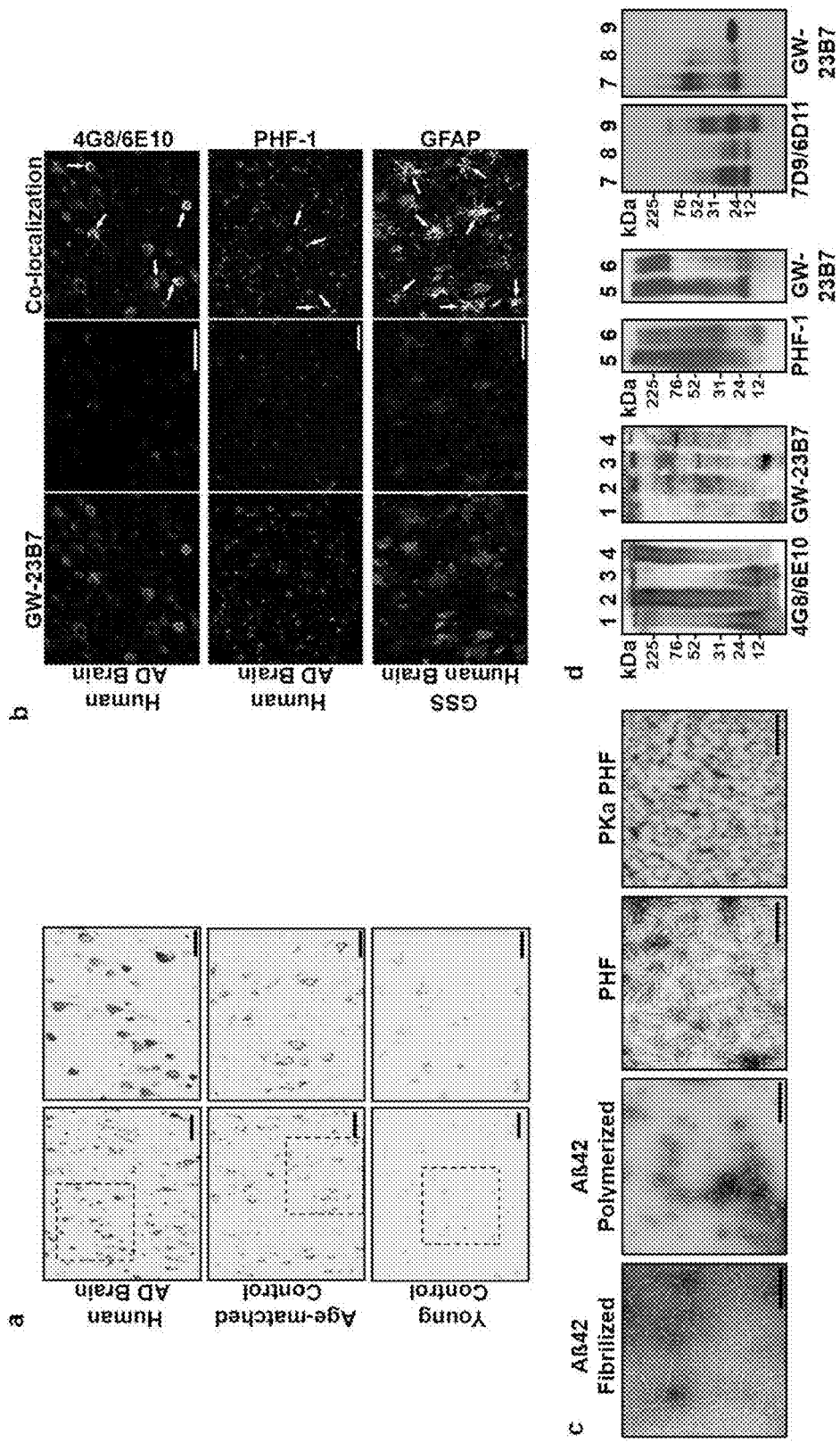
FIGS. 32A-32D depict histochemical reactivity of aβComAb GW-23B7 to Alzheimer's disease (AD), age matched and young control human brains, and Gerstmann-Sträussler-Scheinker (GSS) prion disease; and recognition of pathological conformers on immunoblots.

To determine the pathology specificity of the cross-reactivity that by ELISA and SPR was shown to be related to the shared β-sheet secondary structure present in both oligomeric forms of Aβ and ptau, the GW-23B7 was used for immunohistochemistry in samples from human brains of either known cases of Alzheimer's disease, age matched brain from patients with no clinical cognitive manifestations, and brains from young adults with no known neuropathology. The aβComAb GW-23B7 reacted strongly with intra- and extracellular material in the AD brains consistent with dystrophic neurons and processes as seen in FIG. 32A top panel. The age matched control showed positive but lighter cytoplasmic stain only in scattered neurons (FIG. 32A middle panel), and the brain from the young control with no neuropathology showed no apparent reactivity in all areas scanned (FIG. 31A bottom panel). The proved specificity of the GW-23B7 for human AD pathology was further analyzed to determine the nature of the cross-reactivity. The aβComAb GW-23B7 co-localized in the human AD brain not only with extracellular material of Aβ nature as determined by 4G8/6E10 antibodies, but interestingly with intracellular Aβ in certain neurons (FIG. 32B top panel); most probably the reactivity due to interaction with oligomeric forms of Aβ as demonstrated in immunoblots of electron microscopy (EM) corroborated samples (FIGS. 32C and 32D). The same AD brain showed co-localization of GW-23B7 and PHF-1 in the cytoplasm of neurons (FIG. 32B middle, right panel); again the cross-reactivity was corroborated on immunoblots of EM confirmed samples of oligomer laced human PHF (FIG. 32C, 32D). To further assess cross-reactivity with generic β-sheet in oligomeric conformers, samples from a brain of an unrelated NDD Gerstmann-Sträussler-Scheinker (GSS) a human prion disease, were included. The GW-23B7 strongly co-localized with the typical histopathological gliosis of prion disease where the prion particles with extremely high β-sheet content are associated to the GFAP in astrocytes (FIG. 32B bottom, right panel); the identity of the reaction to $PrP^{res}$ was confirmed by immunoblot (FIG. 32D).

Figures 33A, 33B, 33C:
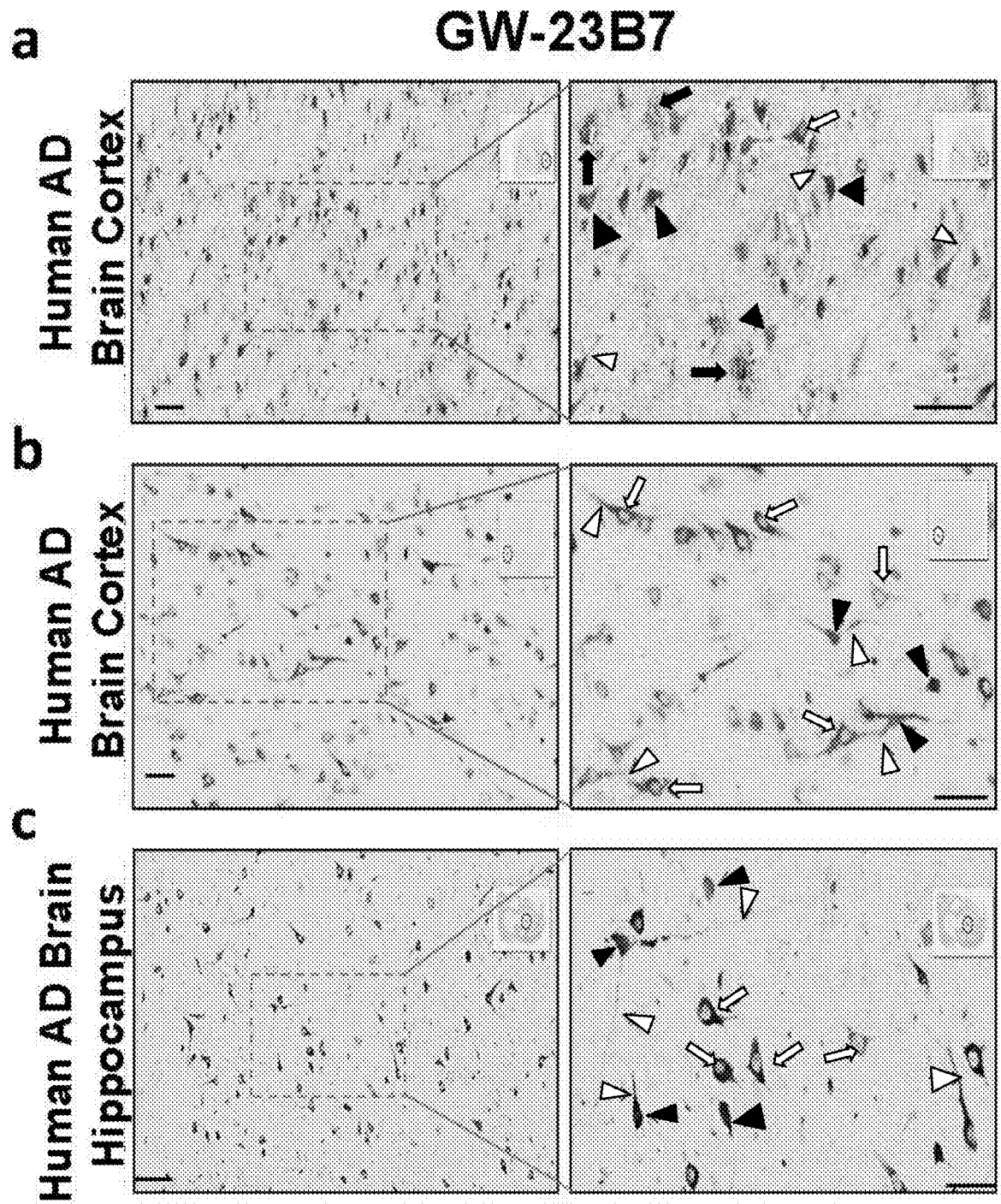
FIGS. 33A-33C depict conformational monoclonal antibody GW-23B7 immunoreactivity on human Alzheimer's disease brains. All slides are from human AD brains.

The IgM aβComAb GW-23B7 was further analyzed on histological samples of human cortex and hippocampus of AD brains where most of the pathology would be located and the primary target for potential immunotherapy. The GW-23B7 detected, in both cortex and hippocampus, cytoplasmic changes in neurons retaining cell shape and membrane integrity through the whole spectrum to dystrophic neurons loosing membrane identity and leaking scatter punctuated material to the extracellular milieu. Processes were also evident and potentially along axons, dendrites, budding and synaptic zones; some of the neurons had even compromised nuclei (FIGS. 33A, 33B, 33C).

Figures 34A, 34B, 34C:
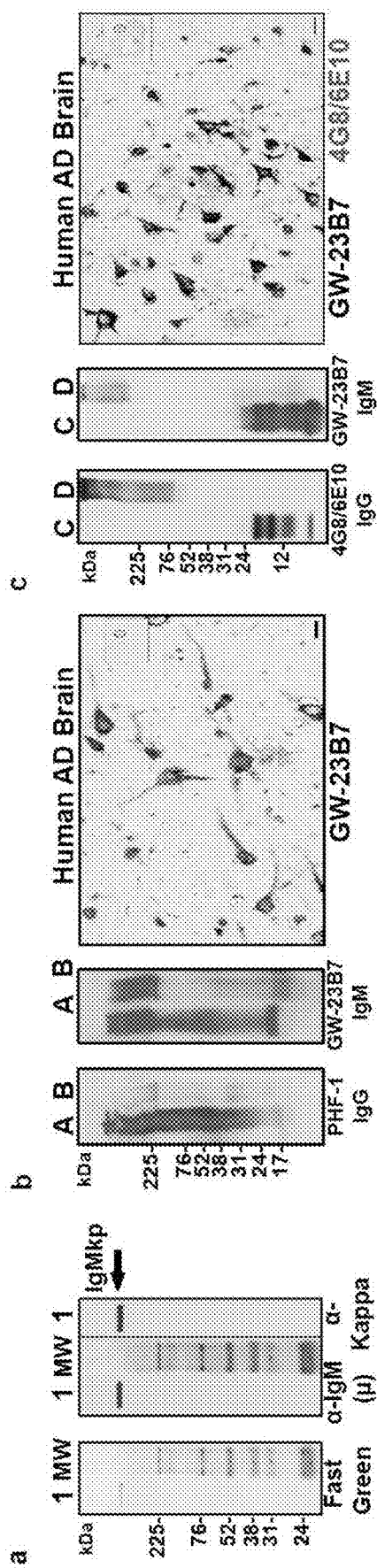
FIGS. 34A-34C depicts molecular integrity and AD pathology recognition of the purified AβComAb GW-23B7 infused on old 3xTg mice.

The specific cross-reactivity of aβComAb GW-23B7 to potentially toxic neuropathological conformers responsible for the prion-like spread of disease without targeting a particular self-sequence primary structure, lead to the possibility of using GW-23B7 for immunotherapeutical infusion experiments in AD animal models. The mAb to be inoculated passed the criteria of being >99% pure IgMk pentameric (FIG. 34A), reactive with oligomeric/fibrillar forms of real human PHF in immunoblots and detect intra and extracellular tau pathology in a human AD brain (FIG. 34B), cross-reactive with oligomeric forms of Aβ in immunoblots, and capable of co-localization with material related to amyloid plaques in a human AD brain (FIG. 34C).

The AD 3×Tg APP/PS1 P301L mouse model with both Aβ and tau pathology was selected for testing. The animals were at least 16 month old to assure a flourish and fast developing Aβ and tau pathology in all animals used for the experiment. Two groups of ten animals each were infused intraperitoneally (i.p.) with either aβComAb GW-23B7 in sterile saline or saline vehicle alone as per protocol in FIG. 35A. Due to the high molecular weight of the pentameric IgM and the uncertainty of the interaction with the blood brain barrier (BBB) two more groups of 12 animals each were also infused i.p. as shown in the bottom part of the protocol in FIG. 35A. Four animals of each group were sacrificed at 6, 24 and 48 hours post-infusion respectively. Each animal was thoroughly perfused with PBS as explained infra to devoid all brain capillary vessels of residual immunoglobulin carrying blood. A whole hemisphere of each animal was homogenized and centrifuged to retain the soluble brain material (FIG. 35A).

Soluble material was concentrated at least 400 times and the samples from each group pooled for immunoblot analysis. FIG. 35B shows protein reversible stain (top panel) to ascertain comparable protein load of each pool. The middle panel shows the anti-mouse μH chain specific reactivity before and after reduction; the intact pentameric IgM and the identity of the reduced chain at 76 kDa molecular weight. The bottom panel shows the reactivity with anti-mouse kappa L chain antisera detecting the intact IgMk in the same pentameric position and also the normal polyclonal IgGk at around 150 kDa. The densitometric analysis of each band is shown in the graph on the right of FIG. 35B. At all times checked, animals infused with aβComAb GW-23B7 had a significant higher concentration of IgM pentameric than the control group. The IgM in the GW-23B7 infused group was noticeable already at 6 hours post-infusion, peaked at 24 hours as demonstrated by both anti-pt and the anti-kappa antisera, maintaining a substantial increase after 48 hours (FIG. 35B right graph). The control group had similar concentration of IgM at all times checked; and all groups infused or control had comparable concentrations of IgG compared to the increased IgMk in the GW-23B7 infused group as determined by the kappa L chains detected in both classes of immunoglobulins (FIG. 35B bottom panel); showing the IgM increase in the infused animals was real and not an artifact of the procedure. These results show IgM pentameric can go through the BBB and eventually act inside the brain.

The two groups were infused for two months as per protocol on FIG. 35A, after which all animals already 18 month old showed no difference in the locomotor tests (FIGS. 36A-36B). The two groups were later tested at the same time for behavioral changes determined by radial arm maze. The GW-23B7 treated animals showed a significant cognitive rescue compared to the control group (FIG. 35C). Immediately after, all animals were sacrificed at 19 month of age and organs and brains collected and divided for histology and biochemistry as per standard procedures described herein.

FIG. 37A shows representative samples of hippocampus and subiculum from brains in the GW-23B7 infused or the control groups. The striking difference in the mostly extracellular Aβ deposited material is reflected in the quantitation of the amyloid burden between the two groups on FIG. 37B. On the other hand the microscopy and the quantitation analysis does not show a difference between the intensity and the number of cells with PHF-1 stain in both groups (FIG. 37A right panel, 37B right graph).

Conversely, the brain homogenates that would have collected the soluble or semi-soluble conformers from all parts of the brain showed a different panorama. The Aβ40 and Aβ42 showed a significant decline in the GW-23B7 infused animals that can be attributed in part to a significant reduction of recognizable aggregated Aβ (FIG. 37C three left graphs), a sign of toxic oligomers reduced in treated animals. More relevant is the specific significant drop of the toxic spreadable form of tau pTau-Thr 231 in the treated animals while the total soluble tau shows only a trend to a slight decrease in the treated animals (FIG. 37C two right graphs).

To assess the possible identity of the potential soluble oligomeric forms of Aβ and tau which were modified by the immunotherapy, the soluble portion of the brain homogenates was run on gels and blotted (FIG. 38A). The membrane, with representative animals from both groups, was stained with a reversible Fast Green and showed comparable loads among all samples and in an extended range of molecular weights (top left panel). The same membrane was blotted with 4G8/6E10 to detect aggregated Aβ (top right panel), with PHF-1 to detect abnormal tau conformers (bottom left panel), and with the same GW-23B7 that was used for immunotherapeutically infuse animals (bottom right panel). The potential oligomeric forms to be analyzed were color coded and quantitated densitometrically after proper scan of the films. The graph results are shown on FIG. 38B. Only one band at 110 kDa showed identity for both Aβ and tau and was also recognized by the GW-23B7. All three antibodies showed a significant decrease of this heterooligomer in the treated animals (top row three left graphs). From 54 to 62 kDa three bands were detected by PHF-1 and showed a significant decrease in the GW-23B7 treated animals (bottom row graphs). The 54 kDa (green) decrease was also confirmed by GW-23B7, the 57 kDa could only be measured with PHF-1 and the decrease of the 62 kDa was only significant when measure by PHF-1. A band of high molecular weight of around 190 kDa was seen only by the GW-23B7 and significantly decreased in the treated animals.

Discussion

Neurodegenerative diseases and Alzheimer's disease in particular have been recognized and studied for more than 100 years, yet most therapeutic approaches have yielded little or null success. Recently, immunotherapy for AD was deemed to be a potent valuable option; however, even the most up to date trials have shown poor or discouraging results.

The approach for the treatment of AD described herein follows the rationale that only a therapy addressing together both hallmarks of the disease, i.e., the Aβ and tau pathologies, might have some chances of success.

The first consideration for this rationale was to have, if possible, an immune reaction to a generic trait present on both so different pathologic conformers. It is clear now that oligomers with mobility to spread prion-like are the disease culprits more than the precipitated amyloid Aβ in extracellular plaques and the tau-PHF inside neurons. These two extremely different neuroconformers only share in common—as with the toxic oligomers in Parkinson and Prion diseases—the dominant β-sheet secondary structure produced during the conversion in the brain of the self-physiological protein/peptides to pathologic oligo-conformers. An extremely difficult feat, was the development of an immunogen with no sequence similarity to any mammal protein/peptide, and polymerization of this immunogen into extremely stable oligomers with more than 90% β-sheet structure and no tendency to develop fibrillary forms. This immunogen was proven to prevent pathology in three different mouse models of AD covering the whole range of Aβ, tau and vascular amyloid pathologies. The successful immunogen was used to inoculate mice and produce hybridomas selected exclusively with at least three different neuroconformers having in common only β-sheet dominant structures in their oligomers. A few families of monoclonals that cross-reacted with different pathological conformers were rescued and called anti-β-sheet secondary structure conformational monoclonal antibodies (aβComAb) to differentiate them from other anti-conformation monoclonals raised against a specific primary and tertiary structure that produces very limited cross-reactivity in the best of cases.

The focus of this example is aβComAb GW-23B7. This mAb has been extensively studied and purified showing a good binding affinity to oligomeric forms of Aβ1-42 and oligomers from real PHF extracted from a human AD brain (FIGS. 30-33). The potential anti-β-sheet cross-reactivity was confirmed by also detecting prion oligomers and the co-localization with different pathological components in human brains of AD and prion disease (FIGS. 32A-32D). To translate it into a therapeutic agent GW-23B7 was purified and shown to still conserve the specific cross-reactivities (FIGS. 34A-34C).

Usually, high molecular weight bands are not detected by commercial antibodies due probably to the specific epitopes being buried in larger compact aggregates of more than one neuroconformer. On the other hand, the aβComAb GW-23B7 essentially detects the β-sheet structures in oligomers that grow by the zipper-like binding site that buries one epitope while producing a newly-formed epitope-binding motif, ensuring the growth of the oligomers until they get compacted, fibrillized and precipitated as amyloid. To be able to recognize this type of oligomers has two potential advantages; the first being of diagnostic value of an active pathology disease-spread marker, and the second, and may be later the most important one, the recognition of therapeutic targets that can be used to stop and reverse a disease spread progress as it was shown in the 3×Tg AD animal model.

Lately, there have been reports blaming high molecular weight oligomers that are extremely toxic for rapid progression of disease and the fatal demise. The aβComAb GW-23B7 or others, alone or in combination, derived from the same family of anti-secondary structure monoclonals produced as described herein provide a potential solution for the treatment of the most aggressive stages of neurodegenerative diseases when spread runs out of the controls of metabolic checks and balances in the brain.

Although preferred embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow.

What is claimed is:

1. An antibody or binding fragment thereof that binds β-sheet secondary structure of pathologic monomeric or oligomeric non-fibrillar proteins/peptides, said antibody or binding fragment thereof comprising:
    (a) a heavy chain variable region, wherein said heavy chain variable region comprises a complementarity-determining region 1 (H-CDR1) comprising the amino acid sequence of SEQ ID NO: 23, a complementarity-determining region 2 (H-CDR2) comprising the amino acid sequence of SEQ ID NO: 27, and a complementarity-determining region 3 (H-CDR3) comprising the amino acid sequence of SEQ ID NO: 31; and a light chain variable region, wherein said light chain variable region comprises a complementarity-determining region 1 (L-CDR1) comprising the amino acid sequence of SEQ ID NO: 35, a complementarity-determining region 2 (L-CDR2) comprising the amino acid sequence of SEQ ID NO: 40, and a complementarity-determining region 3 (L-CDR3) comprising the amino acid sequence of SEQ ID NO: 45;
    (b) a heavy chain variable region, wherein said heavy chain variable region comprises a H-CDR1 comprising the amino acid sequence of SEQ ID NO: 24, a H-CDR2 comprising the amino acid sequence of SEQ ID NO: 28, and a H-CDR3 comprising the amino acid sequence of SEQ ID NO: 32; and a light chain variable region, wherein said light chain variable region comprises a L-CDR1 comprising the amino acid sequence of SEQ ID NO: 36, a L-CDR2 comprising the amino acid sequence of SEQ ID NO: 41, and a L-CDR3 comprising the amino acid sequence of SEQ ID NO: 46;
    (c) a heavy chain variable region, wherein said heavy chain variable region comprises a H-CDR1 comprising the amino acid sequence of SEQ ID NO: 25, a H-CDR2 comprising the amino acid sequence of SEQ ID NO: 29, and a H-CDR3 comprising the amino acid sequence of SEQ ID NO: 33; and a light chain variable region, wherein said light chain variable region comprises a L-CDR1 comprising the amino acid sequence of SEQ ID NO: 37, a L-CDR2 comprising the amino acid sequence of SEQ ID NO: 42, and a L-CDR3 comprising the amino acid sequence of SEQ ID NO: 47;
    (d) a heavy chain variable region, wherein said heavy chain variable region comprises a H-CDR1 comprising the amino acid sequence of SEQ ID NO: 26, a H-CDR2 comprising the amino acid sequence of SEQ ID NO: 30, and a H-CDR3 comprising the amino acid sequence of SEQ ID NO: 34; and a light chain variable region, wherein said light chain variable region comprises a L-CDR1 comprising the amino acid sequence of SEQ ID NO: 39, a L-CDR2 comprising the amino acid sequence of SEQ ID NO: 44, and a L-CDR3 comprising the amino acid sequence of SEQ ID NO: 49;
    (e) a heavy chain variable region, wherein said heavy chain variable region comprises a H-CDR1 comprising the amino acid sequence of SEQ ID NO: 50, a H-CDR2 comprising the amino acid sequence of SEQ ID NO: 51, and a H-CDR3 comprising the amino acid sequence of SEQ ID NO: 52; and a light chain variable region, wherein said light chain variable region comprises a L-CDR1 comprising the amino acid sequence of SEQ ID NO: 53, a L-CDR2 comprising the amino acid sequence of SEQ ID NO: 54, and a L-CDR3 comprising the amino acid sequence of SEQ ID NO: 55;

(f) a heavy chain variable region comprising the H-CDR1 comprises the amino acid sequence of SEQ ID NO: 23, the H-CDR2 comprising the amino acid sequence of SEQ ID NO: 27, and the H-CDR3 comprising the amino acid sequence of SEQ ID NO: 31; a light chain variable region, wherein said light chain variable region comprises a L-CDR1 comprising the amino acid sequence of SEQ ID NO: 38, a L-CDR2 comprising the amino acid sequence of SEQ ID NO: 43, and a L-CDR3 comprising the amino acid sequence of SEQ ID NO: 48; and (g) a heavy chain variable region, wherein said heavy chain variable region comprises a H-CDR1 comprising the amino acid sequence of SEQ ID NO: 50, a H-CDR2 comprising the amino acid sequence of SEQ ID NO: 51, and a H-CDR3 comprising the amino acid sequence of SEQ ID NO: 52; and a light chain variable region, wherein said light chain variable region comprises a L-CDR1 comprising the amino acid sequence of SEQ ID NO: 53, a L-CDR2 comprising the amino acid sequence of SEQ ID NO: 112, and a L-CDR3 comprising the amino acid sequence of SEQ ID NO: 55.

2. The antibody or binding fragment thereof of claim 1 comprising:
the heavy chain variable region comprising the H-CDR1 comprising the amino acid sequence of SEQ ID NO: 23, the H-CDR2 comprising the amino acid sequence of SEQ ID NO: 27, and the H-CDR3 comprising the amino acid sequence of SEQ ID NO: 31 and the light chain variable region comprising the complementarity-determining region 1 (L-CDR1) comprising the amino acid sequence of SEQ ID NO: 35, the complementarity-determining region 2 (L-CDR2) comprising the amino acid sequence of SEQ ID NO: 40, and the complementarity-determining region 3 (L-CDR3) comprising the amino acid sequence of SEQ ID NO: 45.

3. The antibody or binding fragment thereof of claim 1 comprising:
the heavy chain variable region comprising the H-CDR1 comprising the amino acid sequence of SEQ ID NO: 23, the H-CDR2 comprising the amino acid sequence of SEQ ID NO: 27, and the H-CDR3 comprising the amino acid sequence of SEQ ID NO: 31, and the light chain variable region comprising the L-CDR1 comprising the amino acid sequence of SEQ ID NO: 38, the L-CDR2 comprising the amino acid sequence of SEQ ID NO: 43, and the L-CDR3 comprising the amino acid sequence of SEQ ID NO: 48.

4. The antibody or binding fragment thereof of claim 1 comprising:
the heavy chain variable region comprising the H-CDR1 comprising the amino acid sequence of SEQ ID NO: 24, the H-CDR2 comprising the amino acid sequence of SEQ ID NO: 28, and the H-CDR3 comprising the amino acid sequence of SEQ ID NO: 32, and the light chain variable region comprising the L-CDR1 comprising the amino acid sequence of SEQ ID NO: 36, the L-CDR2 comprising the amino acid sequence of SEQ ID NO: 41, and the L-CDR3 comprising the amino acid sequence of SEQ ID NO: 46.

5. The antibody or binding fragment thereof of claim 1 comprising:
the heavy chain variable region comprising the H-CDR1 comprising the amino acid sequence of SEQ ID NO: 25, the H-CDR2 comprising the amino acid sequence of SEQ ID NO: 29, and the H-CDR3 comprising the amino acid sequence of SEQ ID NO: 33, and the light chain variable region comprising the L-CDR1 comprising the amino acid sequence of SEQ ID NO: 37, the L-CDR2 comprising the amino acid sequence of SEQ ID NO: 42, and the L-CDR3 comprising the amino acid sequence of SEQ ID NO: 47.

6. The antibody or binding fragment thereof of claim 1 comprising:
the heavy chain variable region comprising the H-CDR1 comprising the amino acid sequence of SEQ ID NO: 26, the H-CDR2 comprising the amino acid sequence of SEQ ID NO: 30, and the H-CDR3 comprising the amino acid sequence of SEQ ID NO: 34, and the light chain variable region comprising the L-CDR1 comprising the amino acid sequence of SEQ ID NO: 39, the L-CDR2 comprising the amino acid sequence of SEQ ID NO: 44, and the L-CDR3 comprising the amino acid sequence of SEQ ID NO: 49.

7. The antibody or binding fragment thereof of claim 1 comprising:
the heavy chain variable region comprising the H-CDR1 comprising the amino acid sequence of SEQ ID NO: 50, the H-CDR2 comprising the amino acid sequence of SEQ ID NO: 51, and the H-CDR3 comprising the amino acid sequence of SEQ ID NO: 52, and the light chain variable region comprising the L-CDR1 comprising the amino acid sequence of SEQ ID NO: 53, the L-CDR2 comprising the amino acid sequence of SEQ ID NO: 54, and the L-CDR3 comprising the amino acid sequence of SEQ ID NO: 55.

8. The antibody or binding fragment thereof of claim 1 comprising:
the heavy chain variable region comprising the H-CDR1 comprising the amino acid sequence of SEQ ID NO: 50, the H-CDR2 comprising the amino acid sequence of SEQ ID NO: 51, and the H-CDR3 comprising the amino acid sequence of SEQ ID NO: 52, and the light chain variable region comprising the L-CDR1 comprising the amino acid sequence of SEQ ID NO: 53, the L-CDR2 comprising the amino acid sequence of SEQ ID NO: 112, and the L-CDR3 comprising the amino acid sequence of SEQ ID NO: 55.

9. The antibody or binding fragment thereof of claim 1, wherein said antibody or binding fragment thereof comprises
(a) a heavy chain variable region comprising an amino acid sequence that is at least 80% identical to SEQ ID NO: 2 and a light chain variable region comprising an amino acid sequence that is at least 80% identical to SEQ ID NO: 4;
(b) a heavy chain variable region comprising an amino acid sequence that is at least 80% identical to SEQ ID NO: 6 and a light chain variable region comprising an amino acid sequence that is at least 80% identical to SEQ ID NO: 8;
(c) a heavy chain variable region comprising an amino acid sequence that is at least 80% identical to SEQ ID NO: 10 and a light chain variable region comprising an amino acid sequence that is at least 80% identical to SEQ ID NO: 12;

(d) a heavy chain variable region comprising an amino acid sequence that is at least 80% identical to SEQ ID NO: 2 and a light chain variable region comprising an amino acid sequence that is at least 80% identical to SEQ ID NO: 18;
(e) a heavy chain variable region comprising an amino acid sequence that is at least 80% identical to SEQ ID NO: 20 and a light chain variable region comprising an amino acid sequence that is at least 80% identical to SEQ ID NO: 22;
(f) a heavy chain variable region comprising an amino acid sequence that is at least 80% identical to SEQ ID NO: 14 and a light chain variable region comprising an amino acid sequence that is at least 80% identical to SEQ ID NO: 16; or
(g) a heavy chain variable region comprising an amino acid sequence that is at least 80% identical to SEQ ID NO: 14 and a light chain variable region comprising an amino acid sequence that is at least 80% identical to SEQ ID NO: 109.

10. The antibody or binding fragment thereof of claim 9, wherein said antibody or binding fragment thereof comprises:
(a) a heavy chain variable region comprising the amino acid sequence of SEQ ID NO: 2 and a light chain variable region comprising the amino acid sequence of SEQ ID NO: 4;
(b) a heavy chain variable region comprising the amino acid sequence of SEQ ID NO: 6 and a light chain variable region comprising the amino acid sequence of SEQ ID NO: 8;
(c) a heavy chain variable region comprising the amino acid sequence of SEQ ID NO: 10 and a light chain variable region comprising the amino acid sequence of SEQ ID NO: 12;
(d) a heavy chain variable region comprising the amino acid sequence of SEQ ID NO: 2 and a light chain variable region comprising the amino acid sequence of SEQ ID NO: 18;
(e) a heavy chain variable region comprising the amino acid sequence of SEQ ID NO: 20 and a light chain variable region comprising the amino acid sequence of SEQ ID NO: 22;
(f) a heavy chain variable region comprising the amino acid sequence of SEQ ID NO: 14 and a light chain variable region comprising the amino acid sequence of SEQ ID NO: 16; or
(g) a heavy chain variable region comprising the amino acid sequence of SEQ ID NO: 14 and a light chain variable region comprising the amino acid sequence of SEQ ID NO: 109.

11. The antibody or binding fragment thereof of claim 1, wherein said antibody or binding fragment thereof is a murine antibody or a humanized antibody.

12. The antibody or binding fragment thereof of claim 1, wherein said antibody or binding fragment thereof is selected from the group consisting of a disulfide linked Fv, a scFv, a CDR-grafted antibody, a diabody, a multispecific antibody, a Fab, a Fab', a bispecific antibody, a F(ab')$_2$, and a Fv.

13. An isolated polynucleotide encoding the antibody or binding fragment thereof of claim 1.

14. A pharmaceutical composition comprising:
the antibody or binding fragment thereof of claim 1, and a pharmaceutical carrier.

15. A method of binding pathological oligomeric proteins or peptides having a β-sheet secondary structure in a subject, said method comprising:
administering to the subject the pharmaceutical composition of claim 14, wherein said composition is administered in an amount effective to bind pathological oligomeric proteins or peptides having β-sheet secondary structure in the subject.

16. The method of claim 15, wherein the subject has a condition selected from the group consisting of Alzheimer's disease (AD), preclinical AD, Down syndrome (DS), frontotemporal dementia (FTD), Lewy Body Dementia (LBD), Parkinson's disease (PD), hereditary cerebral hemorrhage with amyloidosis (HCHWA), kuru, Creutzfeldt-Jakob disease (CJD), chronic wasting disease (CWD), Gerstmann-Straussler-Scheinker disease (GSS), spongiform encephalopathy, Scrapie (Sc), Huntington's disease (HD), fatal familial insomnia, British familial dementia, Danish familial dementia, frontotemporal lobar degeneration associated with protein tau (FTLD-tau), frontotemporal lobar degeneration associated with protein FUS (FTLD-FUS), Amyotrophic lateral sclerosis (ALS), Mild Cognitive Impairment (MCI), familial corneal amyloidosis, Familial corneal dystrophies, medullary thyroid carcinoma, insulinoma, type 2 diabetes, isolated atrial amyloidosis, pituitary amyloidosis, aortic amyloidosis, plasma cell disorders, familial amyloidosis, senile cardiac amyloidosis, inflammation-associated amyloidosis, familial Mediterranean fever (FMF), dialysis-associated amyloidosis, systemic amyloidosis, familial systemic amyloidosis, motor neuron disease, traumatic brain injury (TBI), and chronic traumatic encephalopathy.

17. A method of diagnosing an amyloid disease in a subject, said method comprising:
detecting, in the subject, the presence of an amyloidogenic protein or peptide using a diagnostic reagent, wherein the diagnostic reagent comprises the antibody or binding fragment thereof of claim 1, and
diagnosing the amyloid disease in the subject based on said detecting.

18. A method of identifying a subject's risk for developing a condition mediated by an amyloidogenic protein or peptide, said method comprising:
detecting, in the subject, the presence of an amyloidogenic protein or peptide using a diagnostic reagent, wherein the diagnostic reagent comprises the antibody or binding fragment thereof of claim 1, and
identifying the subject's risk of developing the condition mediated by the amyloidogenic protein or peptide based on said detecting.

19. A diagnostic kit comprising:
the antibody or binding fragment thereof of claim 1 and a detectable label.

* * * * *